(12) United States Patent
Nishiyama et al.

(10) Patent No.: US 7,196,199 B2
(45) Date of Patent: Mar. 27, 2007

(54) PHENOXYPROPYLAMINE COMPOUNDS

(75) Inventors: Akira Nishiyama, Tokyo (JP);
Masahiro Bougauchi, Tokyo (JP);
Takanobu Kuroita, Tokyo (JP);
Masanori Minoguchi, Tokyo (JP)

(73) Assignee: Mitsubishi Pharma Corporation, Osaka (JP)

( * ) Notice: Subject to any disclaimer, the term of this patent is extended or adjusted under 35 U.S.C. 154(b) by 478 days.

(21) Appl. No.: 10/740,418

(22) Filed: Dec. 22, 2003

(65) Prior Publication Data

US 2004/0138227 A1    Jul. 15, 2004

Related U.S. Application Data

(60) Division of application No. 09/990,389, filed on Nov. 23, 2001, now Pat. No. 6,720,320, which is a continuation-in-part of application No. PCT/JP00/03279, filed on May 22, 2000.

(30) Foreign Application Priority Data

| May 24, 1999 | (JP) | ................................. 11-142750 |
| Jun. 14, 1999 | (JP) | ................................. 11-166160 |
| Sep. 29, 1999 | (JP) | ................................. 11-277384 |
| Jan. 25, 2000 | (JP) | ................................. 2000-18080 |

(51) Int. Cl.
C07D 413/04 (2006.01)
C07D 413/14 (2006.01)

(52) U.S. Cl. ...................................... 548/143; 548/144
(58) Field of Classification Search ................ 548/143, 548/144
See application file for complete search history.

(56) References Cited

U.S. PATENT DOCUMENTS

| 3,810,760 A | 5/1974 | Kampfer et al. |
| 3,816,131 A | 6/1974 | Kampfer et al. |
| 3,929,793 A | 12/1975 | Popelak et al. |
| 4,191,765 A | 3/1980 | Fritsch et al. |
| 4,670,439 A | 6/1987 | Witte et al. |
| 4,861,897 A | 8/1989 | Press et al. |
| 5,281,624 A | 1/1994 | Gehlert et al. |
| 5,436,337 A | 7/1995 | Abraham et al. |
| 5,500,431 A | 3/1996 | Audia et al. |
| 6,376,491 B1 | 4/2002 | Aoki et al. |

FOREIGN PATENT DOCUMENTS

| EP | 0 156 331 | 10/1985 |
| EP | 0 722 941 | 7/1996 |
| EP | 0 814 084 | 12/1997 |
| EP | 0 905 133 | 3/1999 |
| HU | 209 753 | 2/1995 |
| HU | 215 519 | 1/1999 |
| JP | 47-18538 | 9/1972 |
| JP | 50-41880 | 4/1975 |
| JP | 52-90307 | 7/1977 |
| JP | 52-92610 | 8/1977 |
| JP | 53-12827 | 2/1978 |
| JP | 55-100361 | 7/1980 |
| JP | 58-121214 | 7/1983 |
| JP | 60-202872 | 10/1985 |
| JP | 61-43183 | 3/1986 |
| JP | 61-057572 | 3/1986 |
| JP | 61-218582 | 9/1986 |
| JP | 8-508270 | 9/1993 |
| JP | 7-17952 | 1/1995 |
| JP | 8-509228 | 10/1996 |
| JP | 9-136877 | 5/1997 |
| JP | 11-158175 | 6/1999 |
| JP | 2000-86603 | 3/2000 |
| WO | 80/00152 | 2/1980 |
| WO | 92/18089 | 10/1992 |
| WO | 94/22842 | 10/1994 |

(Continued)

OTHER PUBLICATIONS

Katsumi, I., et al. "Studies on Styrene Derivatives. I. Synthesis and Antiinflammatory Activities of α-Benzylidene-γ-butyrolactone Derivatives", Chem. Pharm. Bull., vol. 34, No. 1 (1986), pp. 121-129.

(Continued)

*Primary Examiner*—Fiona T. Powers
(74) *Attorney, Agent, or Firm*—Wenderoth, Lind & Ponack, L.L.P.

(57) ABSTRACT

The present invention relates to a phenoxypropylamine compound of the formula (I)

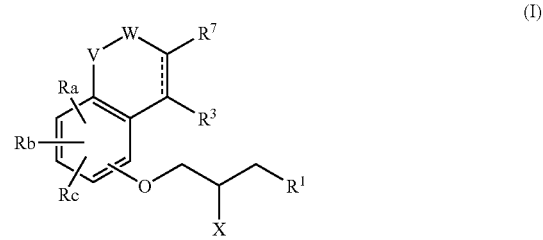

wherein each symbol is as defined in the specification, an optically active compound thereof or a pharmaceutically acceptable salt thereof and hydrates thereof, which simultaneously show selective affinity for and antagonistic activity against 5-HT$_{1A}$ receptor, as well as 5-HT reuptake inhibitory activity, and can be used as antidepressants quick in expressing an anti-depressive effect.

3 Claims, No Drawings

FOREIGN PATENT DOCUMENTS

| | | |
|---|---|---|
| WO | 95/24200 | 9/1995 |
| WO | 97/00249 | 1/1997 |
| WO | 99/55672 | 11/1999 |
| WO | 00/37464 | 6/2000 |
| WO | WO-2002/42297 A1 * | 5/2002 |

OTHER PUBLICATIONS

Shiba, T., et al. "Synthesis of Specifically Iodine-131- and Carbon-14-Labeled Thyroxine", J. Org. Chem., vol. 27 (1962), pp. 1773-1778; with chemical abstract thereof.

Bharathi, K., et al. "Synthesis, Pharmacological Evaluation and QSAR Studies of 4,5-Dihydro-4-[(substituted Phenyl) Methylene]-5-oxo-2-Phenyl/methyl-1H-Imidazole-1-Acetic Acids", Indian Journal of Pharmaceutical Sciences, vol. 61, No. 3 (1999), pp. 186-189.

Zawadowski, T., et al. "Synteza Nowych, Aminoalkanolowych Pochodnych Benzofuranu O Spodziewanym Dzia Laniu β-Adrenolitycznym", Acta Poloniae Pharmaceutica, vol. 46, No. 3 (1989), pp. 201-208; with chemical abstract thereof.

Besenfelder, E. "High Performance Liquid Chromatographic Determination of Picumast and two Active Metabolites in Plasma using On-line Sample Preparation", Biomedical Chromatography, vol. 5 (1997), pp. 32-37; with chemical abstract thereof.

Covello, M., et al. "Nuovi iodorganici di sintesi Iodobenzalidantoine e iodobenzaltioidantoine", Rend. Accad. Sci. Fis. Mal., vol. 35 (1968), pp. 156-164; with chemical abstract thereof.

Meltzer, R.I., et al. "Reaction of 4-Hydroxy-3,5-diiodophenylpyruvic Acid with 3,5-Diiodotyrosine", J. Org. Chem., vol. 26 (1961), pp. 1977-1979; with chemical abstract thereof.

* cited by examiner

PHENOXYPROPYLAMINE COMPOUNDS

This application is a divisional of Ser. No. 09/990,389 filed Nov. 23, 2001, now U.S. Pat. No. 6,720,320, which is a continuation-in-part of International Application No. PCT/JP00/03279 filed May 22, 2000.

TECHNICAL FIELD

The present invention relates to a compound that acts on 5-hydroxytryptamine (5-HT) neurotransmission. More particularly, the present invention relates to a novel phenoxypropylamine compound having selective affinity for and simultaneous antagonistic activity against a 5-hydroxytryptamine 1A (5-HT$_{1A}$) receptor in the central nervous system, as well as a 5-HT reuptake inhibitory activity, which is useful as a pharmaceutical agent, and to a therapeutic agent for depression and the like, which contains this compound. 5-Hydroxytryptamine (5-HT) is also known as "serotonin".

BACKGROUND ART

As a compound having an antagonistic activity against 5-HT$_{1A}$ receptor as well as an inhibitory activity on the reuptake of 5-HT, there are known, for example, 1-(4-indolyloxy)-3-(4-(3,4-methylenedioxyphenyl)piperidino)-2-propanol derivative (EP 0722941), 4-(4-fluorophenyl)-1-((6-(methylamino)indan-1-yl)methyl)piperidine derivative (WO 95/33721), 3,6-dihydro-N-methyl-N-(5-chloro-2-pyridyl)-4-(1-naphthalenyl)-1-(2H)pyridine propanamine derivative (U.S. Pat. No. 5,472,966), 3-(5-chlorobenzo[b]thiophen-3-yl)-5,6-dihydroimidazo[2,1-b]thiazol derivative (WO 97/02269), S-(−)-N-(2-(3-(2-naphthyl)pyrrolidino)ethyl)-N-(2-pyridyl) cyclohexanecarboxamide derivative (WO 97/40038), (R)-3-(N-cyclopentyl-N-n-propylamino)-8-fluoro-5-(N-methylcarbamoyl)-3,4-dihydro-2H-1-benzopyran derivative (WO 96/33710), 3-(2-(4-methylpiperazin-1-yl)benzylidene)-1,3-dihydroindol-2-one derivative (WO 97/36867), (S)-1-(4-indolyloxy)-3-[4-hydroxy-4-(2-naphthyl)piperidino]-propan-2-ol derivative (WO 97/48698) and the like.

JP-A-62-116557 discloses substituted benzyllactams, such as 2-hydroxy-1-[2-((2-oxo-4-pyrrolidinyl)methyl)phenoxy]-3-(4-diphenylmethyl-piperazin-1-yl)propane and the like, which have a binding ability with a serotonin receptor and a muscarinic acetylcholine receptor, and which can be used for the treatment of senile dementia, Alzheimer's disease, cerebrovascular dementia and the like.

Various diseases of the central nervous system (e.g., depression, anxiety) are considered to be caused by disorders of noradrenalin (NA) and 5-hydroxytryptamine (5-HT), which are neurotransmitters. Accordingly, augmentation of 5-HTergic neurotransmission is considered to mainly influence depressive mood and anxious, whereas augmentation of noradrenergic neurotransmission is considered to influence retardation in depressive patients. The pharmaceutical agents, such as imipramine, desipramine and the like, which are most frequently used for the treatment of depression, are considered to act on depressive patients by improving neurotransmission of one or both of these NA and 5-HT.

The activity of 5-HT is considered to relate to a number of various types of psychiatric disorders. In addition, 5-HT has been considered to be responsible for various conditions (e.g., eating disorder, gastrointestinal injury, control of cardiovascular system and sexual behavior). However, conventional antidepressants, such as imipramine, desipramine and the like, are defective in that they require 3–4 weeks or even longer time for the expression of an anti-depressive effect, which poses clinical problems.

A combined use of various pharmaceutical agents has been considered in an attempt to accelerate expression of effects of antidepressants or to increase their efficacy (Journal of Clinical Psychiatry, Vol. 57; Suppliment 7; pp 25–31). Therein, a noticeably shortened time for clinical expression of the effect by concurrent use of a selective serotonin (5-HT) reuptake inhibitor (SSRI) and a 5-HT$_{1A}$ antagonist, pindolol, has been reported (Journal of Clinical Psychopharmacology, Vol. 17, No. 6, pp. 446–450). It is known that the amount of 5-HT release in the brain does not increase much by SSRI alone, but when combined with a 5-HT$_{1A}$ antagonist, the amount increases markedly (Neurochemical Research, Vol. 21, No. 5, 1996, pp. 557–562). Under such circumstances, the "5-HT enhancement hypothesis" was proposed with regard to the expression of the action of antidepressants by Blier and de Montigny (Trends in Pharmacological Sciences, 1994, vol. 15, pp. 220–226). The 5-HT enhancement hypothesis means that the effector mechanism of antidepressant rests in the enhancement of 5-HT release at a terminal. It is based on the understanding that the conventional antidepressants decrease the 5-HT release by single administration, but increase the 5-HT release and express an anti-depressive effect only when they are administered consecutively. From those mentioned above, it is expected that a drug that promotes 5-HT release in the brain from the first can be a rapid onset antidepressant. In other words, a compound concurrently having a serotonin reuptake inhibitory action and a 5-HT$_{1A}$ antagonistic action is considered to be an antidepressant showing quick expression of an anti-depressive effect, namely, a rapid onset antidepressant.

It is an object of the present invention to find a subgroup of 5-hydroxytryptamine (5-HT) receptor, namely, a compound simultaneously having selective affinity for and antagonistic activity against 5-HT$_{1A}$ receptor in the central nervous system in mammals inclusive of human, which compound also having a 5-HT reuptake inhibitory activity.

It is therefore an object of the present invention to provide a compound that expresses an anti-depressive effect quickly, which is a so-called rapid onset antidepressant, and a compound useful for the treatment of 5-HT mediated diseases in the central nervous system, such as schizophrenia, anxiety neurosis, obsessive-compulsive disorder (OCD), panic disorder, social anxiety disorder, seasonal emotional disorder, Anorexia Nervosa, Bulimia Nervosa, nocturnal enuresis, children's hyperlocomotion, post-traumatic stress disorder (PTSD), senile dementia, hemicrania, stroke, Alzheimer's disease, recognition disorder, hypertension, gastrointestinal injury, feeding disorders, premenstrual syndrome (PMS), abnormal body temperature regulation, sexual disorder and pain, as well as for the treatment of abnormality in the cardiovascular system, treatment of drug abuse and the like.

SUMMARY OF THE INVENTION

The present inventors have conducted intensive studies, and as a result, found that a novel phenoxypropylamine compound of the formula (I), an optical isomer thereof and a pharmaceutically acceptable salt thereof have selective affinity for and simultaneous antagonistic activity against a 5-hydroxytryptamine 1A (5-HT$_{1A}$) receptor, as well as 5-HT reuptake inhibitory activity, and can be a useful pharmaceutical agent that meets the above-mentioned objects, which resulted in the completion of the present invention. Moreover, the present inventors have also found novel compounds of the formulas (II) and (III) to be mentioned below, which are the synthetic intermediates for the phenoxypropylamine compound.

Accordingly, the present invention provides the following.

1. A phenoxypropylamine compound of the formula (I)

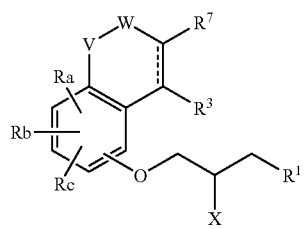
(I)

wherein each symbol in the formula means as follows:
a bond represented by a solid line and a dotted line shows a double bond or a single bond;
X is a hydrogen atom, a hydroxy group, a $C_1$–$C_8$ alkoxy group, an acyloxy group or an oxo group;

provided that when $R^1$ is a group of the following formula (2),
X should not be a hydrogen atom;
$R^1$ is a group of the following formula

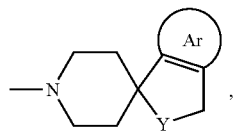
(1)

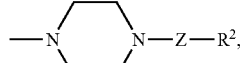
(2)

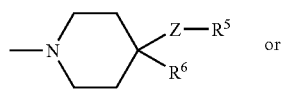
(3)

or

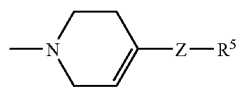
(4)

wherein
Y is O or S,
Ar is optionally substituted aromatic hydrocarbon,
$R^2$ is optionally substituted aryl group or optionally substituted aromatic heterocyclic group,
$R^5$ is optionally substituted aryl group or optionally substituted aromatic heterocyclic group,
Z is void or —$CH_2$—, and
$R^6$ is hydrogen atom, hydroxy group, acetamido group, carboxyl group, alkoxycarbonyl group, cyano group or $C_1$–$C_8$ alkoxy group;
$R^3$ is a hydrogen atom, a $C_1$–$C_{18}$ alkyl group or a halogen atom;
V is —$CH_2$—, —O—, —S— or the formula —N($R^4$)— wherein $R^4$ is hydrogen atom, $C_1$–$C_{18}$ alkyl group or optionally substituted aralkyl group;
W is void or —$CH_2$— or —C(=O)—;

$R^7$ is a $C_1$–$C_4$ hydroxyalkyl group, an acyl group, an optionally substituted saturated or unsaturated heterocyclic group, an optionally substituted fused heterocyclic group, a $C_1$–$C_4$ alkylsulfonyl group or the formula -Q-$R^9$
wherein
Q is —C((=O)—, —C(=S)—, —$CH_2$— or —S(=O)$_2$—, and
$R^9$ is a group of the following formula

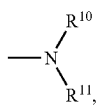
(5)

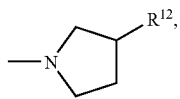
(6)

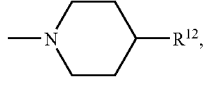
(7)

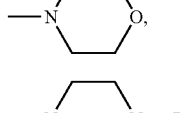
(8)

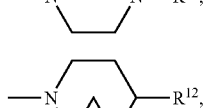
(9)

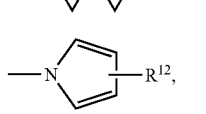
(10)

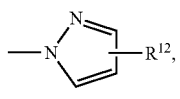
(11)

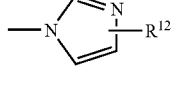
(12)

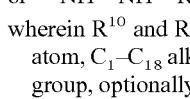
(13)

or —NH—NH—$R^{15}$ wherein $R^{10}$ and $R^{11}$ are each independently hydrogen atom, $C_1$–$C_{18}$ alkyl group, optionally substituted aryl group, optionally substituted aralkyl group or alkoxy group, $R^{12}$ is hydrogen atom, optionally substituted aryl group, $C_1$–$C_{18}$ alkyl group, $C_1$–$C_8$ alkoxy group or acyl group, and $R^{15}$ is hydrogen atom, phenyl group, $C_1$–$C_4$ alkyl group, $C_1$–$C_2$ halogenated alkyl group, halogen atom, $C_2$–$C_4$ alkenyl group, $C_1$–$C_4$ hydroxyalkyl group, alkoxyalkyl group, alkyloxycarbonyl group, optionally substituted amino group, acetamido group, carboxyl group, acyl group, optionally substituted alkyloxy group, alkylthio group or cyano group;

provided that when $R^1$ is a group of the above formula (2), $R^7$ should not be $C_1$–$C_4$ hydroxyalkyl group or acyl group, and $R^{10}$ and $R^{11}$ are not each hydrogen atom at the same time; or R⁷ and W in combination may form a ring of the following formula

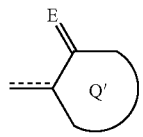
(14)

wherein
E is oxygen atom or sulfur atom, and
Q' is an optionally substituted 4 to 7-membered heterocycle having 1 or 2 hetero atom(s) selected from the group consisting of nitrogen atom and oxygen atom in the ring, in which case V is hydrogen atom; and
Ra, Rb and Rc are each independently a hydrogen atom, a $C_1$–$C_{18}$ alkyl group, a hydroxy group, a $C_1$–$C_8$ alkoxy group,
a halogen atom, an acyl group, a nitro group or an amino group;
provided that when R⁷ and W are bonded to form a ring of the above formula (14), Ra, Rb and Rc are not each hydroxy group or $C_1$–$C_8$ alkoxy group;
an optically active compound thereof, a pharmaceutically acceptable salt thereof or a hydrate thereof.

2. The compound of the aforementioned 1, which is represented by the formula (I)

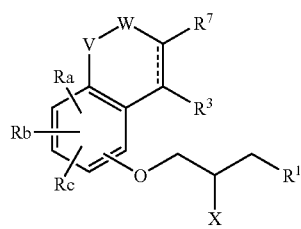
(I)

wherein each symbol in the formula means as follows:
a bond represented by a solid line and a dotted line shows a double bond;
X is a hydrogen atom, a hydroxy group, a $C_1$–$C_8$ alkoxy group, an acyloxy group or an oxo group;
R¹ is a group of the following formula

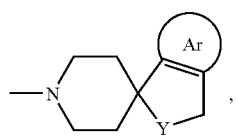
(1)

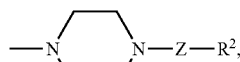
(2)

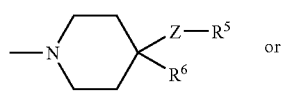
(3)

or

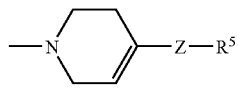
(4)

wherein
Y is O or S,
Ar is optionally substituted benzene or naphthalene,
R² is optionally substituted aryl group or optionally substituted aromatic heterocyclic group,
R⁵ is optionally substituted aryl group or optionally substituted aromatic heterocyclic group,
Z is void or —CH₂—, and
R⁶ is hydrogen atom, hydroxy group, acetamido group, carboxyl group, alkoxycarbonyl group, cyano group or $C_1$–$C_8$ alkoxy group;
R³ is a hydrogen atom, a $C_1$–$C_{18}$ alkyl group or a halogen atom;
V is —CH₂—, —O—, —S— or the formula —N(R⁴)— wherein R⁴ is hydrogen atom, $C_1$–$C_{18}$ alkyl group or optionally substituted aralkyl group;
W is void or —CH₂— or —C(=O)—;
R⁷ is a $C_1$–$C_4$ hydroxyalkyl group, an acyl group, an optionally substituted saturated or unsaturated heterocyclic group, an optionally substituted fused heterocyclic group, a $C_1$–$C_4$ alkylsulfonyl group or the formula -Q-R⁹ wherein
Q is —C(=O)—, —C(=S)—, —CH₂— or —S(=O)₂—, and
R⁹ is a group of the following formula

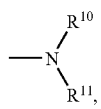
(5)

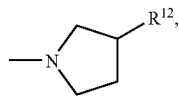
(6)

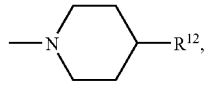
(7)

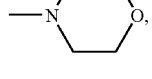
(8)

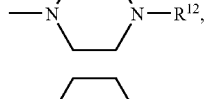
(9)

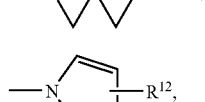
(10)

(11)

-continued

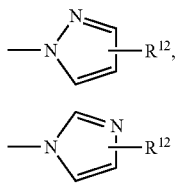
(12)

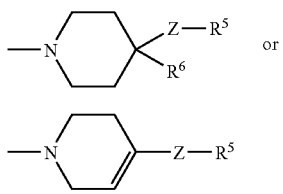 (13)

or —NH—NH—R[15]

wherein R[10] and R[11] are each independently hydrogen atom, $C_1$–$C_{18}$ alkyl group, optionally substituted aryl group, optionally substituted aralkyl group or alkoxy group, R[12] is hydrogen atom, optionally substituted aryl group, $C_1$–$C_{18}$ alkyl group, $C_1$–$C_8$ alkoxy group or acyl group, and R[15] is hydrogen atom, phenyl group, $C_1$–$C_4$ alkyl group, $C_1$–$C_2$ halogenated alkyl group, halogen atom, $C_2$–$C_4$ alkenyl group, $C_1$–$C_4$ hydroxyalkyl group, alkoxyalkyl group, alkyloxycarbonyl group, optionally substituted amino group, acetamido group, carboxyl group, acyl group, optionally substituted alkyloxy group, alkylthio group or cyano group; and Ra, Rb and Rc are each independently a hydrogen atom, a $C_1$–$C_{18}$ alkyl group, a hydroxy group, a $C_1$–$C_8$ alkoxy group, a halogen atom, an acyl group, a nitro group or an amino group;

provided that when R[1] is a group of the above formula (2), R[7] should not be $C_1$–$C_4$ hydroxyalkyl group or acyl group, and R[10] and R[11] are not each hydrogen atom at the same time;

an optically active compound thereof, a pharmaceutically acceptable salt thereof or a hydrate thereof.

3. The compound of the aforementioned 2, which is represented by the formula (I) wherein each symbol in the formula means as follows:

a bond represented by a solid line and a dotted line shows a double bond;

X is a hydroxy group;

R[1] is a group of the following formula

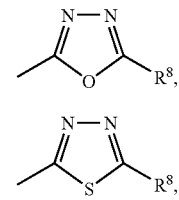
(3)

or

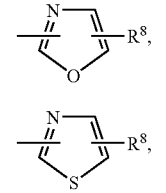
(4)

wherein

R[5] is optionally substituted phenyl group or naphthyl group,

Z is void, and

R[6] is hydrogen atom;

R[3] is a hydrogen atom or a $C_1$–$C_4$ alkyl group;

V is —$CH_2$—, —O—, —S— or —N(R[4])— wherein R[4] is hydrogen atom, $C_1$–$C_6$ alkyl group or optionally substituted aralkyl group;

W is void;

R[7] is a group of the following formula

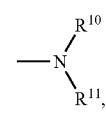
(15)

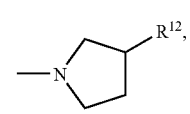
(16)

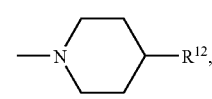
(17)

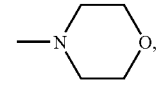
(18)

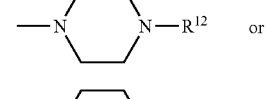

or the formula —CO—R[9]

wherein

R[8] is hydrogen atom, phenyl group, $C_1$–$C_4$ alkyl group, $C_1$–$C_2$ halogenated alkyl group, halogen atom, $C_2$–$C_4$ alkenyl group, $C_1$–$C_4$ hydroxyalkyl group, alkoxyalkyl group, alkyloxycarbonyl group, optionally substituted amino group, acetamido group, carboxyl group, acyl group, optionally substituted alkyloxy group, alkylthio group or cyano group, and R[9] is a group of the following formula (5)

(6)

(7)

(8)

(9)

or (10)

wherein R[10] and R[11] are each independently hydrogen atom, $C_1$–$C_{18}$ alkyl group, optionally substituted aryl group, optionally substituted aralkyl group or alkoxy group, and R[12] is hydrogen atom, optionally substituted aryl group, $C_1$–$C_{18}$ alkyl group, $C_1$–$C_8$ alkoxy group or acyl group; and Ra, Rb and Rc are each a hydrogen atom;

an optically active compound thereof, a pharmaceutically acceptable salt thereof or a hydrate thereof.

4. The compound of the aforementioned 2 or 3, which is represented by the formula (I')

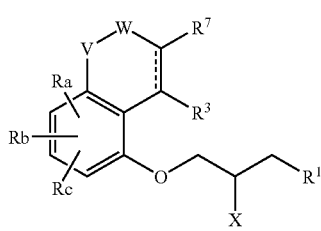

(I')

wherein each symbol is as in the aforementioned 2, an optically active compound thereof, a pharmaceutically acceptable salt thereof or a hydrate thereof.

5. The compound of the aforementioned 2, which is selected from the group consisting of (1) 1-(4-(2-hydroxy-3-(4-(naphthalen-2-yl)piperidino)propyloxy)benzo(b)furan-2-ylcarbonyl)pyrrolidine,
(2) 4-(4-(2-hydroxy-3-(4-(naphthalen-2-yl)piperidino)propyloxy)benzo(b)furan-2-ylcarbonyl)morpholine,
(4) 4-(2-hydroxy-3-(4-(naphthalen-2-yl)piperidino)propyloxy)-N,N-dimethylbenzo(b)furan-2-carboxamide,
(12) 1-(4-(2-hydroxy-3-(4-(naphthalen-2-yl)piperidino)propyloxy)benzo(b)thiophen-2-ylcarbonyl)pyrrolidine, (13) 4-(4-(2-hydroxy-3-(4-(naphthalen-2-yl)piperidino)propyloxy)benzo(b)thiophen-2-ylcarbonyl)morpholine,
(15) 4-(2-hydroxy-3-(4-(naphthalen-1-yl)piperidino)propyloxy)-N,N-dimethylbenzo(b)thiophene-2-carboxamide,
(17) 4-(2-hydroxy-3-(4-(naphthalen-2-yl)piperidino)propyloxy)-N,N-dimethylbenzo(b)thiophene-2-carboxamide,
(20) 4-(7-(2-hydroxy-3-(4-(naphthalen-2-yl)piperidino)propyloxy)benzo(b)furan-2-ylcarbonyl)morpholine,
(21) 7-(2-hydroxy-3-(4-(naphthalen-2-yl)piperidino)propyloxy)-N,N-dimethylbenzo(b)furan-2-carboxamide,
(27) 4-(2-hydroxy-3-(4-(naphthalen-2-yl)piperidino)propyloxy)-N,N-dimethyl-1H-indole-2-carboxamide,
(30) 4-(2-hydroxy-3-(4-(naphthalen-2-yl)piperidino)propyloxy)-N,N-dimethyl-1-methylindole-2-carboxamide,
(35) 1-(2-(5-methyl-1,2,4-oxadiazol-3-yl)benzo(b)furan-4-yloxy)-3-(4-(naphthalen-2-yl)piperidino)-2-propanol,
(37) 1-(2-(5-methyl-1,3,4-oxadiazol-2-yl)benzo(b)furan-4-yloxy)-3-(4-(naphthalen-2-yl)piperidino)-2-propanol,
(38) 1-(2-(5-trifluoromethyl-1,3,4-oxadiazol-2-yl)benzo(b)furan-4-yloxy)-3-(4-(naphthalen-2-yl)piperidino)-2-propanol,
(39) 1-(2-(5-methyl-1,3,4-oxadiazol-2-yl)benzo(b)furan-7-yloxy)-3-(4-(naphthalen-2-yl)piperidino)-2-propanol,
(42) 1-(2-(5-methyl-1,3,4-oxadiazol-2-yl)-1H-indole-4-yloxy)-3-(4-(naphthalen-2-yl)piperidino)-2-propanol,
(44) 1-(2-(3-methyl-1,2,4-oxadiazol-5-yl)benzo(b)furan-4-yloxy)-3-(4-(naphthalen-2-yl)piperidino)-2-propanol,
(48) 1-(2-(5-methyloxazol-2-yl)benzo(b)furan-7-yloxy)-3-(4-(naphthalen-2-yl)piperidino)-2-propanol,
(81) 3-(4-(3,4-dichlorophenyl)piperidino)-1-(2-(5-methyloxazol-2-yl)benzo(b)furan-4-yloxy)-2-propanol,
(88) 1-(4-(3,4-dichlorophenyl)piperidino)-3-(2-(5-methyl-1,3,4-oxadiazol-2-yl)benzo(b)furan-4-yloxy)-2-propanol, and
(93) 3-(4-(3,4-dimethylphenyl)piperidino)-1-(2-(5-ethyl-1,3,4-oxadiazol-2-yl)benzo(b)furan-4-yloxy)-2-propanol, an optically active compound thereof, a pharmaceutically acceptable salt thereof or a hydrate thereof.

6. The compound of the aforementioned 1, which is represented by the formula (I)

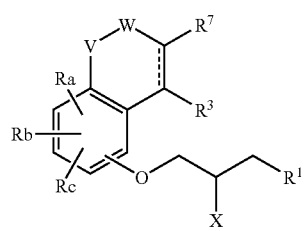

(I)

wherein each symbol in the formula means as follows:
a bond represented by a solid line and a dotted line shows a double bond or a single bond;
X is a hydrogen atom, a hydroxy group, a $C_1$–$C_8$ alkoxy group or an acyloxy group;
$R^1$ is a group of the following formula

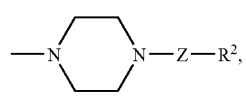

(2)

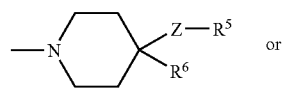

(3)

or

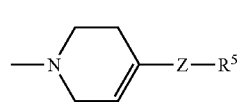

(4)

wherein
$R^2$ is optionally substituted aryl group or optionally substituted aromatic heterocyclic group,
$R^5$ is optionally substituted aryl group or optionally substituted aromatic heterocyclic group,
Z is void or —$CH_2$—, and
$R^6$ is hydrogen atom, hydroxy group or $C_1$–$C_8$ alkoxy group;
$R^3$ is a hydrogen atom, a $C_1$–$C_{18}$ alkyl group or a halogen atom;
$R^7$ and W are bonded to form a ring of the following formula

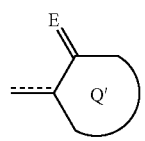

(14)

wherein
E is an oxygen atom or a sulfur atom, and
Q' is an optionally substituted 4 to 7-membered heterocycle having 1 or 2 hetero atom(s) selected from the group consisting of nitrogen atom and oxygen atom in the ring,
and V is hydrogen atom; and
Ra, Rb and Rc are each independently a hydrogen atom, a $C_1$–$C_{18}$ alkyl group, a halogen atom, an acyl group, a nitro group or an amino group;

7. The compound of the aforementioned 6, which is represented by the formula (I) wherein each symbol in the formula means as follows:

a group of the following formula

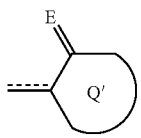
(14)

is a group of the following formula

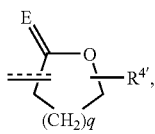
(19)

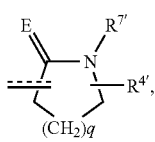
(20)

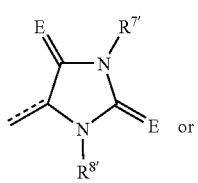
(21)

or

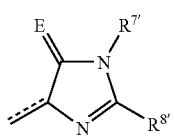
(22)

wherein

E is an oxygen atom or a sulfur atom, q is 0, 1, 2 or 3, $R^{4'}$, $R^{7'}$ and $R^{8'}$ are each independently a hydrogen atom, a $C_1$–$C_{18}$ alkyl group, an optionally substituted aryl group or an optionally substituted aralkyl group, and other symbols are as defined in the aforementioned 6, an optically active compound thereof, a pharmaceutically acceptable salt thereof or a hydrate thereof.

8. The compound of the aforementioned 6, which is represented by the formula (I) wherein each symbol in the formula means as follows:

a bond represented by a solid line and a dotted line shows a double bond;

X is a hydroxy group;

$R^1$ is a group of the following formula

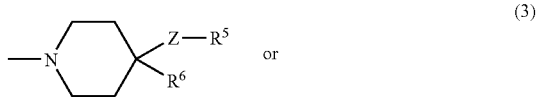
(3)

or

(4)

wherein $R^5$ is optionally substituted phenyl group or naphthyl group,

Z is void, and $R^6$ is hydrogen atom;

$R^3$ is a hydrogen atom or a $C_1$–$C_4$ alkyl group;

a group of the following formula

(14)

is a group of the following formula

(19')

wherein q is 1 and $R^{4'}$ is hydrogen atom or $C_1$–$C_4$ alkyl group; and

Ra, Rb and Rc are each a hydrogen atom;

an optically active compound thereof, a pharmaceutically acceptable salt thereof or a hydrate thereof.

9. The compound of the aforementioned 6, which is represented by the formula (I″)

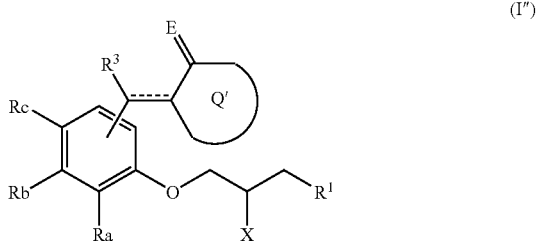
(I″)

wherein each symbol is as defined in the aforementioned 6, an optically active compound thereof, a pharmaceutically acceptable salt thereof or a hydrate thereof.

10. The compound of the aforementioned 6, which is selected from the group consisting of (306) 5-(2'-(2-hydroxy-3-(4-(naphthalen-2-yl)piperidino) propyloxy)benzylidene)-1,3-dimethylimidazolidine-2,4-dione, (307) α-(2'-(2-hydroxy-3-(4-(naphthalen-2-yl)piperidino) propyloxy)benzylidene)-γ-butyrolactone, (308) α-(2'-(2-hydroxy-3-(4-(naphthalen-2-yl)piperidino) propyloxy)benzylidene)-γ-butyrolactone, (309) α-(2'-(2-hydroxy-3-(4-(naphthalen-2-yl)piperidino) propyloxy)benzylidene)-γ-butyrolactone, (310) α-(2'-(3-(4-(3-fluoro-4-methylphenyl)piperidino)-2-hydroxypropyloxy) benzylidene)-γ-butyrolactone, (311) α-(2'-(3-(4-(3,4-dimethylphenyl)piperidino)-2-hydroxypropyloxy) benzylidene)-γ-butyrolactone, (312) α-(2'-(3-(4-(4-chloro-3-fluorophenyl)piperidino)-2-hydroxypropyloxy) benzylidene)-γ-butyrolactone, (313) α-(2'-(3-(4-(4-chloro-3-trifluoromethylphenyl)piperidino)-2-hydroxypropyloxy) benzylidene)-γ-butyrolactone, (314) α-(2'-(2-hydroxy-3-(4-(naphthalen-1-yl)piperidino) propyloxy)benzylidene)-γ-butyrolactone, (315) α-(2'-(2-hydroxy-3-(4-(naphthalen-2-yl)piperidino) propyloxy)benzylidene)-δ-valerolactone, (316) α-(2'-(2-hydroxy-3-(4-(naphthalen-2-yl)piperidino) propyloxy)benzylidene)-γ-valerolactone, (319) 3-(2'-(2-hydroxy-3-(4-(naphthalen-2-yl)piperidino) propyloxy)benzylidene)-2-pyrrolidone, (322) 3-(2'-(2-hydroxy-3-(4-(naphthalen-2-yl)piperidino) propyloxy)benzylidene)-1-methyl-2-pyrrolidone, and (325) α-(2'-(2-hydroxy-3-(4-(6-methoxynaphthalen-2-yl) piperidino) propyloxy) benzylidene)-γ-butyrolactone, an optically active compound thereof, a pharmaceutically acceptable salt thereof or a hydrate thereof.

11. A pharmaceutical agent comprising a compound of the aforementioned 1, an optically active compound thereof, a pharmaceutically acceptable salt thereof or a hydrate thereof.

12. The pharmaceutical agent of the aforementioned 11, which is an agent for the treatment of depression.

13. A pharmaceutical composition comprising at least one member selected from the group consisting of a compound of the aforementioned 1, an optically active compound thereof, a pharmaceutically acceptable salt thereof and a hydrate thereof, and a pharmaceutically acceptable carrier.

14. The pharmaceutical composition of the aforementioned 13, which is an agent for the treatment of depression.

15. A 5HT$_{1A}$ antagonist having a selective serotonin reuptake inhibitory action, which comprises a compound of the aforementioned 1, an optically active compound thereof, a pharmaceutically acceptable salt thereof or a hydrate thereof.

16. A selective serotonin reuptake inhibitor having a 5HT$_{1A}$ antagonistic action, which comprises a compound of the aforementioned 1, an optically active compound thereof, a pharmaceutically acceptable salt thereof or a hydrate thereof.

17. A compound of the formula (II)

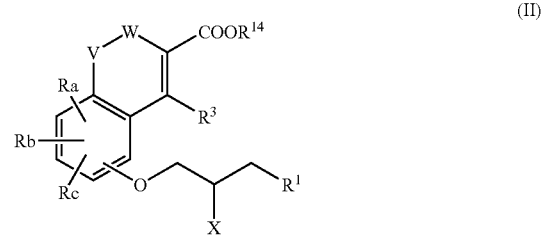

wherein each symbol in the formula means as follows:

X is a hydrogen atom, a hydroxy group, a $C_1$–$C_8$ alkoxy group or an acyloxy group or an oxo group;

$R^1$ is a group of the following formula

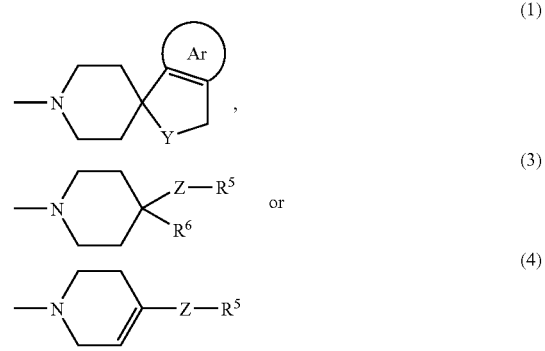

wherein

Y is O or S,

Ar is optionally substituted benzene or naphthalene, $R^2$ is optionally substituted aryl group or optionally substituted aromatic heterocyclic group, $R^5$ is optionally substituted aryl group or optionally substituted aromatic heterocyclic group, Z is void or —CH$_2$—, and $R^6$ is hydrogen atom, hydroxy group, acetamido group, carboxyl group, alkoxycarbonyl group, cyano group or $C_1$–$C_8$ alkoxy group, provided that when V is —N($R^4$)—, $R^6$ should not be hydroxy group;

$R^3$ is a hydrogen atom, a $C_1$–$C_{18}$ alkyl group or a halogen atom;

V is —CH$_2$—, —O—, —S— or the formula —N($R^4$)— wherein $R^4$ is hydrogen atom, $C_1$–$C_{18}$ alkyl group or optionally substituted aralkyl group;

W is void, —CH$_2$— or —C(=O)—;

$R^{14}$ is a hydrogen atom or a $C_1$–$C_4$ alkyl; and

Ra, Rb and Rc are each independently a hydrogen atom, a $C_1$–$C_{18}$ alkyl group, a hydroxy group, a $C_1$–$C_8$ alkoxy group, a halogen atom, an acyl group, a nitro group or an amino group;

an optically active compound thereof, a pharmaceutically acceptable salt thereof or a hydrate thereof.

18. A compound of the formula (III)

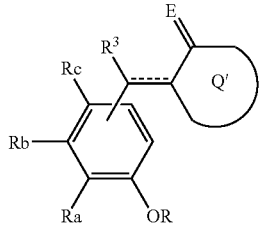
(III)

wherein each symbol is as follows:
R is an allyl group or a 2,3-epoxypropan-1-yl group;
a bond represented by a solid line and a dotted line shows a double bond or a single bond;
E is an oxygen atom or a sulfur atom;
$R^3$ is a hydrogen atom, a $C_1$–$C_{18}$ alkyl group or a halogen atom;
Q' is an optionally substituted 4 to 7-membered heterocycle having 1 or 2 hetero atom(s) selected from the group consisting of nitrogen atom and oxygen atom in the ring; and
Ra, Rb and Rc are each independently a hydrogen atom, a $C_1$–$C_{18}$ alkyl group, a hydroxy group, a $C_1$–$C_8$ alkoxy group, a halogen atom, an acyl group, a nitro group or an amino group;

an optically active compound thereof, a pharmaceutically acceptable salt thereof or a hydrate thereof.

19. The compound of the aforementioned 18, wherein, in the formula (III), each symbol is as follows:
the group of the following formula

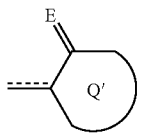
(14)

is a group of the following formula

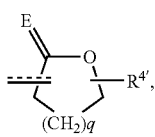
(19)

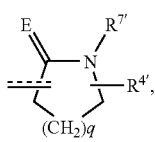
(20)

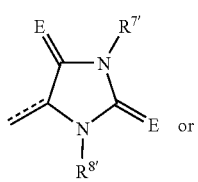
(21)

or

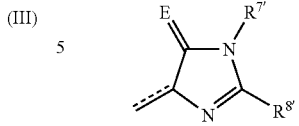
(22)

wherein
E is oxygen atom or sulfur atom,
q is 0, 1, 2 or 3,
$R^{4'}$, $R^{7'}$ and $R^{8'}$ are each independently hydrogen atom, $C_1$–$C_{18}$ alkyl group, optionally substituted aryl group or optionally substituted aralkyl group, and
other symbols are as defined in the aforementioned 18, an optically active compound thereof, a pharmaceutically acceptable salt thereof or a hydrate thereof.

20. A compound selected from the group consisting of
2-(4-methoxybenzo(b)furan-2-yl)-5-methyl-1,3,4-oxadiazole,
2-(4-hydroxybenzo(b)furan-2-yl)-5-methyl-1,3,4-oxadiazole,
(S)-2-(4-glycidyloxybenzo(b)furan-2-yl)-5-methyl-1,3,4-oxadiazole,
2-(7-methoxybenzo(b)furan-2-yl)-5-methyl-1,3,4-oxadiazole,
2-(4-(methoxymethyloxy)benzo(b)thiophen-2-yl)-5-methyl-1,3,4-oxadiazole,
2-(4-hydroxybenzo(b)thiophen-2-yl)-5-methyl-1,3,4-oxadiazole,
4-benzyloxy-2-(5-methyl-1,3,4-oxadiazol-2-yl)-1H-indole,
2-(7-methoxybenzo(b)furan-2-yl)-5-phenyl-1,3,4-oxadiazole,
2-(4-methoxybenzo(b)furan-2-yl)-5-trifluoromethyl-1,3,4-oxadiazole,
2-(4-hydroxybenzo(b)furan-2-yl)-5-trifluoromethyl-1,3,4-oxadiazole,
(S)-2-(4-glycidyloxybenzo(b)furan-2-yl)-5-trifluoromethyl-1,3,4-oxadiazole,
2-(7-methoxybenzo(b)furan-2-yl)-5-trifluoromethyl-1,3,4-oxadiazole,
2-(7-hydroxybenzo(b)furan-2-yl)-5-trifluoromethyl-1,3,4-oxadiazole,
(S)-2-(7-glycidyloxybenzo(b)furan-2-yl)-5-trifluoromethyl-1,3,4-oxadiazole,
N'-(4-methoxybenzo(b)furan-2-ylcarbonyl)propionohydrazide, 2-(4-methoxybenzo(b)furan-2-yl)-5-ethyl-1,3,4-oxadiazole,
2-(4-hydroxybenzo(b)furan-2-yl)-5-ethyl-1,3,4-oxadiazole,
(S)-2-(4-glycidyloxybenzo(b)furan-2-yl)-5-ethyl-1,3,4-oxadiazole,
2-(4-methoxybenzo(b)furan-2-yl)-5-methyl-1,3,4-thiadiazole,
2-(4-hydroxybenzo(b)furan-2-yl)-5-methyl-1,3,4-thiadiazole,
(S)-2-(4-glycidyloxybenzo(b)furan-2-yl)-5-methyl-1,3,4-thiadiazole,
5-ethoxycarbonyl-2-(4-methoxybenzo(b)furan-2-yl)-1,3,4-oxadiazole,
5-ethoxycarbonyl-2-(4-hydroxybenzo(b)furan-2-yl)-1,3,4-oxadiazole,
5-(4-(methoxymethyloxy)benzo(b)furan-2-yl)-2,3-dihydro-1,3,4-oxadiazole-2-thione,
5-(4-(methoxymethyloxy)benzo(b)furan-2-yl)-2-methylthio-1,3,4-oxadiazole, 5-(4-hydroxybenzo(b)furan-2-yl)-2-methylthio-1,3,4-oxadiazole, 5-(4-(methoxymethyloxy)benzo(b)furan-2-yl)-2,3-dihydro-1,3,4-oxadiazol-2-one, 5-(4-(methoxymethyloxy)benzo(b)furan-2-yl)-2-methoxy-1,3,4-oxadiazole, (S)-5-(4-glycidyloxybenzo(b)furan-2-yl)-2-methoxy-1,3,4-oxadiazole, 2-ethoxy-5-(4-(methoxymethyloxy)benzo(b)furan-2-yl)-1,3,4-oxadiazole, (S)-2-ethoxy-5-(4-glycidyloxybenzo(b)furan-2-yl)-1,3,4-oxadiazole, 2-(1-methylethyloxy)-5-(4-(methoxymethyloxy)benzo(b)furan-2-yl)-1,3,4-oxadiazole and (S)-2-(1-methylethyloxy)-5-(4-glycidyloxybenzo(b)furan-2-yl)-1,3,4-oxadiazole.

DETAILED DESCRIPTION OF THE INVENTION

The definitions and examples of each group in the formulas (I), (I'), (I''), (II) and (III) are shown in the following.

The acyloxy group at X is, for example, acetoxy, propionyloxy, butyryloxy, benzoyloxy and the like, preferably acetoxy.

The "aryl group" of the optionally substituted aryl group at Ar, $R^2$, $R^5$, $R^{10}$, $R^{11}$, $R^{12}$, $R^{4'}$, $R^{7'}$ and $R^{8'}$ is, for example, phenyl, naphthyl, tetrahydronaphthyl (e.g., 1,2,3,4-tetrahydronaphthalene-6-yl, 5,6,7,8-tetrahydronaphthalen-2-yl etc.), indanyl (e.g., indan-5-yl etc.), indenyl (e.g., inden-5-yl etc.) and the like, with preference given to phenyl and naphthyl. These may be substituted by one or more, the same or different substituents mentioned below. A hydrogen atom may be added to the double bond of these aryl groups. Examples of the "substituent" include halogen atom (e.g., chlorine atom, fluorine atom etc.), trifluoromethyl, $C_1$–$C_4$ alkyl group (linear or branched chain, such as methyl, ethyl, propyl, isopropyl, butyl etc.), $C_1$–$C_4$ alkoxy group (linear or branched chain, such as methoxy, ethoxy, propoxy, isopropoxy, butoxy etc.), aryl group (e.g., phenyl etc.), aralkyl group (e.g., benzyl etc.), oxo group, alkoxyalkyl group (e.g., methoxyethyl etc.) and the like, with preference given to chlorine atom, fluorine atom, trifluoromethyl, methyl, methoxy, phenyl, benzyl, oxo, ethoxyethyl and the like.

Preferable examples of the optionally substituted aryl group at $R^5$ include naphthyl (1-naphthyl, 2-naphthyl), 4-chloro-3-fluorophenyl, 3-chloro-4-trifluoromethylphenyl, 3,4-dimethylphenyl, 3,4-dichlorophenyl, 2,4- or 3,4-dimethylphenyl, 4-methylphenyl, 4-fluorophenyl, 3-chloro-4-methylphenyl, 4-chloro-3-trifluoromethylphenyl, 6-methoxynaphthyl-2-yl, 4-chlorophenyl, 3,4-difluorophenyl, 3,4-dimethoxyphenyl, 3-chlorophenyl, 4-chloro-3-methylphenyl, 4-chloro-3-methoxyphenyl, 2,5-dichlorophenyl, 4-chloro-3-trifluorophenyl and the like.

Examples of the "aromatic hydrocarbon" of the optionally substituted aromatic hydrocarbon at Ar include benzene, naphthalene and the like, which may be substituted by one or more, the same or different substituents mentioned below. The "substituent" is, for example, halogen atom (e.g., chlorine atom, fluorine atom etc.), trifluoromethyl, $C_1$–$C_4$ alkyl group (linear or branched chain, such as methyl, ethyl, propyl, isopropyl, butyl etc.), $C_1$–$C_4$ alkoxy group (linear or branched chain, such as methoxy, ethoxy, propoxy, isopropoxy, butoxy etc.), aryl group (e.g., phenyl etc.), aralkyl group (e.g., benzyl etc.), oxo group, alkoxyalkyl group (e.g., methoxyethyl etc.) and the like, with preference given to chlorine atom, fluorine atom, trifluoromethyl, methyl, methoxy, phenyl, benzyl, oxo group, methoxyethyl and the like.

The "aromatic heterocyclic group" of the optionally substituted aromatic heterocyclic group at $R^2$ and $R^5$ is, for example, pyridyl, furyl, thienyl, pyrimidinyl, indolyl (e.g., indol-2-yl, indol-6-yl, indol-5-yl etc.), benzo(b)thienyl (e.g., benzo(b)thiophen-2-yl, benzo(b)thiophen-5-yl, 2,3-dihydrobenzo(b)thiophen-6-yl, 2,3-dihydrobenzo(b)thiophen-5-yl etc.), benzo(b)furyl (e.g., benzo(b)furan-2-yl, benzo(b)furan-5-yl, benzo(b)furan-6-yl, 2,3-dihydrobenzo(b)furan-5-yl, 2,3-dihydrobenzo(b)furan-4-yl, 3,4-dihydro-2H-benzo(b)furan-6-yl, 2,3-dihydrobenzo(b)furan-6-yl etc.), 3,4-methylenedioxyphenyl, benzimidazolyl (e.g., 2,3-dihydrobenzimidazol-1-yl etc.), 1,4-benzodioxanyl (e.g., 1,4-benzodioxan-6-yl etc.), chromanyl (e.g., chroman-6-yl, chroman-7-yl etc.), indolinyl (e.g., indolin-5-yl etc.), chromenyl (e.g., 2H-chromen-6-yl, 2H-chromen-7-yl etc.), benzo(b)thiinyl (e.g., 3,4-dihydro-2H-benzo(b)thiin-7-yl, 3,4-dihydro-2H-benzo(b)thiin-6-yl etc.), benzoisoxazolyl (e.g., benzoisoxazol-5-yl, benzo(d)isoxazol-5-yl etc.), benzo(c)furyl (e.g., 1,3-dihydrobenzo(c)furan-5-yl etc.), isochromanyl (e.g., isochroman-7-yl, isochroman-6-yl etc.), quinolinyl (e.g., quinolin-3-yl, quinolin-6-yl etc.), 3,4-dihydro-2H-benzo(b)oxin-6-yl, 3,4-dihydro-2H-benzo(c)oxin-6-yl, isoindolinyl (e.g., isoindolin-5-yl etc.), isoquinolinyl (e.g., isoquinolin-6-yl etc.) and the like, which may be substituted by one to three the same or different substituents mentioned below.

Examples of the "substituent" include halogen atom (e.g., fluorine atom, chlorine atom, bromine atom etc.), haloalkyl (e.g., fluoromethyl, difluoromethyl, trifluoromethyl etc.), $C_1$–$C_4$ alkyl (linear or branched chain, such as methyl, ethyl, propyl, isopropyl, butyl, isobutyl, tert-butyl etc.), $C_1$–$C_8$ alkoxy group (linear or branched chain, such as methoxy, ethoxy, propoxy, isopropoxy, butoxy, isobutoxy, tert-butoxy, pentyloxy, hexyloxy, heptyloxy, octyloxy etc.), hydroxy, nitro, cyano, amino, mono or dialkylamino wherein each alkyl has 1 to 4 carbon atoms (e.g., methylamino, dimethylamino, diethylamino, dipropylamino etc.), acyl (e.g., acetyl, propionyl, butyryl etc.), $C_2$–$C_6$ alkenyl (e.g., vinyl, 1-propenyl, 2-propenyl, 3-propenyl etc.), $C_2$–$C_6$ alkynyl (e.g., ethynyl, 1-propynyl, 2-propynyl etc.), phenyl, phenoxy, benzyloxy, R'—S(O)$_t$— wherein R' is $C_1$–$C_4$ alkyl and t is 0, 1 or 2, Ph-S(O)$_t$— wherein Ph is phenyl and t is as defined above, carbamoyl, N,N-dialkylcarbamoyl (e.g., N,N-dimethylcarbamoyl, N,N-diethylcarbamoyl, N,N-dipropylcarbamoyl etc.), oxo and the like, with preference given to $C_1$–$C_4$ alkyl.

The $C_1$–$C_8$ alkoxy group at X, $R^6$, $R^{12}$, Ra, Rb and Rc is linear or branched chain, such as methoxy, ethoxy, propoxy, isopropoxy, butoxy, isobutoxy, tert-butoxy, pentyloxy, hexyloxy, heptyloxy, octyloxy and the like, with preference given to $C_1$–$C_4$ alkoxy, with particular preference given to methoxy.

The halogen atom at $R^3$, Ra, Rb and Rc is fluorine atom, chlorine atom, bromine atom or iodine atom, preferably fluorine atom and chlorine atom.

The $C_1$–$C_{18}$ alkyl group at $R^3$, $R^4$, $R^{10}$, $R^{11}$, $R^{12}$, Ra, Rb, Rc, $R^{4'}$, $R^{7'}$ and $R^{8'}$ is linear or branched chain, such as methyl, ethyl, propyl, isopropyl, butyl, isobutyl, tert-butyl, pentyl, hexyl, heptyl, octyl, decyl, hexadecyl, octadecyl and the like. Preferably, it is $C_1$–$C_4$ alkyl group at $R^3$, $R^{10}$, $R^{11}$, $R^{12}$, Ra, Rb, Rc, $R^{4'}$, $R^{7'}$, $R^{8'}$, and $C_1$–$C_6$ alkyl group at $R^4$. Particularly preferably, it is methyl, ethyl or isobutyl.

The $C_1$–$C_4$ alkyl group at $R^8$ and $R^{15}$ is linear or branched chain, such as methyl, ethyl, propyl, isopropyl, butyl, isobutyl, tert-butyl and the like, with preference given to methyl, ethyl and isopropyl.

The acyl group at $R^7$, $R^{12}$, Ra, Rb and Rc is, for example, acetyl, propionyl, butyryl, pentanoyl, hexanoyl, benzoyl and the like, particularly preferably $C_2$–$C_3$ acyl group (e.g., acetyl).

The "aralkyl group" of the optionally substituted aralkyl group at $R^4$, $R^{10}$, $R^{11}$, $R^{4'}$, $R^{7'}$ and $R^{8'}$ is a group wherein $C_1$–$C_4$ linear or branched chain alkyl is substituted by phenyl group. Examples thereof include benzyl, 2-phenylethyl, 1-phenylethyl, 1,1-dimethyl-2-phenylethyl, 3-phenylpropyl, 2-phenylpropyl, 1-phenylpropyl, 4-phenylbutyl, 3-phenylbutyl, 2-phenylbutyl, 1-phenylbutyl and the like, with preference given to benzyl, which may be substituted by one or more, the same or different substituents mentioned below. Examples of these substituents include halogen atom (e.g., fluorine atom, chlorine atom, bromine atom etc.), haloalkyl (e.g., fluoromethyl, difluoromethyl, trifluoromethyl etc.), $C_1$–$C_4$ alkyl (linear or branched, such as methyl, ethyl, propyl, isopropyl, butyl, isobutyl, tert-butyl etc.), $C_1$–$C_8$ alkoxy (linear or branched, such as methoxy, ethoxy, propoxy, isopropoxy, butoxy, isobutoxy, tert-butoxy, pentyloxy, hexyloxy, heptyloxy, octyloxy etc.), hydroxy, nitro, cyano, amino and the like. The optionally substituted aralkyl at $R^{4'}$, $R^{7'}$ and $R^{8'}$ is, for example, benzyl, 2-phenylethyl, 1-phenylethyl, 1,1-dimethyl-2-phenylethyl, 3-phenylpropyl, 2-phenylpropyl, 1-phenylpropyl, 4-phenylbutyl, 3-phenylbutyl, 2-phenylbutyl, 1-phenylbutyl and the like, with preference given to benzyl.

The $C_1$–$C_2$ halogenated alkyl group at $R^8$ and $R^{15}$ is, for example, chloromethyl, dichloromethyl, trichloromethyl, bromomethyl, dibromomethyl, fluoromethyl, difluoromethyl, trifluoromethyl, 2,2-difluoroethyl, 2,2,2-trifluoroethyl and the like, preferably trichloromethyl and trifluoromethyl.

The halogen atom at $R^8$ and $R^{15}$ is fluorine atom, chlorine atom, bromine atom or iodine atom, preferably fluorine atom and chlorine atom.

The $C_2$–$C_4$ alkenyl group at $R^8$ and $R^{15}$ is linear or branched chain, such as vinyl, 1-propenyl, allyl, 1-butenyl, 2-butenyl, isopropenyl and the like, with preference given to vinyl, 1-propenyl and isopropenyl.

The $C_1$–$C_4$ hydroxyalkyl group at $R^8$ and $R^{15}$ is, for example, hydroxymethyl, 1-hydroxyethyl, 2-hydroxyethyl, 3-hydroxypropyl, 4-hydroxybutyl, 1-hydroxy-1-methylethyl, 2-hydroxy-1-methylethyl, 1,2-dihydroxy-1-methylethyl and the like, with preference given to hydroxymethyl.

In the alkoxyalkyl group at $R^8$ and $R^{15}$, the "alkoxy" moiety is preferably $C_1$–$C_4$ linear or branched chain alkoxy and the "alkyl" moiety is preferably $C_1$–$C_4$ linear or branched chain alkyl. Examples thereof include methoxymethyl, ethoxymethyl, propyloxymethyl, methoxyethyl, ethoxyethyl and the like, with preference given to methoxymethyl.

In the alkyloxycarbonyl group at $R^8$ and $R^{15}$, the "alkyloxy" moiety is preferably $C_1$–$C_4$ linear or branched chain alkyloxy, such as methoxycarbonyl, ethoxycarbonyl, propyloxycarbonyl, butyloxycarbonyl and the like, with preference given to methoxycarbonyl and ethoxycarbonyl.

The optionally substituted amino group at $R^8$ and $R^{15}$ is preferably amino optionally substituted by one or two, the same or different $C_1$–$C_2$ alkyl. Examples thereof include amino, methylamino, dimethylamino, ethylamino, diethylamino and the like, with preference given to methylamino and dimethylamino.

The acyl group at $R^8$ and $R^{15}$ is, for example, acetyl, propionyl, butyryl, isobutyryl and the like, with preference given to acetyl.

The optionally substituted alkyloxy group at $R^8$ and $R^{15}$ is preferably, $C_1$–$C_4$ linear or branched chain, which may be substituted by one or more, the same or different substituents mentioned below. Examples of these "substituents" include fluorine atom, chlorine atom and the like. Specific examples thereof include methoxy, ethoxy, propoxy, isopropoxy, butyloxy, trifluoromethoxy, 2,2,2-trifluoroethyloxy and the like, with preference given to methoxy and 2,2,2-trifluoroethyloxy.

The alkylthio group at $R^8$ and $R^{15}$ is preferably $C_1$–$C_4$ linear or branched chain, such as methylthio, ethylthio, propylthio, isopropylthio, butylthio and the like, with preference given to methylthio and ethylthio.

The $C_1$–$C_4$ hydroxyalkyl group at $R^7$ is linear or branched chain, such as 1-hydroxymethyl, 1-hydroxyethyl, 1-hydroxypropyl, 2-hydroxypropyl, 1-hydroxybutyl and the like, with preference given to 1-hydroxyethyl.

The $C_1$–$C_4$ alkylsulfonyl group at $R^7$ is linear or branched chain, such as methylsulfonyl, ethylsulfonyl, propylsulfonyl, isopropylsulfonyl, butylsulfonyl and the like, with preference given to ethylsulfonyl.

The optionally substituted saturated or unsaturated heterocyclic group at $R^7$ is a 5 or 6-membered heterocyclic group optionally containing 1–3 hetero atom(s) selected from the group consisting of nitrogen atom, oxygen atom and sulfur atom, such as a group derived from furan, thiophene, pyrrole, pyrazole, oxazole, isoxazole, thiazole, isothiazole, imidazole, furazan, 1,2,4-oxadiazole, 1,3,4-oxadiazole, 1,2,4-thiadiazole, 1,3,4-thiadiazole, pyridine, pyrimidine, pyrazine, pyridazine, oxazoline, thiazoline, imidazoline, tetrahydrofuran, tetrahydrothiophene, pyran and the like. Preferred are groups derived from thiophene, pyrazole, oxazole, isoxazole, thiazole, imidazole, 1,2,4-thiadiazole, 1,3,4-thiadiazole, 1,3,4-oxadiazole and the like and more preferred are groups derived from oxazole, thiazole, 1,3,4-thiadiazole, 1,3,4-oxadiazole and the like. These may be substituted by one or two the same or different substituents mentioned below.

Examples of these substituents include optionally substituted aryl group (e.g., phenyl or naphthyl optionally substituted by halogen atom, amino, nitro, hydroxy, $C_1$–$C_4$ alkyl, $C_1$–$C_4$ alkoxy and the like), $C_1$–$C_{18}$ alkyl group (as defined above, preferably methyl, ethyl, isopropyl, tert-butyl, isobutyl etc.), $C_1$–$C_2$ halogenated alkyl group (as defined above), $C_1$–$C_8$ alkoxy group (as defined above, preferably methoxy, ethoxy, isopropyloxy etc.), halogen atom (e.g., fluorine atom, chlorine atom, bromine atom or iodine atom), $C_2$–$C_4$ alkenyl group (e.g., vinyl, 1-propenyl, allyl, 1-butenyl, 2-butenyl, isopropenyl etc.), $C_1$–$C_4$ hydroxyalkyl group (e.g., hydroxymethyl, 1-hydroxyethyl, 2-hydroxyethyl, 3-hydroxypropyl, 4-hydroxybutyl etc.), alkoxyalkyl group (e.g., methoxymethyl, ethoxymethyl, propyloxymethyl, methoxyethyl, ethoxyethyl etc.), alkyloxycarbonyl group (e.g., methoxycarbonyl, ethoxycarbonyl, propyloxycarbonyl, butyloxycarbonyl etc.), optionally substituted amino group (e.g., amino, methylamino, dimethylamino, ethylamino, diethylamino etc.), acyl group (e.g., acetyl, propionyl, butyryl, isobutyryl etc.), acetamido group, carboxyl group, optionally substituted alkyloxy group (e.g., methoxy, ethoxy, propoxy, isopropoxy, butyloxy, trifluoromethoxy, 2,2,2-trifluoromethoxy etc.), alkylthio group (e.g., methylthio, ethylthio, propylthio, isopropylthio, butylthio etc.), cyano group and the like.

Examples of the optionally substituted fused heterocyclic group at $R^7$ include groups derived from benzofuran, benzothiophene, indole, benzoxazole, benzothiazole, 1,2-benzoisoxazole, 1,2-benzoisothiazole, benzimidazoline and the like, with preference given to benzoxazol-2-yl and benzothiazol-2-yl. These may be substituted by one or more, the same or different substituents mentioned below. Examples of these substituents include halogen atom (e.g., fluorine atom, chlorine atom, bromine atom etc.), haloalkyl group (e.g., fluoromethyl, difluoromethyl, trifluoromethyl etc.), $C_1$–$C_4$ alkyl group (linear or branched, such as methyl, ethyl, propyl, isopropyl, butyl, isobutyl, tert-butyl etc.), $C_1$–$C_8$ alkoxy group (linear or branched, such as methoxy, ethoxy, propoxy, isopropoxy, butoxy, isobutoxy, tert-butoxy, pentyloxy, hexyloxy, heptyloxy, octyloxy etc.), hydroxy group, nitro group, cyano group, amino group and the like.

The alkoxycarbonyl group at $R^6$ is preferably $C_1$–$C_4$ linear or branched chain, such as ethoxycarbonyl, methoxycarbonyl, propoxycarbonyl, butoxycarbonyl and the like, with preference given to ethoxycarbonyl.

The $C_1$–$C_4$ alkyl group at $R^{14}$ is linear or branched, such as methyl, ethyl, propyl, isopropyl, butyl, tert-butyl and the like, with preference given to methyl and ethyl.

The alkoxy group at $R^{10}$ and $R^{11}$ is, for example, linear or branched chain alkoxy having 1 to 4, preferably 1 or 2, carbon atoms, such as methoxy, ethoxy and the like, with preference given to methoxy.

The "cycloalkylene group" of the optionally substituted $C_3$–$C_8$ cycloalkylene group at Y' is, for example, cyclopropylene, cyclobutylene, cyclopentylene, cyclohexylene, cycloheptylene, cyclooctylene and the like. Examples of the substituent include $C_1$–$C_4$ alkyl group (e.g., methyl, ethyl, propyl, isopropyl, butyl, isobutyl, tert-butyl etc.), $C_1$–$C_8$ alkoxy group (e.g., methoxy, ethoxy, propoxy, isopropoxy, butoxy, isobutoxy, tert-butoxy, pentyloxy, hexyloxy, heptyloxy, octyloxy etc.), hydroxy group, oxo group and the like. Examples of the optionally substituted $C_3$–$C_8$ cycloalkylene include 2-methoxycyclopentylene, 2-methylcyclohexylene, 2,6-dimethylcyclohexylene, 3-ethylcycloheptylene, 3-hydroxycycloheptylene and the like, with preference given to 2,6-dimethylcyclohexylene.

The $C_1$–$C_8$ alkylene group at Y' is, for example, linear or branched, such as methylene, ethylene, trimethylene, tetramethylene, pentamethylene, hexamethylene, heptamethylene, octamethylene, methylmethylene, dimethylmethylene, 1-methylethylene, 2-methylethylene, 1,1-dimethylethylene, 2,2-dimethylethylene, ethylmethylene, diethylmethylene, 1-ethylethylene, 2-ethylethylene, 1-methyltrimethylene, 1,1-dimethyltrimethylene, 2-methyltrimethylene, 2,2-dimethyltrimethylene, 3-methyltrimethylene, 3,3-dimethyltrimethylene, 1-ethyltrimethylene, 2-ethyltrimethylene, 3-ethyltrimethylene and the like, with preference given to ethylene, trimethylene and tetramethylene.

The $C_1$–$C_4$ alkyleneoxy group at Y' is, for example, linear or branched, such as methyleneoxy, ethyleneoxy, trimethyleneoxy, tetramethyleneoxy, methylmethyleneoxy, dimethylmethyleneoxy, 1-methylethyleneoxy, 2-methylethyleneoxy, 1,1-dimethylethyleneoxy, 2,2-dimethylethyleneoxy, ethylmethyleneoxy, 1-ethylethyleneoxy, 2-ethylethyleneoxy, 1-methyltrimethyleneoxy, 2-methyltrimethyleneoxy, 3-methyltrimethyleneoxy and the like, with preference given to ethyleneoxy. The alkyleneoxy group here means both —RO— and —OR—, wherein R is $C_1$–$C_4$ alkylene. For example, ethyleneoxy means both —CH$_2$CH$_2$O— and —OCH$_2$CH$_2$—.

The optionally substituted 4 to 7-membered heterocycle having 1 or 2 hetero atom(s) selected from the group consisting of nitrogen atom and oxygen atom in the ring at Q' is, for example, a group derived from 3,5-dihydroimidazole, imidazolidine, pyrrolidine, oxazolidine, oxetane, oxolane, oxane, perhydroazepine, imidazolidine, oxepane, azetidine and the like. Examples of these substituents include $C_1$–$C_{18}$ alkyl group (e.g., methyl, ethyl etc.), $C_2$–$C_4$ alkoxyalkyl group (e.g., 2-methoxyethyl etc.), optionally substituted aryl group (as defined above, e.g., phenyl etc.), optionally substituted aralkyl group (as defined above, e.g., benzyl etc.), oxo group, thioxo group and the like. Preferable examples of the heterocycle group include groups derived from 3,5-dihydro-2-methylimidazole, 3,5-dihydro-2,3-dimethylimidazole, 3,5-dihydro-2-methyl-3-phenylimidazole, 3,5-dihydro-3-ethyl-2-methylimidazole, 3-benzyl-3,5-dihydro-2-methylimidazole, 1,3-dimethylimidazolidine, pyrrolidine, 1-methylpyrrolidine, 1-(2-methoxyethyl)pyrrolidine, oxazolidine and 5,5-dimethyloxane.

The $C_1$–$C_4$ alkyl group at R is, for example, methyl, ethyl, propyl, isopropyl, butyl, isobutyl and the like, with preference given to methyl and ethyl.

Examples of the X include hydrogen atom, hydroxy, methoxy, ethoxy, isopropoxy, acetoxy and the like, with particular preference given to hydroxy.

As $R^1$, a group of the following formula is preferable:

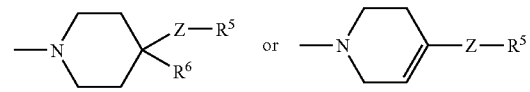

wherein $R^5$ is optionally substituted phenyl group or naphthyl group, Z is void and $R^6$ is hydrogen atom.

Specific examples of $R^1$ include
1-benzylpiperidin-4-ylamino,
4-phenylcyclohexyl-1-ylamino,
4-hydroxy-4-(4-chlorophenyl)piperidino,
4-hydroxy-4-(2-naphthyl)piperidino,
4-hydroxy-4-(benzo(b)thiophen-2-yl)piperidino,
4-benzylpiperidino,
4-(4-fluorobenzyl)piperidino,
4-(4-chlorobenzyl)piperidino,
4-(4-bromobenzyl)piperidino,
4-phenylpiperidino,
4-(4-fluorophenyl)piperidino,
4-(4-chlorophenyl)piperidino,
4-(4-bromophenyl)piperidino,
4-(4-methoxyphenyl)piperidino,
4-(4-methylphenyl)piperidino,
4-(4-trifluoromethylphenyl)piperidino,
4-(3-chlorophenyl)piperidino,
4-(3-fluorophenyl)piperidino,
4-(3-trifluoromethylphenyl)piperidino,
4-(3-bromophenyl)piperidino,
4-(3-methoxyphenyl)piperidino,
4-(3-methylphenyl)piperidino,
4-(2-fluorophenyl)piperidino,
4-(2-chlorophenyl)piperidino,
4-(2-bromophenyl)piperidino,
4-(2-methylphenyl)piperidino,
4-(2-methoxyphenyl)piperidino,
4-(3,4-dichlorophenyl)piperidino,
4-(3,4-dimethylphenyl)piperidino,
4-(3,4-dimethoxyphenyl)piperidino,
4-(3,4-methylenedioxyphenyl)piperidino,
4-(2,3-dimethoxyphenyl)piperidino, 4-(2,3-dimethylphenyl)piperidino,
4-(2,3-dichlorophenyl)piperidino,
4-(3,5-dimethoxyphenyl)piperidino,
4-(3,5-dimethylphenyl)piperidino,
4-(3,5-dichlorophenyl)piperidino,
4-(2,6-dimethoxyphenyl)piperidino,
4-(3,4,5-trimethoxyphenyl)piperidino,
4-(naphthalen-1-yl)piperidino,
4-(naphthalen-2-yl)piperidino,
4-(6-methoxynaphthalen-2-yl)piperidino,
4-(benzo(b)thiophen-2-yl)piperidino,
4-(benzo(b)furan-2-yl)piperidino,
4-(indol-2-yl)piperidino,
4-(4-fluorobenzyl)-3,6-dihydro-2H-pyridin-1-yl,
4-(4-chlorobenzyl)-3,6-dihydro-2H-pyridin-1-yl,
4-(4-bromobenzyl)-3,6-dihydro-2H-pyridin-1-yl,
4-phenyl-3,6-dihydro-2H-pyridin-1-yl,
4-(4-fluorophenyl)-3,6-dihydro-2H-pyridin-1-yl,
4-(4-chlorophenyl)-3,6-dihydro-2H-pyridin-1-yl,
4-(4-bromophenyl)-3,6-dihydro-2H-pyridin-1-yl,
4-(4-methoxyphenyl)-3,6-dihydro-2H-pyridin-1-yl,
4-(4-methylphenyl)-3,6-dihydro-2H-pyridin-1-yl,
4-(4-trifluoromethylphenyl)-3,6-dihydro-2H-pyridin-1-yl,
4-(3-chlorophenyl)-3,6-dihydro-2H-pyridin-1-yl,
4-(3-fluorophenyl)-3,6-dihydro-2H-pyridin-1-yl,
4-(3-trifluoromethylphenyl)-3,6-dihydro-2H-pyridin-1-yl,
4-(3-bromophenyl)-3,6-dihydro-2H-pyridin-1-yl,
4-(3-methoxyphenyl)-3,6-dihydro-2H-pyridin-1-yl,
4-(3-methylphenyl)-3,6-dihydro-2H-pyridin-1-yl,
4-(2-fluorophenyl)-3,6-dihydro-2H-pyridin-1-yl,
4-(2-chlorophenyl)-3,6-dihydro-2H-pyridin-1-yl,
4-(2-bromophenyl)-3,6-dihydro-2H-pyridin-1-yl,
4-(2-methylphenyl)-3,6-dihydro-2H-pyridin-1-yl,
4-(2-methoxyphenyl)-3,6-dihydro-2H-pyridin-1-yl,
4-(3,4-dichlorophenyl)-3,6-dihydro-2H-pyridin-1-yl,
4-(3,4-dimethylphenyl)-3,6-dihydro-2H-pyridin-1-yl,
4-(3,4-dimethoxyphenyl)-3,6-dihydro-2H-pyridin-1-yl,
4-(3,4-methylenedioxyphenyl)-3,6-dihydro-2H-pyridin-1-yl,
4-(2,3-dimethoxyphenyl)-3,6-dihydro-2H-pyridin-1-yl,
4-(2,3-dimethylphenyl)-3,6-dihydro-2H-pyridin-1-yl,
4-(2,3-dichlorophenyl)-3,6-dihydro-2H-pyridin-1-yl,
4-(3,5-dimethoxyphenyl)-3,6-dihydro-2H-pyridin-1-yl,
4-(3,5-dimethylphenyl)-3,6-dihydro-2H-pyridin-1-yl,
4-(3,5-dichlorophenyl)-3,6-dihydro-2H-pyridin-1-yl,
4-(2,6-dimethoxyphenyl)-3,6-dihydro-2H-pyridin-1-yl,
4-(3,4,5-trimethoxyphenyl)-3,6-dihydro-2H-pyridin-1-yl,
4-(naphthalen-1-yl)-3,6-dihydro-2H-pyridin-1-yl,
4-(naphthalen-2-yl)-3,6-dihydro-2H-pyridin-1-yl,
4-(6-methoxynaphthalen-2-yl)-3,6-dihydro-2H-pyridin-1-yl,
4-(benzo(b)thiophen-2-yl)-3,6-dihydro-2H-pyridin-1-yl,
4-(benzo(b)furan-2-yl)-3,6-dihydro-2H-pyridin-1-yl,
4-(indol-2-yl)-3,6-dihydro-2H-pyridin-1-yl,
4-(1,4-benzodioxan-6-yl)piperidino,
4-(2,3-dihydrobenzo(b)furan-5-yl)piperidino,
4-(benzo(b)furan-5-yl)piperidino,
4-(chroman-6-yl)piperidino,
4-(2,3-dihydrobenzo(b)furan-5-yl)piperidino,
4-(2,3-dihydrobenzo(b)furan-6-yl)piperidino,
4-(2,3-dihydrobenzo(b)thiophen-5-yl)piperidino,
4-(2,3-dihydrobenzo(b)thiophen-6-yl)piperidino,
4-(benzo(b)furan-5-yl)piperidino,
4-(benzo(b)furan-6-yl)piperidino,
4-(benzo(b)thiophen-5-yl)piperidino,
4-(benzo(b)thiophen-6-yl)piperidino,
4-(4-methoxy-3-methylphenyl)piperidino,
4-(indan-5-yl)piperidino,
4-(inden-5-yl)piperidino,
4-(1H-indolin-5-yl)piperidino,
4-(1-methylindolin-5-yl)piperidino, 1,3-dihydrobenzo(c)furan-1-spiro-4'-piperidin-1'-yl,
4-(chroman-7-yl)piperidino,
4-(2H-chromen-6-yl)piperidino,
4-(3-chloro-4-methoxyphenyl)piperidino,
4-(4-chloro-3-methoxyphenyl)piperidino,
4-(3-chloro-4-methylphenyl)piperidino,
4-(4-chloro-3-methylphenyl)piperidino,
4-(3-chloro-4-fluorophenyl)piperidino,
4-(4-chloro-3-fluorophenyl)piperidino,
4-(3-chloro-4-trifluoromethylphenyl)piperidino,
4-(4-chloro-3-trifluoromethylphenyl)piperidino,
4-(1H-indol-6-yl)piperidino,
4-(1-methylindol-6-yl)piperidino,
4-(1,3-dihydrobenzo(c)furan-5-yl)piperidino,
4-(3,4-dihydro-1H-benzo(c)oxin-6-yl)piperidino,
4-(3,4-dihydro-2H-benzo(b)thiin-6-yl)piperidino,
4-(3,4-dihydro-2H-benzo(b)thiin-7-yl)piperidino,
4-(2-methyl-2,3-dihydrobenzo(b)furan-5-yl)piperidino,
4-(2,2-dimethyl-2,3-dihydrobenzo(b)furan-5-yl)piperidino,
4-(1-methyl-2-oxoindolin-5-yl)piperidino,
4-(4-chloro-2,2-dimethyl-2,3-dihydrobenzo(b)furan-5-yl)piperidino,
4-(7-chloro-2,2-dimethyl-2,3-dihydrobenzo(b)furan-5-yl)piperidino,
4-(2,2-dimethyl-4-methyl-2,3-dihydrobenzo(b)furan-5-yl)piperidino,
4-(2,2-dimethyl-7-methyl-2,3-dihydrobenzo(b)furan-5-yl)piperidino,
4-(2,4,6-trimethylphenyl)piperidino,
4-(2H-1-oxoisoindolin-5-yl)piperidino,
4-(2-methyl-1-oxoisoindolin-5-yl)piperidino,
4-(quinolin-6-yl)piperidino,
4-(isoquinolin-6-yl)piperidino,
4-(4,5-dimethylthiophen-2-yl)piperidino,
4-(4,5-dichlorothiophen-2-yl)piperidino,
4-(4,5-dimethylfuran-2-yl)piperidino,
4-(4,5-dichlorofuran-2-yl)piperidino,
4-(2-methylpyridin-4-yl)piperidino and the like.
As $R^1$, preferred are
1-benzylpiperidin-4-ylamino,
4-phenylcyclohexyl-1-ylamino,
4-hydroxy-4-(4-chlorophenyl)piperidino,
4-hydroxy-4-(2-naphthyl)piperidino,
4-hydroxy-4-(benzo(b)thiophen-2-yl)piperidino,
4-benzylpiperidino,
4-(4-fluorobenzyl)piperidino,
4-(4-chlorobenzyl)piperidino,
4-(4-bromobenzyl)piperidino,
4-phenylpiperidino,
4-(4-fluorophenyl)piperidino,
4-(4-chlorophenyl)piperidino,
4-(4-bromophenyl)piperidino,
4-(4-methoxyphenyl)piperidino,
4-(4-methylphenyl)piperidino,
4-(4-trifluoromethylphenyl)piperidino,
4-(3-chlorophenyl)piperidino,
4-(3-fluorophenyl)piperidino,
4-(3-trifluoromethylphenyl)piperidino,
4-(3-bromophenyl)piperidino,
4-(3-methoxyphenyl)piperidino,
4-(3-methylphenyl)piperidino,
4-(2-fluorophenyl)piperidino,
4-(2-chlorophenyl)piperidino, 4-(2-bromophenyl)piperidino,
4-(2-methylphenyl)piperidino,
4-(2-methoxyphenyl)piperidino,
4-(3,4-dichlorophenyl)piperidino,
4-(3,4-dimethylphenyl)piperidino,
4-(3,4-dimethoxyphenyl)piperidino,
4-(3,4-methylenedioxyphenyl)piperidino,
4-(2,3-dimethoxyphenyl)piperidino,
4-(2,3-dimethylphenyl)piperidino,
4-(2,3-dichlorophenyl)piperidino,
4-(3,5-dimethoxyphenyl)piperidino,
4-(3,5-dimethylphenyl)piperidino,
4-(3,5-dichlorophenyl)piperidino,
4-(2,6-dimethoxyphenyl)piperidino,
4-(3,4,5-trimethoxyphenyl)piperidino,
4-(naphthalen-1-yl)piperidino,
4-(naphthalen-2-yl)piperidino,
4-(6-methoxynaphthalen-2-yl)piperidino,
4-(benzo(b)thiophen-2-yl)piperidino,
4-(benzo(b)furan-2-yl)piperidino,
4-(indol-2-yl)piperidino,
4-(4-fluorobenzyl)-3,6-dihydro-2H-pyridin-1-yl,
4-(4-chlorobenzyl)-3,6-dihydro-2H-pyridin-1-yl,
4-(4-bromobenzyl)-3,6-dihydro-2H-pyridin-1-yl,
4-phenyl-3,6-dihydro-2H-pyridin-1-yl,
4-(4-fluorophenyl)-3,6-dihydro-2H-pyridin-1-yl,
4-(4-chlorophenyl)-3,6-dihydro-2H-pyridin-1-yl,
4-(4-bromophenyl)-3,6-dihydro-2H-pyridin-1-yl,
4-(4-methoxyphenyl)-3,6-dihydro-2H-pyridin-1-yl,
4-(4-methylphenyl)-3,6-dihydro-2H-pyridin-1-yl,
4-(4-trifluoromethylphenyl)-3,6-dihydro-2H-pyridin-1-yl,
4-(3-chlorophenyl)-3,6-dihydro-2H-pyridin-1-yl,
4-(3-fluorophenyl)-3,6-dihydro-2H-pyridin-1-yl,
4-(3-trifluoromethylphenyl)-3,6-dihydro-2H-pyridin-1-yl,
4-(3-bromophenyl)-3,6-dihydro-2H-pyridin-1-yl,
4-(3-methoxyphenyl)-3,6-dihydro-2H-pyridin-1-yl,
4-(3-methylphenyl)-3,6-dihydro-2H-pyridin-1-yl,
4-(2-fluorophenyl)-3,6-dihydro-2H-pyridin-1-yl,
4-(2-chlorophenyl)-3,6-dihydro-2H-pyridin-1-yl,
4-(2-bromophenyl)-3,6-dihydro-2H-pyridin-1-yl,
4-(2-methylphenyl)-3,6-dihydro-2H-pyridin-1-yl,
4-(2-methoxyphenyl)-3,6-dihydro-2H-pyridin-1-yl,
4-(3,4-dichlorophenyl)-3,6-dihydro-2H-pyridin-1-yl,
4-(3,4-dimethylphenyl)-3,6-dihydro-2H-pyridin-1-yl,
4-(3,4-dimethoxyphenyl)-3,6-dihydro-2H-pyridin-1-yl,
4-(3,4-methylenedioxyphenyl)-3,6-dihydro-2H-pyridin-1-yl,
4-(2,3-dimethoxyphenyl)-3,6-dihydro-2H-pyridin-1-yl,
4-(2,3-dimethylphenyl)-3,6-dihydro-2H-pyridin-1-yl,
4-(2,3-dichlorophenyl)-3,6-dihydro-2H-pyridin-1-yl,
4-(3,5-dimethoxyphenyl)-3,6-dihydro-2H-pyridin-1-yl,
4-(3,5-dimethylphenyl)-3,6-dihydro-2H-pyridin-1-yl,
4-(3,5-dichlorophenyl)-3,6-dihydro-2H-pyridin-1-yl,
4-(2,6-dimethoxyphenyl)-3,6-dihydro-2H-pyridin-1-yl,
4-(3,4,5-trimethoxyphenyl)-3,6-dihydro-2H-pyridin-1-yl,
4-(naphthalen-1-yl)-3,6-dihydro-2H-pyridin-1-yl,
4-(naphthalen-2-yl)-3,6-dihydro-2H-pyridin-1-yl,
4-(6-methoxynaphthalen-2-yl)-3,6-dihydro-2H-pyridin-1-yl,
4-(benzo(b)thiophen-2-yl)-3,6-dihydro-2H-pyridin-1-yl,
4-(benzo(b)furan-2-yl)-3,6-dihydro-2H-pyridin-1-yl,
4-(indol-2-yl)-3,6-dihydro-2H-pyridin-1-yl,
4-(1,4-benzodioxan-6-yl)piperidino,
4-(2,3-dihydrobenzo(b)furan-5-yl)piperidino,
4-(benzo(b)furan-5-yl)piperidino,
4-(chroman-6-yl)piperidino,
4-(2,3-dihydrobenzo(b)furan-5-yl)piperidino,
4-(benzo(b)furan-5-yl)piperidino,
4-(2,2-dimethyl-2,3-dihydrobenzo(b)furan-5-yl)piperidino,
4-(7-chloro-2,2-dimethyl-2,3-dihydrobenzo(b)furan-5-yl)piperidino,
4-(2,2-dimethyl-4-methyl-2,3-dihydrobenzo(b)furan-5-yl)piperidino,
4-(2,2-dimethyl-7-methyl-2,3-dihydrobenzo(b)furan-5-yl)piperidino,
4-(2,4,6-trimethylphenyl)piperidino,
4-(2H-1-oxoisoindolin-5-yl)piperidino,
4-(2-methyl-1-oxoisoindolin-5-yl)piperidino,
4-(quinolin-6-yl)piperidino,
4-(isoquinolin-6-yl)piperidino,
4-(4,5-dimethylthiophen-2-yl)piperidino,
4-(4,5-dichlorothiophen-2-yl)piperidino,
4-(4,5-dimethylfuran-2-yl)piperidino,
4-(4,5-dichlorofuran-2-yl)piperidino,
4-(2-methylpyridin-4-yl)piperidino and the like.
As $R^1$, more preferred are
4-(3,4-dimethylphenyl)piperidin-1-yl,
4-(1-naphthyl)piperidin-1-yl,
4-(2-naphthyl)piperidin-1-yl,
4-(6-methoxynaphthalen-2-yl)piperidin-1-yl,
4-(3,4-dimethylphenyl)-3,6-dihydro-2H-pyridin-1-yl,
4-(1-naphthyl)-3,6-dihydro-2H-pyridin-1-yl,
4-(2-naphthyl)-3,6-dihydro-2H-pyridin-1-yl,
4-(6-methoxynaphthalen-2-yl)-3,6-dihydro-2H-pyridin-1-yl,
4-(benzo(b)furan-5-yl)piperidino,
4-(2,3-dihydrobenzo(b)furan-5-yl)piperidino,
4-(2,2-dimethyl-2,3-dihydrobenzo(b)furan-5-yl)piperidino,
4-(4-chloro-3-fluorophenyl)piperidino,
4-(4-chloro-3-methylphenyl)piperidino,
4-(3,4-dichlorophenyl)piperidino and the like.
As $R^1$,
4-(naphthalen-1-yl)piperidino,
4-(naphthalen-2-yl)piperidino,
4-(naphthalen-1-yl)-3,6-dihydro-2H-pyridin-1-yl,
4-(naphthalen-2-yl)-3,6-dihydro-2H-pyridin-1-yl,
4-(3,4-dichlorophenyl)piperidino,
4-(4-chloro-3-methylphenyl)piperidino,
4-(2,2-dimethyl-2,3-dihydrobenzo(b)furan-5-yl)piperidino
and the like are particularly preferable.
As $R^3$, hydrogen atom and $C_1$–$C_4$ alkyl (e.g., methyl, ethyl, propyl, isopropyl, butyl etc.) are preferable and hydrogen atom is particularly preferable.
W is preferably void.
As $R^7$, a group of the following formula is preferable:

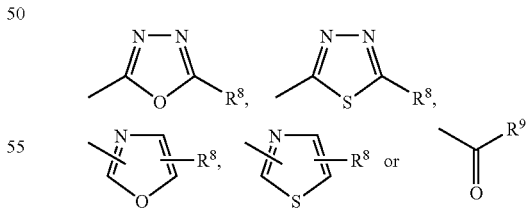

wherein
$R^8$ is hydrogen atom, phenyl group, $C_1$–$C_4$ alkyl group, $C_1$–$C_2$ halogenated alkyl group, halogen atom, $C_2$–$C_4$ alkenyl group, $C_1$–$C_4$ hydroxyalkyl group, alkoxyalkyl group, alkyloxycarbonyl group, optionally substituted amino group, acetamido group, carboxyl group, acyl group, optionally substituted alkyloxy group, alkylthio group or cyano group, and $R^9$ is a group of the following formula

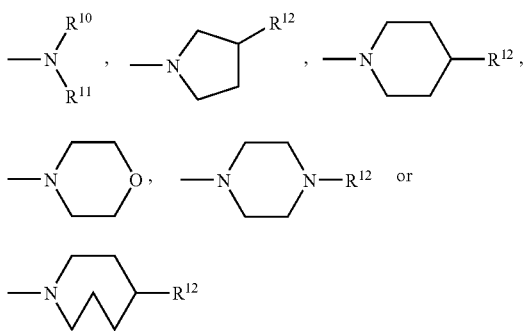

wherein $R^{10}$ and $R^{11}$ are each independently hydrogen atom, $C_1$–$C_{18}$ alkyl group, optionally substituted aryl group, optionally substituted aralkyl group or alkoxy group, and $R^{12}$ is hydrogen atom, optionally substituted aryl group, $C_1$–$C_{18}$ alkyl group, $C_1$–$C_8$ alkoxy group or acyl group.

Ra, Rb and Rc are each specifically hydrogen atom, fluorine atom, chlorine atom, bromine atom, methyl, ethyl, methoxy, methylenedioxy, hydroxy, acetyl and the like, with preference given to all Ra, Rb, Rc being hydrogen atom.

Examples of the group of the following formula

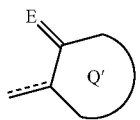

include groups derived from β-propiolactone, γ-butyrolactone, 5,5,-dimethyl-γ-butyrolactone, γ-valerolactone, δ-valerolactone, 6,6-dimethyl-δ-valerolactone, γ-caprolactone, ε-caprolactone, 6,6-dimethyl-δ-caprolactone, 2-azetidinone, 2-pyrrolidinone, δ-valerolactam, ε-caprolactam, hydantoin, 3,5-dihydroimidazol-4-one and the like.

A preferable group of the following formula

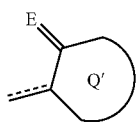

includes the groups of the following formulas

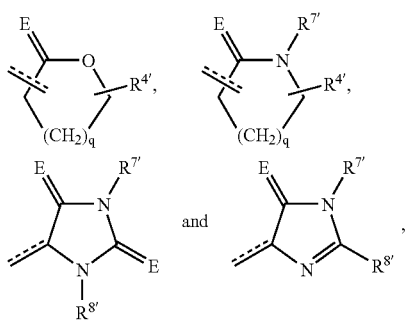

which are specifically groups derived from γ-butyrolactone, δ-valerolactone, 2-pyrrolidinone and the like, with particular preference given to a group of the following formula

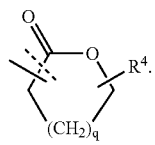

Specific examples are groups derived from γ-butyrolactone and δ-valerolactone.

Preferable embodiment of the formula (I) includes the compounds of the following formulas:

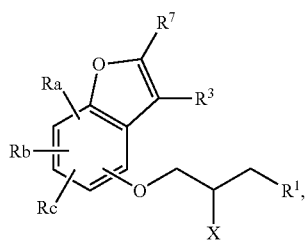

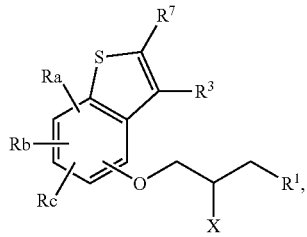

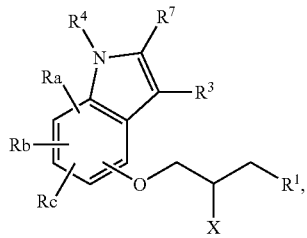

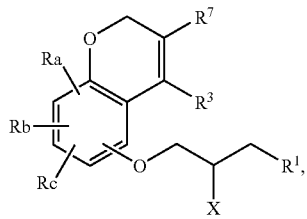

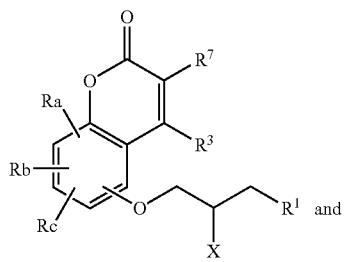

and

-continued

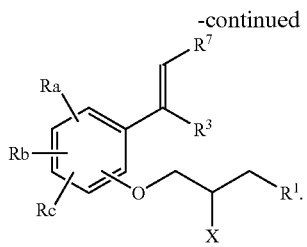

The phenoxypropylamine compound of the present invention is a compound of the following formula (I)

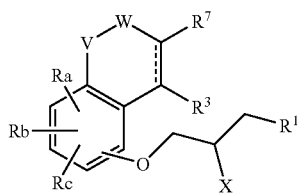

wherein each symbol is as defined above.

The preferable compound of the above-mentioned formula (1) is a compound (compound A) wherein each symbol of the formula (I) is as follows:
a bond represented by a solid line and a dotted line shows a double bond;
X is a hydrogen atom, a hydroxy group, a $C_1$–$C_8$ alkoxy group, an acyloxy group or an oxo group;
$R^1$ is a group of the following formula

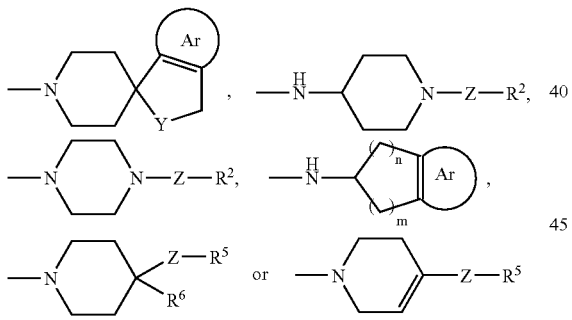

wherein
Y is O or S,
m and n are each independently 0, 1 or 2,
Ar is optionally substituted benzene or naphthalene,
$R^2$ is optionally substituted aryl group or optionally substituted aromatic heterocyclic group,
$R^5$ is optionally substituted aryl group or optionally substituted aromatic heterocyclic group,
Z is void or —$CH_2$—, and
$R^6$ is hydrogen atom, hydroxy group, acetamido group, carboxyl group, alkoxycarbonyl group, cyano group or $C_1$–$C_8$ alkoxy group;
$R^3$ is a hydrogen atom, a $C_1$–$C_{18}$ alkyl group or a halogen atom;
V is —$CH_2$—, —O—, —S— or the formula —N($R^4$)— wherein $R^4$ is hydrogen atom, $C_1$–$C_{18}$ alkyl group or optionally substituted aralkyl group;

W is void or —$CH_2$— or —C(=O)—; or
V and W are each a hydrogen atom without bonding;
$R^7$ is a $C_1$–$C_4$ hydroxyalkyl group, an acyl group, an optionally substituted saturated or unsaturated heterocyclic group, an optionally substituted fused heterocyclic group, a $C_1$–$C_4$ alkylsulfonyl group or the formula -Q-$R^9$ wherein
Q is —C(=O)—, —C(=S)—, —$CH_2$— or S(=O)$_2$—, and
$R^9$ is a group of the following formula

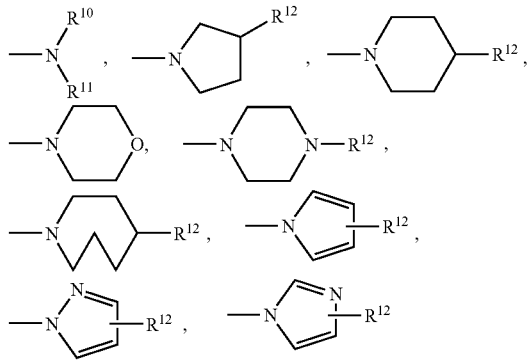

or —NH—NH—$R^{15}$
wherein $R^{10}$ and $R^{11}$ are each independently hydrogen atom, $C_1$–$C_{18}$ alkyl group, optionally substituted aryl group, optionally substituted aralkyl group or alkoxy group, $R^{12}$ is hydrogen atom, optionally substituted aryl group, $C_1$–$C_{18}$ alkyl group, $C_1$–$C_8$ alkoxy group or acyl group, and $R^{15}$ is hydrogen atom, phenyl group, $C_1$–$C_4$ alkyl group, $C_1$–$C_2$ halogenated alkyl group, halogen atom, $C_2$–$C_4$ alkenyl group, $C_1$–$C_4$ hydroxyalkyl group, alkoxyalkyl group, alkyloxycarbonyl group, optionally substituted amino group, acetamido group, carboxyl group, acyl group, optionally substituted alkyloxy group, alkylthio group or cyano group; and
Ra, Rb and Rc are each independently a hydrogen atom, a $C_1$–$C_{18}$ alkyl group, a hydroxy group, a $C_1$–$C_8$ alkoxy group, a halogen atom, an acyl group, a nitro group or an amino group;
provided that when V and W are not directly bonded and V and W are both hydrogen atoms, $R^7$ should not be a group of the formula —CO—$R^9$ wherein $R^9$ is as defined above.

In the above-mentioned compound A, a compound A wherein each symbol of the formula (I) is as follows is more preferable:
a bond represented by a solid line or a dotted line shows a double bond;
X is a hydroxy group;
$R^1$ is a group of the following formula

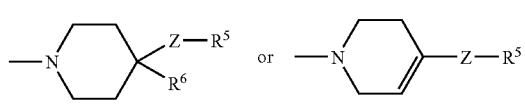

wherein
$R^5$ is optionally substituted phenyl group or naphthyl group,
Z is void, and
$R^6$ is hydrogen atom;

R³ is a hydrogen atom or C₁–C₄ alkyl group;
V is —CH₂—, —O—, —S— or the formula —N(R⁴)—
  wherein R is hydrogen atom, C₁–C₆ alkyl group or optionally substituted aralkyl group;
W is void; or
R⁷ is a group of the following formula

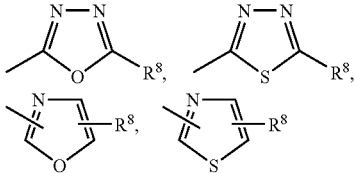

or the formula —CO—R⁹
wherein
R⁸ is hydrogen atom, phenyl group, C₁–C₄ alkyl group, C₁–C₂ halogenated alkyl group, halogen atom, C₂–C₄ alkenyl group, C₁–C₄ hydroxyalkyl group, alkoxyalkyl group, alkyloxycarbonyl group, optionally substituted amino group, acetamido group, carboxyl group, acyl group, optionally substituted alkyloxy group, alkylthio group or cyano group, and
R⁹ is a group of the following formula

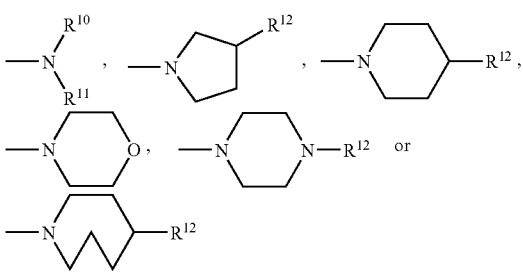

wherein R¹⁰ and R¹¹ are each independently hydrogen atom, C₁–C₁₈ alkyl group, optionally substituted aryl group, optionally substituted aralkyl group or alkoxy group, and R¹² is hydrogen atom, optionally substituted aryl group, C₁–C₁₈ alkyl group, C₁–C₈ alkoxy group or acyl group; and
Ra, Rb and Rc are each a hydrogen atom.

In the above-mentioned compound A, that having the following formula (I') is more preferable:

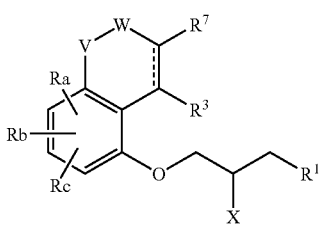

wherein each symbol is as defined for compound A.

Specific examples of the above-mentioned compound A are:
(1) 1-(4-(2-hydroxy-3-(4-(naphthalen-2-yl)piperidino)propyloxy)benzo(b)furan-2-ylcarbonyl)pyrrolidine,
(2) 4-(4-(2-hydroxy-3-(4-(naphthalen-2-yl)piperidino)propyloxy)benzo(b)furan-2-ylcarbonyl)morpholine,
(4) 4-(2-hydroxy-3-(4-(naphthalen-2-yl)piperidino)propyloxy)-N,N-dimethylbenzo(b)furan-2-carboxamide,
(12) 1-(4-(2-hydroxy-3-(4-(naphthalen-2-yl)piperidino)propyloxy)benzo(b)thiophen-2-ylcarbonyl)pyrrolidine,
(13) 4-(4-(2-hydroxy-3-(4-(naphthalen-2-yl)piperidino)propyloxy)benzo(b)thiophen-2-ylcarbonyl)morpholine,
(15) 4-(2-hydroxy-3-(4-(naphthalen-1-yl)piperidino)propyloxy)-N,N-dimethylbenzo(b)thiophene-2-carboxamide,
(17) 4-(2-hydroxy-3-(4-(naphthalen-2-yl)piperidino)propyloxy)-N,N-dimethylbenzo(b)thiophene-2-carboxamide,
(20) 4-(7-(2-hydroxy-3-(4-(naphthalen-2-yl)piperidino)propyloxy)benzo(b)furan-2-ylcarbonyl)morpholine,
(21) 7-(2-hydroxy-3-(4-(naphthalen-2-yl)piperidino)propyloxy)-N,N-dimethylbenzo(b)furan-2-carboxamide,
(27) 4-(2-hydroxy-3-(4-(naphthalen-2-yl)piperidino)propyloxy)-N,N-dimethyl-1H-indole-2-carboxamide,
(30) 4-(2-hydroxy-3-(4-(naphthalen-2-yl)piperidino)propyloxy)-N,N-dimethyl-1-methylindole-2-carboxamide,
(35) 1-(2-(5-methyl-1,2,4-oxadiazol-3-yl)benzo(b)furan-4-yloxy)-3-(4-(naphthalen-2-yl)piperidino)-2-propanol,
(37) 1-(2-(5-methyl-1,3,4-oxadiazol-2-yl)benzo(b)furan-4-yloxy)-3-(4-(naphthalen-2-yl)piperidino)-2-propanol,
(38) 1-(2-(5-trifluoromethyl-1,3,4-oxadiazol-2-yl)benzo(b)furan-4-yloxy)-3-(4-(naphthalen-2-yl)piperidino)-2-propanol,
(39) 1-(2-(5-methyl-1,3,4-oxadiazol-2-yl)benzo(b)furan-7-yloxy)-3-(4-(naphthalen-2-yl)piperidino)-2-propanol,
(42) 1-(2-(5-methyl-1,3,4-oxadiazol-2-yl)-1H-indol-4-yloxy)-3-(4-(naphthalen-2-yl)piperidino)-2-propanol,
(44) 1-(2-(3-methyl-1,2,4-oxadiazol-5-yl)benzo(b)furan-4-yloxy)-3-(4-(naphthalen-2-yl)piperidino)-2-propanol,
(48) 1-(2-(5-methyloxazol-2-yl)benzo(b)furan-7-yloxy)-3-(4-(naphthalen-2-yl)piperidino)-2-propanol,
(81) 3-(4-(3,4-dichlorophenyl)piperidino)-1-(2-(5-methyloxazol-2-yl)benzo(b)furan-4-yloxy)-2-propanol,
(88) 1-(4-(3,4-dichlorophenyl)piperidino)-3-(2-(5-methyl-1,3,4-oxadiazol-2-yl)benzo(b)furan-4-yloxy)-2-propanol, and
(93) 3-(4-(3,4-dimethylphenyl)piperidino)-1-(2-(5-ethyl-1,3,4-oxadiazol-2-yl)benzo(b)furan-4-yloxy)-2-propanol,
wherein the number in the parenthesis affixed to each compound is an Example number.

The preferable compound of the above-mentioned formula (I) also includes a compound (compound B) wherein each symbol of the formula (I) is as follows:
a bond represented by a solid line and a dotted line shows a double bond or a single bond;
X is a hydrogen atom, a hydroxy group, a C₁–C₈ alkoxy group or an acyloxy group;
R¹ is a group of the following formula

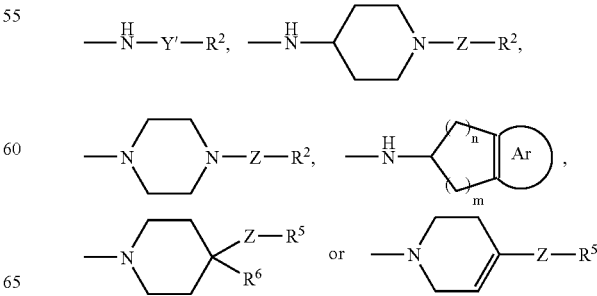

wherein
m and n are each independently 0, 1 or 2,
Ar is optionally substituted aromatic hydrocarbon,
$R^2$ is optionally substituted aryl group or optionally substituted aromatic heterocyclic group,
$R^5$ is optionally substituted aryl group or optionally substituted aromatic heterocyclic group,
Z is void or —$CH_2$—,
$R^6$ is hydrogen atom, hydroxy group or $C_1$–$C_8$ alkoxy group and
Y' is optionally substituted $C_3$–$C_8$ cycloalkylene group, $C_1$–$C_4$ alkyleneoxy group or $C_1$–$C_8$ alkylene group;
$R^3$ is a hydrogen atom, $C_1$–$C_{18}$ alkyl group or halogen atom;
$R^7$ and W are bonded to form the following formula

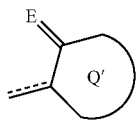

wherein
E is an oxygen atom or a sulfur atom;
Q' is optionally substituted 4 to 7-membered heterocycle having 1 or 2 hetero atom(s) selected from the group consisting of nitrogen atom and oxygen atom in the ring,
and V is hydrogen atom; and
Ra, Rb and Rc are each independently a hydrogen atom, a $C_1$–$C_{18}$ alkyl group, a hydroxy group, a $C_1$–$C_8$ alkoxy group,
a halogen atom, an acyl group, a nitro group or an amino group.
In the above-mentioned compound B, that wherein each symbol is as follows is more preferable:
a group of the following formula

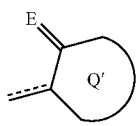

is a group of the following formula

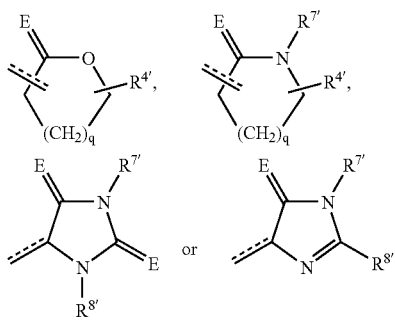

wherein
E is an oxygen atom or a sulfur atom,
q is 0, 1, 2 or 3,
$R^{4'}$, $R^{7'}$ and $R^{8'}$ are each independently a hydrogen atom, a $C_1$–$C_{18}$ alkyl group, an optionally substituted aryl group or an optionally substituted aralkyl group, and
other symbols are as defined in the aforementioned compound B.

In the above-mentioned compound B, that wherein each symbol is as follows is more preferable:
a bond represented by a solid line and a dotted line shows a double bond;
X is a hydroxy group;
$R^1$ is a group of the following formula:

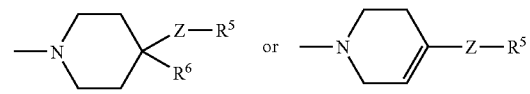

wherein
$R^5$ is optionally substituted phenyl group or naphthyl group,
Z is void, and
$R^6$ is hydrogen atom;
$R^3$ is a hydrogen atom or $C_1$–$C_4$ alkyl group;
a group of the formula

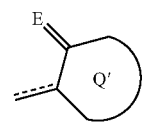

is a group of the following formula

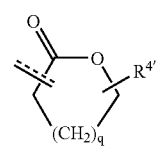

wherein q is 1 and $R^{4'}$ is hydrogen atom or $C_1$–$C_4$ alkyl group); and
Ra, Rb and Rc are each a hydrogen atom.
In the above-mentioned compound B, that having the following formula (I") is particularly preferable:

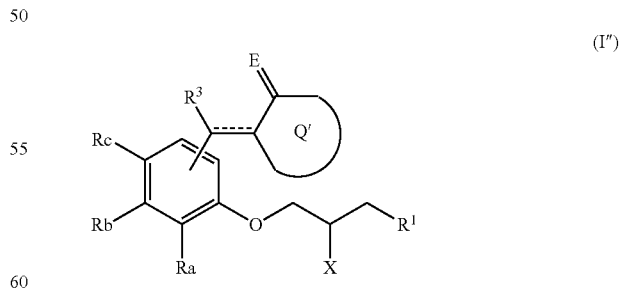

(I")

wherein each symbol is as defined for compound B.
Specific examples of the above-mentioned compound B are as follows:
(306) 5-(2'-(2-hydroxy-3-(4-(naphthalen-2-yl)piperidino)propyloxy)benzylidene)-1,3-dimethylimidazolidine-2,4-dione, (307) α-(2'-(2-hydroxy-3-(4-(naphthalen-2-yl)piperidino) propyloxy)benzylidene)-γ-butyrolactone,
(308) α-(2'-(2-hydroxy-3-(4-(naphthalen-2-yl)piperidino) propyloxy)benzylidene)-γ-butyrolactone,
(309) α-(2'-(2-hydroxy-3-(4-(naphthalen-2-yl)piperidino) propyloxy)benzylidene)-γ-butyrolactone,
(310) α-(2'-(3-(4-(3-fluoro-4-methylphenyl)piperidino)-2-hydroxypropyloxy) benzylidene)-γ-butyrolactone,
(311) α-(2'-(3-(4-(3,4-dimethylphenyl)piperidino)-2-hydroxypropyloxy) benzylidene)-γ-butyrolactone,
(312) α-(2'-(3-(4-(4-chloro-3-fluorophenyl)piperidino)-2-hydroxypropyloxy) benzylidene)-γ-butyrolactone,
(313) α-(2'-(3-(4-(4-chloro-3-trifluoromethylphenyl)piperidino)-2-hydroxypropyloxy) benzylidene)-γ-butyrolactone,
(314) α-(2'-(2-hydroxy-3-(4-(naphthalen-1-yl)piperidino) propyloxy)benzylidene)-γ-butyrolactone,
(315) α-(2'-(2-hydroxy-3-(4-(naphthalen-2-yl)piperidino) propyloxy)benzylidene)-δ-valerolactone,
(316) α-(2'-(2-hydroxy-3-(4-(naphthalen-2-yl)piperidino) propyloxy)benzylidene)-γ-valerolactone,
(319) 3-(2'-(2-hydroxy-3-(4-(naphthalen-2-yl)piperidino) propyloxy)benzylidene)-2-pyrrolidone,
(322) 3-(2'-(2-hydroxy-3-(4-(naphthalen-2-yl)piperidino) propyloxy)benzylidene)-1-methyl-2-pyrrolidone, and
(325) α-(2'-(2-hydroxy-3-(4-(6-methoxynaphthalen-2-yl) piperidino) propyloxy) benzylidene)-γ-butyrolactone, wherein the number in the parenthesis affixed to each compound is an Example number.

A synthetic intermediate of compound A may be a compound of the following formula (II)

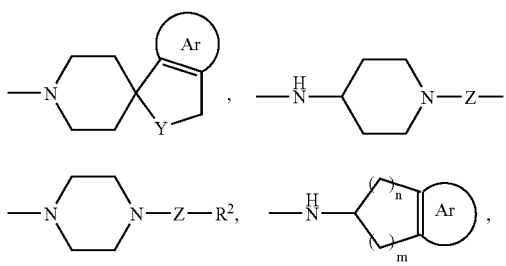

(II)

wherein each symbol in the formula is as defined below:
X is a hydrogen atom, a hydroxy group, a $C_1$–$C_8$ alkoxy group or an acyloxy group or an oxo group;
$R^1$ is a group of the following formula

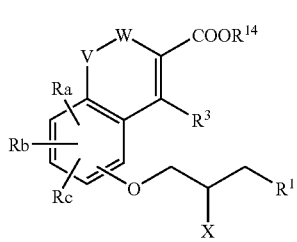

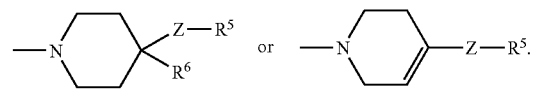

wherein
Y is O or S,
m and n are each independently 0, 1 or 2,
Ar is optionally substituted benzene or naphthalene,
$R^2$ is optionally substituted aryl group or optionally substituted aromatic heterocyclic group,
$R^5$ is optionally substituted aryl group or optionally substituted aromatic heterocyclic group,
Z is void or —$CH_2$—, and
$R^6$ is hydrogen atom, hydroxy group, acetamido group, carboxyl group, alkoxycarbonyl group, cyano group or $C_1$–$C_8$ alkoxy group;
$R^3$ is a hydrogen atom, a $C_1$–$C_{18}$ alkyl group or a halogen atom;
V is —$CH_2$—, —O—, —S— or the formula —N($R^4$)— wherein
$R^4$ is hydrogen atom, $C_1$–$C_{18}$ alkyl group or optionally substituted aralkyl group;
W is void, —$CH_2$— or —C(=O)—; or
V and W are each a hydrogen atom without bonding;
$R^{14}$ is a hydrogen atom or a $C_1$–$C_4$ alkyl; and
Ra, Rb and Rc are each independently a hydrogen atom, a $C_1$–$C_{18}$ alkyl group, a hydroxy group, a $C_1$–$C_8$ alkoxy group, a halogen atom, an acyl group, a nitro group or an amino group.

A synthetic intermediate of compound B may be a compound of the following formula (III)

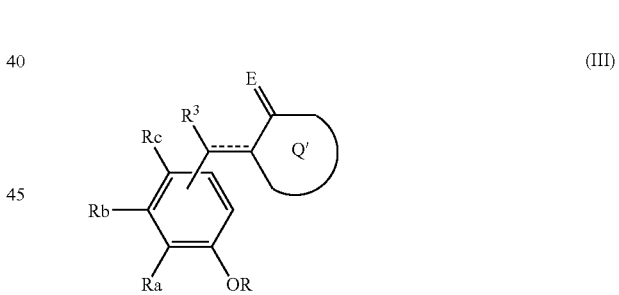

(III)

wherein each symbol in the formula is as defined below:
R is a hydrogen atom, a $C_1$–$C_4$ alkyl group, an allyl group or a 2,3-epoxypropan-1-yl group;
a bond represented by a solid line and a dotted line shows a double bond or a single bond;
E is an oxygen atom or a sulfur atom;
$R^3$ is a hydrogen atom, a $C_1$–$C_{18}$ alkyl group or a halogen atom;
Q' is an optionally substituted 4 to 7-membered heterocycle having 1 or 2 hetero atom(s) selected from the group consisting of nitrogen atom and oxygen atom in the ring; and
Ra, Rb and Rc are each independently a hydrogen atom, a $C_1$–$C_{18}$ alkyl group, a hydroxy group, a $C_1$–$C_8$ alkoxy group, a halogen atom, acyl group, a nitro group or an amino group.

As a synthetic intermediate for the above-mentioned compound B, a compound of the formula (III) wherein each symbol is as defined below is preferable:
the group of the following formula

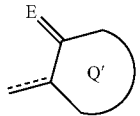

is a group of the following formula

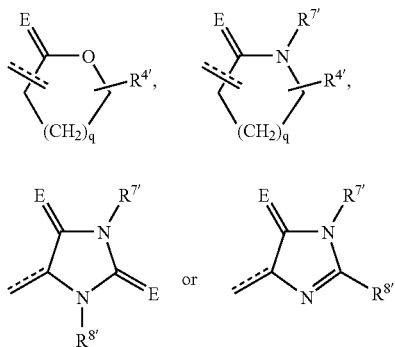

wherein
E is an oxygen atom or a sulfur atom,
q is 0, 1, 2 or 3, and
$R^{4'}$, $R^{7'}$ and $R^{8'}$ are each independently hydrogen atom, $C_1$–$C_{18}$ alkyl group, optionally substituted aryl group or optionally substituted aralkyl group, and
other symbols are as defined with regard to the formula (III).

The pharmaceutically acceptable salts of compounds of the formulas (I), (II) and (III) include acid addition salts with inorganic acids (e.g., hydrochloric acid, hydrobromic acid, sulfuric acid, phosphoric acid, nitric acid etc.) or organic acids (e.g., acetic acid, propionic acid, succinic acid, glycolic acid, lactic acid, malic acid, tartaric acid, citric acid, maleic acid, fumaric acid, methanesulfonic acid, benzenesulfonic acid, p-toluenesulfonic acid, camphorsulfonic acid, ascorbic acid, terephthalic acid, adipic acid etc.).

The compounds of the formulas (I), (II) and (III) and pharmaceutically acceptable salts thereof may be present in the form of a hydrate or a solvate. These hydrates and solvates are also encompassed in the present invention. When the compound of the formula (I) has an asymmetric atom, at least two kinds of optical isomers exist. The optical isomers and racemates thereof are encompassed in the present invention.

The compound of the formula (I) can be synthesized by the following methods. Each symbol in the following reaction formulas is as defined above, unless particularly specified.

The compound of the formula (I) and synthetic intermediates of the formulas (II) and (III) can be produced according to the following reaction formulas A–Z and Q'–T', as well as methods analogous to the following examples and the like. In the formulas, the symbol A refers to a leaving group (or nucleofugal group) well known in the organic synthesis, such as chlorine atom, bromine atom, iodine atom, mesylate, tosylate, nosylate, triflate and the like. Leaving groups (or nucleofugal groups) are well known to those of ordinary skill in the art of organic syntheses.

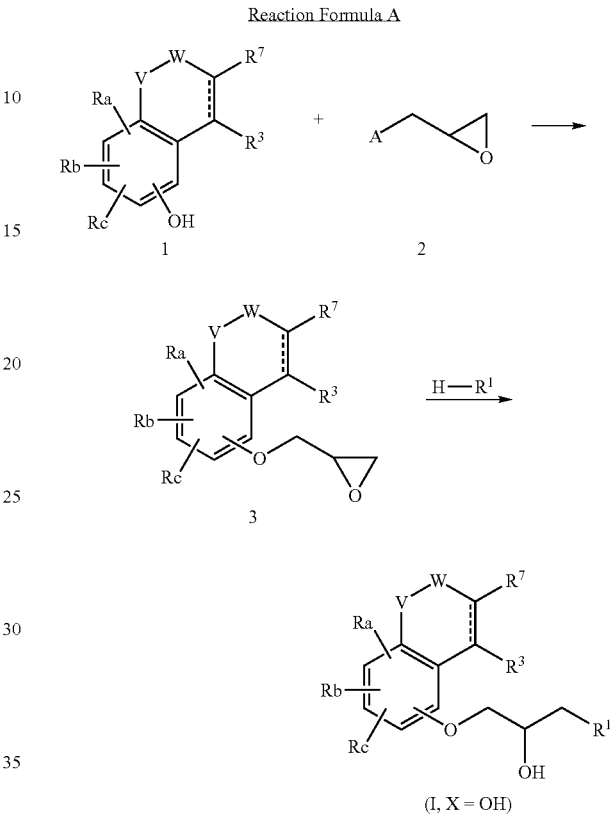

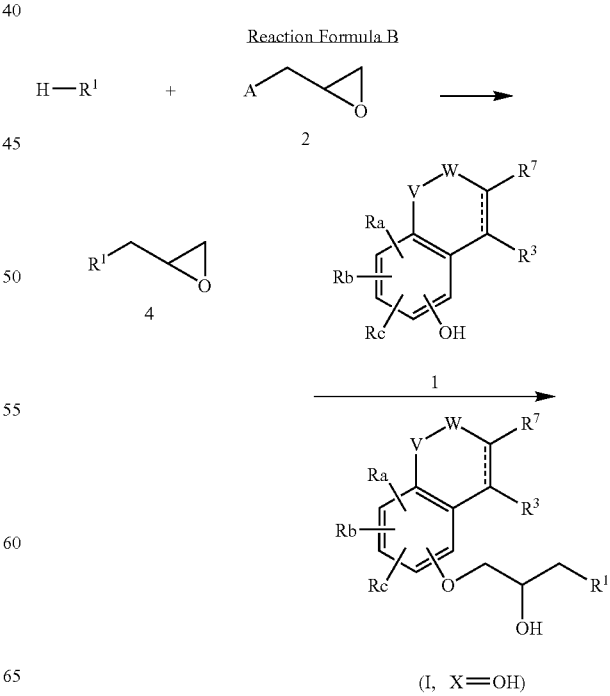

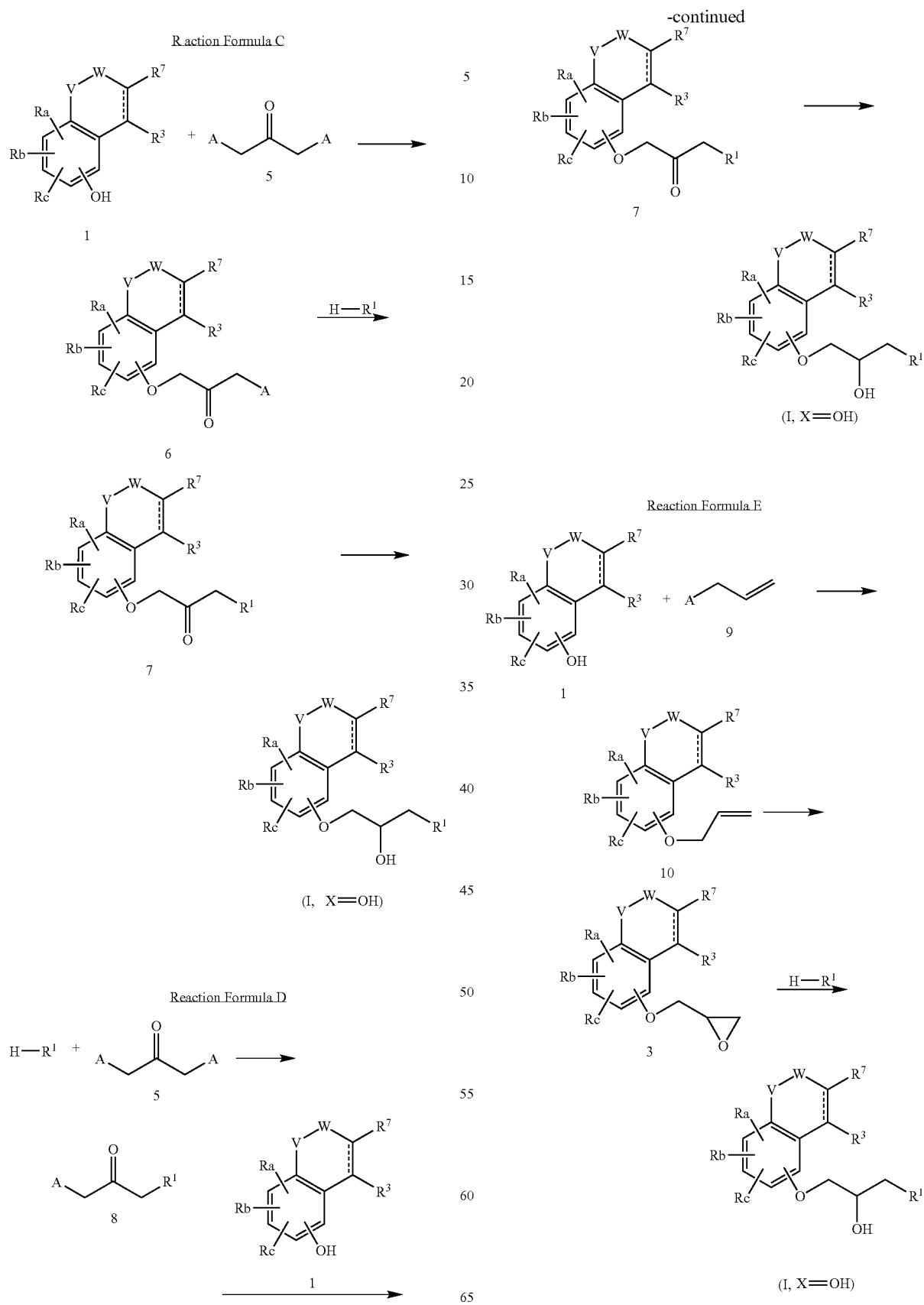

Reaction formula A: A method comprising reacting a phenol derivative 1 and 2,3-epoxypropane compound 2 having a leaving group (or nucleofugal group) at 1-position, followed by reaction with H—$R^1$, Reaction formula B: A method comprising reacting H—$R^1$ and 2,3-epoxypropane compound 2 having a leaving group (or nucleofugal group) at 1-position to give compound 4, which is reacted with a phenol derivative 1, Reaction formula C: A method comprising reacting a phenol derivative 1 and 2-propanone 5 having leaving groups (or nucleofugal groups) at 1,3-position to give compound 6, which is reacted with H—$R^1$ to give a product 7, followed by reduction thereof, Reaction formula D: A method comprising reacting H—$R^1$ and 2-propanone compound 5 having leaving groups (or nucleofugal groups) at 1,3-position to give compound 8, which is reacted with phenol derivative 1 to give a product 7, followed by reduction thereof, Reaction formula E: A method comprising reacting phenol derivative 1 and allyl compound 9 (e.g., 3-allyl bromide etc.) having a leaving group (or nucleofugal group) at 3-position to give a product 10, which is epoxidated and successively reacted with H—$R^1$, and the like. The methods for synthesis of the compound of the formula (I) are not limited to those mentioned above.

Particularly, the optically active compound of the formula (I) (X=OH) can be synthesized by the following reaction formulas F–L and the like. In these reaction formulas, the symbol R* means a part other than carboxyl group of optically active carboxylic acid.

Reaction Formula G

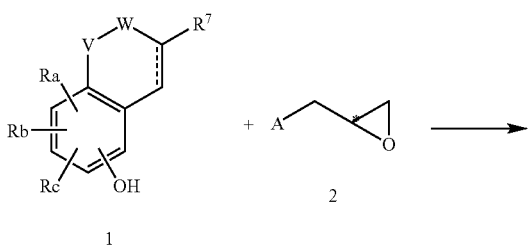

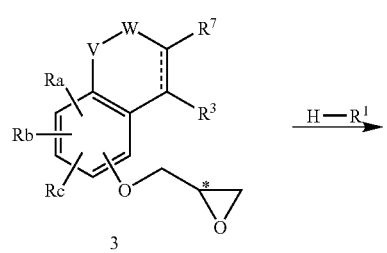

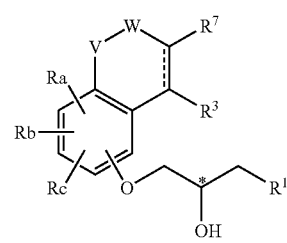

Reaction Formula F

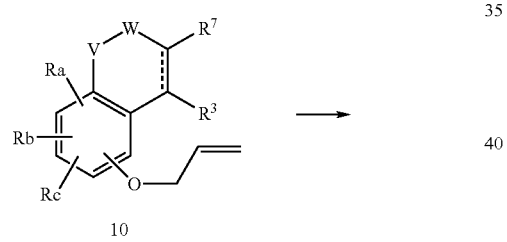

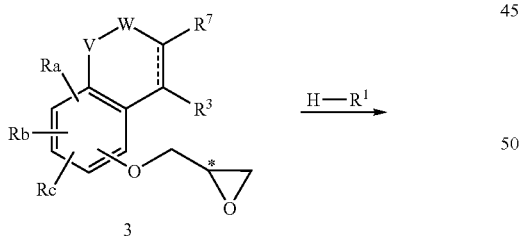

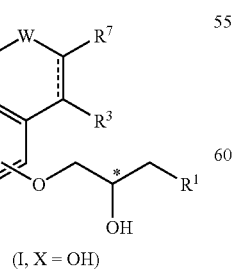

Reaction Formula H

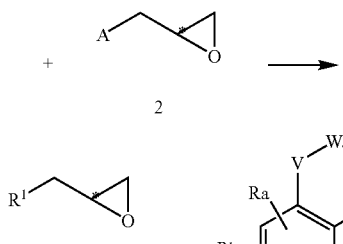

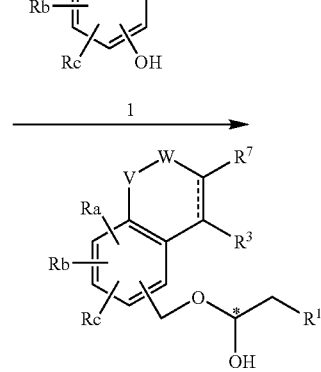

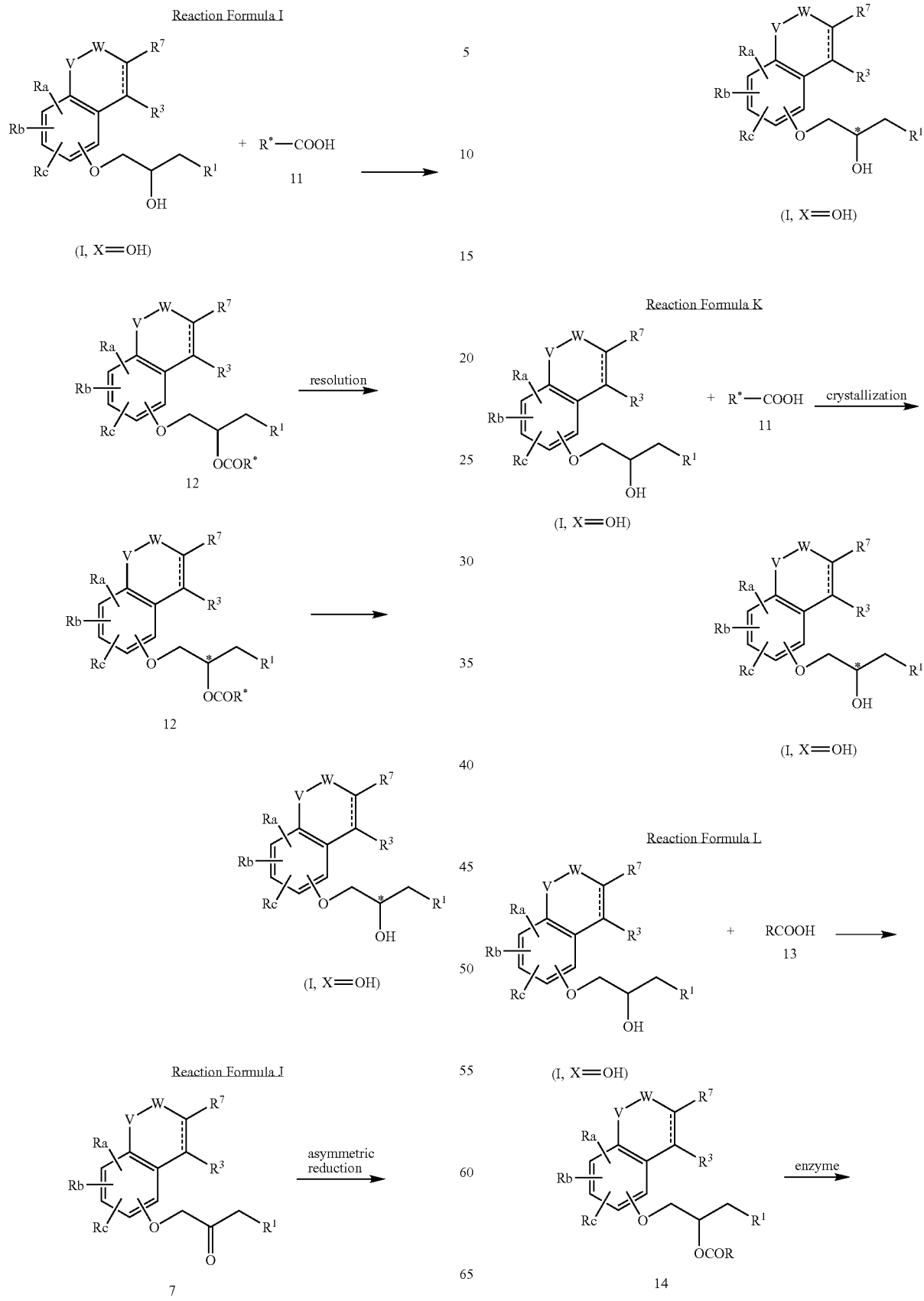

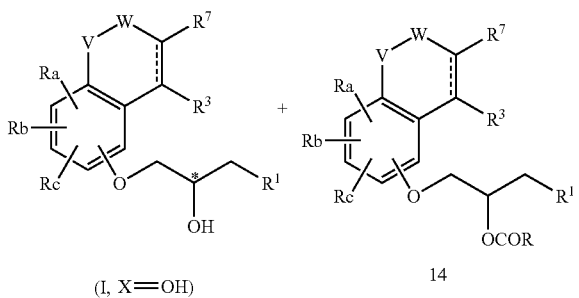

(I, X=OH)    14    15

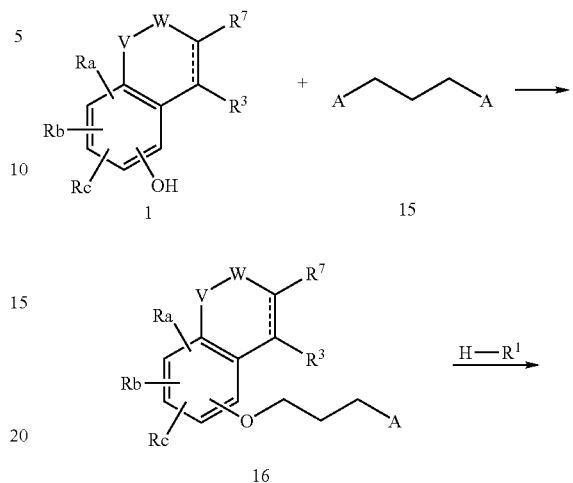

Reaction formula F: A method comprising asymmetric epoxydation of intermediate 10 obtained by the above-mentioned reaction formula E, using optically active base and asymmetric ligand in catalytic or stoichiometric amounts to give optically active intermediate 3, which is reacted with H—$R^1$, Reaction formula G: A method comprising reacting phenol derivative 1 and optically active 2,3-epoxypropane derivative 2 having a leaving group (or nucleofugal group) at 1-position to give compound 3, which is reacted with H—$R^1$, Reaction formula, H: A method comprising reacting H—$R^1$ and optically active 2,3-epoxypropane derivative 2 having a leaving group (or nucleofugal group) at 1-position to give compound 4, which is reacted with phenol derivative 1, Reaction formula I: A method comprising condensing a racemic mixture of the compound of the formula (I) with optically active carboxylic acid 11 to convert the compound to optically active ester 12, which is followed by crystallization, column chromatography and the like to resolve the compound into two diastereomers, Reaction formula J: A method comprising asymmetric reduction of intermediate 7 obtained by the above-mentioned reaction formulas C and D, using a chiral ligand, Reaction formula K: A method comprising forming a salt in a racemic mixture of the compound of the formula (I) and optically active carboxylic acid 11, whereby both isomers are resolved based on difference in crystallinity, Reaction formula L: A method comprising condensing a racemic mixture of the compound of the formula (I) with carboxylic acid 13 to once convert the compound to an ester, and hydrolyzing the ester enantioselectively using an enzyme.

The methods for synthesizing the optically active compound of the formula (I) (X=OH) are not limited to those mentioned above.

A compound of the formula (I) wherein X is hydrogen atom can be synthesized as in the following reaction formulas M–N and the like.

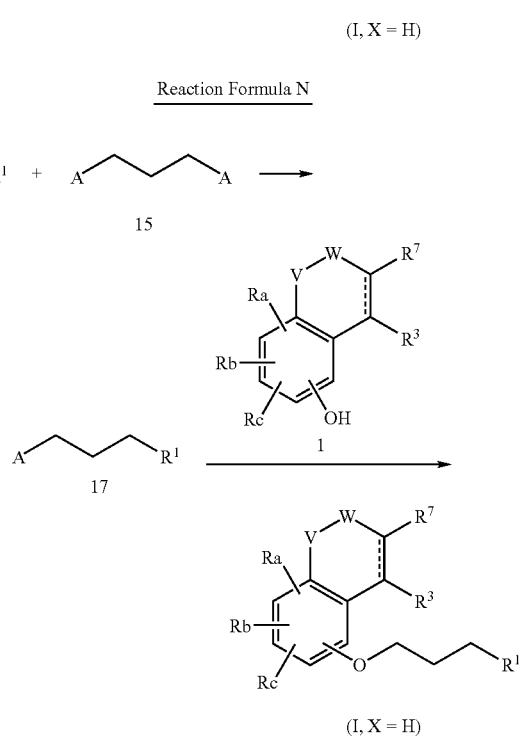

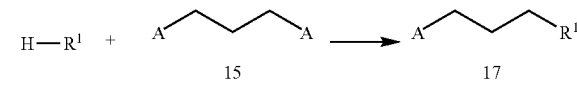

-continued

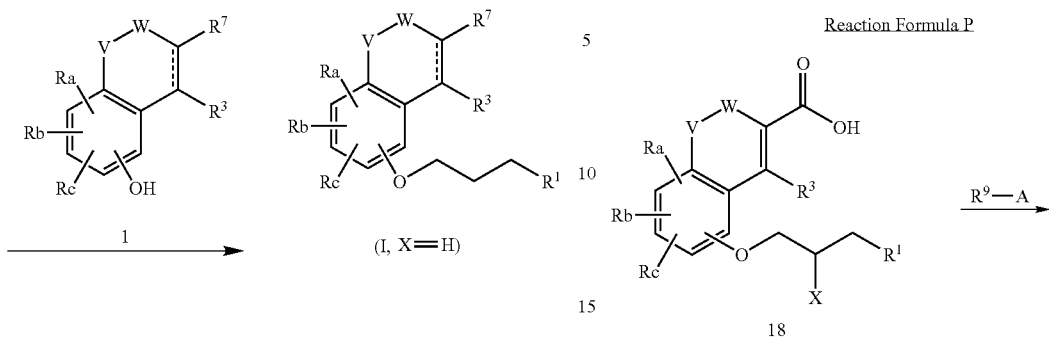

Reaction formula M: A method comprising reacting phenol derivative 1 and propane derivative 15 having leaving groups or nucleofugal groups at 1,3-positions to synthesize intermediate 16, and condensing the intermediate 16 and H—R$^1$ in the presence of deoxidizing agent, Reaction formula N: A method comprising reacting H—R$^1$ and propane derivative 15 having leaving groups or nucleofugal groups at 1,3-positions to synthesize intermediate 17 and condensing the intermediate 17 and phenol derivative 1 in the presence of deoxidizing agent.

Of the compounds of the formula (I), a compound wherein X is alkoxy can be derived from the compound of the formula (I) wherein X is OH as in the following reaction formula O wherein R$^{13}$ is alkyl group.

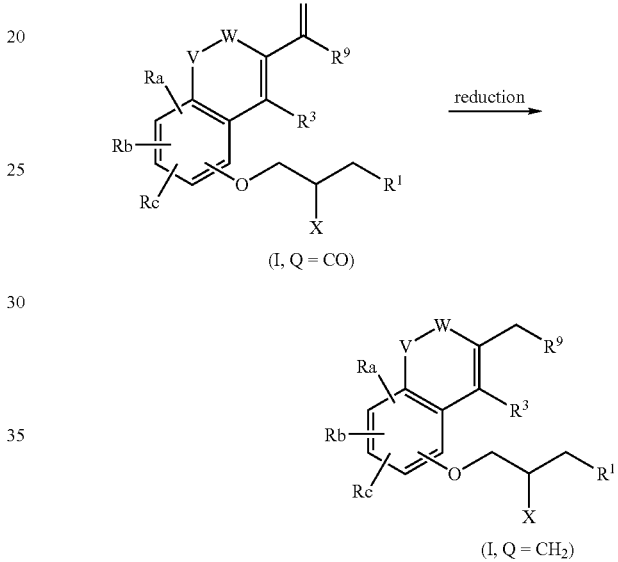

Reaction formula O: A method comprising alkylating hydroxy group of a compound of the formula (I) wherein X is hydroxy group, in the presence of deoxidizing agent.

Of the compounds of the formula (I), a compound wherein R$^7$ is the formula: -Q-R$^9$ wherein Q is —C(=O)— or —CH$_2$— can be derived from carboxylic acid derivative 18, as in the following the reaction formula P.

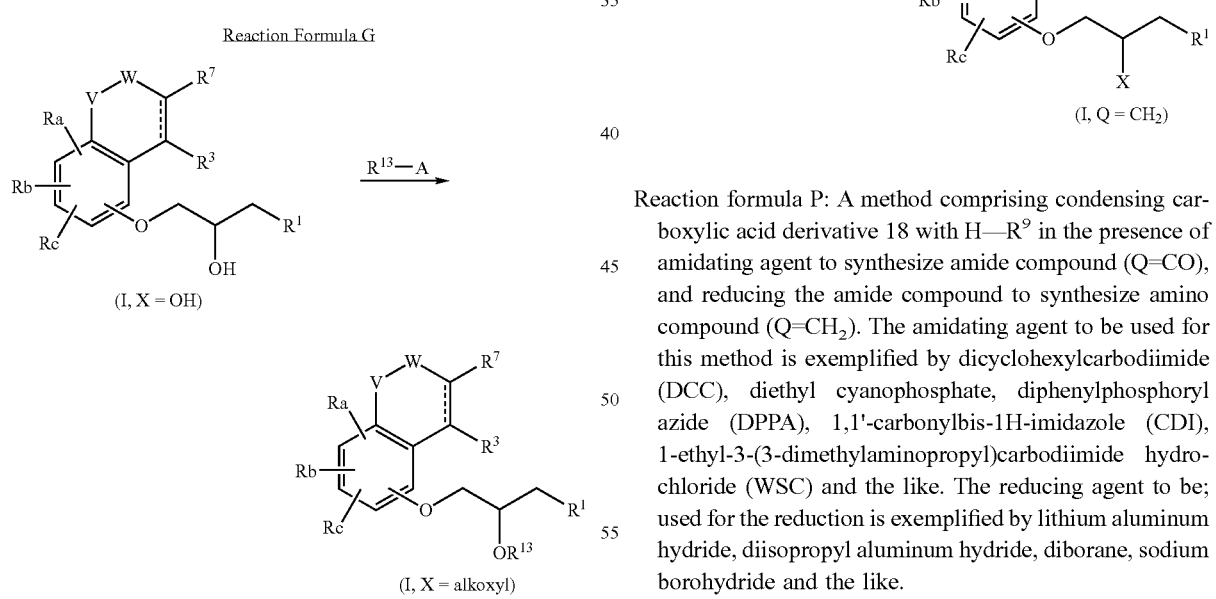

Reaction formula P: A method comprising condensing carboxylic acid derivative 18 with H—R$^9$ in the presence of amidating agent to synthesize amide compound (Q=CO), and reducing the amide compound to synthesize amino compound (Q=CH$_2$). The amidating agent to be used for this method is exemplified by dicyclohexylcarbodiimide (DCC), diethyl cyanophosphate, diphenylphosphoryl azide (DPPA), 1,1'-carbonylbis-1H-imidazole (CDI), 1-ethyl-3-(3-dimethylaminopropyl)carbodiimide hydrochloride (WSC) and the like. The reducing agent to be; used for the reduction is exemplified by lithium aluminum hydride, diisopropyl aluminum hydride, diborane, sodium borohydride and the like.

Of the phenol derivatives 1 used in Reaction formulas A, B, D, E, G, H, M and N, a compound wherein R$^7$ is the formula: -Q-R$^9$ can be synthesized according to the following reaction formulas Q–S and the like. In these reaction formulas, the symbol PG means a protecting group (e.g., methyl, ethyl, methoxymethyl, ethoxymethyl, trimethylsilyl, benzyl, acetyl, benzoyl etc.) that can be eliminated easily in the organic synthesis.

Reaction Formula Q
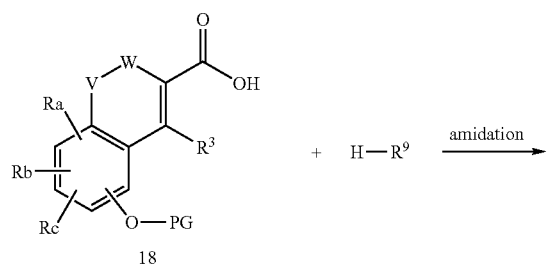
18
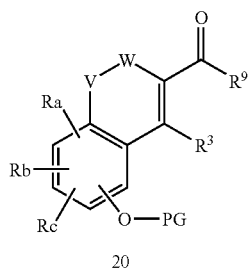
20
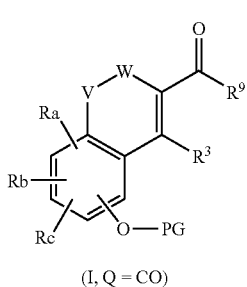
(I, Q = CO)
Reaction Formula R
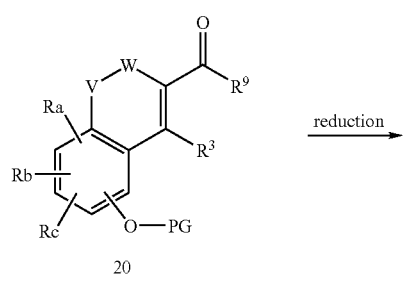
20
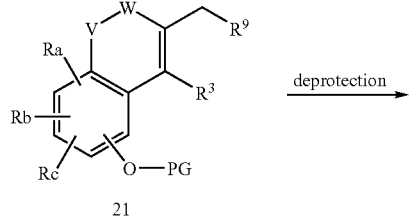
21
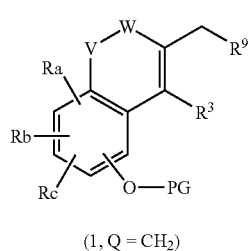
(I, Q = CH₂)
-continued
Reaction Formula S
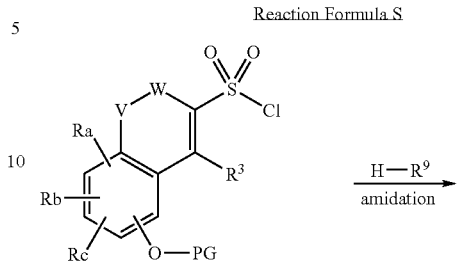
22
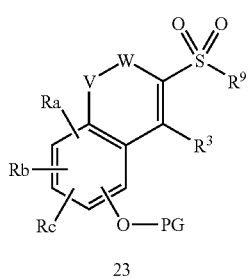
23
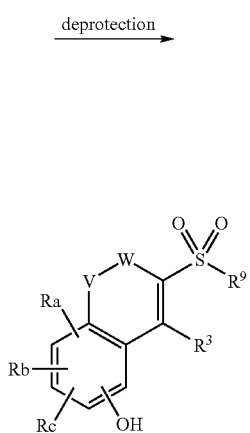
(I, Q = SO₂)
Reaction Formula R
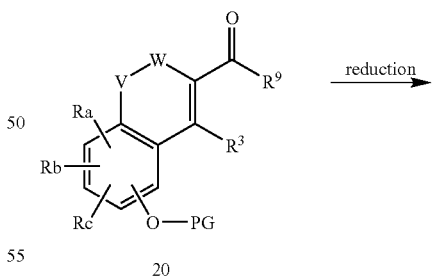
20
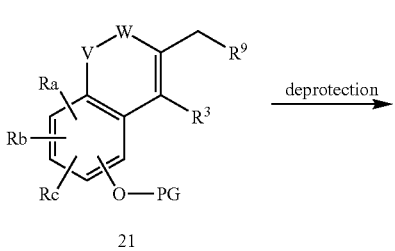
21

-continued

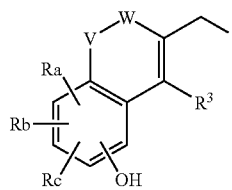

(1, Q=CH$_2$)

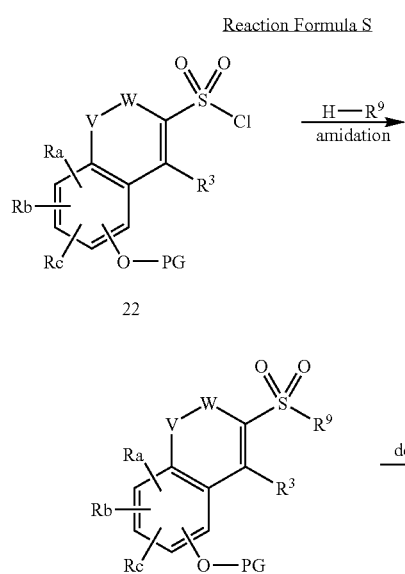

Reaction formula Q: A production method comprising condensing carboxylic acid derivative 19 with H—R$^9$, using amidating agent, and then eliminating the protecting group to give phenol derivative (1, Q=CO). As the amidating agent, dicyclohexylcarbodiimide (DCC), diethyl cyanophosphate, diphenylphosphoryl azide (DPPA), 1,1'-carbonylbis-1H-imidazole (CDI), 1-ethyl-3 (3-dimethylaminopropyl)carbodiimide hydrochloride (WSC) and the like can be used.

Reaction formula R: A production method comprising reducing amide compound 20 with a reducing agent, and eliminating the protecting group to give phenol derivative (1, Q=CH$_2$). As the reducing agent, lithium aluminum hydride, diisopropyl aluminum hydride, diborane, sodium borohydride and the like can be used.

Reaction formula S: A production method comprising condensing, sulfonic chloride derivative 22 with H—R$^9$ using a deoxidizing agent, and eliminating the protecting group to give phenol derivative (1, Q=SO$_2$).

In the following, the reaction formulas T–Z are shown as typical synthetic methods of representative compounds wherein R$^7$ is optionally substituted heterocycle in the reaction formulas A —H, M and N. In these reaction formulas, the symbol PG is as defined above.

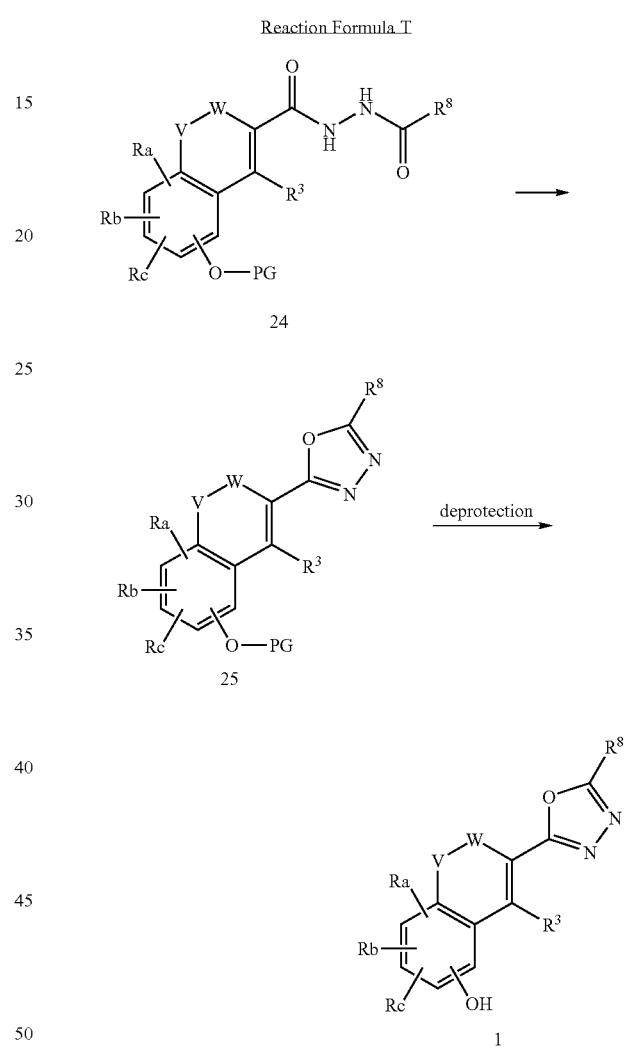

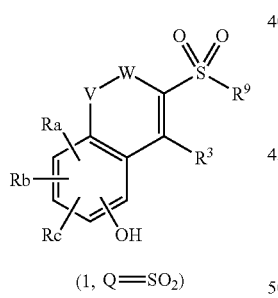

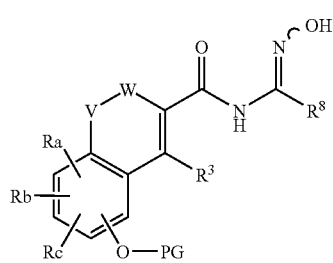

27

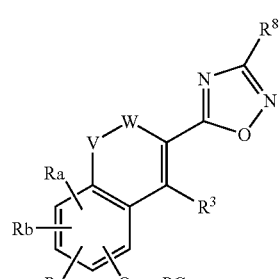

28

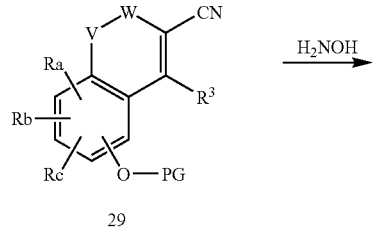

29

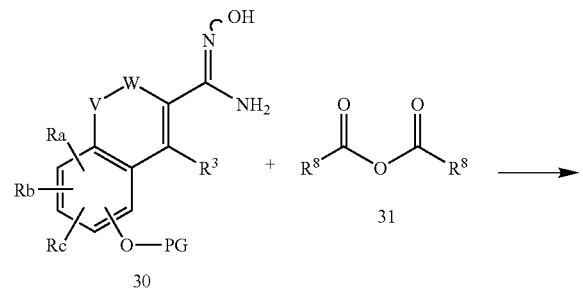

30

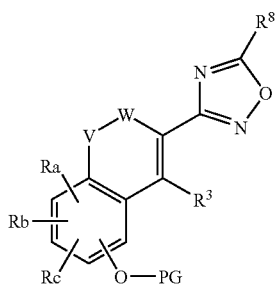

32

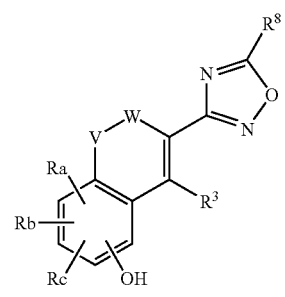

1

Reaction formula T: A production method of phenol derivative 1 having a 1,3,4-oxadiazole ring, which method comprises cyclization of diacylhydrazine derivative 24 with a dehydrating agent, and deprotection. The phenol derivative 1 having a 1,3,4-oxadiazole ring can be also synthesized by reacting azo compound and triphenylphosphine, in the presence of a deoxidizing agent, followed by deprotection. As the dehydrating agent, polyphosphoric acid, oxalyl chloride, phosphorus trichioride, sulfuric acid, phosphorus oxychloride, thionyl chloride, oxalyl chloride and the like can be used. As the azo compound, diethyl azodicarboxylate (DEAD), diisopropyl azodicarboxylate (DIAD) and the like can be used.

Reaction formula U: A production method of phenol derivative 1 having a 1,2,4-oxadiazole ring, which method comprises condensing carboxylic acid derivative 19 and hydroxyimino compound 26 using an amidating agent to give compound 27, which is subjected to cyclization using a dehydrating agent or by heating for dehydration, followed by deprotection. As the dehydrating agent, polyphosphoric acid, phosphorus pentachloride, phosphorus trichloride, sulfuric acid, phosphorus oxychloride, thionyl chloride, oxalyl chloride and the like can be used.

Reaction formula V: A production method of phenol derivative 1 having a 1,2,4-oxadiazole ring, which method comprises condensing nitrile derivative 29 and hydroxylamine to give compound 30, to which acid anhydride 31 is added to allow cyclization by heating for dehydration, followed by deprotection.

Reaction Formula W
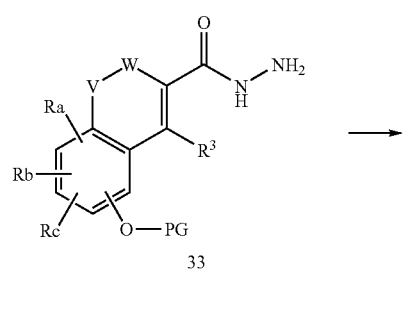
33
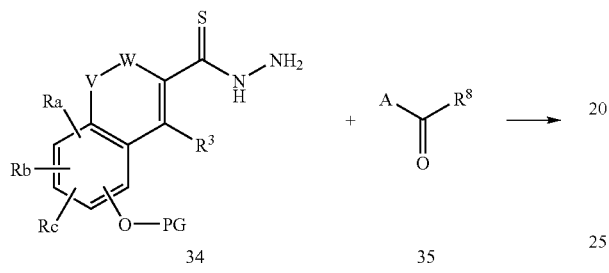
34 + 35
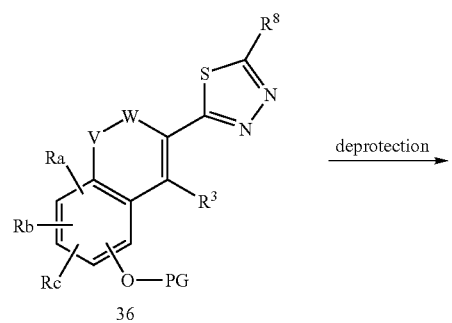
36
Reaction Formula X
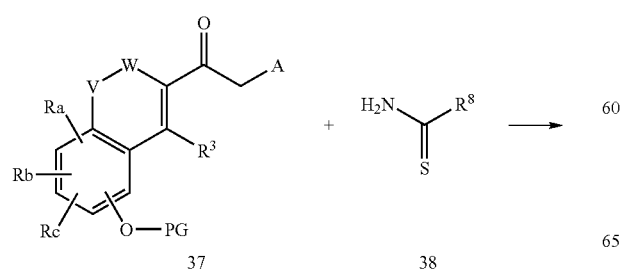
37 + 38
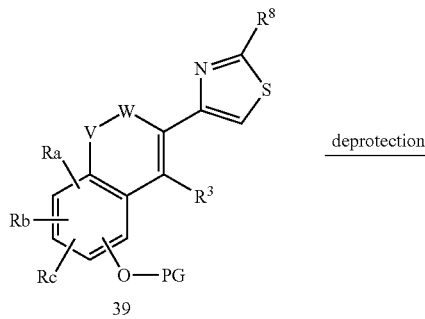
39
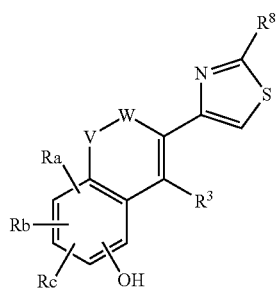
Reaction Formula X
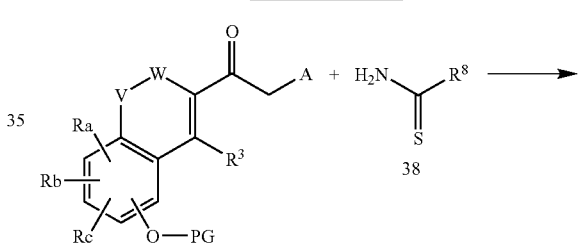
37 + 38
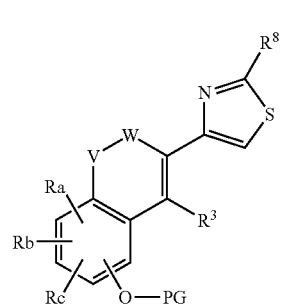
39
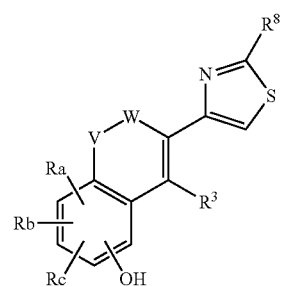

Reaction formula W: A production method of phenol derivative 1 having a 1,3,4-thiadiazole ring, which method comprises conversion of hydrazone compound 33 into thione compound with a sulfidation agent to give compound 34, which is cyclized with compound 35 by heating, followed by deprotection. As the sulfidation agent, Lawesson reagent, diphosphorus pentasulfide and the like can be used.

Reaction formula X: A production method of phenol derivative 1 having a thiazole ring, which method comprises cyclization of compound 37 and thioamide compound 38 by heating, followed by deprotection.

Reaction Formula Y

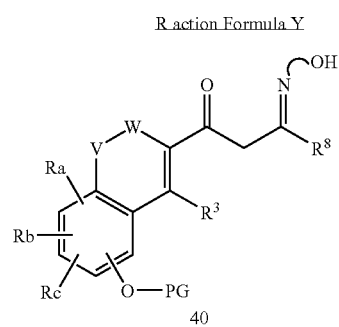
40

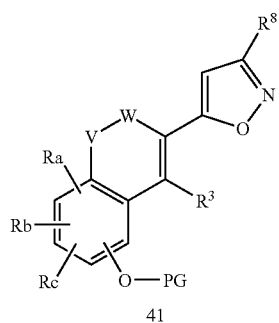
41

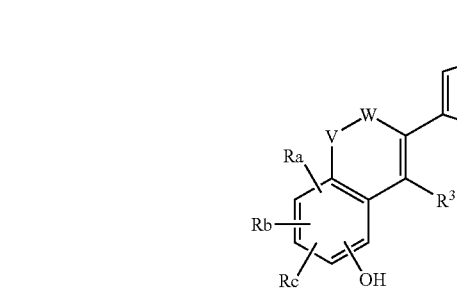

Reaction Formula Z

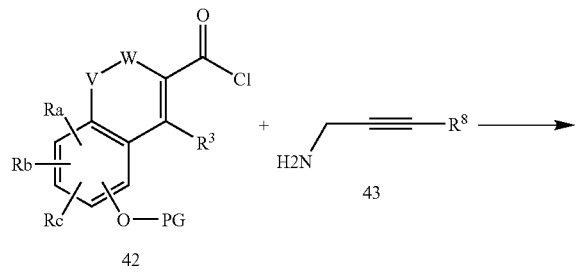

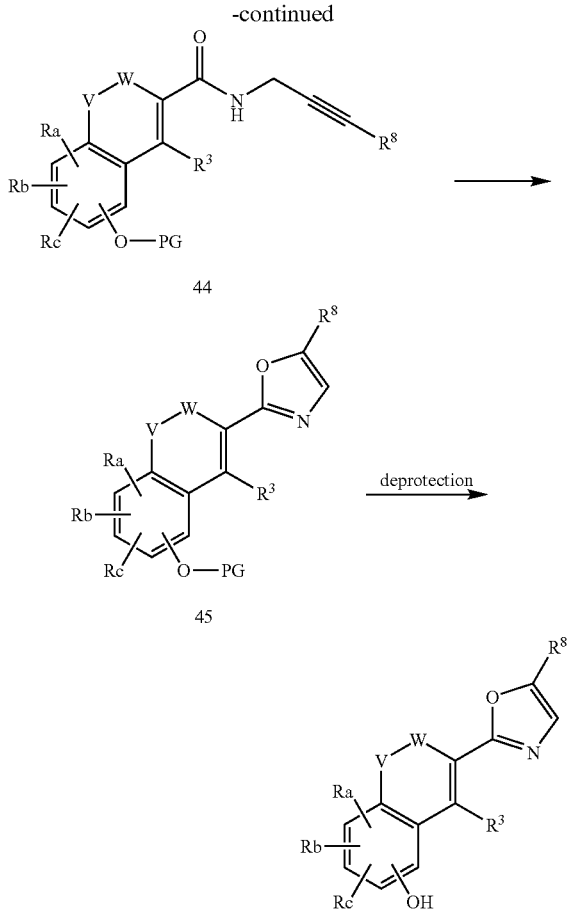

Reaction formula Y: A production method of phenol derivative 1 having a isoxazole ring, which method comprises cyclization of hydroxyimino compound 40, using a dehydrating agent or by heating for dehydration, followed by deprotection. As the dehydrating agent, polyphosphoric acid, phosphorus pentachloride, phosphorus trichloride, sulfuric acid, phosphorus oxychloride, thionyl chloride, oxalyl chloride and the like can be used.

Reaction formula Z: A production method of phenol derivative 1 having an oxazole ring, which method comprises condensing acid halide compound 42 and acetylene compound 43 to give compound 44, followed by cyclization using mercury (II) acetate and deprotection.

Of the phenol derivatives 1 to be used for the reaction formulas A, B, D, E, G, H, M and N, a compound wherein R and W are bonded to form a ring can be also synthesized by the methods of the following reaction formulas Q'–T'.

Reaction Formula Q'

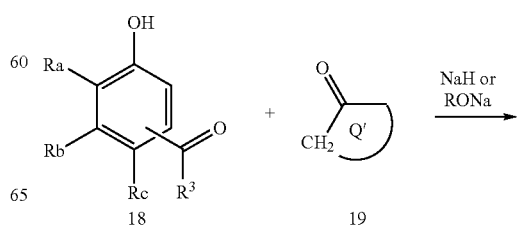

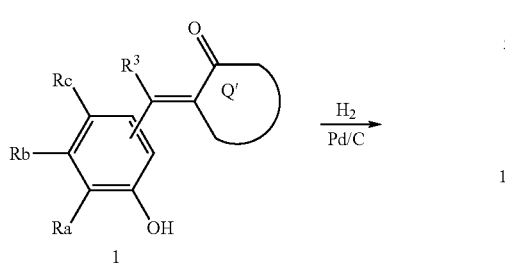

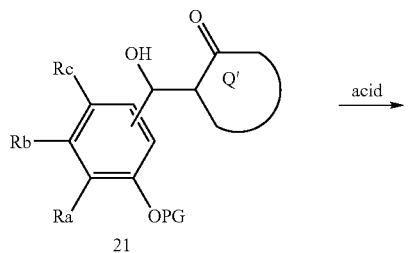

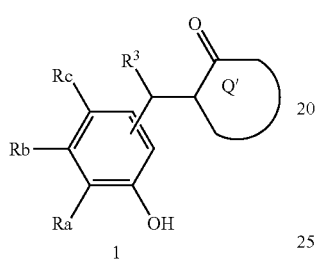

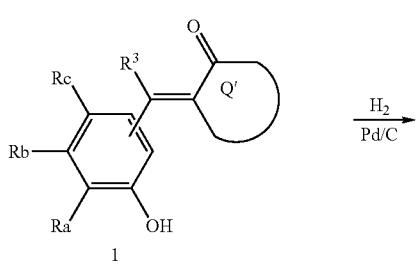

Reaction formula Q': The phenol derivative 1, which is a benzylidene compound, can be synthesized by reacting phenol derivative 18 and carbonyl (thiocarbonyl) derivative 19 in the presence of a base such as sodium hydride, sodium alcoholate and the like. Further, the phenol derivative 1, which is a benzyl compound, can be synthesized by reducing the obtained phenol derivative 1 (benzylidene compound) in the presence of a catalyst such as palladium carbon and the like.

When R and W are bonded to form a ring, which is a lactam or hydantoin (or their sulfur derivatives), and $R^{7'}$ is other than hydrogen atom, phenol derivative 1 can be also synthesized by the method of the reaction formula R'.

Reaction Formula R'

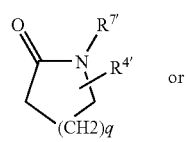

or

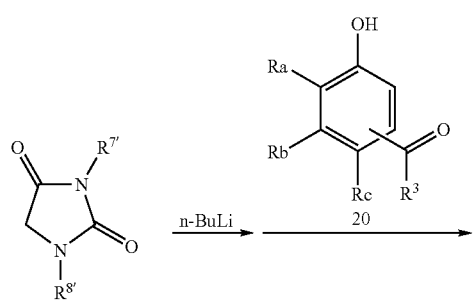

Reaction formula R': Synthesis is available by lithiation of a lactam derivative or hydantoin derivative (or their sulfur derivatives), wherein $R^{7'}$ is other than hydrogen atom, with an organic lithium reagent such as n-BuLi and the like, reacting the same with a phenol derivative 20, wherein hydroxyl group is protected, to once convert to benzyl alcohol compound 21, followed by treatment with an acid. Moreover, by reduction of phenol derivative 1 (benzylidene compound) in the presence of a catalyst such as palladium carbon and the like, phenol derivative 1, which is a benzyl compound, can be synthesized.

The phenol derivative 1 (or its sulfur derivative) containing hydantoin, wherein $R^{7'}$ and $R^{8'}$ are the same substituents, can be also synthesized by the method of the reaction formula S'.

Reaction Formula S'

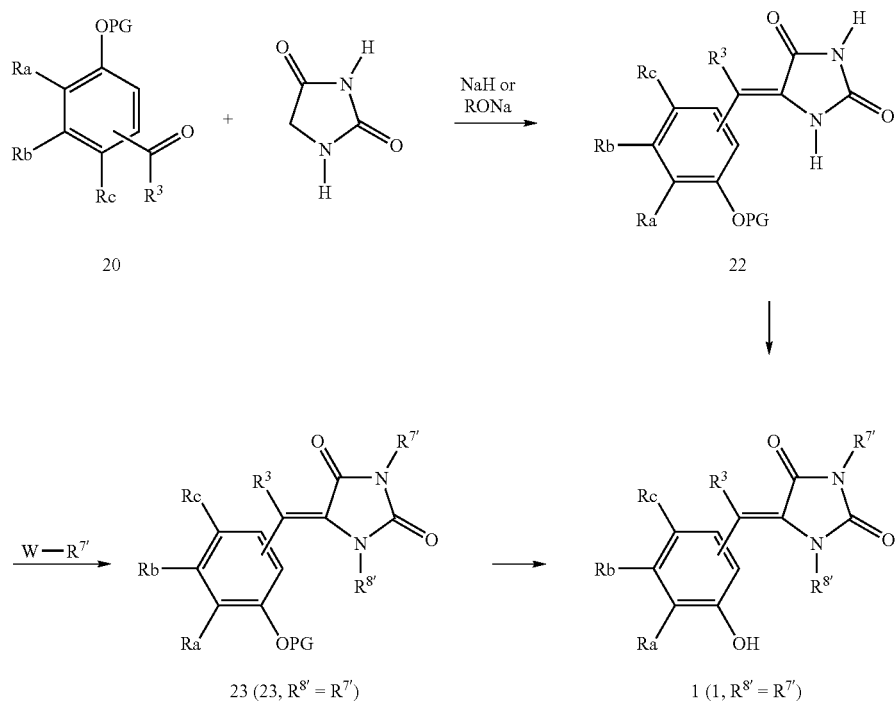

Reaction formula S': The phenol derivative 20, wherein hydroxyl group is protected, is reacted with hydantoin (or its sulfur derivative) along with a base such as sodium hydride, sodium alcoholate and the like to give benzylidene compound 22, followed by deprotection to give phenol derivative 1, wherein $R^{7'}$ and $R^{8'}$ are hydrogen atoms. Moreover, by reacting benzylidene compound 22, which is an intermediate, with W—$R^{7'}$ having a nucleofugal group to synthesize intermediate 23, and deprotecting the same, the phenol derivative 1 (or its sulfur derivative) containing hydantoin, wherein $R^{7'}$ and $R^{8'}$ are the same, can be synthesized.

The phenol derivative 1 (or its sulfur derivative) containing 3,5-dihydroimidazol-4-one can be also synthesized by the method of the reaction formula T'.

Reaction Formula T'

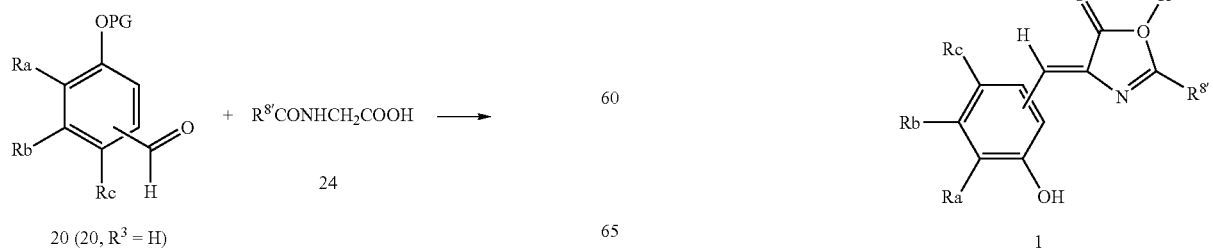

-continued

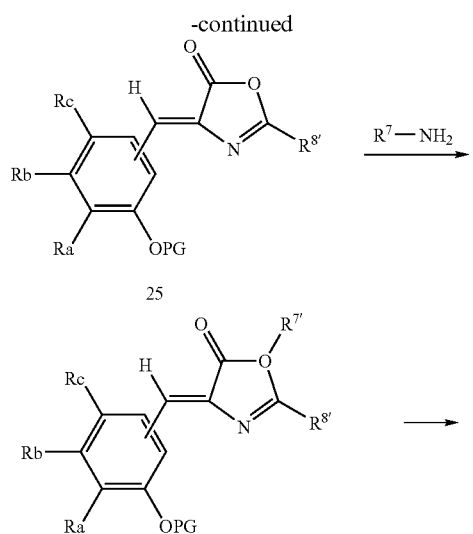

Reaction formula T': The phenol derivative 20, wherein hydroxyl group is protected, is reacted with glycine derivative 24 to give benzylidene compound 25, which is then reacted with amine $R^{7'}$—$NH_2$ to give intermediate 26. This intermediate is deprotected to give phenol derivative 1 (or its sulfur derivative) containing 3,5-dihydroimidazol-4-one.

There are many methods for obtaining phenol derivative 1 other than those mentioned above that are known to synthesis chemists, and therefore, the methods for obtaining the compound are not limited to those shown above.

These reactions and applications ultimately leading to the formula (I) of the present invention are well known to those of ordinary skill in the field of organic chemical synthesis. The improvements to adopt the conditions and reagents for the synthesis of specific compounds of the formula (I) inclusive of the inventive compound, beyond those described, are known to synthesis chemists. For more detailed description, respective synthetic examples are shown under Examples.

The compounds of the formula (I) obtained as mentioned above have selective affinity for as well as simultaneous antagonistic activity against $5\text{-HT}_{1A}$ receptors and have a 5-HT reuptake inhibitory action. Therefore, the compounds can provide effective pharmaceutical agents for diseases accompanying serotoninergic neurotransmission functional disorders. They are also effective as $5HT_{1A}$ antagonists having a selective serotonin reuptake inhibitory action, or as selective serotonin reuptake inhibitors having a $5HT_{1A}$ antagonistic action.

That is, the inventive compounds show quick expression of the anti-depressive effect and are useful as a so-called rapid onset antidepressant. They are also useful for the treatment of mammals inclusive of human for central nervous system diseases mediated by 5-HT, such as schizophrenia, anxiety neurosis, obsessive-compulsive disorder (OCD), panic disorder, social anxiety disorder, seasonal emotional disorder, Anorexia Nervosa, Bulimia Nervosa, nocturnal enuresis, children's hyperlocomotion, post-traumatic stress disorder (PTSD), senile dementia, hemicrania, stroke, Alzheimer's disease, recognition disorder, hypertension, gastrointestinal injury, feeding disorders, premenstrual syndrome (PMS), abnormal body temperature regulation and sexual disorder, pain, as well as abnormal cardiovascular system, drug abuse and the like.

When the compound of the present invention is used as a pharmaceutical agent, a systemic administration of a pharmacologically acceptable amount of the compound of the formula (I) or a pharmacologically acceptable acid addition salt thereof to a mammal is included. The dose requires careful control for each case, and in consideration of the age, body weight and condition of the subject, administration route, as well as nature and severity of disease, the general daily dose in the case of parenteral administration is 0.01–100 mg/kg, preferably 0.1–1 mg/kg, and that in the case of oral administration is 0.5–10 mg/kg, preferably 1–5 mg/kg. The administration method in the present invention includes oral, rectal and parenteral (e.g., intramuscular, intravenous, percutaneous and subcutaneous) administrations.

For anti-depression, the compound of the present invention may be administered as a single therapeutic agent or may be administered as a mixture with other therapeutic agents. For therapy, the compound is generally given as a pharmacological composition containing the compound of the formula (I) or a pharmaceutically acceptable salt thereof in an amount sufficient to show an anti-depressive effect, and a pharmaceutically acceptable carrier. A pharmacological composition containing about 1–500 mg of the active ingredient per unit dose is desirable.

According to a conventional method, it is prepared into tablets, lozenges, capsules, powders, aqueous or oily suspensions, syrups, elixirs, aqueous solutions and the like. The pharmacological composition to be used naturally shows properties that vary depending on the objective administration route. For example, an oral composition may be tablet or capsule, and may contain a conventional excipient such as binder (starch etc.) and moistening agent (sodium laurylsulfate etc.). A solution or suspension of the present invention containing a conventional pharmacological vehicle may be used for parenteral administration, such as an aqueous solution for intravenous injection and oily suspension for intramuscular injection.

EXAMPLES

The present invention is described in detail in the following by Starting Material Synthesis Examples, Examples, Formulation Examples and Experimental Examples. The present invention is not limited in any way by these examples.

Starting Material Synthesis Example 1

(S)-1-(4-glycidyloxybenzo(b)furan-2-ylcarbonyl)pyrrolidine

To a solution (30 ml) of (S)-1-(4-hydroxybenzo(b)furan-2-ylcarbonyl)pyrrolidine (1.3 g) in N,N-dimethylformamide (DMF) were added potassium carbonate (2.2 g) and (S)-glycidyl nosylate (1.7 g), and the mixture was stirred for 10 hr at room temperature, followed by pouring into water. After extraction with ethyl acetate, the organic layer was washed with water, dried over anhydrous magnesium sulfate, and concentrated under reduced pressure. The obtained residue was purified by silica gel column chromatography (hexane/ethyl acetate) to give the title compound (1.2 g) as a yellow oil.

$^1$H-NMR(CDCl$_3$)δ:1.93(penth, J=6.4, 2H), 2.00(penth, J=6.4, 2H), 2.79(dd, J=4.9, 2.9, 1H), 2.93(t, J=4.9, 1H), 3.38–3.43(m, 1H), 3.69(t, J=6.8, 2H), 3.92(t, J=6.8, 2H), 4.08(dd, J=11.2, 5.8, 1H), 4.36(dd, J=11.2, 3.0, 1H), 6.00(d, J=8.3, 1H), 7.15(d, J=8.3, 1H), 7.28(t, J=8.3, 1H), 7.47(s, 1H)

Starting Material Synthesis Example 2

(S)-4-(4-glycidyloxybenzo(b)furan-2-ylcarbonyl)morpholine

To a suspension (30 ml) of sodium hydride (0.52 g) in DMF was dropwise added a solution (30 ml) of 4-(4-hydroxybenzo(b)furan-2-ylcarbonyl)morpholino in DMF at a reaction temperature of 4° C. over 10 min, and the mixture was stirred for 30 min. Thereto was added a solution (10 ml) of (S)-glycidyl nosylate (3.4 g) in DMF, and the mixture was stirred for 30 min and poured into water. After extraction with ethyl acetate, the organic layer was washed with water, dried over anhydrous magnesium sulfate and then concentrated under reduced pressure. The obtained residue was purified by silica gel column chromatography (hexane/ethyl acetate) to give the title compound (1.3 g) as a yellow oil.

$^1$H-NMR(CDCl$_3$)δ:2.81(dd, J=4.9, 2.4, 1H), 2.96(t, J=4.9, 1H), 3.42–3.44(m, 1H), 3.78–4.07(m, 8H), 4.09(dd,

J=10.8, 5.9, 1H), 4.40(dd, J=10.8, 3.0, 1H), 6.69(d, J=8.3, 1H), 7.16(d, J=8.3, 1H), 7.32(t, J=8.3, 1H), 7.44(s, 1H)

Starting Material Synthesis Example 3 methyl(S)-4-glycidyloxybenzo(b)furan-2-carboxylate

To a solution (60 ml) of methyl 4-hydroxybenzo(b)furan-2-carboxylate (3.6 g) in DMF were added (S)-glycidyl nosylate (5.1 g) and potassium carbonate (6.5 g) and the mixture was stirred at room temperature for 8 hr. The reaction mixture was concentrated under reduced pressure and ethyl acetate was added to the residue. The mixture was washed with water, dried over anhydrous magnesium sulfate, and concentrated under reduced pressure to give the title compound (4.1 g) as a yellow crystalline compound.
$^1$H-NMR(CDCl$_3$)δ:2.82(dd, J=4.9, 3.0, 1H), 2.96(t, J=4.9, 1H) 3.41–3.45(m, 1H), 3.97(s, 3H), 4.09(dd, J=10.8, 5.9, 1H), 4.40(dd, J=10.8, 3.0, 1H), 6.69(d, J=8.3, 1H), 7.22(d, J=8.3, 1H), 7.36(t, J=8.3, 1H), 7.68(s, 1H)

Starting Material Synthesis Example 4

4-(8-methoxy-2H-chromen-3-ylcarbonyl)morpholine

To a solution (200 ml) of 8-methoxy-2H-chromene-3-carboxylic acid (10.0 g) in DMF were added triethylamine (8.6 ml) and diethyl cyanophosphate (10.0 ml) and the mixture was stirred at room temperature for 3 hr. The reaction mixture was poured into water and extracted with ethyl acetate. The organic layer was washed with water and dried over anhydrous magnesium sulfate. The solvent was evaporated under reduced pressure and the residue was purified by silica gel column chromatography (chloroform/ethyl acetate) to give the title compound (3.5 g) as a brown oil.
$^1$H-NMR(CDCl$_3$)δ:3.69–3.78(m, 8H), 4.94(s, 2H), 6.60 (s, 1H), 6.71(d, J=5.2, 1H), 6.87–6.90(m, 2H)

Starting Material Synthesis Example 5

4-(8-hydroxy-2H-chromen-3-ylcarbonyl)morpholine

To a solution (70 ml) of 4-(8-methoxy-2H-chromen-3-ylcarbonyl)morpholine (3.5 g) in methylene chloride was added dropwise boron tribromide (9.5 g) at −78° C. The reaction temperature was set to room temperature and the mixture was stirred for 2 hr. The reaction mixture was poured into water and stirred for 1 hr. The organic layer was separated and washed with water and dried over anhydrous magnesium sulfate. The solvent was evaporated under reduced pressure to give the title compound (3.3 g) as brown crystals.
$^1$H-NMR(CDCl$_3$)δ:3.69–3.73(brs, 8H), 4.95(s, 2H), 5.83 (brs, 1H), 6.61(s, 1H), 6.65(d, J=7.3, 1H), 6.83(t, J=7.3, 1H), 7.89(d, J=7.3, 1H)

Starting Material Synthesis Example 6

(S)-4-(8-glycidyloxy-2H-chromen-3-ylcarbonyl)morpholine

By the reactions in the same manner as in Starting Material Synthesis Example 1 using 4-(8-hydroxy-2H-chromen-3-ylcarbonyl)morpholine (3.3 g), potassium carbonate (3.5 g) and (S)-glycidyl nosylate (3.3 g), the title compound (3.1 g) was obtained as a brown oil.
$^1$H-NMR(CDCl$_3$)δ:2.74(dd, J=4.9, 2.4, 1H), 2.91(t, J=4.9, 1H), 3.37–3.39(m, 1H), 3.69–3.73(brs, 8H), 4.03(dd, J=11.7, 5.8, 1H), 4.11–4.13(m, 1H), 4.28(dd, J=11.7, 3.4, 1H), 4.94(s, 2H), 6.60(s, 1H), 6.75(d, J=7.3, 1H), 6.87(t, J=7.3, 1H), 6.91(d, J=7.3, 1H)

Starting Material Synthesis Example 7

8-methoxy-N,N-dimethyl-2H-chromene-3-carboxamide

By the reactions in the same manner as in Starting Material Synthesis Example 4 using 8-methoxy-2H-chromene-3-carboxylic acid (8.0 g), triethylamine (14.0 ml) and diethyl cyanophosphate (8.2 ml), the title compound (3.2 g) was obtained as a brown oil.
$^1$H-NMR(CDCl$_3$)δ:3.83(s, 6H), 4.84(s, 2H), 6.45(d, J=8.3, 1H) 6.50(d, J=8.3, 1H), 6.99(s, 1H), 7.13(t, J=8.3, 2H)

Starting Material Synthesis Example 8

(S)-8-glycidyloxy-N,N-dimethyl-2H-chromene-3-carboxamide

By the reactions in the same manner as in Starting Material Synthesis Example 5 using 8-methoxy-N,N-dimethyl-2H-chromene-3-carboxamide (3.2 g) and boron tribromide (11.0 g), a brown oil (3.0 g) was obtained. To a solution (50 ml) of this brown oil in DMF were added potassium carbonate (3.8 g) and (S)-glycidyl nosylate (3.8 g), and the mixture was stirred at room temperature for 10 hr and poured into water. After extraction with ethyl acetate, the organic layer was washed with water, dried over anhydrous magnesium sulfate and concentrated under reduced pressure. The obtained residue was purified by silica gel column chromatography (hexane/ethyl acetate) to give the title compound (3.2 g) as yellow crystals, melting point 115–117° C.

Starting Material Synthesis Example 9 ethyl 4-benzyloxy-1-methylindole-2-carboxylate

To a solution (100 ml) of ethyl 4-benzyloxy-1H-indole-2-carboxylate (12.0 g) in DMF was added sodium hydride (1.6 g) and the mixture was stirred at room temperature for 10 min. To this reaction mixture was added methyl iodide (2.2 g) and the mixture was stirred for one more hour. The reaction mixture was poured into water and extracted with ethyl acetate. The organic layer was washed with saturated aqueous solution of ammonium chloride and dried over anhydrous magnesium sulfate. The solvent was evaporated under reduced pressure to give the title compound (13.2 g) as a brown oil.
$^1$H-NMR(CDCl$_3$)δ:1.39(t, J=6.9, 3H), 4.06(s, 3H), 4.35 (q, J=6.9, 2H), 5.22(s, 2H), 6.66(d, J=7.8, 1H), 6.98(t, J=7.8, 1H), 7.40(t, J=7.4, 1H), 7.45–7.51(m, 6H)

Starting Material Synthesis Example 10 ethyl 4-hydroxy-1-methylindole-2-carboxylate

To a solution (200 ml) of ethyl 4-benzyloxy-1-methylindole-2-carboxylate (13.0 g) in ethanol was added 10% palladium-carbon (1.3 g), and the mixture was stirred at room temperature for 8 hr under a hydrogen atmosphere. The palladium-carbon was filtered off with celite and the reaction mixture was concentrated under reduced pressure to give the title compound (8.0 g) as a brown oil.

$^1$H-NMR(CDCl$_3$)δ:1.40(t, J=6.9, 3H), 4.05(s, 3H), 4.37 (q, J=6.9, 2H), 6.52(d, J=7.8, 1H), 6.95(t, J=7.8, 1H), 7.19(t, J=7.4, 1H), 7.41(s, 1H)

Starting Material Synthesis Example 11

Ethyl 4-benzyloxy-1-(2-methylpropyl)indole-2-carboxylate

By the reactions in the same manner as in Starting Material Synthesis Example 9 using ethyl 4-benzyloxy-1H-indole-2-carboxylate (10.0 g), sodium hydride (1.6 g) and isobutyl iodide (3.3 ml), the title compound (6.0 g) was obtained as a brown oil.

$^1$H-NMR(CDCl$_3$)δ:0.89(d, J=6.3, 6H), 1.39(t, J=7.3, 3H), 2.22(penth, J=6.3, 1H), 4.25–4.42(m, 2H), 4.35(q, J=7.3, 1H), 5.21(s, 2H), 6.54(d, J=7.8, 1H), 7.00(d, J=7.8, 1H), 7.20(t, J=7.8, 1H), 7.33–7.1 (m, 5H)

Starting Material Synthesis Example 12 ethyl 4-hydroxy-1-(2-methylpropyl)indole-2-carboxylate

By the reactions in the same manner as in Starting Material Synthesis Example 10 using ethyl 4-benzyloxy-1-(2-methylpropyl)indole-2-carboxylate (6.0 g) and 10% palladium-carbon (0.6 g), the title compound was obtained as pale-brown crystals.

$^1$H-NMR(CDCl$_3$)δ:0.89(d, J=6.3, 6H), 1.40(t, J=7.3, 3H), 2.21(penth, J=6.3, 1H), 4.25–4.42(m, 2H), 4.35(q, J=7.3, 1H), 6.49(d, J=7.8, 1H), 6.96(d, J=7.8, 1H), 7.16(t, J=7.8, 1H), 7.42(s, 1H)

Starting Material Synthesis Example 13

3-chloro-6-methoxy-N,N-dimethylbenzo(b)thiophene-2-carboxamide 3.0 g of 3-chloro-6-methoxy-benzo(b)thiophene-2-carboxylic acid (7.0 g) synthesized from 4-methoxycinnamic acid (10.0 g) and thionyl chloride (15 ml) according to the method described in J. Med. Chem. 1992, 35, 958–965 was reacted with dimethylamine hydrochloride and triethylamine in THF to give the title compound (1.9 g) as a brown oil.

$^1$H-NMR(CDCl$_3$):3.09(bs, 3H), 3.12(bs, 3H), 3.89(s, 3H), 7.10(d, 1H, J=8.8), 7.26(s, 1H), 7.71(d, 1H, J=8.8)

Starting Material Synthesis Example 14

(S)-3-chloro-6-glycidyloxy-N,N-dimethylbenzo(b)thiophene-2-carboxamide

3-Chloro-6-methoxy-N,N-dimethylbenzo(b)thiophene-2-carboxamide (1.9 g) was dissolved in methylene chloride (100 ml) and the mixture was cooled to −78° C. Boron tribromide (4 ml) was added dropwise, and after the temperature rose to room temperature, the mixture was poured into water and extracted with chloroform. The organic layer was dried over anhydrous magnesium sulfate, and after filtration, the solvent was evaporated under reduced pressure. The obtained residue was dissolved in DMF (40 ml). By the reactions in the same manner as in Starting Material Synthesis Example 1 using potassium carbonate (3.0 g) and (S)-glycidyl nosylate (2.1 g), the title compound (10 g) was obtained as a brown oil.

$^1$H-NMR(CDCl$_3$):2.80(dd, 1H, J=4.8, 2.9), 2.95(t, 1H, J=4.8) 3.11(bs, 3H), 3.17(bs, 3H), 3.41(m, 1H), 4.00(dd, 1H, J=5.9, 10.8), 4.35(dd, 1H, J=3.0, 11.5), 7.13(dd, 1H, J=2.5, 8.7), 7.26(s, 1H), 7.72(d, 1H, J=8.8)

Starting Material Synthesis Example 15

4-(methoxymethyloxy)benzo(b)thiophene-2-carboxylic acid 4-(Methoxymethyloxy)benzo(b)thiophene (83 g) was dissolved in THF (700 ml) and the mixture was cooled to −78° C. At this temperature, a solution (363 ml) of n-butyllithium in hexane was added dropwise. The temperature was raised to 0° C. and then cooled again to −35° C., and carbon dioxide was bubbled. After the completion of the reaction, the reaction mixture was poured into water, and in the presence of ice, hydrochloric acid was added to adjust its pH to 1 and the mixture was extracted with ethyl acetate. The organic layer was dried over anhydrous magnesium sulfate, and after filtration, the solvent was evaporated under reduced pressure to give the title compound (80 g).

$^1$H-NMR(CDCl$_3$):3.55(s, 3H), 5.37(s, 2H)., 7.04(d, 1H, J=7.8) 7.41(t, 1H, J=7.8), 7.50(d, 1H, J=8.2), 8.36(s, 1H)

Starting Material Synthesis Example 16

4-(methoxymethyloxy)-N,N-dimethylbenzo(b)thiophene-2-carboxamide 4-(Methoxymethyloxy)benzo(b)thiophene-2-carboxylic acid (9.6 g) obtained in Starting Material Synthesis Example 15 was dissolved in dimethylformamide (75 ml). Triethylamine (17 ml) and dimethylamine hydrochloride (4.9 g) were added and the mixture was stirred. After 15 min, diethyl cyanophosphate (10 ml) was added, and the mixture was stirred at room temperature for 3 hr. Aqueous hydrochloric acid was added under cooling to make the reaction mixture acidic (pH 1), and then the mixture was stirred at 45° C. for 5 hr. The reaction mixture was poured into water, extracted three times with ethyl acetate and the organic layer was dried over anhydrous magnesium sulfate. After filtration, the solvent was evaporated under reduced pressure. To the obtained residue was added 6N aqueous hydrochloric acid and the mixture was stirred with heating at 50° C. for 1 hr. The reaction mixture was extracted with ethyl acetate and the organic layer was dried over anhydrous magnesium sulfate. The solvent was evaporated under reduced pressure to give the title compound (9.0 g).

$^1$H-NMR(CDCl$_3$):3.17(bs, 3H), 3.28(bs, 3H), 6.76(d, 1H, J=7.8), 7.23(t, 1H, J=7.8), 7.36(d, 1H, J=7.8), 7.81(s, 1H)

Starting Material Synthesis Example 17

(S)-4-glycidyloxy-N,N-dimethylbenzo(b)thiophene-2-carboxamide

To a solution of N,N-dimethyl-4-(hydroxymethyloxy)benzo(b)thiophene-2-carboxamide (9.0 g) in DMF (100 ml) was added potassium carbonate (8.0 g), and (S)-glycidyl nosylate (8.0 g) was further added. The mixture was stirred at 60° C. for 2 hr. The reaction mixture was concentrated under reduced pressure and water was added. The mixture was extracted with ethyl acetate and the organic layer was dried over anhydrous sodium sulfate and concentrated under reduced pressure. The obtained crystals were recrystallized from ethyl acetate to give the title compound (7.5 g).

$^1$H-NMR(CDCl$_3$):2.81(dd, 1H, J=2.4, 4.9), 2.96(t, 1H, J=4.4), 3.00–3.21(bs, 6H), 3.44–3.48(m, 1H), 4.08(dd, 1H, J=5.8, 11.2), 4.41(dd, 1H, J=2.4, 11.2), 6.76(d, 1H, J=7.8), 7.32(t, 1H, J=7.8), 7.45(d, 1H, J=8.3), 7.73(s, 1H)

Starting Material Synthesis Example 18

(S)-4-(4-glycidyloxybenzo(b)thiophen-2-ylcarbonyl)morpholine

By the reactions in the same manner as in Starting Material Synthesis Example 16 using 4-(methoxymethyloxy)benzo(b)thiophene-2-carboxylic acid (3.5 g), morpholine (1.0 g) and diethyl cyanophosphate (3.1 g), 4-(4-hydroxybenzo(b)thiophene-2-carbonyl)morpholine (3.2 g) was obtained as a brown oil. By the reactions in the same manner as in Starting Material Synthesis Example 1 using the brown oil (2.0 g) and (S)-glycidyl nosylate (2.1 g), the title compound (2.0 g) was obtained as brown crystals.

$^1$H-NMR(CDCl$_3$):2.81(dd, 1H, J=11.9, 4.8), 2.97(t, 1H, J=4.8), 3.42–3.48(m, 1H), 3.86–3.95(bs, 8H), 4.05(dd, 1H, J=5.6, 11.2), 4.43(dd, 1H, J=2.9, 11.4), 6.77(d, 1H, J=8.3), 7.33(t, 1H, J=7.8), 7.45(d, 1H, J=7.8), 7.68(s, 1H)

The structural formulas of the compounds obtained from the starting material synthesis examples 1 to 18 are shown in the following.

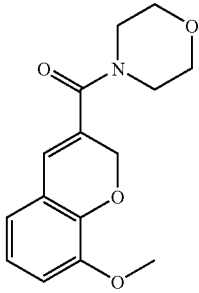

1

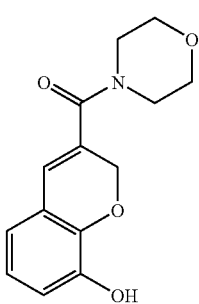

2

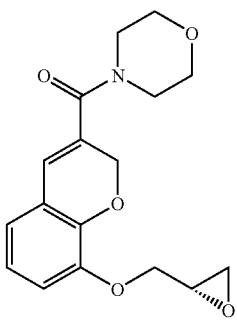

3

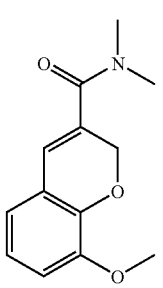

4

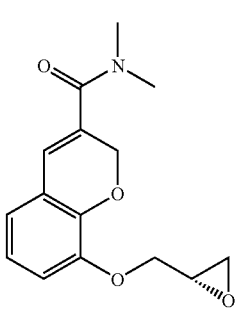

5

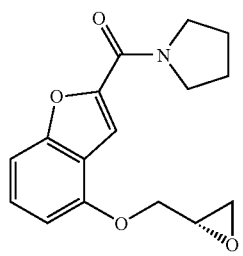

6

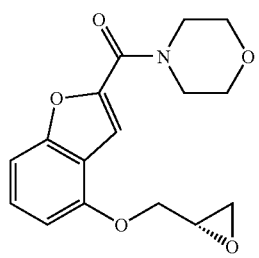

7

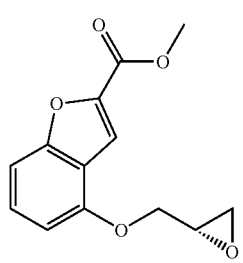

8

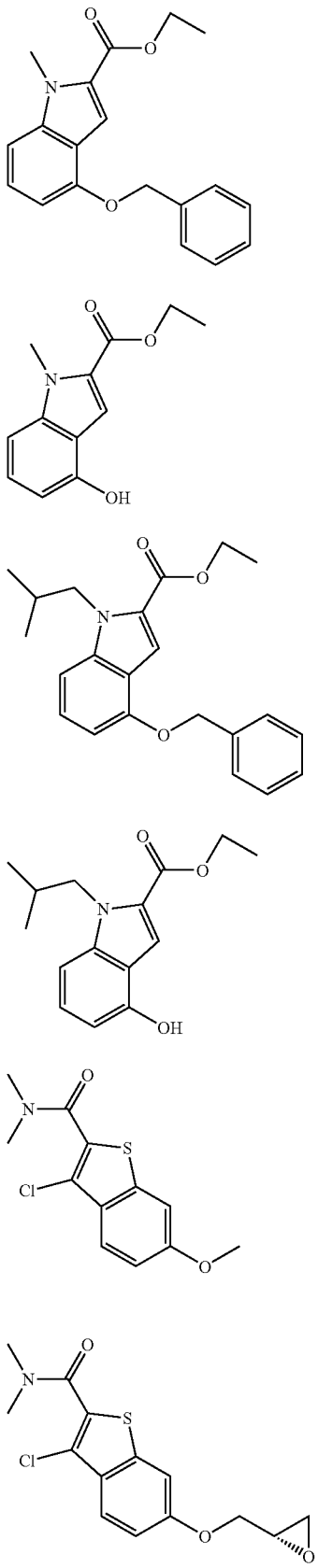

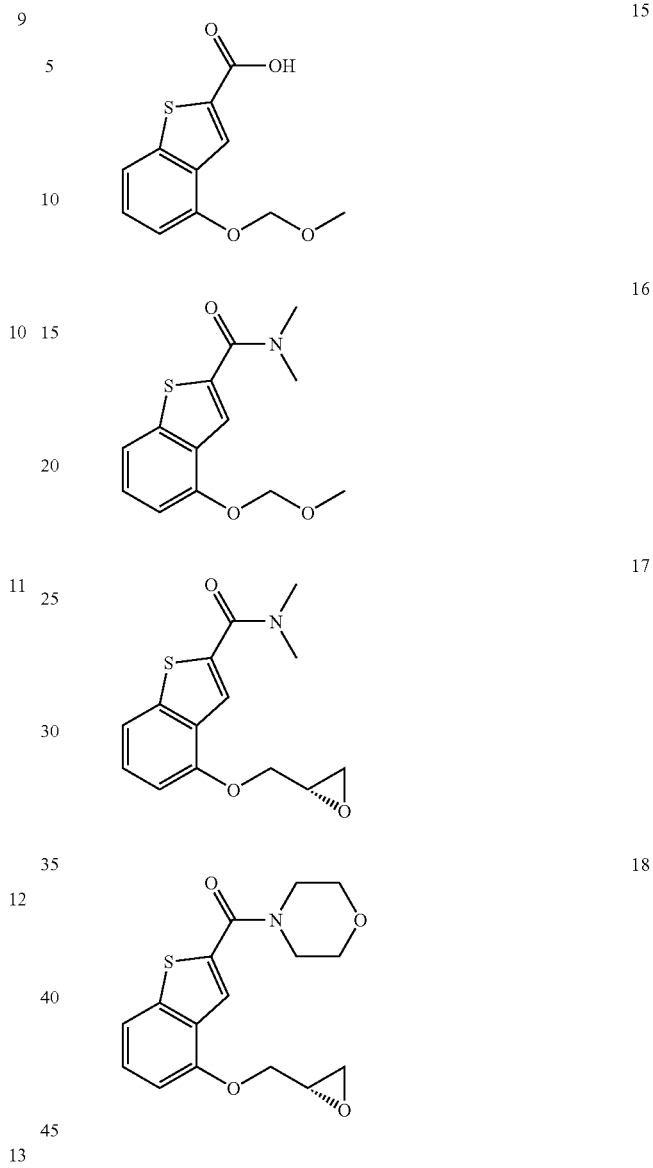

Starting Material Synthesis Example 19

(S)-1-(4-glycidyloxybenzo(b)thiophen-2-ylcarbonyl)pyrrolidine

By the reactions in the same manner as in Starting Material Synthesis Example 16 using 4-(methoxymethyloxy)benzo(b)thiophene-2-carboxylic acid (3.0 g), pyrrolidine (0.75 g) and diethyl cyanophosphate (2.5 g), 1-(4-hydroxybenzo(b)thiophene-2-carbonyl)pyrrolidine (2.4 g) was obtained as a brown oil. By the reactions in the same manner as in Starting Material Synthesis Example 1 using the brown oil (2.0 g) and (S)-glycidyl nosylate (2.0 g), the title compound (0.45 g) was obtained as brown crystals.

$^1$H-NMR(CDCl$_3$):1.98–2.10(bs, 4H), 2.80(dd, 1H, J=2.9, 4.9), 2.96(t, 1H, J=4.2), 3.42–3.48(m, 1H), 3.70(bs, 2H), 3.87(bs, 2H), 4.07(dd, 1H, J=4.8, 11.2), 4.41(dd, 1H, J=2.9, 11.2), 6.74(d, 1H, J=7.8), 7.32(t, 1H, J=7.8), 7.44(d, 1H, J=8.3), 8.00(s, 1H)

Starting Material Synthesis Example 20

(S)-4-glycidyloxy-N-methoxy-N-methylbenzo(b)thiophene-2-carboxamide

By the reactions in the same manner as in Starting Material Synthesis Example 16 using 4-(methoxymethyloxy)benzo(b)thiophene-2-carboxylic acid (4.5 g), N,O-dimethylhydroxylamine hydrochloride (2.1 g) and diethyl cyanophosphate (3.2 g), 4-hydroxy-N-methoxy-N-methylbenzo(b)thiophene-2-carboxamide (4.0 g) was obtained as a brown oil. By the reactions in the same manner as in Starting Material Synthesis Example 1 using the brown oil (2.0 g) and (S)-glycidyl nosylate (2.0 g), the title compound (1.1 g) was obtained as brown crystals.
$^1$H-NMR(CDCl$_3$):2.78(dd, 1H, J=2.8, 4.8), 2.98(t, 1H, J=4.2), 3.42(s, 3H), 3.43–3.48(m, 1H), 3.83(s, 3H), 4.10(dd, 1H, J=4.9, 11.2), 4.36(dd, 1H, J=3.5, 11.3), 6.74(d, 1H, J=7.8), 7.33(t, 1H, J=8.3), 7.44(d, 1H, J=8.3), 8.40(s, 1H)

Starting Material Synthesis Example 21

Methyl(S)-4-(2-hydroxy-3-(4-(naphthalen-2-yl)piperidino)propyloxy)benzo(b)furan-2-carboxylate To a solution (70 ml) of methyl(S)-4-glycidyloxybenzo(b)furan-2-carboxylate (4.1 g) obtained in Starting Material Synthesis Example 3 in methanol (70 ml) was added 4-(naphthalen-2-yl)piperidine (3.5 g) at room temperature, and the mixture was refluxed under heating for 2 hr. The solvent was evaporated under reduced pressure and the obtained residue was purified by silica gel column chromatography (chloroform:methanol) to give the title compound (5.6 g) as yellow crystals, melting point 118–119° C.

Starting Material Synthesis Example 22

(S)-4-(2-hydroxy-3-(4-(naphthalen-2-yl)piperidino)propyloxy)benzo(b)furan-2-carboxylic acid To a solution (140 ml) of methyl(S)-4-(2-hydroxy-3-(4-(naphthalen-2-yl)piperidino)propyloxy)benzo(b)furan-2-carboxylate (5.6 g) in methanol was added 2.0 M aqueous potassium hydroxide solution (100 ml) and the mixture was refluxed under heating for 2 hr. The reaction mixture was poured into water and the aqueous solution was made acidic (pH=1) with conc. hydrochloric acid. The solution was extracted with a mixed solvent of chloroform-methanol (2:1) and the organic layer was washed with saturated brine, dried over anhydrous magnesium sulfate and concentrated under reduced pressure. The obtained residue was crystallized from ethyl acetate, and the crystals were collected by filtration and dried to give hydrochloride (4.7 g) of the title compound as pale-yellow crystals, melting point 234–235° C. (decomposition)

Starting Material Synthesis Example 23 ethyl (S)-7-(2-hydroxy-3-(4-(naphthalen-2-yl)piperidino)propyloxy)benzo(b)furan-2-carboxylate By the reactions in the same manner as in Starting Material Synthesis Example 11 using ethyl (S)-7-(glycidyloxy)benzo(b)furan-2-carboxylate (5.3 g) and 4-(naphthalen-2-yl)piperidine (3.0 g), the title compound (5.2 g) was obtained as a brown oil.
$^1$H-NMR(CDCl$_3$)δ:1.41(t, J=7.3, 3H), 1.87–1.98(m, 4H), 2.23(t, J=7.3, 1H), 2.25–2.63(m, 1H), 2.48–2.79(m, 4H), 3.05(d, J=10.7, 1H), 3.05(d, J=10.7, 1H), 3.23(d, J=10.7, 1H), 4.10–4.28(m, 3H), 4.45(q, J=7.3, 2H), 6.72(d, J=8.3, 1H), 7.21(d, J=8.3, 1H), 7.35–7.49(m, 4H), 7.67–7.70(m, 2H), 7.75–7.82(m, 3H)

Starting Material Synthesis Example 24

(S)-7-(2-hydroxy-3-(4-(naphthalen-2-yl)piperidino)propyloxy)benzo(b)furan-2-carboxylic acid To a solution of ethyl (S)-7-(2-hydroxy-3-(4-(naphthalen-2-yl)piperidino)propyloxy)benzo(b)furan-2-carboxylate (5.2 g) in methanol (50 ml) was added 10% saturated aqueous sodium hydroxide solution (50 ml) and the mixture was refluxed under heating for 1 hr. The reaction mixture was made acidic (pH 1) with conc. hydrochloric acid and extracted with chloroform. The organic layer was washed with water and dried over anhydrous sodium sulfate. The solvent was evaporated under reduced pressure to give the title compound (4.0 g) as a brown oil.
$^1$H-NMR(DMSO-d$_6$)δ:1.81–2.20(m, 4H), 2.80–3.17(m, 2H), 4.01(dd, J=9.3, 3.4, 1H), 4.12(dd, J=9.3, 3.4, 1H), 6.75(d, J=8.3, 1H), 7.19(d, J=8.3, 1H), 7.48(t, J=8.3, 1H), 7.44–7.51(m, 3H), 7.77(s, 1H), 7.87–7.90(m, 3H), 8.04(s, 1H)

Starting Material Synthesis Example 25

(S)-4-(2-hydroxy-3-(4-(naphthalen-2-yl)piperidino)propyloxy)-1H-indole-2-carboxylic acid To a solution of ethyl 4-hydroxy-1H-indole-2-carboxylate (1.3 g) in DMF (50 ml) were added potassium carbonate and (S)-glycidyl nosylate (1.0 g) and the mixture was stirred one day. The reaction mixture was poured into water and extracted with ethyl acetate. The organic layer was washed with water and dried over anhydrous magnesium sulfate and the solvent was evaporated under reduced pressure to give ethyl (S)-4-glycidyloxy-1H-indole-2-carboxylate (1.8 g) as a brown oil. This was dissolved in methanol (50 ml) and the solution was refluxed under heating with 4-(naphthalen-2-yl)piperidine (1.5 g) for 3 hr. The solvent was evaporated under reduced pressure to give ethyl (S)-4-(2-hydroxy-3-(4-(naphthalen-2-yl)piperidino)propyloxy)-1H-indole-2-carboxylate (1.4 g) as pale-brown crystals (melting point 115–117° C.). By the reactions in the same manner as in Starting Material Synthesis Example 22, the title compound (1.1 g) was obtained as white crystals, melting point 171–173° C.

Starting Material Synthesis Example 26

(S)-4-(2-hydroxy-3-(4-(naphthalen-2-yl)piperidino)propyloxy)-1-methylindole-2-carboxylic acid By the reactions in the same manner as in Starting Material Synthesis Example 25 using ethyl 4-hydroxy-1-methylindole-2-carboxylate (4.0 g) obtained in Starting Material Synthesis Example 10, (S)-glycidyl nosylate (4.5 g) and 4-(naphthalen-2-yl)piperidine (4.3 g), ethyl (S)-4-(2-hydroxy-3-(4-(naphthalen-2-yl)piperidino)propyloxy)-1-(2-methylpropyl)-1-methylindole-2-carboxylate (5.8 g) was obtained. This was dissolved in ethanol (40 ml). Water (40 ml) and potassium hydroxide (4.5 g) were added, and the mixture was refluxed for 2.5 hr. From the obtained reaction mixture, ethanol was evaporated under reduced pressure and 1N aqueous hydrochloric acid solution (40 ml) was added under ice-cooling. The mixture was extracted with chloroform. The obtained organic layer was washed with saturated brine and dried over anhydrous magnesium sulfate. The solvent was evaporated under reduced pressure and isopropyl ether was added to the obtained oil. The obtained crystals were collected by filtration to give the title compound (4.2 g) as pale-yellow crystals, melting point 158–161° C.

Starting Material Synthesis Example 27

(S)-4-(2-hydroxy-3-(4-(naphthalen-2-yl)piperidino) propyloxy)-1-(2-methylpropyl)indole-2-carboxylic acid By the reactions in the same manner as in Starting Material Synthesis Example 25 using ethyl 4-hydroxy-1-(2-methylpropyl)indole-2-carboxylate (5.0 g) obtained in Starting Material Synthesis Example 12, (S)-glycidyl nosylate (4.5 g) and 4-(naphthalen-2-yl)piperidine (5.3 g), ethyl (S)-4-(2-hydroxy-3-(4-(naphthalen-2-yl)piperidino)propyloxy)-1-(2-methylpropyl)indole-2-carboxylate (7.5 g) was obtained. This was dissolved in ethanol (40 ml) and water (30 ml) and potassium hydroxide (4.0 g) were added. The mixture was refluxed for 2.5 hr. From the obtained reaction mixture, ethanol was evaporated under reduced pressure and 1N aqueous hydrochloric acid solution (30 ml) was added under ice-cooling. The mixture was extracted with chloroform. The obtained organic layer was washed with saturated brine and dried over anhydrous magnesium sulfate. The solvent was evaporated under reduced pressure and isopropyl ether was added to the obtained oil. The obtained crystals were collected by filtration to give the title compound (6.7 g) as pale-yellow crystals.
$^1$H-NMR(CD$_3$OD)δ:0.84–0.86(m, 7H), 2.15–2.23(m, 5H), 3.11–3.65(m, 4H), 3.65(m, 2H), 4.18–4.25(m, 2H), 4.40(d, J=7.3, 2H), 4.58(m, 1H), 6.60(d, J=7.8, 1H), 7.10(d, J=8.3, 1H), 7.24(dd, J=7.8, 8.3, 1H), 7.46–7.47(m, 4H), 7.74–7.86(m, 4H)

Starting Material Synthesis Example 28

1-(hydroxyimino)-1-(4-methoxybenzo(b)furan-2-yl) methylamine

To a solution (40 ml) of 4-methoxybenzo(b)furan-2-carbonitrile (2.8 g) in ethanol were added hydroxylamine hydrochloride (1.2 g) and sodium hydrogencarbonate (3.0 g). The mixture was refluxed under heating for 1.5 hr. The inorganic material was filtered off and the reaction mixture was concentrated under reduced pressure to give the title compound (3.4 g) as brown crystals.
$^1$H-NMR(CDCl$_3$)δ:3.94(s, 3H), 6.68(d, J=7.8, 1H), 7.13 (d, J=7.8, 1H), 7.19(s, 1H), 7.26(t, J=7.8, 1H)

Starting Material Synthesis Example 29

3-(4-methoxybenzo(b)furan-2-yl)-5-methyl-1,2,4-oxadiazole 1-(Hydroxyimino)-1-(4-methoxybenzo(b)furan-2-yl)methylamine (3.4 g) was dissolved in acetic anhydride (40 ml) and the mixture was refluxed under heating for 14 hr. The reaction mixture was concentrated under reduced pressure and the obtained residue was recrystallized from acetonitrile to give the title compound (1.1 g) as pale-as brown crystals.

$^1$H-NMR(CDCl$_3$)δ:2.68(s, 3H), 3.97(s, 3H), 6.70(d, J=8.3, 1H), 7.22(d, J=8.3, 1H), 7.33(t, J=8.3, 1H), 7.58(s, 1H)

Starting Material Synthesis Example 30

3-(4-hydroxybenzo(b)furan-2-yl)-5-methyl-1,2,4-oxadiazole

By the reactions in the same manner as in Starting Material Synthesis Example 5 using 3-(4-methoxybenzo(b)furan-2-yl)-5-methyl-1,2,4-oxadiazole (1.1 g) and boron tribromide (4.2 ml), the title compound (0.75 g) was obtained as yellow crystals.
$^1$H-NMR(DMSO-d$_6$)δ:2.65(s, 3H), 6.68(d, J=7.8, 1H), 7.12(d, J=8.3, 1H), 7.23(dd, J=7.8, 8.3, 1H), 7.60(s, 1H), 10.30(s, 1H)

Starting Material Synthesis Example 31

(S)-3-(4-glycidyloxybenzo(b)furan-2-yl)-5-methyl-1,2,4-oxadiazole

By the reactions in the same manner as in Starting Material Synthesis Example 1 using 3-(4-hydroxybenzo(b)furan-2-yl)-5-methyl-1,2,4-oxadiazole (0.75 g) and (S)-glycidyl nosylate (0.93 g), the title compound (0.45 g) was obtained as white crystals.
$^1$H-NMR(CDCl$_3$)δ:2.69(s, 3H), 2.83(dd, J=4.9, 2.5, 1H), 2.96(t, J=4.9, 1H), 3.43–3.45(m, 1H), 4.13(dd, J=11.2, 4.4, 1H), 4.40(dd, J=11.2, 3.0, 1H), 6.71(d, J=7.8, 1H), 7.25(d, J=8.3, 1H), 7.32(dd, J=8.3, 7.8, 1H), 7.62(s, 1H)

Starting Material Synthesis Example 32

1-(hydroxyimino)-1-(7-methoxybenzo(b)furan-2-yl) methylamine

By the reactions in the same manner as in Starting Material Synthesis Example 28 using 7-methoxybenzo(b)furan-2-carbonitrile (3.0 g), hydroxylamine hydrochloride (1.4 g) and sodium hydrogencarbonate (2.1 g), the title compound (3.3 g) was obtained as brown crystals.
$^1$H-NMR(CD$_3$OD)δ:3.97(s, 3H), 6.89–6.91(m, 1H), 7.11–7.17(m, 3H)

Starting Material Synthesis Example 33

3-(7-methoxybenzo(b)furan-2-yl)-5-methyl-1,2,4-oxadiazole

By the reactions in the same manner as in Starting Material Synthesis Example 29 using 1-(hydroxyimino)-1-(7-methoxybenzo(b)furan-2-yl)methylamine (3.3 g), the title compound (1.7 g) was obtained as white crystals.
$^1$H-NMR(CDCl$_3$)δ:2.68(s, 3H), 4.03(s, 3H), 6.90(d, J=7.8, 1H), 7.21(d, J=7.8, 1H), 7.25(t, J=7.8, 1H), 7.45(s, 1H)

The structural formulas of the compounds obtained in Starting Material Synthesis Examples 19 to 33 are shown in the following.

19
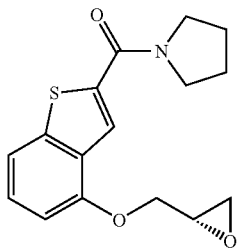
20
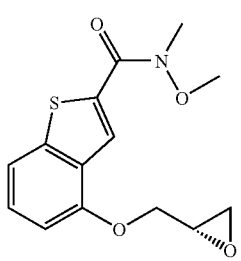
21
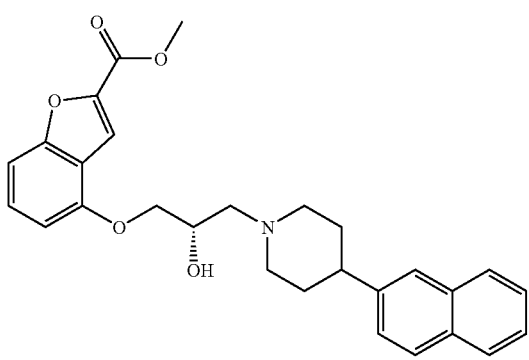
22
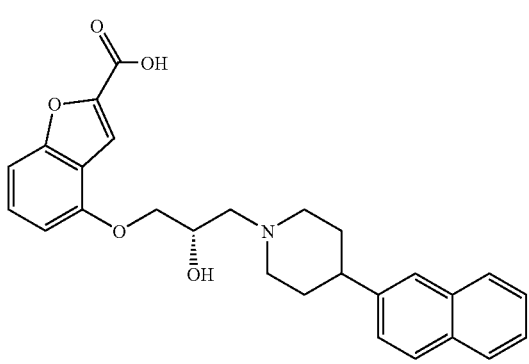
-continued
23
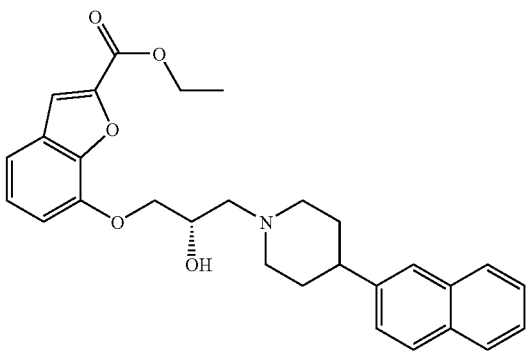
24
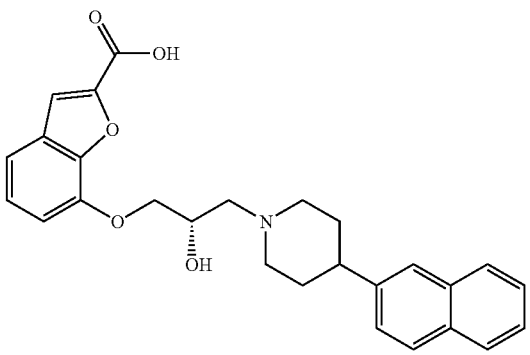
25
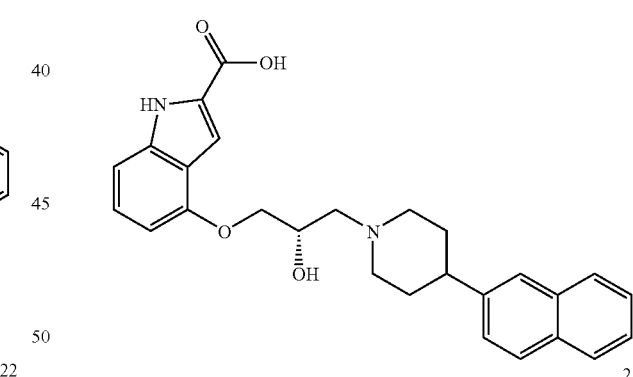
26
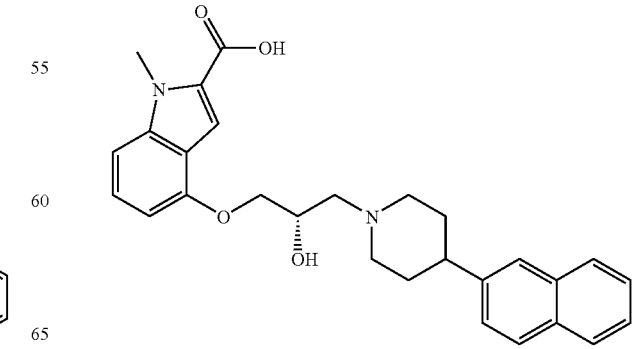

27

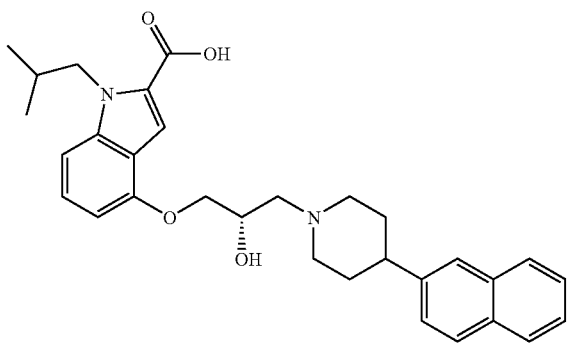

28

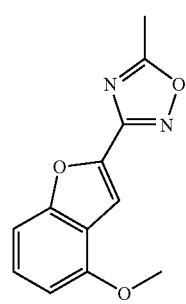

29 30

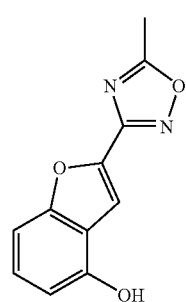

31

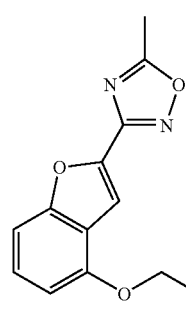

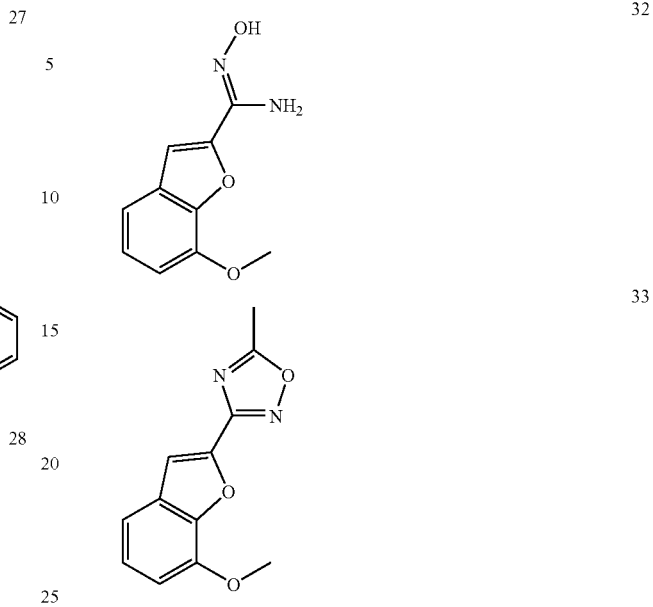

32

33

Starting Material Synthesis Example 34

3-(7-hydroxybenzo(b)furan-2-yl)-5-methyl-1,2,4-oxadiazole

By the reactions in the same manner as in Starting Material Synthesis Example 5 using 3-(7-methoxybenzo(b)furan-2-yl)-5-methyl-1,2,4-oxadiazole (1.7 g) and boron tribromide (6.5 ml), the title compound (1.5 g) was obtained as white crystals.

$^1$H-NMR(DMSO-d$_6$)δ:2.65(s, 3H), 6.68(d, J=7.8, 1H), 7.12(d, J=8.3, 1H), 7.23(dd, J=7.8, 8.3, 1H), 7.60(s, 1H), 10.30(s, 1H)

Starting Material Synthesis Example 35

(S)-3-(7-glycidyloxybenzo(b)furan-2-yl)-5-methyl-1,2,4-oxadiazole

By the reactions in the same manner as in Starting Material Synthesis Example 1 using 3-(7-hydroxybenzo(b)furan-2-yl)-5-methyl-1,2,4-oxadiazole (1.5 g) and (S)-glycidyl nosylate (1.8 g), the title compound (1.7 g) was obtained as white crystals.

$^1$H-NMR(CDCl$_3$)δ:2.69(s, 3H), 2.81(dd, J=4.9, 2.4, 1H), 2.94(t, J=4.9, 1H), 3.46–3.48(m, 1H), 4.26(dd, J=11.2, 5.4, 1H), 4.46(dd, J=11.2, 3.4, 1H), 6.95(d, J=7.8, 1H), 7.21(t, J=7.8, 1H), 7.29(d, J=7.8, 1H), 7.46(s, 1H)

Starting Material Synthesis Example 36

N'-(4-methoxybenzo(b)furan-2-ylcarbonyl)acetohydrazide

To a solution (700 ml) of 4-methoxybenzo(b)furan-2-carboxylic acid (43.4 g) in THF was added 1,1'-carbonylbis-1H-imidazole (CDI) (38.4 g) and the mixture was stirred at room temperature for 1 hr. Acetohydrazine (17.6 g) was added to this reaction mixture, and the mixture was stirred for 1 more hr. The reaction mixture was poured into water, and the precipitated crystals were collected by filtration and dried to give the title compound (38.4 g) as pale-brown crystals.

$^1$H-NMR(DMSO-d$_6$)δ:1.91(s, 3H), 3.93(s, 3H), 6.86(d, J=7.8, 1H), 7.25(d, J=7.8, 1H), 7.42(t, J=7.8, 1H), 7.61(s, 1H), 9.92(s, 1H), 10.46(s, 1H)

Starting Material Synthesis Example 37

2-(4-methoxybenzo(b)furan-2-yl)-5-methyl-1,3,4-oxadiazole

To a solution (400 ml) of N'-(4-methoxybenzo(b)furan-2-ylcarbonyl)acetohydrazide (15.6 g) in 1,2-dichloroethane were added triethylamine (21 ml) and triphenylphosphine (19.8 g) and the reaction temperature was set to 5° C. To this reaction mixture was added dropwise diethyl azodicarboxylate (40% toluene solution) (33 ml) over 15 min. The reaction temperature was set to room temperature and the mixture was stirred for 1.5 hr and washed with saturated aqueous solution of ammonium chloride. After partitioning, the obtained organic layer was dried over anhydrous magnesium sulfate and the solvent was evaporated under reduced pressure. The obtained residue was concentrated under reduced pressure and purified by silica gel column chromatography (chloroform/ethyl acetate) to give the title compound (4.6 g) as pale-yellow crystals.

$^1$H-NMR(CDCl$_3$)δ:2.65(s, 3H), 3.97(s, 3H), 6.72(d, J=8.3, 1H), 7.22(d, J=8.3, 1H), 7.36(t, J=8.3, 1H), 7.56(s, 1H)

Starting Material Synthesis Example 38

2-(4-hydroxybenzo(b)furan-2-yl)-5-methyl-1,3,4-oxadiazole

By the reactions in the same manner as in Starting Material Synthesis Example 5 using 2-(4-methoxybenzo(b)furan-2-yl)-5-methyl-1,3,4-oxadiazole (6.5 g) and boron tribromide (27 ml), the title compound (3.3 g) was obtained as yellow crystals.

$^1$H-NMR(DMSO-d$_6$)δ:2.60(s, 3H), 6.71(d, J=8.3, 1H), 7.16(d, J=8.3, 1H), 7.29(t, J=8.3, 1H), 7.68(s, 1H)

Starting Material Synthesis Example 39

(S)-2-(4-glycidyloxybenzo(b)furan-2-yl)-5-methyl-1,3,4-oxadiazole

By the reactions in the same manner as in Starting Material Synthesis Example 1 using 2-(4-hydroxybenzo(b)furan-2-yl)-5-methyl-1,3,4-oxadiazole (3.3 g) and (S)-glycidyl nosylate (3.7 g), the title compound (1.1 g) was obtained as white crystals.

$^1$H-NMR(CDCl$_3$)δ:2.65(s, 3H), 2.83(dd, J=4.9, 2.4, 1H), 2.96(t, J=4.9, 1H), 3.43–3.46(m, 1H), 4.09(dd, J=11.2, 5.8, 1H), 4.42(dd, J=11.2, 2.9, 1H), 6.72(d, J=8.3, 1H), 7.23(d, J=8.3, 1H), 7.34(t, J=8.3, 1H), 7.59(s, 1H)

Starting Material Synthesis Example 40

2-(7-methoxybenzo(b)furan-2-yl)-5-methyl-1,3,4-oxadiazole

7-Methoxybenzo(b)furan-2-carboxylic acid (10 g) was dissolved in tetrahydrofuran (100 ml) and CDI (12.6 g) and acetohydrazine (4.0 g) were added. The mixture was stirred at room temperature for 2 hr. The reaction mixture was poured into ice water and extracted with ethyl acetate. The organic layer was dried over anhydrous sodium sulfate and concentrated under reduced pressure to give an oily product (19 g). This oily product (19 g) was dissolved in 1,2-dichloroethane (300 ml) and triphenylphosphine (39 g) and triethylamine (25 ml) were added. The mixture was stirred under ice-cooling. Diisopropyl azodicarboxylate (40% toluene solution) (75 g) was added and then the mixture was stirred at room temperature for 3 hr. The reaction mixture was poured into ice water and extracted with chloroform. The organic layer was dried over anhydrous sodium sulfate and concentrated under reduced pressure. The residue was purified by silica gel column chromatography (hexane/ethyl acetate) to give the title compound (8.0 g) as pale-yellow crystals.

$^1$H-NMR(CDCl$_3$)δ:2.65(s, 3H), 4.05(s, 3H), 6.92(d, J=7.8, 1H) 7.23–7.28(m, 2H), 7.51(s, 1H)

Starting Material Synthesis Example 41

N'-(4-(methoxymethyloxy)benzo(b)thiophen-2-ylcarbonyl)acetohydrazide 4-(Methoxymethyloxy)benzothiophene-2-carboxylic acid (7 g) was dissolved in tetrahydrofuran (100 ml) and CDI (7.3 g) and acetohydrazine (2.4 g) was added. The mixture was stirred at room temperature for 3 hr. The precipitated crystals were collected by filtration to give the title compound (3.9 g).

$^1$H-NMR(DMSO-d$_6$)δ:1.99(s, 3H), 3.32(bs, 2H), 3.51(s, 3H), 5.37(s, 2H), 7.03(d, J=7.8, 1H), 7.36(t, J=7.8, 1H), 7.52(d, J=7.8, 1H), 8.32(s, 1H)

Starting Material Synthesis Example 42

2-(4-(methoxymethyloxy)benzo(b)thiophen-2-yl)-5-methyl-1,3,4-oxadiazole

N'-(4-(Methoxymethyloxy)benzo(b)thiophen-2-ylcarbonyl)acetohydrazide (2.4 g) was dissolved in 1,2-dichloroethane (50 ml) and triphenylphosphine (3.2 g) and triethylamine (2 ml) were added. The mixture was stirred under ice-cooling. Diethyl azodicarboxylate (40% toluene solution) (5.2 g) was added and the mixture was stirred at room temperature for 1 hr. The reaction mixture was poured into ice water and extracted with chloroform. The organic layer was dried over anhydrous sodium sulfate and concentrated under reduced pressure. The residue was purified by silica gel column chromatography (hexane/ethyl acetate) to give the title product (1.4 g) as pale-yellow crystals.

$^1$H-NMR(CDCl$_3$)δ:2.61(s, 3H), 3.54(s, 3H), 5.38(s, 2H), 7.05(d, J=7.8, 1H), 7.38(t, J=7.8, 1H), 7.52(d, J=7.8, 1H), 8.12(s, 1H)

Starting Material Synthesis Example 43

2-(4-hydroxybenzo(b)thiophen-2-yl)-5-methyl-1,3,4-oxadiazole 2-(4-(Methoxymethyloxy)benzo(b)thiophen-2-yl)-5-methyl-1,3,4-oxadiazole (1.4 g) was dissolved in a mixed solvent (10 ml) of acetic acid-water (1:1) and the mixture was heated at 80° C. for 4 hr. The reaction mixture was poured into ice water and extracted with ethyl acetate. The organic layer was washed with water, dried over anhydrous sodium sulfate and concentrated under reduced pressure to give an oily compound (1.4 g).

$^1$H-NMR(DMSO-d$_6$)δ:2.61(s, 3H), 6.83(d, J=7.8, 1H), 7.32(t, J=7.8, 1H), 7.44(d, J=7.8, 1H), 8.07(s, 1H), 10.44(bs, 1H)

Starting Material Synthesis Example 44

N'-(4-benzyloxy-1H-indol-2-ylcarbonyl)acetohydrazide

Ethyl 4-benzyloxyindol-2-carboxylate (10 g) was dissolved in a mixed solvent (200 ml) of dioxane-water (1:1) and potassium hydroxide (3.8 g) was added. The mixture was refluxed under heating for 2 hr. The reaction mixture was poured into ice water, made acidic with hydrochloric acid and extracted with ethyl acetate. The organic layer was washed with brine, dried over anhydrous sodium sulfate and concentrated under reduced pressure to give 4-benzyloxyindol-2-carboxylic acid as pale-yellow crystals (9.0 g). The crystals were dissolved in dimethylformamide (100 ml) and 1-ethyl-3-(3-dimethylaminopropyl)carbodiimide hydrochloride (WSC, 7.6 g), 1-hydroxybenzotriazole hydrochloride (HOBt, 6.9 g), triethylamine (7.0 ml) and acetohydrazine (2.6 g) were added thereto. The mixture was stirred at room temperature for 6 hr. The reaction mixture was poured into ice water and the precipitated crystals were collected by filtration to give the title compound (10 g).

$^1$H-NMR(DMSO-d$_6$)δ:1.93(s, 3H), 5.22(s, 2H), 6.62(d, J=7.8, 1H), 7.04(d, J=7.8, 1H), 7.11(t, J=7.8, 1H), 7.36–7.45 (m, 5H), 7.54(s, 1H), 9.85(s, 1H), 10.20(s, 1H), 11.67(s, 1H)

Starting Material Synthesis Example 45

4-benzyloxy-2-(5-methyl-1,3,4-oxadiazol-2-yl)-1H-indole

N'-(4-Benzyloxy-1H-indol-2-ylcarbonyl)acetohydrazide (7.5 g) was dissolved in tetrahydrofuran (250 ml) and triphenylphosphine (9.0 g) and triethylamine (6 ml) were added. The mixture was stirred under ice-cooling. Diisopropyl azodicarboxylate (40% toluene solution) (17.7 g) was added and the mixture was stirred at 50° C. for 2 hr. The reaction mixture was poured into ice water and extracted with chloroform. The organic layer was dried over anhydrous sodium sulfate and concentrated under reduced pressure. The residue was purified by silica gel column chromatography (hexane/ethyl acetate) to give the title compound (6.0 g) as yellow crystals.

$^1$H-NMR(DMSO-d$_6$)δ:2.59(s, 3H), 5.25(s, 2H), 6.65(d, J=7.8, 1H), 7.07(d, J=7.8, 1H), 7.15(m, 2H), 7.34(m, 1H), 7.41(m, 2H), 7.53(m, 2H), 12.21(s, 1H)

Starting Material Synthesis Example 46

N'-(7-methoxybenzo(b)furan-2-ylcarbonyl)benzohydrazide

7-Methoxybenzo(b)furan-2-ylcarbohydrazide (10 g) was dissolved in dichloromethane (100 ml) and triethylamine (9.0 ml) and benzoyl chloride (7.8 g) were added thereto. The mixture was stirred at room temperature for 3 hr. The reaction mixture was poured into ice water and extracted with ethyl acetate. The organic layer was washed with water, dried over anhydrous sodium sulfate and concentrated under reduced pressure. The residue was purified by silica gel column chromatography (chloroform/methanol) to give the title compound (5.0 g) as white crystals.

$^1$H-NMR(DMSO-d$_6$)δ:4.00(s, 3H), 7.08(d, J=7.8, 1H), 7.27(t, J=7.8, 1H), 7.35(d, J=7.8, 1H), 7.47–7.60(m, 3H), 7.68(s, 1H), 7.94(m, 2H), 10.57(s, 1H), 10.76(s, 1H)

Starting Material Synthesis Example 47

2-(7-methoxybenzo(b)furan-2-yl)-5-phenyl-1,3,4-oxadiazole

N'-(7-Methoxybenzo(b)furan-2-ylcarbonyl)benzohydrazide (5.0 g) was dissolved in thionyl chloride (20 ml) and the mixture was stirred with heating at 80° C. for 1 hr. Thionyl chloride was evaporated under reduced pressure and water was added to the residue. The mixture was extracted with ethyl acetate and the organic layer was washed with saturated aqueous solution of sodium hydrogencarbonate, dried over anhydrous sodium sulfate and concentrated under reduced pressure to give the title compound (3.7 g) as pale-yellow crystals.

$^1$H-NMR(DMSO-d$_6$)δ:4.02(s, 3H), 7.12(d, J=7.8, 1H), 7.29(t, J=7.8, 1H), 7.38(d, J=7.8, 1H), 7.63–7.68(m, 3H), 7.88(s, 1H), 8.13(m, 2H)

Starting Material Synthesis Example 48

N'-(4-methoxybenzo(b)furan-2-ylcarbonyl)trifluoroacetohydrazide

To a solution (250 ml) of 4-methoxybenzo(b)furan-2-ylcarbohydrazide (9.5 g) in methylene chloride was added trifluoroacetic anhydride (8.5 ml), and the mixture was stirred at room temperature for 2 hr. The reaction mixture was concentrated under reduced pressure and the residue was crystallized from hexane. The crystals were collected by filtration and dried to give the title compound (10.5 g) as yellow crystals.

$^1$H-NMR(DMSO-d$_6$)δ:3.94(s, 3H), 6.89(d, J=8.3, 1H), 7.28(d, J=8.3, 1H), 7.45(t, J=8.3, 1H), 7.66(s, 1H), 11.04(s, 1H), 11.70(s, 1H)

Starting Material Synthesis Example 49

2-(4-methoxybenzo(b)furan-2-yl)-5-trifluoromethyl-1,3,4-oxadiazole

By the reactions in the same manner as in Starting Material Synthesis Example 37 using N'-(4-methoxybenzo(b)furan-2-ylcarbonyl)trifluoroacetohydrazide (5.2 g), triethylamine (7.2 ml), triphenylphosphine (9.0 g) and diethyl azodicarboxylate (40% toluene solution, 6.2 ml), the title compound (4.0 g) was obtained as pale-yellow crystals.

$^1$H-NMR(CDCl$_3$)δ:3.98(s, 3H), 6.71(d, J=8.3, 1H), 7.18 (d, J=8.3, 1H), 7.48(t, J=8.3, 1H), 7.95(s, 1H)

Starting Material Synthesis Example 50

2-(4-hydroxybenzo(b)furan-2-yl)-5-trifluoromethyl-1,3,4-oxadiazole

By the reactions in the same manner as in Starting Material Synthesis Example 5 using 2-(4-methoxybenzo(b)furan-2-yl)-5-trifluoromethyl-1,3,4-oxadiazole (4.0 g) and boron tribromide (15 ml), the title compound (3.6 g) was obtained as yellow crystals.

¹H-NMR(DMSO-d₆)δ:6.73(d, J=8.3, 1H), 7.22(d, J=8.3, 1H), 7.36(t, J=8.3, 1H), 10.52(s, 1H)

Starting Material Synthesis Example 51

(S)-2-(4-glycidyloxybenzo(b)furan-2-yl)-5-trifluoromethyl-1,3,4-oxadiazole

By the reactions in the same manner as in Starting Material Synthesis Example 1 using 2-(4-hydroxybenzo(b)furan-2-yl)-5-trifluoromethyl-1,3,4-oxadiazole (3.3 g) and (S)-glycidyl nosylate (3.7 g), the title compound (1.1 g) was obtained as white crystals.
¹H-NMR(CDCl₃)δ:2.83(dd, J=4.9, 2.4, 1H), 2.99(t, J=4.9, 1H) 3.44–3.46(m, 1H), 4.12(dd, J=11.2, 5.9, 1H), 4.44(dd, J=11.2, 2.9, 1H), 6.76(d, J=8.3, 1H), 7.27(d, J=8.3, 1H), 7.42(t, J=8.3, 1H), 7.83(s, 1H)

Starting Material Synthesis Example 52

N'-(7-methoxybenzo(b)furan-2-ylcarbonyl)trifluoroacetohydrazide

To a solution (300 ml) of 7-methoxybenzo(b)furan-2-ylcarbohydrazide (14.0 g) in methylene chloride was added trifluoroacetic anhydride (11.5 ml) and the mixture was stirred at room temperature for 1 hr. The reaction mixture was concentrated under reduced pressure and the residue was crystallized from hexane, collected by filtration and dried to give the title compound (16.1 g) as white crystals.
¹H-NMR(DMSO-d₆)δ:7.11(d, J=7.8, 1H), 7.28(t, J=7.8, 1H), 7.35(d, J=7.8, 1H), 7.69(s, 1H), 11.10(s, 1H)

Starting Material Synthesis Example 53

2-(7-methoxybenzo(b)furan-2-yl)-5-trifluoromethyl-1,3,4-oxadiazole

To a solution (280 ml) of N'-(7-methoxybenzo(b)furan-2-ylcarbonyl)trifluoroacetohydrazide (14.6 g) in 1,2-dichloroethane were added thionyl chloride (4.2 ml) and DMF (0.1 ml) and the mixture was refluxed under heating for 4.5 hr. The solvent was evaporated under reduced pressure and the obtained residue was purified by silica gel column chromatography (chloroform/ethyl acetate) to give the title compound (2.4 g) as pale-yellow crystals.
¹H-NMR(CDCl₃)δ:4.06(s, 3H), 6.99(d, J=6.9, 1H), 7.22 (d, J=6.9, 1H), 7.26–7.31(m, 2H), 7.72(s, 1H)

The structural formulas of the compounds obtained in Starting Material Synthesis Examples 34 to 53 are shown in the following.

34

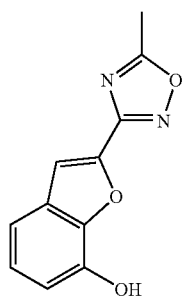

35

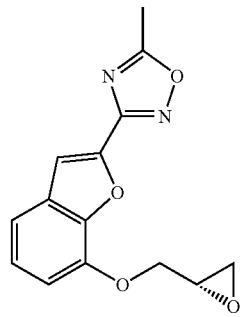

36

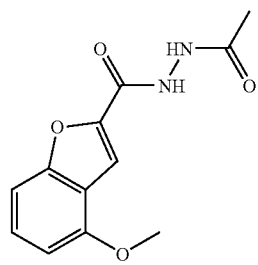

37

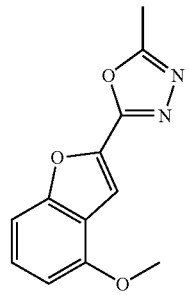

38

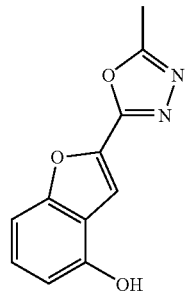

39

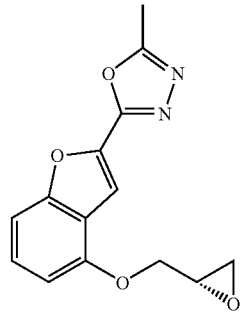

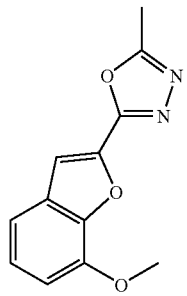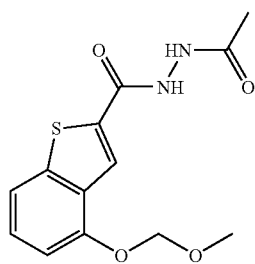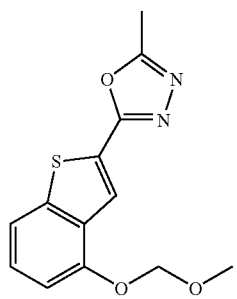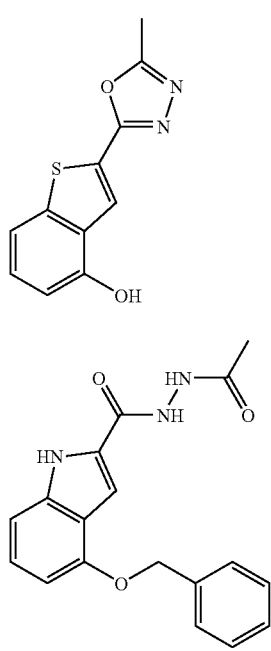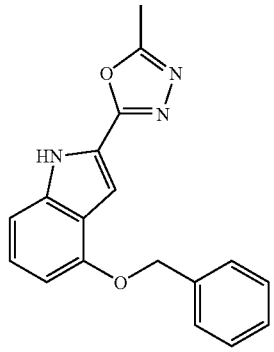

-continued

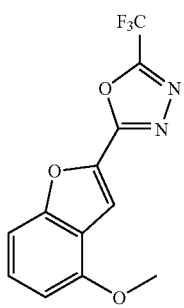

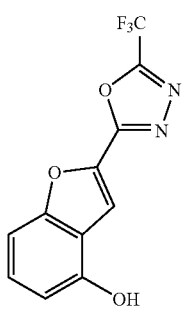

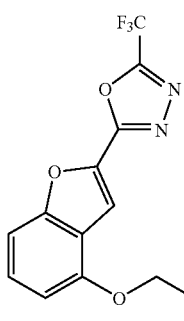

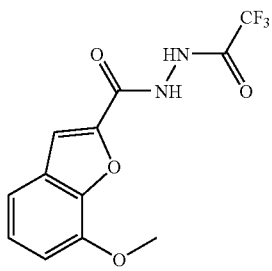

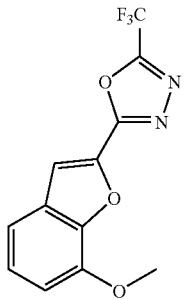

Starting Material Synthesis Example 54

2-(7-hydroxybenzo(b)furan-2-yl)-5-trifluoromethyl-1,3,4-oxadiazole

By the reactions in the same manner as in Starting Material Synthesis Example 5 using 2-(7-methoxybenzo(b)furan-2-yl)-5-trifluoromethyl-1,3,4-oxadiazole (2.4 g) and boron tribromide (5.0 ml), the title compound (2.2 g) was obtained as yellow crystals.

$^1$H-NMR(DMSO-d$_6$)δ:6.96(d, J=7.3, 1H), 7.19(t, J=7.3, 1H), 7.29(t, d=7.3, 1H), 8.00(s, 1H), 10.50(s, 1H)

Starting Material Synthesis Example 55

(S)-2-(7-glycidyloxybenzo(b)furan-2-yl)-5-trifluoromethyl-1,3,4-oxadiazole

By the reactions in the same manner as in Starting Material Synthesis Example 1 using 2-(7-hydroxybenzo(b)furan-2-yl)-5-trifluoromethyl-1,3,4-oxadiazole (2.4 g) and (S)-glycidyl nosylate (2.2 g), the title compound (1.0 g) was obtained as white crystals.

$^1$H-NMR(CDCl$_3$)δ:2.81–2.85(m, 1H), 2.96–2.98(m, 1H), 3.42–3.50(m, 1H), 4.23(dd, J=11.2, 5.8, 1H), 4.52(dd, J=11.2, 3.4, 1H), 7.04(d, J=7.8, 1H), 7.30(t, J=7.8, 1H), 7.33(d, J=7.8, 1H), 7.71(s, 1H)

Starting Material Synthesis Example 56

5-(4-methoxybenzo(b)furan-2-yl)-3-methyl-1,2,4-oxadiazole

To a solution (50 ml) of 4-methoxybenzo(b)furan-2-carboxylic acid (1.9 g) in THF were added thionyl chloride (0.9 ml) and DMF (0.1 ml), and the mixture was refluxed under heating for 20 min. The solvent was evaporated under reduced pressure and the obtained residue was dissolved in pyridine (50 ml) and acetamide oxime hydrochloride (1.3 g) was added. The mixture was refluxed under heating for 1 hr and the solvent was evaporated under reduced pressure. The obtained residue was purified by silica gel column chromatography (chloroform:ethyl acetate=6:1) to give the title compound (1.0 g) as pale-yellow crystals.

$^1$H-NMR(CDCl$_3$)δ:2.51(s, 3H), 3.98(s, 3H), 6.73(d, J=7.8, 1H) 7.24(d, J=8.3, 1H), 7.38(dd, J=7.8, 8.3, 1H), 7.73(s, 1H)

Starting Material Synthesis Example 57

5-(4-hydroxybenzo(b)furan-2-yl)-3-methyl-1,2,4-oxadiazole

By the reactions in the same manner as in Starting Material Synthesis Example 5 using 5-(4-methoxybenzo(b)furan-2-yl)-3-methyl-1,2,4-oxadiazole (0.98 g) and boron tribromide (3.1 ml), the title compound (0.72 g) was obtained as yellow crystals.

$^1$H-NMR(CD$_3$OD)δ:2.44(s, 3H), 6.69(d, J=8.3, 1H), 7.10 (d, J=8.3, 1H), 7.31(t, J=8.3, 1H), 7.79(s, 1H)

Starting Material Synthesis Example 58

(S)-5-(4-glycidyloxybenzo(b)furan-2-yl)-3-methyl-1,2,4-oxadiazole

By the reactions in the same manner as in Starting Material Synthesis Example 1 using 5-(4-hydroxybenzo(b)furan-2-yl)-3-methyl-1,2,4-oxadiazole (3.3 g) and (S)-glycidyl nosylate (3.7 g), the title compound (1.1 g) was obtained as white crystals.

$^1$H-NMR(CDCl$_3$)δ:2.51(s, 3H), 2.83(dd, J=4.8, 2.4, 1H), 2.96(t, J=4.8, 1H), 3.42–3.46(m, 1H), 4.11(dd, J=11.2, 5.8, 1H), 4.42(dd, J=11.2, 2.9, 1H), 6.73(d, J=8.3, 1H), 7.26(d, J=8.3, 1H), 7.39(t, J=8.3, 1H), 7.78(s, 1H)

Starting Material Synthesis Example 59 methyl 4-hydroxybenzo(b)thiophene-2-carboxylate 4-(Methoxymethyloxy)benzo(b)thiophene-2-carboxylic acid (7 g) was dissolved in methanol (140 ml) and thionyl chloride (2.0 ml) was added under ice-cooling. The mixture was refluxed under heating for 2 hr and the reaction mixture was concentrated under reduced pressure. Water was added and the mixture was extracted with ethyl acetate. The organic layer was dried over anhydrous magnesium sulfate, and after filtration, the solvent was evaporated under reduced pressure to give the title compound (6.0 g).

$^1$H-NMR(CDCl$_3$):3.95(s, 3H), 6.82(d, 1H, J=4.8), 7.23–7.38(m, 2H), 8.30(s, 1H)

Starting Material Synthesis Example 60

5-(4-hydroxybenzo(b)thiophen-2-yl)-3-methyl-1,2,4-oxadiazole

Methyl 4-hydroxybenzo(b)thiophene-2-carboxylate (6.0 g) was dissolved in dimethylformamide (80 ml) and sodium hydride (1.7 g) was added under ice-cooling. The mixture was stirred for 30 min and chloromethyl methyl ether (3 g) was added. The mixture was stirred at room temperature for 3 hr. The reaction mixture was poured into water and extracted with ethyl acetate. The organic layer was dried over anhydrous magnesium sulfate, and after filtration, the solvent was evaporated under reduced pressure. Tetrahydrofuran (100 ml) was added and the reaction mixture was ice-cooled, and sodium hydride (1.6 g) and acetamide oxime (3.0 g) were added in the presence of molecular sieves (4A). The mixture was refluxed under heating for 30 min and the tetrahydrofuran solution obtained earlier was added to the solution. The mixture was refluxed under heating for 1 hr, and after cooling, poured into water and extracted with ethyl acetate. The organic layer was dried over anhydrous magnesium sulfate, and after filtration, the solvent was evaporated under reduced pressure. Thereto were added tetrahydrofuran (35 ml) and 6N hydrochloric acid (20 ml), and the mixture was stirred at 50° C. for 30 min. The reaction mixture was poured into water, and the mixture was extracted with ethyl acetate. The organic layer was dried over anhydrous magnesium sulfate, and after filtration, the solvent was evaporated under reduced pressure to give the title compound (2.4 g).

$^1$H-NMR(CDCl$_3$):2.50(s, 3H), 5.70(bs, 1H), 6.78(d, 1H, J=7.6), 7.34(t, 1H, J=7.8), 7.47(d, 1H, J=8.3), 8.33(s, 1H)

Starting Material Synthesis Example 61

(S)-5-(4-glycidyloxybenzo(b)thiophen-2-yl)-3-methyl-1,2,4-oxadiazole

Synthesized according to a method similar to the method of Starting Material Synthesis Example 1.

$^1$H-NMR(CDCl$_3$):2.48(s, 3H), 2.83(dd, 1H, J=2.4, 4.9), 2.98(t, 1H, J=4.4), 3.42–3.48(m, 1H), 4.14(dd, 1H, J=5.9, 11.3), 4.41(dd, 1H, J=3.0, 10.8), 6.80(d, 1H, J=7.8), 7.40(t, 1H, J=7.8), 7.48(d, 1H, J=8.3), 8.35(s, 1H)

Starting Material Synthesis Example 62

1-(4-methoxybenzo(b)furan-2-yl)butan-1,3-dione

2-Acetyl-4-methoxybenzo(b)furan (2.4 g) was dissolved in ethyl acetate (50 ml), and sodium hydride (1.5 g) was added under ice-cooling. The mixture was stirred at room temperature for 10 min, and the mixture was refluxed under heating for 1 hr. After cooling, the mixture was poured into water and extracted with ethyl acetate. The organic layer was dried over anhydrous magnesium sulfate, and after filtration, the solvent was evaporated under reduced pressure. The residue was purified by silica gel column chromatography (hexane/ethyl acetate) to give the title compound (0.7 g).

$^1$H-NMR(CDCl$_3$):2.21(s, 3H), 3.96(s, 3H), 6.25(s, 1H), 6.68(d, 1H, J=7.8), 6.68(d, 1H, J=7.6), 7.15(d, 1H, J=7.8), 7.33(t, 1H, J=7.8), 7.56(s, 1H)

Starting Material Synthesis Example 63

(S)-3-(4-glycidyloxybenzo(b)furan-2-yl)-1,5-dimethylpyrazole 1-(4-Methoxybenzo(b)furan-2-yl)butan-1,3-dione (1.0 g) was dissolved in methanol (30 ml) and methylhydrazine (0.3 g) was added thereto. The mixture was refluxed under heating for 20 min. The reaction solvent was evaporated under reduced pressure, and the residue was purified by silica gel column chromatography (hexane/acetone). To the obtained oil was added methylene chloride (30 ml), and the mixture was cooled to −40° C., and boron tribromide (1 ml) was added dropwise. After the completion of the reaction, the mixture was poured into water and extracted with ethyl acetate. The organic layer was dried over anhydrous magnesium sulfate, and after filtration, the solvent was evaporated under reduced pressure to give 3-(4-hydroxybenzo(b)furan-2-yl)-1,5-dimethylpyrazole (0.85 g) as a brown oil. Using this and (S)-glycidyl nosylate (0.75 g) and in the same manner as in Starting Material Synthesis Example 1, the title compound (0.53 g) was obtained as a brown oil.

$^1$H-NMR(CDCl$_3$):2.33(s, 3H), 2.82(dd, 1H, J=2.8, 4.8), 2.94(t, 1H, J=4.4), 3.86(s, 3H), 4.13(dd, 1H, J=5.4, 11.2), 4.36(dd, 1H, J=3.4, 11.2), 6.40(s, 1H), 6.65(d, 1H, J=6.3), 7.06(s, 1H), 7.08–7.12(m, 2H)

Starting Material Synthesis Example 64

4-methoxymethylbenzo(b)thiophene-2-carboxylic acid

To a solution (400 ml) of 4,5,6,7-tetrahydrobenzo(b)thiophen-4-one (70.0 g) in methanol was added dropwise a solution (200 ml) of bromine (75.0 g) in methanol at room temperature. After the completion of the reaction, the reaction mixture was poured into water and extracted with chloroform, and the solvent was evaporated under reduced pressure. The obtained residue was dissolved in DMF (500 ml) and lithium bromide (30.0 g) was added. The reaction mixture was stirred with heating at a reaction temperature of 110° C. for 1 hr. The reaction mixture was poured into ice water, extracted with chloroform, the extract was dried over magnesium sulfate and concentrated under reduced pressure to give 4-hydroxymethylbenzo(b)thiophene (50.5 g). This was dissolved in DMF (300 ml) and boron hydride (15.0 g) was added. The mixture was stirred at room temperature for 1 hr. To this reaction mixture was added dropwise methoxymethyl chloride (16.5 g). After the completion of the reaction, the reaction mixture was poured into water and extracted with ethyl acetate. The organic layer was dried and concentrated under reduced pressure. The residue was dissolved in THF (400 ml) and n-BuLi (1.6M hexane solution) (250 ml) was added dropwise at −78° C. After the mixture was stirred for 30 min, and carbonic acid gas was blown in until the reaction ended. The reaction mixture was poured into water, and the aqueous layer was made acidic with hydrochloric acid, and after extraction with ethyl acetate, the solvent was evaporated under reduced pressure to give the title compound as white crystals, melting point 212–214° C.

Starting Material Synthesis Example 65

2-(7-hydroxybenzo(b)furan-2-yl)-5-methyloxazole

7-Methoxybenzo(b)furan-2-carboxylic acid (6.0 g) was dissolved in chloroform (30 ml), and dimethylformamide (1 ml) was added. Thionyl chloride (4.0 ml) was added, and the mixture was stirred with heating at 50° C. for 2 hr. The reaction solvent was evaporated under reduced pressure, and tetrahydrofuran (100 ml) was added. The mixture was cooled and a solution of propargylamine (1.65 g) and triethylamine (12 ml) in tetrahydrofuran was added dropwise with stirring. The mixture was stirred at room temperature for 2 hr, and poured into water and extracted with ethyl acetate. The organic layer was dried over anhydrous magnesium sulfate, and after filtration, the solvent was evaporated under reduced pressure. This product (4 g) was dissolved in acetic acid (40 ml) and mercury (II) acetate (0.5 g) was added. The mixture was refluxed for 2 hr. After cooling, acetic acid was evaporated under reduced pressure and aqueous potassium carbonate solution was added, and the mixture was extracted with ethyl acetate. The organic layer was dried over anhydrous magnesium sulfate, and after filtration, the solvent was evaporated under reduced pressure to give pale-yellow crystals (1.5 g). The crystals were dissolved in methylene chloride (30 ml), and the mixture was cooled to −20° C. Boron tribromide (0.8 ml) was added dropwise and the mixture was stirred at 0° C. for 1 hr. The reaction mixture was poured into water, and extracted with tetrahydrofuran. The organic layer was dried over anhydrous magnesium sulfate, and after filtration, the solvent was evaporated under reduced pressure to give the title compound (1.0).

$^1$H-NMR(DMSO-d$_6$):2.42(s, 3H), 6.92–6.95(m, 2H), 7.01–7.13(m, 1H), 7.18–7.35(m, 1H), 7.63(d, 1H, J=2.8)

Starting Material Synthesis Example 66

5-(7-methoxybenzo(b)furan-2-yl)-3-methylisoxazole

Thionyl chloride (10 ml) was added dropwise to methanol (100 ml) with stirring under ice-cooling. 7-Methoxybenzo(b)furan-2-carboxylic acid (10 g) was successively added, and the mixture was refluxed under heating for 1 hr. After cooling, the solvent was evaporated under reduced pressure and the precipitated yellow crystals were collected by filtration to give methyl 7-methoxybenzo(b)furan-2-carboxylate (11.2 g). This was used in the next reaction without purification. Acetone oxime (4.8 g) was dissolved in tetrahydrofuran (100 ml), and butyllithium (1.6M hexane solution) (80 ml) was added dropwise to this solution at −5° C. with stirring. Thereafter, the mixture was stirred under ice-cooling for 1 hr, and a solution (50 ml) of methyl 7-methoxybenzo(b)furan-2-carboxylate (11.2 g) in tetrahydrofuran was added. The mixture was stirred at room temperature for 20 hr. A solution of sulfuric acid (28 g) dissolved in tetrahydrofuran (120 ml)-water (30 ml) was prepared, into which the reaction mixture was poured. The mixture was refluxed under heating for 2 hr. After cooling, the reaction mixture was poured into ice water and extracted with chloroform. The organic layer was dried over anhydrous sodium sulfate and concentrated under reduced pressure, and the residue was purified by silica gel column chromatography (hexane/ethyl acetate) to give the title compound (2.1 g).

$^1$H-NMR(CDCl$_3$)δ:2.38(s, 3H), 4.04(s, 3H), 6.57(s, 1H), 6.88(d, J=7.8, 1H), 7.22(m, 3H)

Starting Material Synthesis Example 67

4-(4-methoxybenzo(b)furan-2-yl)-2-methylthiazole

To a solution (30 ml) of 4-methoxybenzo(b)furan-2-yl α-bromomethyl ketone (2.7 g) in ethanol was added thioacetamide (0.75 g), and the mixture was refluxed under heating for 6 hr. The precipitated crystals were collected by filtration and dried to give the title compound (2.7 g) as pale-brown crystals.

$^1$H-NMR(DMSO-d$_6$)δ:2.72(s, 3H), 3.91(s, 3H), 6.81(d, J=7.3, 1H) 7.13(s, 1H), 7.21(d, J=7.3, 1H), 7.27(t, J=7.3, 1H), 7.90(s, 1H)

Starting Material Synthesis Example 68

2-(2'-hydroxystyryl)-5-methyl-1,3,4-oxadiazole 2-(Methoxymethyloxy)cinnamic acid (4.0 g) and CDI (3.1 g) were successively added to tetrahydrofuran (40 ml) and the mixture was stirred. One hour later, acetylhydrazide (1.4 g) was added, and the mixture was stirred for 3 more hr. The reaction mixture was poured into water and extracted with ethyl acetate to give an oil (3.5 g). This oil was dissolved in dichloroethane (300 ml) and triphenylphosphine (5 g) and triethylamine (3.3 ml) were added to this solution. Then DEAD (8.3 g) was added under ice-cooling. The mixture was stirred at room temperature for 2 hr, and aqueous potassium carbonate solution was added, and reaction mixture was extracted with chloroform. The organic solvent was dried and concentrated, and the residue was purified by silica gel column chromatography (hexane/acetone) to give an oil (2.2 g). This oil was stirred with heating in a mixed solvent of water (20 ml) and hydrochloric acid (20 ml) for 2 hr, and after cooling, poured into water. The mixture was extracted with ethyl acetate to give the title compound (1.5 g) as a brown oil.

$^1$H-NMR(CDCl$_3$):2.58(s, 3H), 6.45(bs, 1H), 6.90(t, J=7.8, 1H), 6.98(d, J=7.5, 1H), 7.19(d, J=7.5, 1H), 7.40(t, J=8.0, 1H), 7.42(d, J=15.8, 1H), 7.68(d, J=15.8, 1H)

Starting Material Synthesis Example 69

2-(2'-hydroxystyryl)benzothiazole

Salicylaldehyde (6.1 g) and 2-methylthiazole (7.5 g) were mixed and conc. hydrochloric acid (1.5 ml) was added thereto. The mixture was stirred with heating at 100° C. for 9 hr. The reaction mixture was cooled, and aqueous potassium hydroxide solution was added. The aqueous layer was washed with ether and made acidic with hydrochloric acid and extracted again with ethyl acetate. The organic solvent was dried and concentrated to give the title compound (2.5 g) as pale-yellow crystals, melting point 235–236° C.

Starting Material Synthesis Example 70

5-(2'-hydroxystyryl)-3-methyl-1,2,4-oxadiazole

Acetamide oxime (7.5 g), molecular sieves (4A) (10 g) and sodium hydride (5 g) were added to tetrahydrofuran (200 ml) and the mixture was refluxed under heating. To this reaction mixture was added dropwise ethyl 2-(methoxymethyloxy)cinnamate (12 g) and the mixture was continuously heated for 2 hr. After cooling, the mixture was poured on ice and extracted with ethyl acetate. The organic layer was concentrated under reduced pressure. Thereto were added tetrahydrofuran (10 ml) and 6N hydrochloric acid (20 ml) and the mixture was stirred with heating at 50° C. for 30 min to allow precipitation of crystals. The crystals were collected by filtration and dried to give the title compound (6.0 g) as white crystals, melting point 184–186° C.

Starting Material Synthesis Example 71

(S)-(4-glycidyloxy)benzo(b)furan-2-yl methyl ketone

To a suspension (40 ml) of sodium hydride (0.22 g) in DMF was added dropwise a solution (10 ml) of 4-hydroxybenzo(b)furan-2-yl methyl ketone (0.80 g) in DMF under ice-cooling and the mixture was stirred at room temperature for 30 min. To this reaction mixture was added dropwise a solution (10 ml) of (S)-glycidyl nosylate (1.4 g) in DMF under ice-cooling, and the mixture was stirred for 2 hr. The reaction mixture was poured into ice water and extracted with ethyl acetate. The organic layer was washed with water and dried over anhydrous magnesium sulfate. The solvent was evaporated under reduced pressure and the residue was purified by silica gel column chromatography (hexane/ethyl acetate) to give the title compound (0.61 g) as yellow crystals.

$^1$H-NMR(CDCl$_3$):2.60(s, 3H), 2.82(dd, J=4.4, 5.9, 1H), 2.97(t, J=4.4, 1H), 3.43–3.46(m, 1H), 4.09(dd, J=10.8, 5.9, 1H), 4.42(dd, J=10.8, 3.0, 1H), 6.69(d, J=7.8, 1H), 7.20(d, J=8.3, 1H), 7.39(t, J=8.3, 1H), 7.65(s, 1H)

Starting Material Synthesis Example 72

(S)-4-glycidyloxy-3-methylbenzo(b)furan-2-yl methyl ketone

To a suspension (60 ml) of sodium hydride (1.4 g) in DMF was added dropwise a solution (30 ml) of 4-hydroxy-3-methylbenzo(b)furan-2-yl methyl ketone (6.1 g) in DMF under ice-cooling and the mixture was stirred at room temperature for 30 min. To this reaction mixture was added dropwise under ice-cooling a solution (30 ml) of (S)-glycidyl nosylate (9.1 g) in DMF, and the mixture was stirred for 2 hr. The reaction mixture was poured into ice water and extracted with ethyl acetate. The organic layer was washed with water and dried over anhydrous magnesium sulfate. The solvent was evaporated under reduced pressure and the residue was purified by silica gel column chromatography (hexane/ethyl acetate) to give the title compound (3.1 g) as pale-yellow crystals.

$^1$H-NMR(CDCl$_3$):2.59(s, 3H), 2.79(s, 3H), 2.83(dd, J=4.9, 2.3, 1H), 2.96(t, J=4.3, 1H), 3.43–3.45(m, 1H), 4.08 (dd, J=11.2, 5.4, 1H), 4.37(dd, J=11.2, 3.0, 1H), 6.62(d, J=7.8, 1H), 7.11(d, J=8.3, 1H), 7.34(t, J=8.3, 1H);

The structural formulas of the compounds obtained in Starting Material Synthesis Examples 54 to 72 are shown in the following.

54

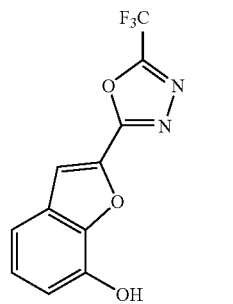

55

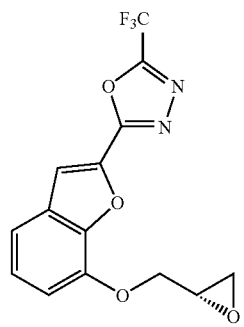

56

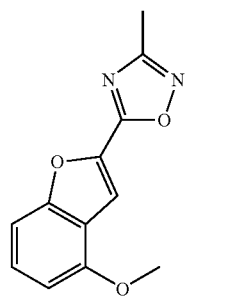

57

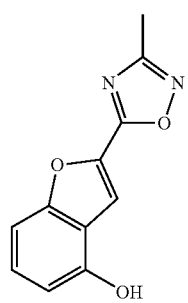

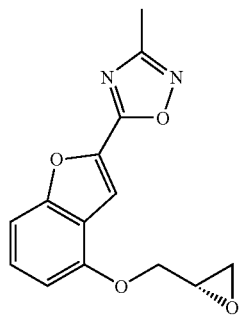
58
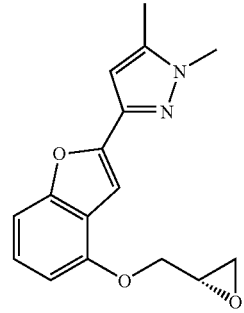
63
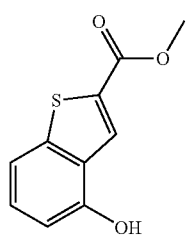
59
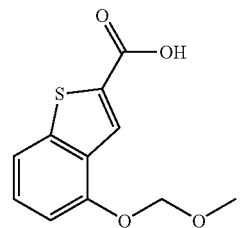
64
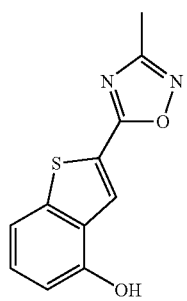
60
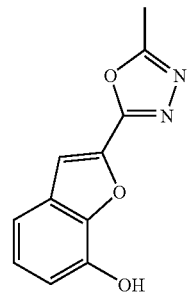
65
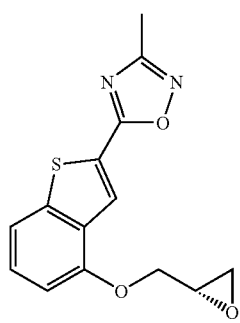
61
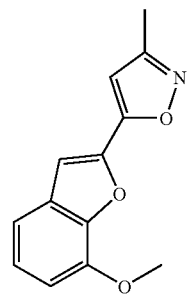
66
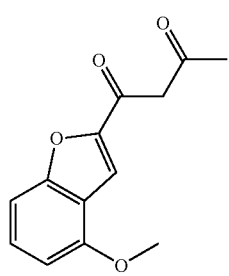
62
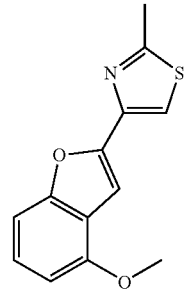
67

-continued

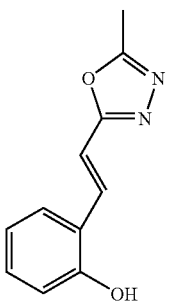
68

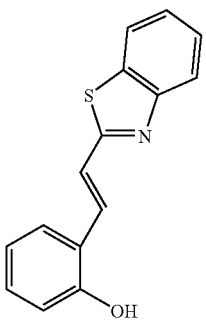
69

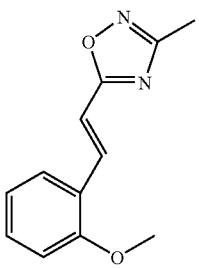
70

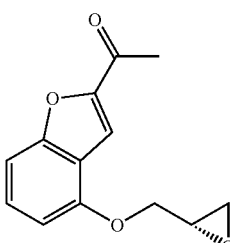
71

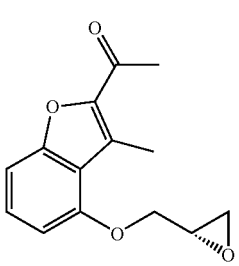
72

Starting Material Synthesis Example 73

N'-(4-methoxybenzo(b)furan-2-ylcarbonyl)propionohydrazide

To a solution (200 ml) of (4-methoxybenzo(b)furan-2-ylcarbonyl)hydrazide (8.5 g) in THF was added propionic anhydride (8.1 g) and the mixture was stirred at room temperature for 1 hr. The reaction mixture was concentrated under reduced pressure and the residue was crystallized from diisopropyl ether, collected by filtration and dried to give the title compound (8.3 g) as brown crystals.

$^1$H-NMR(DMSO-$d_6$)δ:1.05(t, J=7.8, 3H), 2.19(q, J=7.8, 2H), 3.93(s, 3H), 6.86(d, J=7.8, 1H), 7.25(d, J=8.3, 1H), 7.41(t, J=8.3, 1H), 7.62(s, 1H), 9.89(s, 1H), 10.46(s, 1H)

Starting Material Synthesis Example 74

2-(4-methoxybenzo(b)furan-2-yl)-5-ethyl-1,3,4-oxadiazole

N'-(4-Methoxybenzo(b)furan-2-ylcarbonyl)propionohydrazide (8.3 g) obtained in Starting Material Synthesis Example 73 was added to phosphorus oxychloride (60 ml) and the mixture was stirred at 90° C. for 1 hr. After cooling, the reaction mixture was poured into ice water and extracted with ethyl acetate. After washing with water, the organic layer was dried over anhydrous magnesium sulfate and concentrated under reduced pressure to give the title compound (4.5 g) as yellow crystals.

$^1$H-NMR(CDCl$_3$)δ:1.46(t, J=7.8, 3H), 2.99(q, J=7.8, 2H), 3.97(s, 3H), 6.72(d, J=7.8, 1H), 7.22(d, J=8.3, 1H), 7.36(t, J=8.3, 1H), 7.57(s, 1H)

Starting Material Synthesis Example 75

2-(4-hydroxybenzo(b)furan-2-yl)-5-ethyl-1,3,4-oxadiazole

To a solution (60 ml) of 2-(4-methoxybenzo(b)furan-2-yl)-5-ethyl-1,3,4-oxadiazole (4.5 g) obtained in Starting Material Synthesis Example 74 in methylene chloride was added boron tribromide (11.8 ml), and the mixture was stirred at room temperature for 2 hr. The reaction mixture was poured into ice water and stirred for 1 hr and extracted with a mixed solvent of chloroform-methanol (2:1). After washing with water, the organic layer was dried over anhydrous magnesium sulfate and concentrated under reduced pressure to give the title compound (3.1 g) as pale-yellow crystals.

$^1$H-NMR(DMSO-$d_6$)δ:1.33(t, J=7.8, 3H), 2.96(q, J=7.8, 2H), 6.71(d, J=8.3, 1H), 7.16(d, J=8.8, 1H), 7.29(t, J=8.3, 1H), 7.69(s, 1H), 10.37(s, 1H)

Starting Material Synthesis Example 76

(S)-2-(4-glycidyloxybenzo(b)furan-2-yl)-5-ethyl-1,3,4-oxadiazole

By the reactions in the same manner as in Starting Material Synthesis Example 1 using 2-(4-hydroxybenzo(b)furan-2-yl)-5-ethyl-1,3,4-oxadiazole (3.1 g) obtained in Starting Material Synthesis Example 75, (S)-glycidyl nosylate (3.5 g) and potassium carbonate (5.6 g), the title compound (3.8 g) was obtained as pale-yellow crystals.

$^1$H-NMR(CDCl$_3$): 1.47(t, J=7.8, 3H), 2.83(dd, J=3.9, 2.4, 1H), 2.96(t, J=3.9, 1H), 2.99(q, J=7.8, 2H), 3.42–3.48(m, 1H), 4.11(dd, J=11.3, 5.9, 1H), 4.42(dd, J=11.3, 3.0, 1H), 6.72(d, J=8.3, 1H), 7.25(d, J=8.3, 1H), 7.32(t, J=8.3, 1H), 7.61(s, 1H)

Starting Material Synthesis Example 77

5-(4-methoxybenzo(b)furan-2-yl)-3-methylisoxazole

To a solution (160 ml) of acetone oxime (5.0 g) in THF was added dropwise n-butyllithium (1.6 M hexane solution) over 15 min under ice-cooling and the mixture was stirred for 1 hr. Thereto was added dropwise a solution (60 ml) of methyl 4-methoxybenzo(b)furan-2-carboxylate (6.7 g) in THF and the mixture was stirred at room temperature for 2 hr. The reaction mixture was poured into ice water, and conc. sulfuric acid (4 ml) was added carefully. The mixture was stirred for 20 min more. The aqueous layer was neutralized with sodium hydrogencarbonate and extracted with ethyl acetate. After washing with water, the organic layer was dried over anhydrous magnesium sulfate and the solvent was evaporated under reduced pressure to give the title compound (3.0 g) as yellow crystals.
$^1$H-NMR(CDCl$_3$)δ:2.38(s, 3H), 3.96(s, 3H), 6.46(s, 1H), 6.69(d, =7.8, 1H), 7.15(d, J=8.3, 1H), 7.29(t, J=8.3, 1H), 7.32(s, 1H)

Starting Material Synthesis Example 78

5-(4-hydroxybenzo(b)furan-2-yl)-3-methylisoxazole

By the reactions in the same manner as in Starting Material Synthesis Example 5 using 5-(4-methoxybenzo(b)furan-2-yl)-3-methylisoxazole (3.0 g) and boron tribromide (7.6 ml), the title compound (2.6 g) was obtained as pale-yellow crystals.
$^1$H-NMR(DMSO-d$_6$)δ:2.30(s, 3H), 6.68(d, J=7.8, 1H), 6.85(s, 1H) 7.10(d, J=8.3, 1H), 7.22(t, J=8.3, 1H), 7.49(s, 1H)

Starting Material Synthesis Example 79

(S)-5-(4-glycidyloxybenzo(b)furan-2-yl)-3-methyl-isoxazole

By the reactions in the same manner as in Starting Material Synthesis Example 1 using 5-(4-hydroxybenzo(b)furan-2-yl)-3-methylisoxazole (2.6 g), (S)-glycidyl nosylate (3.1 g) and potassium carbonate (5.0 g), the title compound (2.8 g) was obtained as brown crystals.
$^1$H-NMR(CDCl$_3$)δ:2.82(dd, J=4.9, 2.4, 1H), 2.96(t, J=4.9, 1H), 3.43–3.46(m, 1H), 4.11(dd, J=11.2, 5.4, 1H), 4.39(dd, J=11.2, 3.0, 1H), 6.49(s, 1H), 6.70(d, J=8.3, 1H), 7.17(d, J=8.3, 1H), 7.28(t, J=8.3, 1H), 7.36(s, 1H)

Starting Material Synthesis Example 80

2-(4-methoxybenzo(b)furan-2-yl)-5-methyl-1,3,4-thiadiazole

To a solution (50 ml) of N'-(4-methoxybenzo(b)furan-2-ylthiocarbonyl)acetohydrazide (1.1 g) in toluene was added methanesulfonic acid (1.0 ml) and the mixture was stirred at 80° C. for 30 min. The reaction mixture was concentrated under reduced pressure and the residue was dissolved in ethyl acetate and aqueous potassium carbonate solution, followed by partitioning. After washing with water, the organic layer was dried over anhydrous magnesium sulfate and the solvent was evaporated under reduced pressure to give the title compound (0.82 g) as yellow crystals.
$^1$H-NMR(CDCl$_3$)δ:2.85(s, 3H), 3.97(s, 3H), 6.70(d, J=7.8, 1H) 7.18(d, J=8.3, 1H), 7.32(t, J=8.3, 1H), 7.57(s, 1H)

Starting Material Synthesis Example 81

2-(4-hydroxybenzo(b)furan-2-yl)-5-methyl-1,3,4-thiadiazole

By the reactions in the same manner as in Starting Material Synthesis Example 5 using 2-(4-methoxybenzo(b)furan-2-yl)-5-methyl-1,3,4-thiadiazole (0.98 g) and boron tribromide (2.3 ml), the title compound (0.89 g) was obtained as pale-yellow crystals.
$^1$H-NMR(DMSO-d$_6$)δ:2.80(s, 3H), 6.70(d, J=7.3, 1H), 7.13(d, J=8.3, 1H), 7.25(t, J=8.3, 1H), 7.67(s, 1H)

Starting Material Synthesis Example 82

(S)-2-(4-glycidyloxybenzo(b)furan-2-yl)-5-methyl-1,3,4-thiadiazole

By the reactions in the same manner as in Starting Material Synthesis Example 1 using 2-(4-hydroxybenzo(b)furan-2-yl)-5-methyl-1,3,4-thiadiazole (1.1 g), (S)-glycidyl nosylate (1.2 g) and potassium carbonate (3.0 g), the title compound (1.0 g) was obtained as yellow crystals.
$^1$H-NMR(CDCl$_3$)δ:2.82(dd, J=4.9, 3.0, 1H), 2.96(t, J=4.9, 1H), 3.42–3.46(m, 1H), 4.13(dd, J=10.8, 5.9, 1H), 4.40(dd, J=10.8, 3.0, 1H), 6.71(d, J=7.8, 1H), 7.20(d, J=8.3, 1H), 7.31(t, J=8.3, 1H), 7.61(s, 1H)

Starting Material Synthesis Example 83

N-propargyl-4-methoxybenzo(b)furan-2-carboxamide

4-Methoxybenzo(b)furan-2-carboxylic acid (44.0 g) and propargylamine (12 g) were dissolved in dimethylformamide (200 ml), and WSC (48.0 g), HOBt (43.0 g) and triethylamine (50 ml) were added thereto at room temperature. The mixture was stirred for 4 hr. The reaction mixture was poured into ice water and extracted with ethyl acetate. The organic layer was washed with saturated aqueous solution of ammonium chloride, dried over anhydrous sodium sulfate and concentrated under reduced pressure to give the title compound as yellow crystals (45.0 g).
$^1$H-NMR(CDCl$_3$)δ:3.32(s, 1H), 3.92(s, 3H), 4.06(m, 2H), 6.65(d, J=7.8, 1H), 7.18(d, J=7.8, 1H), 7.26(t, J=7.8, 1H), 7.36(s, 1H), 8.86(m, 1H)

Starting Material Synthesis Example 84

4-methoxy-2-(5-methyl-1,3-oxazol-2-yl)benzo(b)furan

To a solution (200 ml) of N-propargyl-4-methoxybenzo(b)furan-2-carboxamide (45.0 g) obtained in Starting Material Synthesis Example 83 in acetic acid was added mercury acetate (7.0 g), and the mixture was refluxed under heating for 3 hr. After cooling, the solvent was evaporated under reduced pressure and water was added. The mixture was neutralized with potassium carbonate and extracted with ethyl acetate. The solvent was evaporated under reduced pressure and the residue was purified by silica gel column chromatography (chloroform) to give the title compound (15.0 g) as yellow crystals.
$^1$H-NMR(CDCl$_3$)δ:2.42(s, 3H), 3.96(s, 3H), 6.70(d, J=7.8, 1H) 6.90(s, 1H), 7.20(d, J=7.8, 1H), 7.29(t, J=7.8, 1H), 7.38(s, 1H)

Starting Material Synthesis Example 85

2-(4-hydroxybenzo(b)furan-2-yl)-5-methyloxazole

To a solution (100 ml) of 4-methoxy-2-(5-methyl-1,3-oxazol-2-yl)benzo(b)furan (15.0 g) obtained in Starting Material Synthesis Example 84 in dichloromethane was added dropwise boron tribromide (14 ml) under ice-cooling. The mixture was stirred at room temperature for 3 hr and poured into ice water. The mixture was stirred at room temperature for 3 more hr. The crystals were collected by filtration and dissolved in ethyl acetate. 1N HCl was added and the mixture was stirred one day. The organic layer was washed with saturated aqueous solution of sodium hydrogencarbonate, dried over anhydrous sodium sulfate and concentrated under reduced pressure to give the title compound (11.0 g) as yellow crystals.

$^1$H-NMR(DMSO-d$_6$)δ:2.41(s, 3H), 6.68(d, J=7.8, 1H), 7.04(s, 1H), 7.10(d, J=7.8, 1H), 7.21(t, J=7.8, 1H), 7.45(s, 1H), 10.17(bs, 1H)

The structural formulas of the compounds obtained in Starting Material Synthesis Examples 73 to 85 are shown in the following.

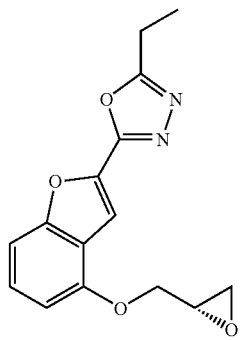

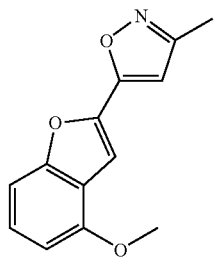

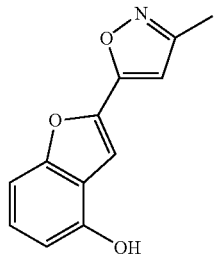

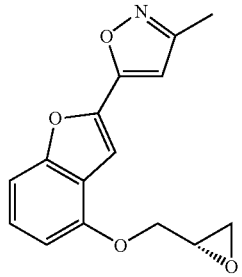

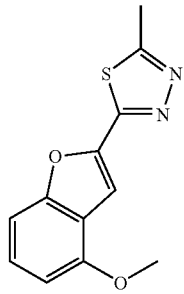

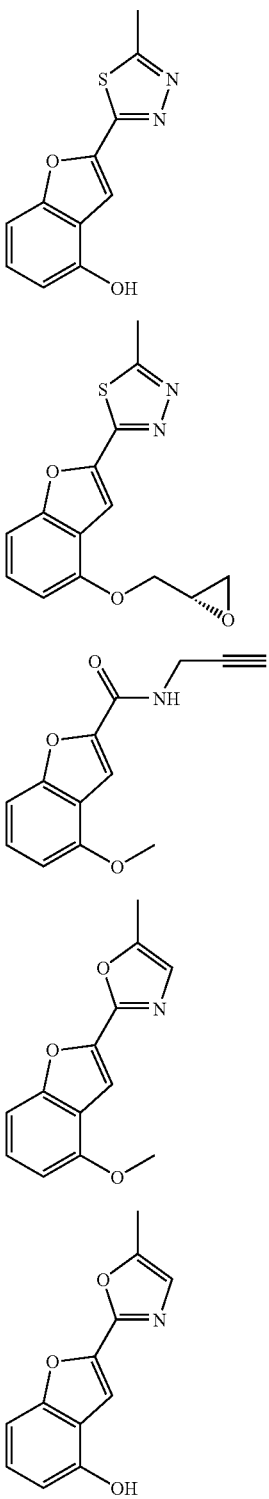

Starting Material Synthesis Example 86

4-methoxy-2-(trimethylstannyl)benzo(b)furan

To a solution of 4-methoxybenzo(b)furan (2.50 g) in THF (50 ml) was added n-butyllithium (1.54 M hexane solution) (16.5 ml) at −78° C. and the mixture was stirred at the same temperature for 20 min. To this solution was added trimethyltin chloride (5.00 g) and the mixture was further stirred at the same temperature for 1 hr. The reaction mixture was warmed to room temperature and water (200 ml) was added. The mixture was extracted with ethyl acetate, and the obtained organic layer was washed with water and saturated brine and dried over magnesium sulfate. This solution was concentrated under reduced pressure to give the title compound (5.86 g) as pale-yellow crystals.

$^1$H-NMR(CDCl$_3$)δ:0.35(s, 3H), 3.90(s, 3H), 6.58(d, J=5.0, 1H) 6.98(s, 1H), 7.10–7.40(m, 2H)

Starting Material Synthesis Example 87

2-(5-ethylthiophen-2-yl)-4-methoxybenzo(b)furan

To a solution of 4-methoxy-2-(trimethylstannyl)benzo(b) furan (3.00 g) and 2-bromo-5-ethylthiophene (1.84 g) in THF (25 ml) was added bistriphenylphosphinepalladium dichloride (224 mg), and the mixture was stirred with refluxing overnight. After cooling, ethyl acetate was added to the reaction mixture and the mixture was filtered through celite. The filtrate was washed with water and saturated brine, and the organic layer was dried over magnesium sulfate and concentrated under reduced pressure. The residue was purified by silica gel column chromatography to give the title compound (1.04 g) as a yellow oil.

$^1$H-NMR(CDCl$_3$)δ:1.32(t, J=8.0, 3H), 2.84(q, J=8,2H), 3.93(s, 3H), 6.60–6.65(m, 2H), 6.75(d, J=2.0, 1H), 6.85(s, 1H), 7.15(d, J=7.0, 1H), 7.18–7.23(m, 2H)

Starting Material Synthesis Example 88

2-(5-ethylthiophen-2-yl)-4-hydroxybenzo(b)furan

By the reactions in the same manner as in Starting Material Synthesis Example 5 using 2-(5-ethylthiophen-2-yl)-4-methoxybenzo(b)furan (1.00 g) and boron tribromide (1.0 ml), the title compound (774 mg) was obtained as colorless crystals, melting point 87–90° C.

Starting Material Synthesis Example 89

(S)-2-(5-ethylthiophen-2-yl)-4-glycidyloxybenzo(b) furan

By the reactions in the same manner as in Starting Material Synthesis Example 1 using 2-(5-ethylthiophen-2-yl)-4-hydroxybenzo(b)furan (750 mg), (S)-glycidyl nosylate (875 mg) and potassium carbonate (1.27 g), a crude product of the title compound was quantitatively obtained as a yellow oil.

$^1$H-NMR(CDCl$_3$)δ:1.32(t, J=8.0, 3H), 2.83(dd, J=3.9, 2.4, 1H), 2.96(t, J=3.9, 1H), 2.75–2.95(m, 2H), 3.35–3.45 (m, 1H), 4.05(dd, J=11.0, 6.0, 1H), 4.34(dd, J=11.0, 3.0, 1H), 6.62(dd, J=8.0, 1.0, 1H), 6.75(d, J=1.0, 1H), 6.88(s, 1H), 7.10–7.20(m, 2H)

Starting Material Synthesis Example 90

4-methoxy-2-(1-methylimidazol-2-yl)benzo(b)furan

By the reactions in the same manner as in Starting Material Synthesis Example 87 using 4-methoxy-2-(trimethylstannyl)benzo(b)furan (5.26 g), 2-bromo-1-methylimidazole (2.72 g) and bistriphenylphosphinepalladium dichloride (593 mg), the title compound (2.06 g) was obtained as a yellow oil.

$^1$H-NMR(CDCl$_3$)δ:3.97(s, 6H), 6.69(d, J=8.0, 1H), 7.22 (d, J=8.0, 1H), 6.96(s, 1H), 7.24(d, J=8.0, 1H), 7.20–7.35(m, 4H)

Starting Material Synthesis Example 91

4-hydroxy-2-(1-methylimidazol-2-yl)benzo(b)furan

By the reactions in the same manner as in Starting Material Synthesis Example 5 using 4-methoxy-2-(1-methylimidazol-2-yl)benzo(b)furan (2.00 g) and boron tribromide (2.0 ml), the title compound (1.21 g) was obtained as pale-yellow crystals, melting point >265° C. (decomposition)

Starting Material Synthesis Example 92

(S)-4-glycidyloxy-2-(1-methylimidazol-2-yl)benzo(b)furan

By the reactions in the same manner as in Starting Material Synthesis Example 1 using 4-hydroxy-2-(1-methylimidazol-2-yl)benzo(b)furan (1.10 g), (S)-glycidyl nosylate (1.33 g) and potassium carbonate (2.13 g), a crude product of the title compound was quantitatively obtained as a pale-yellow oil.

$^1$H-NMR(CDCl$_3$)δ:2.75–2.80(m, 1H), 2.92(d, J=4.0, 2H), 3.42–3.45(m, 1H), 4.11(dd, J=11.0, 6.0, 1H), 4.37(dd, J=11.0, 2.0, 1H), 6.67(d, J=8.0, 1H), 6.95(s, 1H), 7.10–7.30 (m, 4H)

Starting Material Synthesis Example 93

N-propargyl-4-(methoxymethyloxy)benzo(b)thiophene-2-carboxamide

By the reactions in the same manner as in Starting Material Synthesis Example 83 using 4-(methoxymethyloxy)benzo(b)furan-2-carboxylic acid (10.0 g), propargylamine (2.31 g), WSC (8.87 g), HOBt (7.71 g) and triethylamine (8.76 ml), the title compound (7.15 g) was obtained as pale-brown crystals.

$^1$H-NMR(CDCl$_3$)δ:3.31(s, 1H), 3.45(s, 3H), 4.06(br.s, 2H), 5.38(s, 2H), 7.04(d, J=8.0, 1H), 7.38(t, J=8.0, 1H), 7.60(d, J=8.0, 1H), 8.25(s, 1H), 9.26(m, 1H)

Starting Material Synthesis Example 94

4-hydroxy-2-(5-methyloxazol-2-yl)benzo(b)thiophene

By the reactions in the same manner as in Starting Material Synthesis Example 5 using N-propargyl-4-(methoxymethyloxy)benzo(b)thiophene-2-carboxamide (6.00 g) and mercury acetate (765 mg), the title compound (2.41 g) was obtained as yellow crystals, melting point 188–189° C.

Starting Material Synthesis Example 95

(S)-4-glycidyloxy-2-(5-methyloxazol-2-yl)benzo(b)thiophene

By the reactions in the same manner as in Starting Material Synthesis Example 1 using 4-hydroxy-2-(5-methyloxazol-2-yl)benzo(b)thiophene (2.20 g), (S)-glycidyl nosylate (2.38 g) and potassium carbonate (3.18 g), a crude product of the title compound was quantitatively obtained as pale-yellow crystals.

$^1$H-NMR(CDCl$_3$)δ:2.84(dd, J=5.0, 3.0, 1H), 2.96(t, J=5.0, 1H), 3.40–3.48(m, 1H), 4.12(dd, J=11.0, 6.0, 1H), 4.39(dd, J=11.0, 2.0, 1H), 6.76(d, J=8.0, 1H), 6.85(s, 1H), 7.33(d, J=8.0, 1H), 7.45(d, J=8.0, 1H), 8.03(s, 1H)

Starting Material Synthesis Example 96

2-(4,4-dimethyloxazolin-2-yl)-4-methoxybenzo(b)furan

To a solution of 4-methoxybenzo(b)furan-2-carboxylic acid (15.0 g) in dichloromethane (300 ml) were added DMF (6 ml) and thionyl chloride (17.1 ml), and the mixture was stirred with refluxing for 2 hr. The solvent was evaporated under reduced pressure to give acid chloride.

This acid chloride was dissolved in dichloromethane (150 ml) and added dropwise to a solution of 2-amino-2-methyl-1-propanol (10.4 g) in dichloromethane (150 ml) at 0° C. The mixture was stirred at room temperature for 2 hr and saturated sodium hydrogencarbonate (500 ml) was added. The mixture was extracted with chloroform and the organic layer was washed with water and saturated brine and dried over magnesium sulfate. The solvent was evaporated under reduced pressure and the residue was purified by silica gel column chromatography to give an amide compound (14.7 g).

To the obtained amide compound was added thionyl chloride (75 ml) and the mixture was stirred at room temperature for 5 hr and poured into saturated aqueous solution of sodium hydrogencarbonate (500 ml). 10% Sodium hydroxide was added to this mixed solution until it reached pH 12 and the mixture was extracted with ethyl acetate. The organic layer was washed with water and saturated brine and dried over magnesium sulfate. The solvent was evaporated under reduced pressure to give the title compound (7.81 g) as a yellow oil.

$^1$H-NMR(CDCl$_3$)δ:1.40(s, 6H), 3.92(s, 3H), 4.12(s, 2H), 6.65(d, J=8.0, 1H), 7.15(d, J=8.0, 1H), 7.28(t, J=8.0, 1H), 7.33(s, 1H)

Starting Material Synthesis Example 97

2-(4,4-dimethyloxazolin-2-yl)-4-hydroxybenzo(b)furan

By the reactions in the same manner as in Starting Material Synthesis Example 5 using 2-(4,4-dimethyloxazolin-2-yl)-4-methoxybenzo(b)furan (6.11 g) and boron tribromide (6.11 ml), the title compound (5.03 g) was obtained as pale-yellow crystals, melting point 187–188° C.

The structural formulas of the compounds obtained in Starting Material Synthesis Examples 86 to 97 are shown in the following.

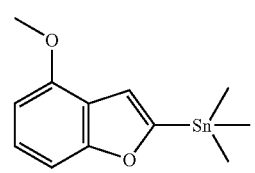

86

-continued

87 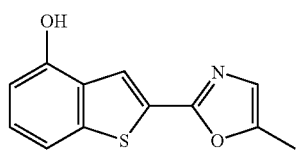

88 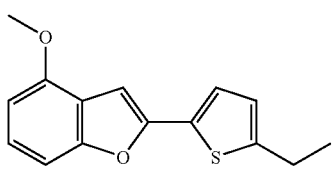

89 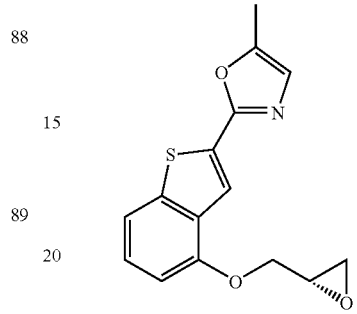

90 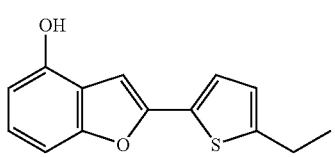

91 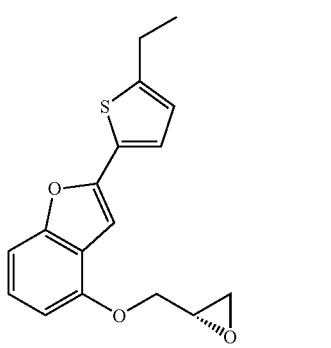

92 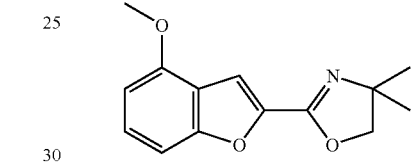

93 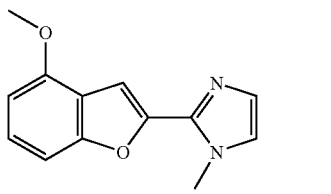

94 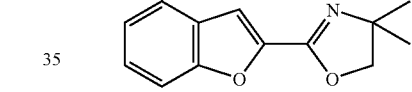

95 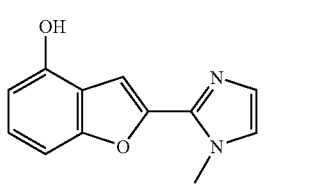

96 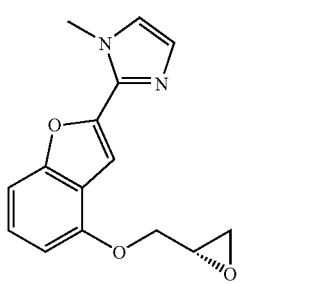

97 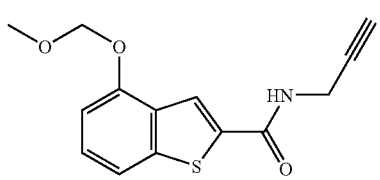

Starting Material Synthesis Example 98

(S)-4-glycidyloxy-2-(4,4-dimethyloxazolin-2-yl)benzo(b)furan

By the reactions in the same manner as in Starting Material Synthesis Example 1 using 2-(4,4-dimethyloxazolin-2-yl)-4-hydroxybenzo(b)furan (1.50 g), (S)-glycidyl nosylate (1.68 g) and potassium carbonate (2.69 g), a crude product of the title compound was quantitatively obtained as a pale-yellow oil.

$^1$H-NMR(CDCl$_3$)δ:1.40(s, 6H), 2.75–2.80(m, 1H), 2.92(t, J=4.0, 1H), 3.35–3.45(m, 1H), 4.00–4.20(m, 1H), 4.13(s, 2H), 4.36(dd, J=11.0, 2.0, 1H), 6.65(d, J=8.0, 1H), 7.18(d, J=8.0, 1H), 7.28(t, J=8.0, 1H), 7.37(s, 1H)

Starting Material Synthesis Example 99

2-(ethylsulfonyl)-4-methoxybenzo(b)furan

To a solution of 4-methoxybenzo(b)furan (5.00 g) in THF (40 ml) was added n-butyllithium (1.54 M hexane solution) (24.1 ml) at −78° C., and the mixture was stirred at the same temperature for 30 min. To this solution was added sulfur (1.19 g) and the mixture was stirred further at the same temperature for 30 min. Then, bromoethane (4.16 ml) was added and this reaction mixture was stirred at room temperature for 1 hr. A saturated aqueous solution of ammonium chloride (100 ml) was added, and the mixture was extracted with ethyl acetate. The obtained organic layer was washed with water and saturated brine and dried over magnesium sulfate. This solution was concentrated under reduced pressure to give a sulfide compound (3.50 g).

To a solution of this sulfide compound (3.50 g) in dichloromethane (50 ml) was added m-chloroperoxybenzoic acid (70%, 9.13 g) at 0° C., and the mixture was stirred at room temperature for 1 hr. Saturated sodium hydrogencarbonate (50 ml) and saturated sodium thiosulfate (50 ml) were added to the reaction mixture and the mixture was extracted with ethyl acetate. The obtained organic layer was washed with water and saturated brine and dried over magnesium sulfate. The solvent was evaporated under reduced pressure and the residue was purified by silica gel column chromatography to give the title compound (3.53 g) as pale-brown crystals.

$^1$H-NMR(CDCl$_3$)δ:1.34(t, J=8.0, 1H), 3.29(q, J=8.0, 1H), 3.94(s, 3H), 6.72(d, J=8.0, 1H), 7.16(d, J=8, 1H), 7.40(t, J=8.0, 1H), 7.61(s, 1H)

Starting Material Synthesis Example 100

2-(ethylsulfonyl)-4-hydroxybenzo(b)furan

By the reactions in the same manner as in Starting Material Synthesis Example 5 using 2-(ethylsulfonyl)-4-methoxybenzo(b)furan (3.50 g) and boron tribromide (7.0 ml), the title compound (2.85 g) was obtained as colorless crystals, melting point 145–147° C.

Starting Material Synthesis Example 101

(S)-2-(ethylsulfonyl)-4-glycidyloxybenzo(b)furan

By the reactions in the same manner as in Starting Material Synthesis Example 1 using 2-(ethylsulfonyl)-4-hydroxybenzo(b)furan (2.75 g), (S)-glycidyl nosylate (3.48 g) and potassium carbonate (5.05 g), a crude product of the title compound (3.62 g) was obtained as a pale-yellow oil.

$^1$H-NMR(CDCl$_3$)δ:1.34(t, J=8.0, 1H), 2.79(dd, J=4.0, 2.0, 2H), 2.94(t, J=4.0, 1H), 3.29(q, J=8.0, 1H), 3.35–3.45 (m, 1H), 4.08(dd, J=10.0, 4.0, 2H), 4.39(dd, J=10.0, 2.0, 1H), 6.72(d, J=8.0, 1H), 7.18(d, J=8.0, 1H), 7.39(t, J=8.0, 1H), 7.65(s, 1H)

Starting Material Synthesis Example 102

2-(N,N-dimethylsulfamoyl)-4-methoxybenzo(b)furan

To a solution of 4-methoxybenzo(b)furan (5.00 g) in THF (40 ml) was added n-butyllithium (1.54 M hexane solution, 24.1 ml) at −78° C. and the mixture was stirred at the same temperature for 30 min. To this solution was added sulfuryl chloride (9.13 g) and the mixture was stirred further at 0° C. for 1 hr. The reaction mixture was concentrated under reduced pressure and the condensate was dissolved in acetone (30 ml). This was added dropwise at room temperature to a mixed solution of aqueous dimethylamine solution (50%, 20 g) and acetone (50 ml), and the mixture was stirred at room temperature for 1 hr and extracted with ethyl acetate. The obtained organic layer was washed with water and saturated brine and dried over magnesium sulfate. The solvent was evaporated under reduced pressure and the residue was purified by silica gel column chromatography to give the title compound (1.32 g) as a yellow oil.

$^1$H-NMR(CDCl$_3$)δ:2.88(s, 6H), 3.94(s, 3H), 6.71(d, J=8.0, 1H), 7.14(d, J=8.0, 1H), 7.35(t, J=8.0, 1H), 7.45(s, 1H)

Starting Material Synthesis Example 103

2-(N,N-dimethylsulfamoyl)-4-hydroxybenzo(b)furan

By the reactions in the same manner as in Starting Material Synthesis Example 5 using 2-(N,N-dimethylsulfamoyl)-4-methoxybenzo(b)furan (1.30 g) and boron tribromide (2.6 ml), the title compound (1.20 g) was obtained as colorless crystals, melting point 150–153° C.

Starting Material Synthesis Example 104

(S)-2-(N,N-dimethylsulfamoyl)-4-glycidyloxybenzo(b)furan

By the reactions in the same manner as in Starting Material Synthesis Example 1 using 2-(N,N-dimethylsulfamoyl)-4-methoxybenzo(b)furan (1.10 g), (S)-glycidyl nosylate (1.30 g) and potassium carbonate (1.89 g), a crude product of the title compound was quantitatively obtained as a pale-yellow oil.

$^1$H-NMR(CDCl$_3$)δ:2.80(dd, J=4.0, 1.0, 2H), 2.88(s, 6H), 2.94(dd, J=4.0, 1.0, 1H), 3.35–3.45(m, 1H), 4.07(dd, J=11.0, 4.0, 2H), 4.39(dd, J=11.0, 1.0, 1H), 6.71(d, J=8.0, 1H), 7.16(d, J=8.0, 1H), 7.35(t, J=8.0, 1H), 7.47(s, 1H)

Starting Material Synthesis Example 105

N-(2-oxobutyl)-4-methoxybenzo(b)furan-2-carboxamide

To a solution of 4-methoxybenzo(b)furan-2-carboxylic acid (10.0 g) in dichloromethane (100 ml) were added DMF (4 ml) and thionyl chloride (11.4 ml), and the mixture was stirred with refluxing for 2 hr. The solvent was evaporated under reduced pressure to give acid chloride.

This acid chloride was dissolved in THF (50 ml) and added dropwise to a solution of 1-amino-2-butanol (10.0 g) in THF (130 ml) at 0° C. The mixture was stirred at room temperature for 3 hr and water (200 ml) was added. The mixture was extracted with ethyl acetate and the organic layer was washed with water and saturated brine and dried over magnesium sulfate. The solvent was evaporated under reduced pressure and purified by silica gel column chromatography to give an amide compound (7.48 g) as a brown oil.

A solution of the obtained amide compound (3.00 g) in dichloromethane (20 ml) was added dropwise to a suspension of pyridinium chlorochromate (7.39 g) and molecular sieve (4A)(7.50 g) in dichloromethane (120 ml) at room temperature, and the mixture was stirred at room temperature for 2 hr. Ether (300 ml) was added to the reaction mixture and the mixture was dried over magnesium sulfate and filtered through celite. The filtrate was concentrated under reduced pressure and purified by silica gel column chromatography (chloroform-methanol) to give the title compound (2.14 g) as a yellow oil.

$^1$H-NMR(CDCl$_3$)δ:1.15(t, J=8.0, 3H), 2.54(q, J=8.0, 2H), 3.47(d, J=2.0, 1H), 3.94(s, 3H), 4.35(d, J=2.0, 2H), 6.66(d, J=8.0, 1H), 7.12(d, J=8.0, 1H), 7.32(t, J=8.0, 1H), 7.55(s, 1H)

Starting Material Synthesis Example 106

2-(5-ethyloxazol-2-yl)-4-methoxybenzo(b)furan

To a solution of N-(2-oxobutyl)-4-methoxybenzo(b)furan-2-carboxamide (2.00 g) in THF (60 ml) was added Burgess reagent (7.30 g), and the mixture was stirred with refluxing. Water (200 ml) was added to the reaction mixture and the mixture was extracted with ether. The organic layer was washed with water and saturated brine, and dried over magnesium sulfate. The solvent was evaporated under reduced pressure and the residue was purified by silica gel column chromatography to give the title compound (1.56 g) as colorless crystals, melting point 88–87° C.

Starting Material Synthesis Example 107

2-(5-ethyloxazol-2-yl)-4-hydroxybenzo(b)furan

By the reactions in the same manner as in Starting Material Synthesis Example 5 using 2-(5-ethyloxazol-2-yl)-4-methoxybenzo(b)furan (2.00 g) and boron tribromide (2.0 ml), the title compound (1.24 g) was obtained as colorless crystals.

$^1$H-NMR(CDCl$_3$)δ:1.33(t, J=8.0, 3H), 2.79(q, J=8.0, 2H), 6.04(br.s, 1H), 6.68(d, J=8.0, 1H), 6.92(s, 1H), 7.15(d, J=8.0, 1H), 7.21(t, J=8.0, 1H), 7.42(s, 1H)

Starting Material Synthesis Example 108

(S)-2-(5-ethyloxazol-2-yl)-4-glycidyloxybenzo(b)furan

By the reactions in the same manner as in Starting Material Synthesis Example 1 using 2-(5-ethyloxazol-2-yl)-4-hydroxybenzo(b)furan (1.10 g), (S)-glycidyl nosylate (1.24 g) and potassium carbonate (1.99 g), a crude product of the title compound (1.36 g) was obtained as pale-yellow crystals.

$^1$H-NMR(CDCl$_3$)δ:1.34(t, J=8.0, 3H), 2.70–2.2.85(m, 3H), 2.96(t, J=3.0, 1H), 3.40–3.45(m, 1H), 4.14(dd, J=11.0, 4.0, 2H), 4.40(dd, J=11.0, 1.0, 1H), 6.70(d, J=8.0, 1H), 6.91(s, 1H), 7.20–7.30(m, 2H), 7.44(s, 1H)

Starting Material Synthesis Example 109

N'-(4-hydroxybenzo(b)furan-2-ylcarbonyl)acetohydrazide

N'-(4-Methoxybenzo(b)furan-2-ylcarbonyl)acetohydrazide (4.0 g) obtained in Starting Material Synthesis Example 36 was dissolved in dichloromethane (40 ml) and boron tribromide (4.0 ml) was added dropwise while stirring under ice-cooling. Then the mixture was stirred at room temperature for 5 hr, and the reaction mixture was poured into ice water. The mixture was further stirred as it was at room temperature for 1 hr. The precipitated crystals were collected by filtration, dissolved in chloroform, washed with saturated aqueous solution of sodium hydrogencarbonate, dried over anhydrous sodium sulfate and concentrated under reduced pressure to give the title compound (2.5 g) as yellow crystals.

$^1$H-NMR(DMSO-d$_6$)δ:1.93(s, 3H), 6.69(d, J=7.8, 1H), 7.07(d, J=7.8, 1H), 7.27(t, J=7.8, 1H), 7.65(s, 1H), 9.92(s, 1H), 10.29(s, 1H), 10.43(s, 1H)

Starting Material Synthesis Example 110

N-ethoxalyl-N'-(4-methoxybenzofuran-2-ylcarbonyl)hydrazide

4-Methoxybenzo(b)furan-2-ylcarbonylhydrazide (9.0 g) was dissolved in dichloromethane (100 ml) and triethylamine (7.0 ml) and ethyl chloroglyoxylate (6.0 g) were added. The mixture was stirred at room temperature for 4 hr. The reaction mixture was poured into ice water and extracted with ethyl acetate. The organic layer was washed with water, dried over anhydrous sodium sulfate and concentrated under reduced pressure. The residue was purified by silica gel column chromatography (chloroform/methanol) to give the title compound (7.0 g) as pale-yellow crystals.

$^1$H-NMR(DMSO-d$_6$)δ:1.33(t, J=8.0, 3H), 3.95(s, 3H), 4.32(q, J=8.0, 2H), 6.87(d, J=7.8, 1H), 7.26(d, J=7.8, 1H), 7.44(t, J=7.8, 1H), 7.65(s, 1H), 10.82(s, 1H), 10.96(s, 1H)

Starting Material Synthesis Example 111

5-ethoxycarbonyl-2-(4-methoxybenzo(b)furan-2-yl)-1,3,4-oxadiazole

N-Ethoxalyl-N'-(4-methoxybenzofuran-2-ylcarbonyl)hydrazide (7.0 g) was dissolved in phosphorus oxychloride (20 ml) and the mixture was heated at 80° C. for 7 hr. Phosphorus oxychloride was evaporated under reduced pressure and water was added to the residue. The mixture was extracted with ethyl acetate. The organic layer was washed with saturated aqueous solution of sodium hydrogencarbonate, dried over anhydrous sodium sulfate and concentrated under reduced pressure. The residue was purified by silica gel column chromatography (chloroform) to give the title compound (5.0 g) as yellow crystals.

$^1$H-NMR(CDCl$_3$)δ:1.49(t, J=8.0, 3H), 3.98(s, 3H), 4.57 (d, J=8.0, 2H), 6.73(d, J=7.8, 1H), 7.24(d, J=7.8, 1H), 7.41(t, J=7.8, 1H), 7.79(s, 1H)

Starting Material Synthesis Example 112

5-ethoxycarbonyl-2-(4-hydroxybenzo(b)furan-2-yl)-1,3,4-oxadiazole

5-Ethoxycarbonyl-2-(4-methoxybenzo(b)furan-2-yl)-1,3,4-oxadiazole (5.0 g) was dissolved in dichloromethane (40 ml) and boron tribromide (4.0 ml) was added dropwise with stirring under ice-cooling. Then, the mixture was stirred at room temperature for 5 hr, and the reaction mixture was poured into ice water. The mixture was stirred at it was at room temperature for 1 hr. The crystals were collected by filtration and dissolved in chloroform. The solution was washed with saturated aqueous solution of sodium hydrogencarbonate, dried over anhydrous sodium sulfate and concentrated under reduced pressure to give the title compound (2.5 g) as yellow crystals.

$^1$H-NMR(DMSO-d$_6$)δ:1.40(t, J=8.0, 3H), 4.48(d, J=8.0, 2H), 6.74(d, J=7.8, 1H), 7.19(d, J=7.8, 1H), 7.35(t, J=7.8, 1H), 7.90(s, 1H), 10.46(bs, 1H)

The structural formulas of the compounds obtained in Starting Material Synthesis Examples 98 to 112 are shown in the following.

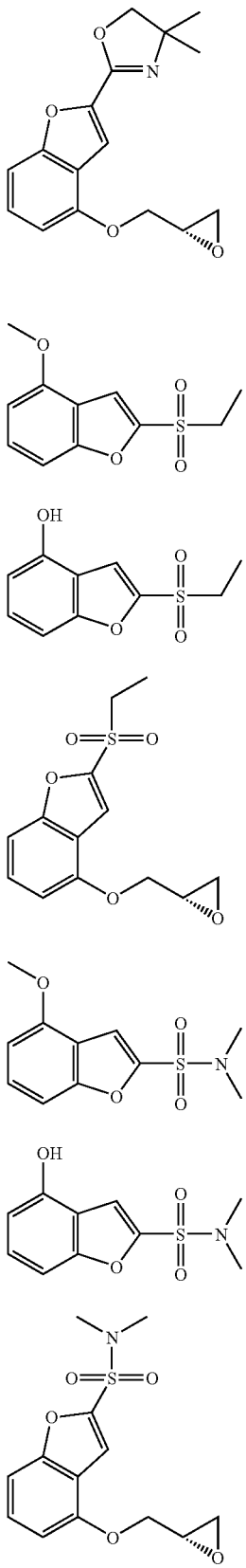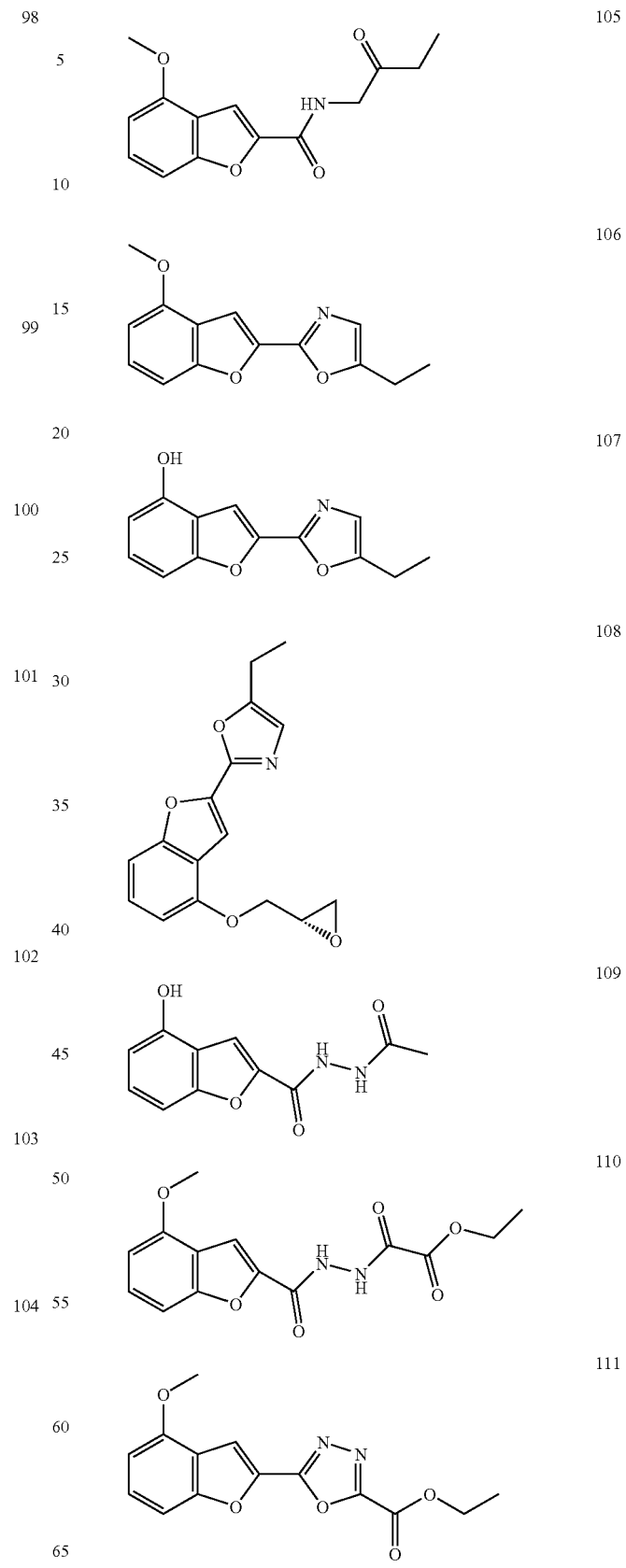

-continued

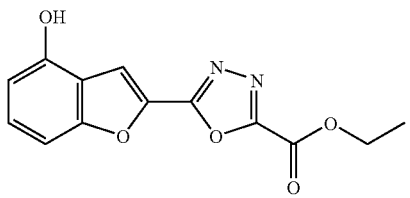

112

Starting Material Synthesis Example 113

5-(4-(methoxymethyloxy) benzo(b)furan-2-yl)-2,3-dihydro-1,3,4-oxadiazole-2-thione To a solution (80 ml) of 4-(methoxymethyloxy)benzo(b)furan-2-ylcarbohydrazide (5.3 g) in ethanol were added carbon disulfide (2.6 g) and potassium hydroxide (1.6 g) and the mixture was refluxed under heating for 7 hr. The reaction mixture was concentrated under reduced pressure and water was added to the residue. The pH was adjusted to 4 with ammonium chloride. After standing, the precipitated crystals were collected by filtration and dried to give the title compound (4.6 g) as yellow crystals.

$^1$H-NMR(CD$_3$OD)δ:3.44(s, 3H), 5.27(s, 2H), 6.90(d, J=7.8, 1H) 7.15(d, J=8.3, 1H), 7.25(t, J=7.8, 1H), 7.35(s, 1H)

Starting Material Synthesis Example 114

5-(4-(methoxymethyloxy)benzo(b)furan-2-yl)-2-methylthio-1,3,4-oxadiazole

To a suspension (40 ml) of sodium hydride (0.8 g) in THF was added dropwise a solution (30 ml) of 5-(4-(methoxymethyloxy)benzo(b)furan-2-yl)-2,3-dihydro-1,3,4-oxadiazole-2-thione (4.6 g) in DMF at room temperature, and the mixture was stirred for 40 min. To this reaction mixture was added dropwise methyl iodide at room temperature, and the mixture was further stirred for 1 hr. The reaction mixture was poured into ice water and extracted with ethyl acetate. The organic layer was washed with water and dried. The solvent was evaporated under reduced pressure to give the title compound (2.5 g) as brown crystals.

$^1$H-NMR(CDCl$_3$)δ:2.81(s, 3H), 3.54(s, 3H), 5.34(s, 2H), 6.97(d, J=7.8, 1H), 7.27(d, J=8.3, 1H), 7.35(t, J=7.8, 1H), 7.58(s, 1H)

Starting Material Synthesis Example 115

5-(4-hydroxybenzo(b)furan-2-yl)-2-methylthio-1,3,4-oxadiazole

To a solution (20 ml) of 5-(4-(methoxymethyloxy)benzo(b)furan-2-yl)-2-methylthio-1,3,4-oxadiazole (1.0 g) in THF was added 2N aqueous hydrochloric acid (3.0 ml), and the mixture was refluxed under heating for 7 hr. The solvent was evaporated under reduced pressure to give the title compound (0.62 g) as yellow crystals.

$^1$H-NMR(DMSO-d$_6$)δ:2.78(s, 3H), 6.71(d, J=7.9, 1H), 7.16(d, J=8.3, 1H), 7.29(t, J=8.3, 1H), 7.71(s, 1H), 10.42 (brs, 1H)

Starting Material Synthesis Example 116

5-(4-(methoxymethyloxy)benzo(b)furan-2-yl)-2,3-dihydro-1,3,4-oxadiazol-2-one

To a solution (20 ml) of 4-(methoxymethyloxy)benzo(b)furan-2-ylcarbohydrazide (1.0 g) in 1,2-dimethoxyethane were added triphosgene (1.0 g) and triethylamine (1.8 ml), and the mixture was stirred at room temperature for 20 min. The reaction mixture was poured into 2N saturated aqueous sodium hydroxide solution and soluble part of the organic layer was removed with ethyl acetate. The aqueous layer was made acidic with hydrochloric acid and extracted with ethyl acetate. This organic layer was washed with water and dried. The solvent was evaporated under reduced pressure to give the title compound (1.0 g) as white crystals.

$^1$H-NMR(DMSO-d$_6$)δ:3.43(s, 3H), 5.36(s, 2H), 7.00(d, J=7.8, 1H), 7.37(d, J=8.3, 1H), 7.40(t, J=7.8, 1H), 7.53(s, 1H)

Starting Material Synthesis Example 117

5-(4-(methoxymethyloxy)benzo(b)furan-2-yl)-2-methoxy-1,3,4-oxadiazole

To a suspension of sodium hydride (0.17 g) in DMF was added dropwise a solution (20 ml) of 5-(4-(methoxymethyloxy)benzo(b)furan-2-yl)-2,3-dihydro-1,3,4-oxadiazol-2-one (1.0 g) obtained in Starting Material Synthesis Example 116 in DMF at room temperature, and the mixture was stirred for 30 min. Thereto was added methyl iodide (0.26 ml), and the mixture was further stirred for 30 min. The reaction mixture was poured into ice water and extracted with ethyl acetate. The extract was washed with water and dried. The solvent was evaporated under reduced pressure to give the title compound (0.80 g) as pale-yellow crystals.

$^1$H-NMR(CDCl$_3$)δ:3.54(s, 3H), 3.55(s, 3H), 5.33(s, 2H), 6.97(d, J=7.8, 1H), 7.23(d, J=8.3, 1H), 7.34(t, J=7.8, 1H), 7.42(s, 1H)

Starting Material Synthesis Example 118

(S)-5-(4-glycidyloxybenzo(b)furan-2-yl)-2-methoxy-1,3,4-oxadiazole

To a solution (20 ml) of 5-(4-(methoxymethyloxy)benzo(b)furan-2-yl)-2-methoxy-1,3,4-oxadiazole (0.80 g) obtained in Starting Material Synthesis Example 117 in THF was added 2N hydrochloric acid (15 ml), and the mixture was refluxed under heating for 2 hr. The reaction mixture was concentrated under reduced pressure to give crude crystals of 5-(4-hydroxybenzo(b)furan-2-yl)-2-methoxy-1,3,4-oxadiazole. This was dissolved in DMF (30 ml) and (S)-glycidyl nosylate (0.83 g) and potassium carbonate (0.89 g) were added. The mixture was stirred at room temperature for 14 hr. This reaction mixture was poured into ice water, and the precipitated crystals were collected by filtration, washed with water and dried to give the title compound (0.50 g) as brown crystals.

$^1$H-NMR(DMSO-d$_6$)δ:2.81(dd, J=4.9, 2.5, 1H), 2.87(t, J=4.9, 1H) 3.35–3.46(m, 1H), 3.42(s, 3H), 4.04(dd, J=11.3, 5.9, 1H), 4.53(dd, J=11.3, 2.0, 1H), 6.92(d, J=8.3, 1H), 7.31(d, J=8.3, 1H), 7.41(t, J=8.3, 1H), 7.57(s, 1H)

Starting Material Synthesis Example 119

2-ethoxy-5-(4-(methoxymethyloxy)benzo(b)furan-2-yl)-1,3,4-oxadiazole

By the reactions in the same manner as in Starting Material Synthesis Example 117 using sodium hydride (0.37 g), 5-(4-(methoxymethyloxy)benzo(b)furan-2-yl)-2,3-dihydro-1,3,4-oxadiazol-2-one (2.0 g) and ethyl iodide (0.73 ml), the title compound (1.9 g) was obtained as pale-yellow crystals.

$^1$H-NMR(CDCl$_3$)δ:1.44(t, J=7.3, 3H), 3.54(s, 3H), 3.90 (q, J=7.3, 2H), 5.33(s, 2H), 6.97(d, J=7.8, 1H), 7.23(d, J=8.3, 1H), 7.32(t, J=7.8, 1H), 7.42(s, 1H)

Starting Material Synthesis Example 120

(S)-2-ethoxy-5-(4-glycidyloxybenzo(b)furan-2-yl)-1,3,4-oxadiazole

To a solution (40 ml) of 2-ethoxy-5-(4-(methoxymethyloxy)benzo(b)furan-2-yl)-1,3,4-oxadiazole (2.0 g) obtained in the same manner as in Starting Material Synthesis Example 119 in THF was added 2N hydrochloric acid (40 ml), and the mixture was refluxed under heating for 2 hr. The reaction mixture was concentrated under reduced pressure to give crude crystals of 2-ethoxy-5-(4-hydroxybenzo(b)furan-2-yl)-1,3,4-oxadiazole. This was dissolved in DMF (40 ml) and (S)-glycidyl nosylate (1.7 g) and potassium carbonate (3.5 g) were added. The mixture was stirred at room temperature for 14 hr. This reaction mixture was poured into ice water, and after extraction with ethyl acetate, the extract was washed with water and dried. The solvent was evaporated under reduced pressure and the residue was purified by silica gel column chromatography (chloroform/ethyl acetate) to give the title compound (1.0 g) as white crystals.

$^1$H-NMR(CDCl$_3$)δ:1.44(t, J=7.3, 3H), 2.81(dd, J=4.9, 2.9, 1H), 2.97(t, J=4.3, 1H), 3.42–3.46(m, 1H), 3.90(q, J=7.3, 2H), 4.10(dd, J=11.2, 5.9, 1H), 4.40(dd, J=11.2, 2.9, 1H), 6.72(d, J=8.3, 1H), 7.21(d, J=8.3, 1H), 7.34(t, J=8.3, 1H), 7.44(s, 1H)

Starting Material Synthesis Example 121

2-(1-methylethyloxy)-5-(4-(methoxymethyloxy)benzo(b)furan-2-yl)-1,3,4-oxadiazole By the reactions in the same manner as in Starting Material Synthesis Example 117 using sodium hydride (0.28 g), 5-(4-(methoxymethyloxy)benzo(b)furan-2-yl)-2,3-dihydro-1,3,4-oxadiazol-2-one (1.5 g) and 2-iodopropane (1.1 g), the title compound (1.5 g) was obtained as brown crystals.

$^1$H-NMR(CDCl$_3$)δ:1.47(d, J=6.3, 6H), 3.54(s, 3H), 4.44 (penth, J=6.3, 1H), 5.33(s, 2H), 6.96(d, J=7.8, 1H), 7.25(d, J=8.3, 1H), 7.33(t, J=7.8, 1H), 7.42(s, 1H)

Starting Material Synthesis Example 122

(S)-2-(1-methylethyloxy)-5-(4-glycidyloxybenzo(b)furan-2-yl)-1,3,4-oxadiazole

To a solution (30 ml) of 2-(1-methylethyloxy)-5-(4-(methoxymethyloxy)benzo(b)furan-2-yl)-1,3,4-oxadiazole (1.5 g) obtained in Starting Material Synthesis Example 121 in THF was added 4N hydrochloric acid (15 ml), and the mixture was refluxed under heating for 3 hr. The reaction mixture was concentrated under reduced pressure to give crude crystals of 2-(1-methylethyloxy)-5-(4-hydroxybenzo(b)furan-2-yl)-1,3,4-oxadiazole. This was dissolved in DMF (30 ml) and (S)-glycidyl nosylate (1.2 g) and potassium carbonate (3.2 g) were added. The mixture was stirred at room temperature for 5 hr. This reaction mixture was poured into ice water, and after extraction with ethyl acetate, the extract was washed with water and dried. The solvent was evaporated under reduced pressure and the residue was purified by silica gel column chromatography (chloroform/ethyl acetate) to give the title compound (1.3 g) as white crystals.

$^1$H-NMR(CDCl$_3$)δ:1.35(d, J=6.3, 6H), 2.81(dd, J=4.9, 2.9, 1H), 2.88(t, J=4.3, 1H), 3.40–3.42(m, 1H), 4.04(dd, J=11.7, 6.4, 1H), 4.30(penth, J=6.3, 1H), 4.53(dd, J=11.7, 1.9, 1H), 6.91(d, J=8.3, 1H), 7.33(d, J=7.8, 1H), 7.41(t, J=8.3, 1H), 7.55(s, 1H)

Starting Material Synthesis Example 123

4-(2'-methoxybenzylidene)-2-methyl-4H-oxazol-5-one

Anisaldehyde (11.3 g), N-acetylglycine (9.8 g) and sodium acetate (8.2 g) were dissolved in acetic anhydride (200 ml) and the mixture was heated at 100° C. for 10 hr. After cooling, the precipitated yellow crystals were collected by filtration to give the title compound (9.52 g), melting point 151–153° C.

The structural formulas of the compounds obtained in Starting Material Synthesis Examples 113 to 123 are shown in the following.

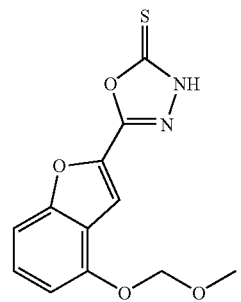

113

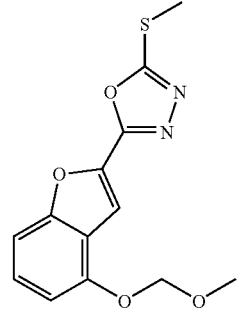

114

115
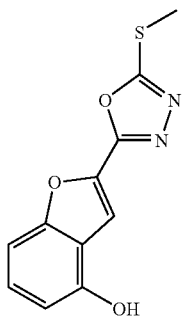
116
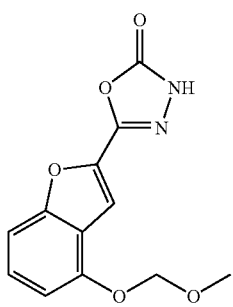
117
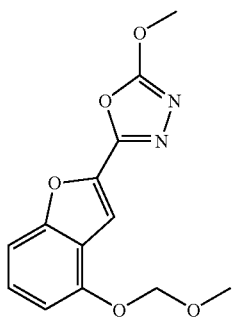
118
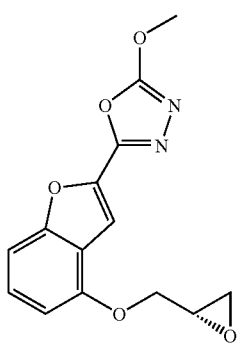
119
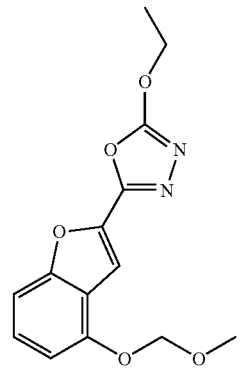
120
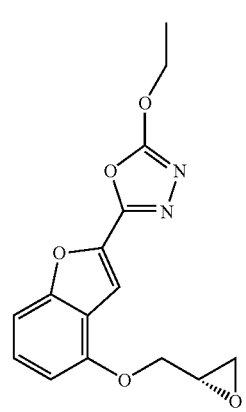
121
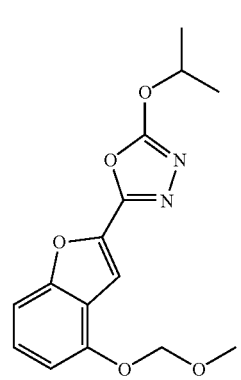
122
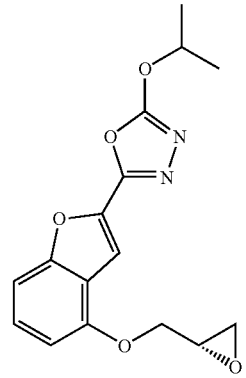

-continued

123

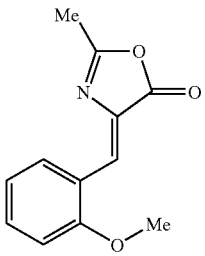

Example 1

(S)-1-(4-(2-hydroxy-3-(4-(naphthalen-2-yl)piperidino)propyloxy)benzo(b)furan-2-ylcarbonyl)pyrrolidine (S)-1-(4-Glycidyloxybenzo(b)furan-2-ylcarbonyl)pyrrolidine (1.2 g) obtained in Starting Material Synthesis Example 1 was dissolved in methanol (40 ml) and 4-(naphthalen-2-yl)piperidine (0.85 g) was added. The mixture was refluxed under heating for 8 hr. The reaction mixture was evaporated under reduced pressure and the obtained residue was purified by silica gel column chromatography (chloroform/methanol) to give the title compound (1.6 g) as a brown oil.
$^1$H-NMR(CDCl$_3$)δ: 1.81–2.20(m, 8H), 2.22(t, J=11.7, 1H), 2.56–2.96(m, 1H), 2.62–2.79(m, 3H), 3.03(d, J=10.8, 1H), 3.22(d, J=10.8, 1H), 4.10–4.28(m, 3H), 6.73(d, J=8.3, 1H), 7.16(d, J=8.3, 1H), 7.33(t, J=8.3, 1H), 7.35–7.50(m, 3H), 7.51–7.55(m, 1H), 7.67(s, 1H), 7.81(d, J=8.8, 3H)

Example 2

(S)-4-(4-(2-hydroxy-3-(4-(naphthalen-2-yl)piperidino)propyloxy)benzo(b)furan-2-ylcarbonyl)morpholine (S)-4-(4-Glycidyloxybenzo(b)furan-2-ylcarbonyl)morpholine (1.3 g) obtained in Starting Material Synthesis Example 2 was dissolved in methanol (40 ml) and 4-(naphthalen-2-yl)piperidine (0.91 g) was added. The mixture was refluxed under heating for 8 hr and the reaction solvent was evaporated under reduced pressure. The obtained residue was purified by silica gel column chromatography (chloroform/methanol) to give the title compound (1.8 g) as a brown oil.
$^1$H-NMR(CDCl$_3$)δ: 1.86–1.99(m, 4H), 2.21(t, J=11.7, 1H), 2.53(t, J=11.2, 1H), 2.59–2.74(m, 3H), 3.03(d, J=10.8, 1H), 3.22(d, J=10.8, 1H), 3.70–4.03(m, 8H), 4.10–4.27(m, 3H), 6.73(d, J=8.3, 1H), 7.15(d, J=8.3, 1H), 7.33(t, J=8.3, 1H), 7.37–7.41(m, 3H), 7.49(s, 1H), 7.67(s, 1H), 7.81(d, J=8.8, 3H)

Example 3

(S)-4-(2-hydroxy-3-(4-(naphthalen-2-yl)piperidino)propyloxy)-N-methylbenzo(b)furan-2-carboxamide To a solution (13 ml) of (S)-4-(2-hydroxy-3-(4-(naphthalen-2-yl)piperidino)propyloxy)benzo(b)furan-2-carboxylic acid (0.12 g) obtained in Starting Material Synthesis Example 22 in DMF were added methylamine hydrochloride (0.18 g), triethylamine (0.1 ml) and diethyl cyanophosphate (0.1 ml), and the mixture was stirred for 1 hr at room temperature. The reaction mixture was poured into water and extracted with ethyl acetate. The organic layer was washed with saturated aqueous ammonium chloride solution and water and dried over anhydrous magnesium sulfate. The solvent was evaporated under reduced pressure and the obtained residue was purified by silica gel column chromatography (chloroform/methanol) to give the title compound (0.05 g) as a brown oil.
$^1$H-NMR(CDCl$_3$)δ: 1.84–1.97(m, 4H), 2.20(t, J=11.7, 1H), 2.45–2.55(m, 1H), 2.59–2.79(m, 3H), 2.99–3.06(m, 1H), 3.03(d, J=5.3, 3H), 3.20(d, J=9.7, 1H), 4.11–4.20(m, 3H), 6.60(br, 1H), 6.70(d, J=8.3, 1H), 7.08(d, J=8.3, 1H), 7.31(t, J=8.3, 1H), 7.35–7.41(m, 3H), 7.59(s, 1H), 7.65(s, 1H), 7.78(d, J=8.8, 3H)

Example 4

(S)-4-(2-hydroxy-3-(4-(naphthalen-2-yl)piperidino)propyloxy)-N,N-dimethylbenzo(b)furan-2-carboxamide By the reactions as in the same manner as in Example 3 using (S)-4-(2-hydroxy-3-(4-(naphthalen-2-yl)piperidino)propyloxy)benzo(b)furan-2-carboxylic acid (0.8 g) obtained in Starting Material Synthesis Example 22, dimethylamine hydrochloride (0.15 g), triethylamine (0.49 ml) and diethyl cyanophosphate (0.33 ml), the title compound (0.61 g) was obtained as a brown oil.
$^1$H-NMR(CDCl$_3$)δ: 1.84–2.00(m, 4H), 2.22(t, J=11.0, 1H), 2.49–2.55(m, 1H), 2.65–2.77(m, 3H), 3.03(brd, J=10.7, 1H), 3.16(brs, 3H), 3.22(brd, J=10.7, 1H), 3.36(brs, 3H), 4.14–4.24(m, 3H), 6.72(d, J=8.3, 1H), 7.16(d, J=8.3, 1H), 7.31(t, J=8.3, 1H), 7.39–7.48(m, 3H), 7.67(s, 1H), 7.80(d, J=8.8, 3H)

Example 5

(S)-4-(2-hydroxy-3-(4-(naphthalen-2-yl)piperidino)propyloxy)-N,N-diethylbenzo(b)furan-2-carboxamide By the reactions in the same manner as in as in Example 3 using (S)-4-(2-hydroxy-3-(4-(naphthalen-2-yl)piperidino)propyloxy)benzo(b)furan-2-carboxylic acid Starting Material Synthesis Example 22, diethylamine (0.24 ml) and diethyl cyanophosphate (0.5 ml), the title compound (0.61 g) was obtained as a brown oil.
$^1$H-NMR(CDCl$_3$)δ: 1.19–1.40(m, 6H), 1.82–2.00(m, 4H), 2.22(t, J=12.2, 1H), 2.49–2.55(m, 1H), 2.64–2.76(m, 3H), 3.04(brd, J=11.3, 1H), 3.21(brd, J=11.3, 1H), 3.43–3.70(m, 4H), 4.12–4.24(m, 3H), 6.72(d, J=8.3, 1H), 7.14(d, J=8.3, 1H), 7.30(t, J=8.3, 1H), 7.38–7.48(m, 3H), 7.67(s, 1H), 7.80(d, J=8.3, 3H)

Example 6

(S)-4-(2-hydroxy-3-(4-(naphthalen-2-yl)piperidino)propyloxy)-N-methoxy-N-methylbenzo(b)furan-2-carboxamide By the reactions in the same manner as in Example 3 using (S)-4-(2-hydroxy-3-(4-(naphthalen-2-yl)piperidino)propyloxy)benzo(b)furan-2-carboxylic acid (0.8 g) obtained in Starting Material Synthesis Example 22, N,O-dimethylhydroxylamine hydrochloride (0.24 g), triethylamine (1.0 ml) and diethyl cyanophosphate (0.27 ml), the title compound (0.64 g) was obtained as a brown oil.

$^1$H-NMR(CDCl$_3$)δ: 1.86–1.99(m, 4H), 2.22(t, J=10.2, 1H), 2.49–2.53(m, 1H), 2.63–2.74(m, 3H), 3.04(brd, 11.7, 1H), 3.22(brd, 11.7, 1H), 3.42(s, 3H), 3.92(s, 3H)4.14–4.27 (m, 3H), 6.72(d, J=7.8, 1H), 7.23(d, J=7.8, 1H), 7.34(t, J=7.8, 1H), 7.38–7.48(m, 3H), 7.63(s, 1H), 7.67(s, 1H), 7.79–7.82(m, 3H)

Example 7

(S)-4-(8-(2-hydroxy-3-(4-(naphthalen-2-yl)piperidino)propyloxy)-2H-chromen-3-ylcarbonyl)morpholine By the reactions in the same manner as in Example 1 using (S)-4-(8-glycidyloxy-2H-chromen-3-ylcarbonyl)morpholine (3.1 g) obtained in Starting Material Synthesis Example 6 and 4-(naphthalen-2-yl)piperidine (2.5 g), the title compound (3.5 g) was obtained as a brown oil.

$^1$H-NMR(CDCl$_3$)δ: 1.86–1.99(m, 4H), 2.21(t, J=11.7, 1H), 2.49–2.56(m, 1H), 2.63–2.74(m, 3H), 3>03 (d, J=11.7, 1H), 3.22(d, J=11.7, 1H), 3.42(s, 3H), 3.84(s, 3H), 4.14–4.27(m, 3H), 6.72(d, J=8.3, 1H), 7.23(d, J=8.3, 1H), 7.43(d, J=8.3, 1H), 7.44–7.48(m, 2H), 7.63(s, 1H), 7.68(s, 1H), 7.78–7.82(m, 3H)

Example 8

(S)-4-(8-(2-hydroxy-3-(4-(naphthalen-2-yl)piperidino)propyloxy)-2H-chromen-3-ylmethyl)morpholine maleate To a suspension of lithium aluminum hydride (0.55 g) in THF was added aluminum chloride (0.63 g) and the mixture was stirred at room temperature for 1 hr. The reaction mixture was made to become 4° C. and a solution of (S)-4-(8-(2-hydroxy-3-(4-(naphthalen-2-yl)piperidino)propyloxy)-2H-chromen-3-ylcarbonyl)morpholine (2.5 g) in THF (50 ml) was added dropwise. The mixture was stirred for 30 min and hydrous THF was added. The mixture was further stirred for 30 min at room temperature and the precipitated insoluble matter was filtered off through celite. The solvent was evaporated under reduced pressure to give a brown oil. This was dissolved in ethanol and maleic acid was added. The precipitated crystals were collected by filtration and dried to give the title compound (1.3 g) as pale-yellow crystals, melting point 164–166° C.

Example 9

(S)-8-(2-hydroxy-3-(4-(naphthalen-2-yl)piperidino)propyloxy)-N,N-dimethyl-2H-chromene-3-carboxamide By the reactions in the same manner as in Example 1 using (S)-8-glycidyloxy-N,N-dimethyl-2H-chromene-3-carboxamide (3.2 g) obtained in Starting Material Synthesis Example 8 and 4-(naphthalen-2-yl)piperidine (1.5 g), the title compound (3.7 g) was obtained as a brown oil.

$^1$H-NMR(CDCl$_3$)δ: 1.86–1.96(m, 4H), 2.19(t, J=11.7, 1H), 2.43–2.55(m, 1H), 2.59–2.89(m, 3H), 2.96(s, 3H), 2.97(s, 3H), 2.90–3.32(m, 2H), 4.07–4.32(m, 3H), 6.61(s, 1H), 6.73(d, J=8.3, 1H), 6.86(t, J=8.3, 1H), 6.93(d, J=8.3, 1H), 7.35–7.47(m, 3H), 7.66(s, 1H), 7.78–7.80(m, 3H)

Example 10

(S)-3-chloro-6-(2-hydroxy-3-(4-(naphthalen-2-yl)piperidino)propyloxy)-N,N-dimethylbenzo(b)thiophene-2-carboxamide By the reactions in the same manner as in Example 1, the title compound (0.4 g) was obtained from (S)-3-chloro-6-glycidyloxy-N,N-dimethylbenzo(b)thiophene-2-carboxamide (0.6 g) obtained in Starting Material Synthesis Example 14 and 4-(naphthalen-2-yl)piperidine (0.45 g).

$^1$H-NMR(CDCl$_3$)δ: 1.87–1.96(m, 3H), 2.05–2.22(m, 1H), 2.52–2.70(m, 4H), 3.03–3.22(m, 10H), 4.08–4.20(m, 3H), 7.13–7.16(m, 1H), 7.30(d, 1H, J=1.9), 7.39(d, 1H, J=8.8), 7.43–7.48(m, 2H), 7.60(s, 1H), 7.72(d, 1H, J=8.3), 7.77–7.82(m, 3H, J=8.3)

The structural formulas of the compounds obtained in Examples 1 to 10 are shown in the following.

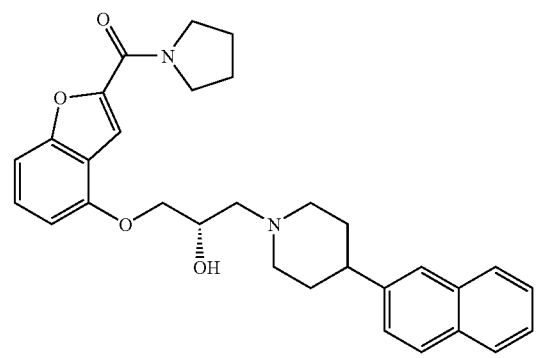

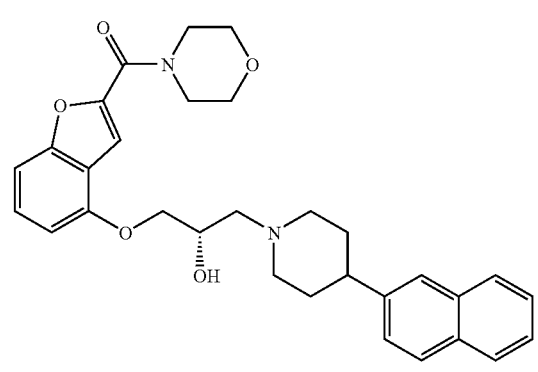

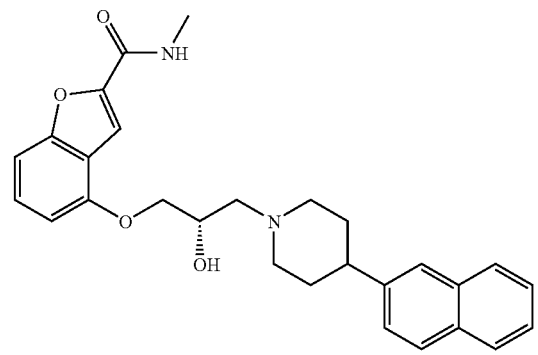

4

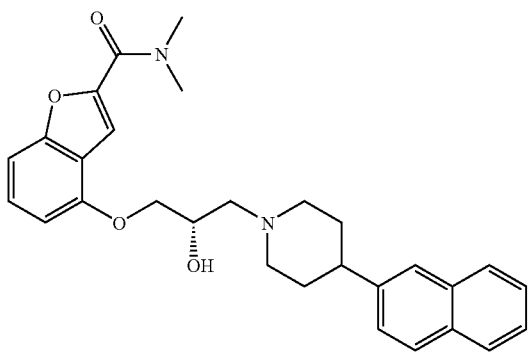

5

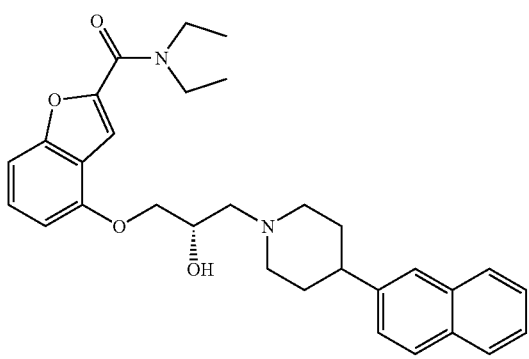

6

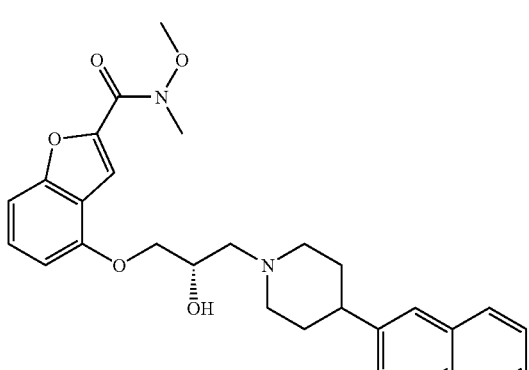

7

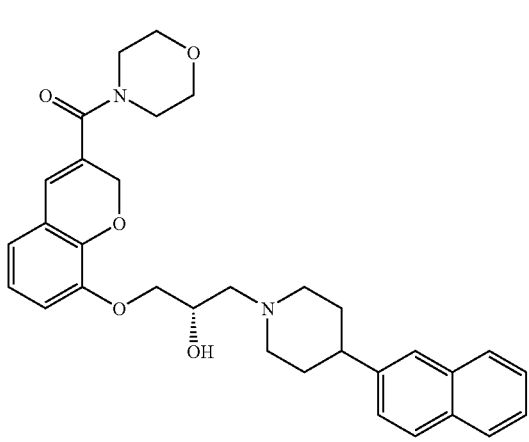

8

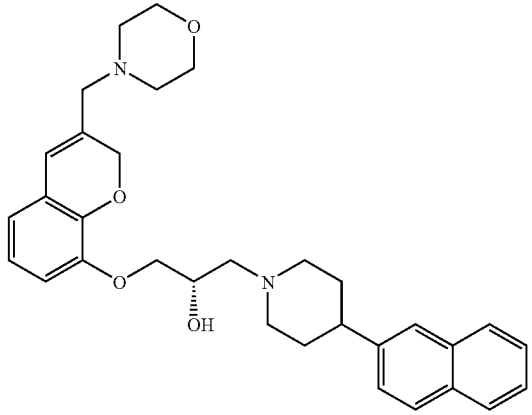

9

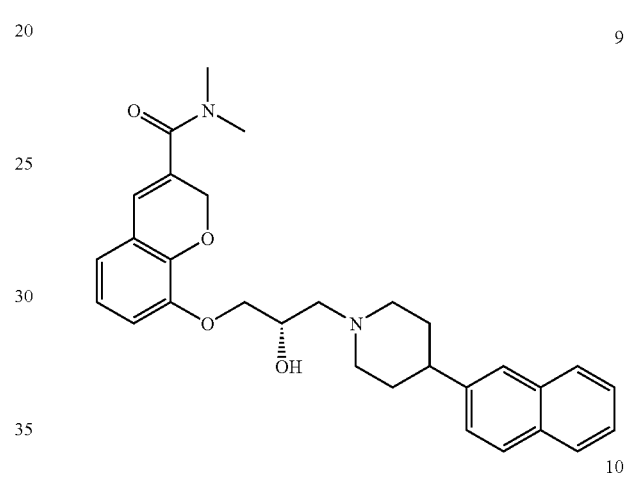

10

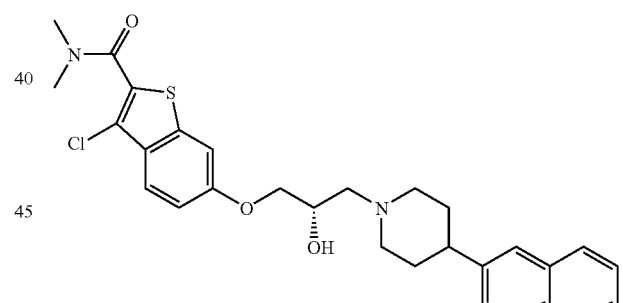

Example 11

(S)-3-chloro-6-(2-hydroxy-3-(4-(naphthalen-1-yl)piperidino)propyloxy)-N,N-dimethylbenzo(b)thiophene-2-carboxamide By the reactions in the same manner as in Example 1 using (S)-3-chloro-6-glycidyloxy-N,N-dimethylbenzo(b)thiophene-2-carboxamide (0.6 g) obtained in Starting Material Synthesis Example 14 and 4-(naphthalene-1-yl)piperidine (0.45 g), the title compound (0.5 g) was obtained as a brown oil.

$^1$H-NMR(CDCl$_3$)δ: 1.81–2.33(m, 3H), 2.30–2.37(m, 1H), 2.62–2.70(m, 4H), 3.11–3.17(m, 8H), 3.21–3.25(m, 1H), 3.35–3.44(m, 1H), 4.02–4.15(m, 2H), 4.18–4.22(m,

1H), 7.15(d, 1H, J=6.8), 7.30(s, 1H), 7.40–7.49(m, 4H), 7.75–7.79(m, 2H), 7.88(d, 1H, J=7.8), 8.10(d, 1H, J=8.3)

Example 12

(S)-1-(4-(2-hydroxy-3-(4-(naphthalen-2-yl)piperidino)propyloxy)benzo(b)thiophen-2-ylcarbonyl) pyrrolidine 2 methanesulfonate monohydrate By the reactions in the same manner as in Example 1 using (S)-1-(4-glycidyloxybenzo(b)thiophen-2-ylcarbonyl) pyrrolidine (4.0 g) obtained in similar manner as in Starting Material Synthesis Example 19 and 4-(naphthalen-2-yl) piperidine (2.2 g), a brown oil (4.2 g) was obtained. This was dissolved in ethyl acetate and methanesulfonic acid was added. The precipitated crystals were collected by filtration and dried to give the title compound (3.3 g) as pale-yellow crystals, melting point 88–90° C.

Example 13

(S)-4-(4-(2-hydroxy-3-(4-(naphthalen-2-yl)piperidino)propyloxy)benzo(b)thiophen-2-ylcarbonyl) morpholine By the reactions in the same manner as in Example 1, the title compound (0.7 g) was obtained from (S)-4-(4-glycidyloxybenzo(b)thiophen-2-ylcarbonyl)morpholine (1.2 g) obtained in Starting Material Synthesis Example 18 and 4-(naphthalen-2-yl)piperidine (1.0 g), melting point 82–86° C.

Example 14

(S)-4-(2-hydroxy-3-(4-(naphthalen-2-yl)piperidino)propyloxy)-N-methoxy-N-methylbenzo(b)thiophene-2-carboxamide By the reactions in the same manner as in Example 1, the title compound (0.8 g) was obtained as a brown oil from (S)-4-glycidyloxy-N-methoxy-N-methylbenzo(b)thiophene-2-carboxamide (1.1 g) obtained in Starting Material Synthesis Example 20 and 4-(naphthalen-2-yl)piperidine (0.8 g).
$^{1}$H-NMR(CDCl$_{3}$)δ: 1.86–1.99(m, 4H), 2.23(t, 1H, J=9.8), 2.47–2.55(m, 1H), 2.63–2.74(m, 3H), 3.05(d, 1H, J=11.2), 3.23(d, 1H, J=11.2), 3.43(s, 3H), 3.83(s, 3H), 4.11–4.15(m, 1H), 4.20–4.27(m, 2H), 6.79(d, 1H, J=7.8), 7.35–7.48(m, 5H), 7.68(s, 1H), 7.81(d, 3H, J=8.3), 8.42(s, 1H)

Example 15

(S)-4-(2-hydroxy-3-(4-(naphthalen-1-yl)piperidino)propyloxy)-N,N-dimethylbenzo(b)thiophene-2-carboxamide By the reactions in the same manner as in Example 1, the title compound (0.4 g) was obtained from (S)-4-glycidyloxy-N,N-dimethylbenzo(b)thiophene-2-carboxamide (0.5 g) obtained in Starting Material Synthesis Example 17 and 4-(naphthalen-1-yl)piperidine (0.4 g), as pale-yellow crystals, melting point 97–100° C.

Example 16

(S)-4-(2-hydroxy-3-(4-(6-methoxynaphthalen-2-yl)piperidino)propyloxy)-N,N-dimethylbenzo(b)thiophene-2-carboxamide By the reactions in the same manner as in Example 1, the title compound (1.2 g) was obtained from (S)-4-glycidyloxy-N,N-dimethylbenzo(b)thiophene-2-carboxamide (1.7 g) obtained in Starting Material Synthesis Example 17 and 4-(6-methoxynaphthalen-2-yl)piperidine (1.5 g).
$^{1}$H-NMR(CDCl$_{3}$)δ: 1.82–2.00(m, 3H), 2.07–2.23(m, 1H), 2.52–2.57(m, 1H), 2.63–2.75(m, 3H), 3.02–3.05(m, 1H), 1.10–3.20(bs, 6H), 3.91(s, 3H), 40.09–4.23(m, 3H), 6.79(d, 1H, J=7.9), 7.11(s, 1H), 7.14(d, 1H, J=2.5), 7.30–7.37(m, 2H), 7.44(d, 1H, J=7.8), 7.59(s, 1H), 7.69(s, 1H), 7.70(s, 1H), 7.74(s, 1H)

Example 17

(S)-4-(2-hydroxy-3-(4-(naphthalen-2-yl)piperidino)propyloxy)-N,N-dimethylbenzo(b)thiophene-2-carboxamide (L)-tartrate By the reactions in the same manner as in Example 1, a brown oil (1.9 g) was obtained from (S)-4-glycidyloxy-N,N-dimethylbenzo(b)thiophene-2-carboxamide (1.2 g) obtained in Starting Material Synthesis Example 17 and 4-(naphthalen-2-yl)piperidine (0.9 g). This was dissolved in ethanol and (L)-tartaric acid was added. The precipitated crystals were collected by filtration and dried to give the title compound (1.2 g) as white crystals, melting point 173–175° C.

Example 18

(S)-4-(2-hydroxy-3-(4-(naphthalen-1-yl)-3,6-dihydro-2H-pyridin-1-yl)propyloxy)-N,N-dimethylbenzo(b)thiophene-2-carboxamide By the reactions in the same manner as in Example 1 using (S)-4-glycidyloxy-N,N-dimethylbenzo(b)thiophene-2-carboxamide (2.0 g) obtained in Starting Material Synthesis Example 17 and 4-(naphthalen-1-yl)-3,6-dihydro-2H-pyridine (2.0 g), the title compound (0.8 g) was obtained.
$^{1}$H-NMR(CDCl$_{3}$)δ: 2.63–2.81(m, 6H), 3.05–3.40(m, 6H), 2.98–3.02(m, 1H), 3.41–3.44(m, 1H), 4.17–4.23(m, 2H), 4.25–4.33(m, 1H), 6.25(s, 1H), 6.79(d, 1H, J=7.9), 7.32(t, 1H, J=7.9), 7.40–7.58(m, 2H), 7.60(d, 1H, J=10.2), 7.74–7.83(m, 6H)

Example 19

(S)-7-(2-hydroxy-3-(4-(naphthalen-2-yl)piperidino)propyloxy)-N-methylbenzo(b)furan-2-carboxamide By the reactions in the same manner as in Example 3 using (S)-7-(2-hydroxy-3-(4-(naphthalen-2-yl)piperidino)propyloxy)benzo(b)furan-2-carboxylic acid (1.0 g) obtained in Starting Material Synthesis Example 24, methylamine (0.15 g), triethylamine (0.63 ml) and diethyl cyanophosphate (0.37 ml), the title compound (0.75 g) was obtained as a brown oil.
$^{1}$H-NMR(CDCl$_{3}$)δ: 1.85–1.97(m, 4H), 2.20(t, J=11.7, 1H), 2.45–2.55(m, 1H), 2.59–2.79(m, 3H), 2.99–3.06(m, 1H), 3.04(d, J=5.3, 3H), 3.20(d, J=9.7, 1H), 4.07–4.27(m, 3H), 4.18–4.38(s, m), 6.82(br, 1H), 6.94(d, J=8.3, 1H), 7.18(t, J=8.3, 1H), 7.31(t, J=8.3, 1H), 7.37–7.46(m, 3H), 7.66(s, 1H), 7.79(d, J=8.8, 3H)

Example 20

(S)-4-(7-(2-hydroxy-3-(4-(naphthalen-2-yl)piperidino)propyloxy)benzo(b)furan-2-ylcarbonyl)morpholine By the reactions in the same manner as in Example 3 using (S)-7-(2-hydroxy-3-(4-(naphthalen-2-yl)piperidino)propyloxy)benzo(b)furan-2-carboxylic acid (1.0 g) obtained in Starting Material Synthesis Example 24, morpholine (0.19 g), triethylamine (0.63 ml) and diethyl cyanophosphate (0.37 ml), the title compound (0.60 g) was obtained as a brown oil.

$^1$H-NMR(CDCl$_3$)δ: 1.86–1.99(m, 4H), 2.22(t, J=11.7, 1H), 2.53–2.58(m, 1H), 2.59–2.80(m, 3H), 3.03(d, J=10.8, 1H), 3.23(d, J=10.8, 1H), 3.72–4.03(m, 8H), 4.20–4.36(m, 3H), 6.96(d, J=8.3, 1H), 7.22(t, J=8.3, 1H), 7.25(d, J=8.3, 1H), 7.37–7.41(m, 3H), 7.49(s, 1H), 7.66(s, 1H), 7.81(d, J=8.8, 3H)

The structural formulas of the compounds obtained in Examples 11 to 20 are shown in the following.

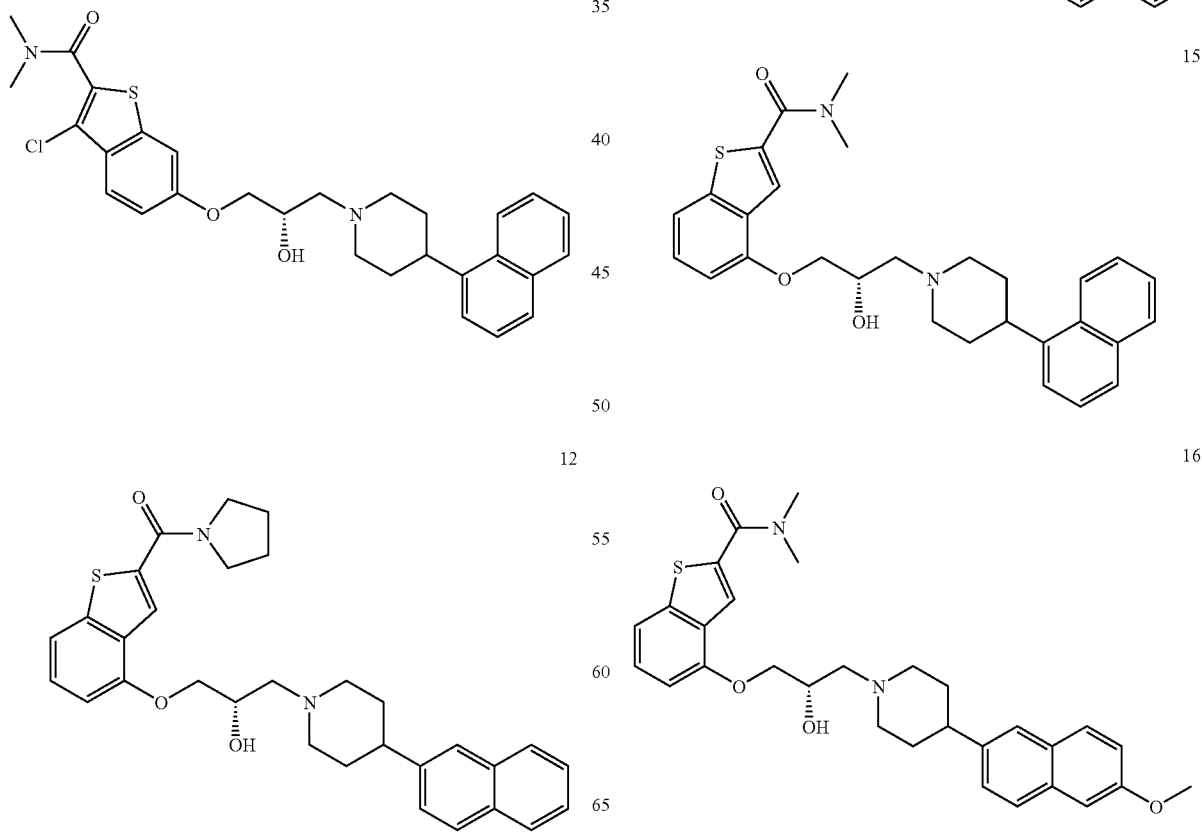

17

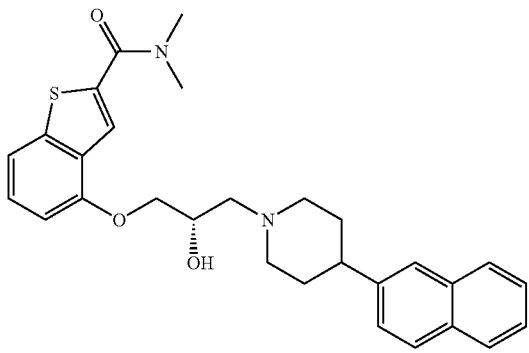

18

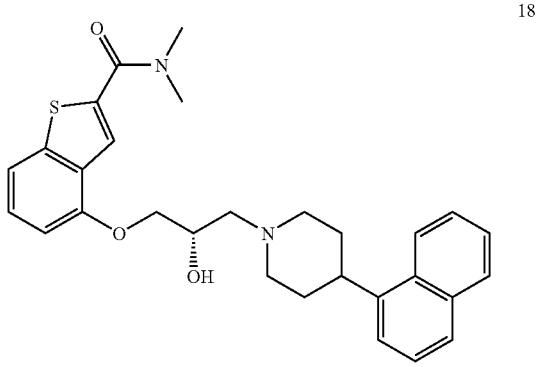

19

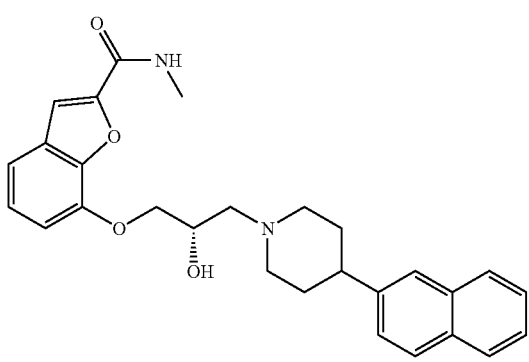

20

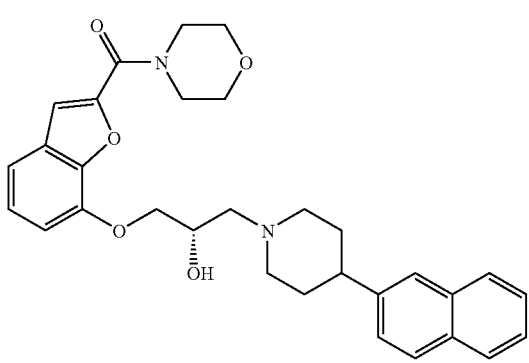

Example 21

(S)-7-(2-hydroxy-3-(4-(naphthalen-2-yl)piperidino)propyloxy)-N,N-dimethylbenzo(b)furan-2-carboxamide By the reactions in the same manner as in Example 3 using (S)-7-(2-hydroxy-3-(4-(naphthalen-2-yl)piperidino)propyloxy)benzo(b)furan-2-carboxylic acid (1.0 g) obtained in Starting Material Synthesis Example 24, dimethylamine hydrochloride (0.18 g), triethylamine (0.63 ml) and diethyl cyanophosphate (0.37 ml), the title compound (0.60 g) was obtained as a brown oil.

$^1$H-NMR(CDCl$_3$)δ: 1.81–2.01(m, 4H), 2.18–2.29(m, 1H), 2.44–2.58(m, 1H), 2.61–2.78(m, 3H), 2.88(s, 3H), 2.95(s, 3H), 3.03(d, J=10.8, 1H), 3.24(d, J=10.8, 1H), 4.20–4.37(m, 3H), 6.95(d, J=7.8, 1H), 7.19(t, J=7.8, 1H), 7.25(d, J=7.8, 1H), 7.31(s, 1H), 7.38–7.48(m, 3H), 7.66(s, 1H), 7.80(d, J=8.8, 3H)

Example 22

(S)-7-(2-hydroxy-3-(4-(naphthalen-2-yl)piperidino)propyloxy)-N-methoxy-N-methylbenzo(b)furan-2-carboxamide By the reactions in the same manner as in Example 3 using (S)-7-(2-hydroxy-3-(4-(naphthalen-2-yl)piperidino)propyloxy)benzo(b)furan-2-carboxylic acid (1.0 g) obtained in Starting Material Synthesis Example 24, N,O-dimethylhydroxylamine (0.21 g), triethylamine (0.63 ml) and diethyl cyanophosphate (0.37 ml), the title compound (0.62 g) was obtained as a brown oil.

$^1$H-NMR(CDCl$_3$)δ: 1.83–2.01 m, 4H), 2.21–2.29((m, 1H), 2.43–2.58(m, 1H), 2.63–2.78(m, 3H), 3.03(brd, J=10.8, 1H), 3.23(d, J=10.8, 1H), 3.42(s, 3H), 3.86(s, 3H), 4.21–4.38(m, 3H), 6.98(d, J=7.8, 1H), 7.20(t, J=7.8, 1H), 7.38–7.48(m, 3H), 7.66(s, 1H), 7.80(d, J=8.8, 3H)

Example 23

(S)-1-(4-(2-hydroxy-3-(4-(naphthalen-2-yl)piperidino)propyloxy)-1H-indol-2-ylcarbonyl)-4-methylpiperazine By the reactions in the same manner as in Example 3 using (S)-4-(2-hydroxy-3-(4-(naphthalen-2-yl)piperidino)propyloxy)-1H-indole-2-carboxylic acid (0.70 g) obtained in Starting Material Synthesis Example 25, N-methylpiperazine (0.16 g), triethylamine (0.44 ml) and diethyl cyanophosphate (0.27 ml), the title compound (0.65 g) was obtained as a brown oil.

$^1$H-NMR(CDCl$_3$)δ: 1.73–2.04(m, 4H), 2.16–2.20(m, 1H), 2.34(s, 3H), 2.49–2.79(m, 7H), 3.03(d, J=10.7, 1H), 3.15–3.36(m, 5H), 4.10–4.37(m, 3H), 6.54(d, J=8.3, 1H), 6.93(s, 1H), 7.00(d, J=8.3, 1H), 7.18(t, J=8.3, 1H), 7.38–7.46(m, 3H), 7.67(s, 1H), 7.78(m, 3H), 9.29(s, 1H)

Example 24

(S)-4-(4-(2-hydroxy-3-(4-(naphthalen-2-yl)piperidino)propyloxy)-1H-indol-2-ylcarbonyl)morpholine hydrochloride By the reactions in the same manner as in Example 3 using (S)-4-(2-hydroxy-3-(4-(naphthalen-2-yl)piperidino)propyloxy)-1H-indole-2-carboxylic acid (0.70 g) obtained in Starting Material Synthesis Example 25, morpholine (0.14 g), triethylamine (0.44 ml) and diethyl cyanophosphate (0.27 ml), a brown oil (0.66 g) was obtained. This was dissolved in acetone and 1N solution of hydrochloric acid in methanol was added. The precipitated crystals were collected by filtration and dried to give the title compound (0.65 g) as white crystals, melting point 169–171° C.

Example 25

(S)-1-(4-(2-hydroxy-3-(4-(naphthalen-2-yl)piperidino)propyloxy)-1H-indol-2-ylcarbonyl)pyrrolidine 3/2 hydrochloride By the reactions in the same manner as in Example 3 using (S)-4-(2-hydroxy-3-(4-(naphthalen-2-yl)piperidino)propyloxy)-1H-indole-2-carboxylic acid (0.70 g) obtained in Starting Material Synthesis Example 25, pyrrolidine (0.11 g), triethylamine (0.44 ml) and diethyl cyanophosphate (0.27 ml), the title compound (0.24 g) was obtained as white crystals, melting point 158–161° C.

Example 26

(R)-1-(4-(2-hydroxy-3-(4-(naphthalen-2-yl)piperidino)propyloxy)-1H-indol-2-ylcarbonyl)pyrrolidine By the reactions in the same manner as in Example 3 using (R)-4-(2-hydroxy-3-(4-(naphthalen-2-yl)piperidino)propyloxy)-1H-indole-2-carboxylic acid (1.0 g) obtained by the reactions in the same manner as in Starting Material Synthesis Example 25 from (R)-glycidyl nosylate, pyrrolidine (0.30 g), triethylamine (3.0 ml) and diethyl cyanophosphate (0.30 ml), the title compound (0.54 g) was obtained as white crystals, melting point 211–212° C.

Example 27

(R)-4-(2-hydroxy-3-(4-(naphthalen-2-yl)piperidino)propyloxy)-N,N-dimethyl-1H-indole-2-carboxamide By the reactions in the same manner as in Example 3 using (R)-4-(2-hydroxy-3-(4-naphthalen-2-yl)piperidino)propyloxy)-1H-indole-2-carboxylic acid (1.0 g) obtained by the reactions in the same manner as in Starting Material Synthesis Example 25 from (R)-glycidyl nosylate, dimethylamine hydrochloride (0.3 g), triethylamine (3.0 ml) and diethyl cyanophosphate (0.3 ml), the title compound (0.24 g) was obtained as white crystals, melting point 158–160° C.

Example 28

4-(2-hydroxy-3-(2-(2-naphthoxy)ethylamino)propyloxy)-1H-indole-2-carboxamide

By the reactions in the same manner as in Example 1 using 4-glycidyloxy-1H-indole-2-carboxamide (0.70 g) and 2-(2-naphthoxy)ethylamine (0.70 g), the title compound (0.57 g) was obtained as white crystals, melting point 125–126° C.

Example 29

(S)-4-(2-hydroxy-3-(4-(naphthalen-2-yl)piperidino)propyloxy)-1-methyl-N-methylindole-2-carboxamide By the reactions in the same manner as in Example 3 using (S)-4-(2-hydroxy-3-(4-(naphthalen-2-yl)piperidino)propyloxy)-1-methylindole-2-carboxylic acid (1.0 g) obtained in Starting Material Synthesis Example 26, methylamine hydrochloride (0.2 g), triethylamine (1.0 ml) and diethyl cyanophosphate (0.5 ml), a yellow oil (0.8 g) was obtained. To this oil was added isopropyl ether and the precipitated crystals were collected by filtration to give the title compound (0.5 g) as pale-yellow crystals, melting point 180–183° C.

$^1$H-NMR(CDCl$_3$)δ: 1.87–1.96(m, 4H), 2.19–2.50(m, 1H), 2.50–2.80(m, 4H), 2.90–3.20(m, 4H), 3.21(m, 1H), 4.04(s, 3H), 4.14–4.18(m, 3H), 6.19(brs, 1H), 6.55(d, J=7.8, 1H), 6.98–7.08(m, 2H), 7.20–7.22(m, 1H), 7.38–7.46(m, 3H), 7.66(m, 1H), 7.79–7.81(m, 3H)

Example 30

(S)-4-(2-hydroxy-3-(4-(naphthalen-2-yl)piperidino)propyloxy)-1-methyl-N,N-dimethylindole-2-carboxamide By the reactions in the same manner as in Example 3 using (S)-4-(2-hydroxy-3-(4-(naphthalen-2-yl)piperidino)propyloxy)-1-methylindole-2-carboxylic acid (0.6 g) obtained in Starting Material Synthesis Example 26, dimethylamine hydrochloride (0.3 g), triethylamine (1.0 ml) and diethyl cyanophosphate (0.5 ml), the title compound (0.6 g) was obtained as pale-yellow crystals, melting point 146–148° C.

$^1$H-NMR(CDCl$_3$)δ: 1.84–1.93(m, 4H), 2.16–2.20(m, 1H), 2.50–2.80(m, 4H), 3.00–3.40(m, 8H), 3.81(s, 3H), 4.10–4.30(m, 3H), 6.54(d, J=8.4, 1H), 6.77(s, 1H), 6.96(d, J=8.3, 1H), 7.18(dd, J=7.8, 7.8, 1H), 7.24(s, 1H), 7.36–7.45 (m, 3H), 7.64(s, 1H), 7.78(d, J=7.8, 2H)

The structural formulas of the compounds obtained in Examples 21 to 30 are shown in the following.

21

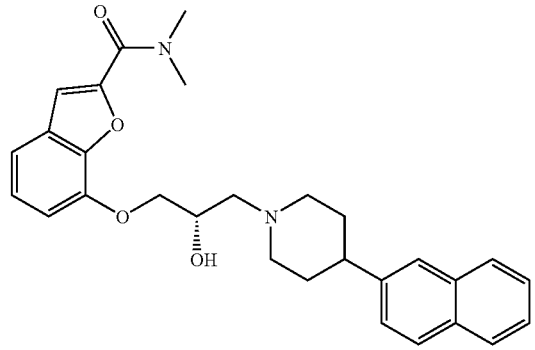

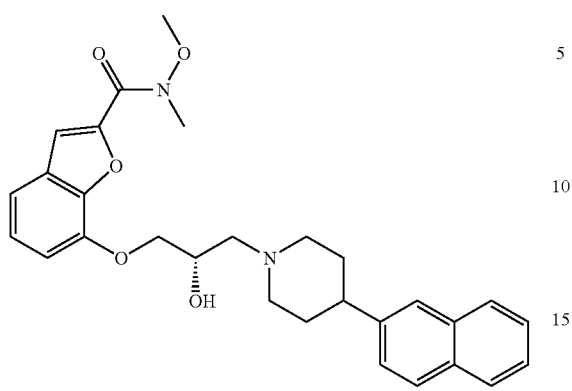
22
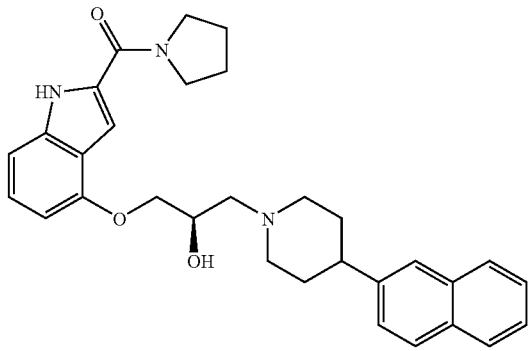
26
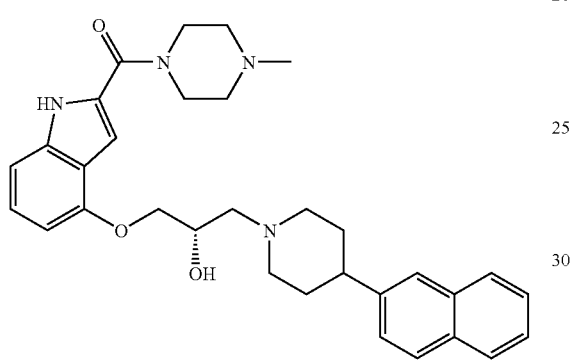
23
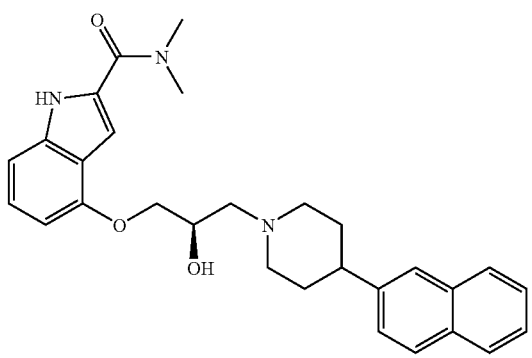
27
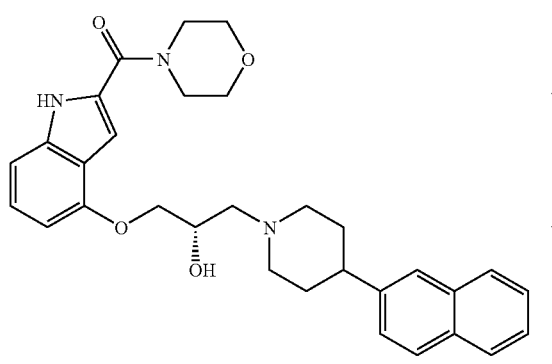
24
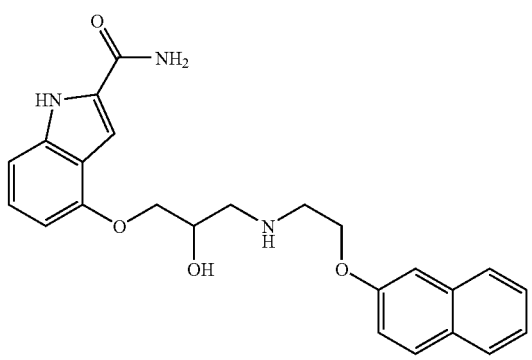
28
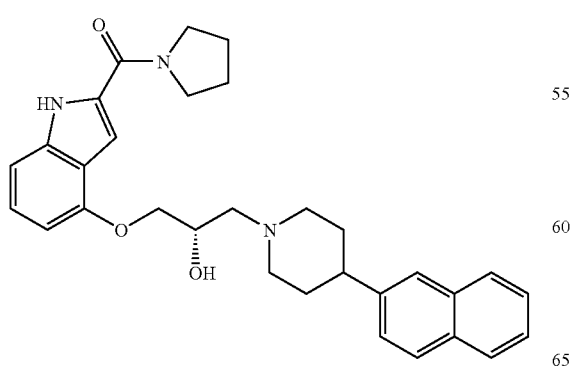
25
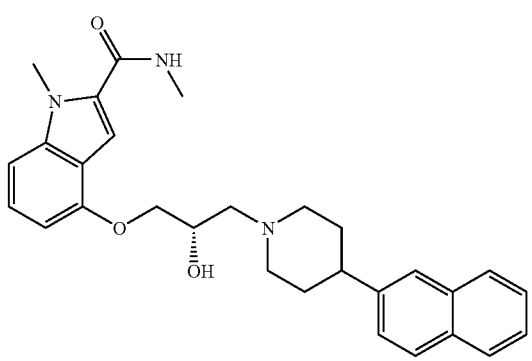
29

Example 31

(S)-1-(4-(2-hydroxy-3-(4-(naphthalen-2-yl)piperidino)propyloxy)-1-methylindole-2-carbonyl)pyrrolidine

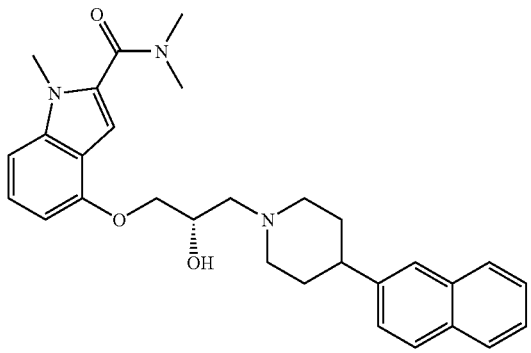

By the reactions in the same manner as in Example 3 using (S)-4-(2-hydroxy-3-(4-(naphthalen-2-yl)piperidino)propyloxy)-1-methylindole-2-carboxylic acid (1.8 g) obtained in Starting Material Synthesis Example 26, pyrrolidine (0.5 ml), triethylamine (0.5 ml) and diethyl cyanophosphate (1.5 ml), the title compound (0.2 g) was obtained as a yellow oil.
$^1$H-NMR(CDCl$_3$)δ: 1.84–2.04(m, 9H), 2.23(m, 1H), 2.50 (m, 1H), 2.66–2.80(m, 2H), 3.00–3.30(m, 2H), 3.60–3.80 (m, 4H), 3.92(s, 3H), 4.00–4.30(m, 3H), 6.55(d, J=7.8, 1H), 6.89(s, 1H), 6.99(d, J=8.3, 1H), 7.22(dd, J=7.8, 8.3, 1H), 7.38(s, 1H), 7.40–7.47(m, 3H), 7.66(s, 1H), 7.80(d, J=7.3, 2H)

Example 32

(S)-4-(2-hydroxy-3-(4-(naphthalen-2-yl)piperidino)propyloxy)-N-methyl-1-(2-methylpropyl)indole-2-carboxamide hydrochloride 1/2 hydrate By the reactions in the same manner as in Example 3 using (S)-4-(2-hydroxy-3-(4-(naphthalen-2-yl)piperidino)propyloxy)-1-(2-methylpropyl)indole-2-carboxylic acid (1.0 g) obtained in Starting Material Synthesis Example 27, methylamine hydrochloride (0.2 g), triethylamine (0.7 ml) and diethyl cyanophosphate (0,5 ml), a yellow oil (0.8 g) was obtained. A 1N solution of hydrochloric acid in isopropyl was added to this oil in isopropyl ether. The precipitated crystals were collected by filtration and dried to give the title compound (0.7 g) as pale-yellow crystals, melting point 108–110° C.
$^1$H-NMR(CD$_3$OD)δ: 1.10–1.12(m, 7H), 2.09–2.24(m, 5H), 2.91(s, 3H) 3.11–3.60(m, 4H), 3.84–3.92(m, 2H), 4.15–4.25(m, 2H), 4.37(d, J=7.4, 2H), 4.57(m, 1H), 6.60(d, J=7.8, 1H), 7.09(d, J=8.3, 1H), 7.16–7.22(m, 2H), 7.43–7.46 (m, 3H), 7.74–7.867 (m, 4H)

Example 33

(S)-4-(2-hydroxy-3-(4-(naphthalen-2-yl)piperidino)propyloxy)-N,N-dimethyl-1-(2-methylpropyl)indole-2-carboxamide hydrochloride 1/2 hydrate By the reactions in the same manner as in Example 3 using (S)-4-(2-hydroxy-3-(4-(naphthalen-2-yl)piperidino)propyloxy)-1-(2-methylpropyl)indole-2-carboxylic acid (1.0 g) obtained in Starting Material Synthesis Example 27, dimethylamine hydrochloride (0.2 g), triethylamine (0.7 ml) and diethyl cyanophosphate (0.5 ml), the title compound (0.6 g) was obtained as pale-yellow crystals, melting point 108–110° C. $^1$H-NMR(CD$_3$OD)δ: 1.10–1.12(m, 7H), 2.03 (m, 1H), 2.10–2.30(m, 4H) 3.00–3.40(m, 8H), 3.40–3.60(m, 2H), 3.80–3.95(m, 2H), 4.12(d, J=7.8, 2H), 4.20–4.25(m, 2H), 4.57(m, 1H), 6.62(d, J=7.8, 1H), 6.87(s, 1H), 7.10(d, J=8.3, 1H), 7.17(dd, J=7.8, 8.3 m, 1H), 7.43–7.49(m, 3H), 7.74–7.86(m, 4H)

Example 34

(S)-1-(4-(2-hydroxy-3-(4-(naphthalen-2-yl)piperidino)propyloxy)-1-(2-methylpropyl)indole-2-carbonyl)pyrrolidine hydrochloride By the reactions in the same manner as in Example 3 using (S)-4-(2-hydroxy-3-(4-(naphthalen-2-yl)piperidino)propyloxy)-1-(2-methylpropyl)indole-2-carboxylic acid (1.0 g) obtained in Starting Material Synthesis Example 27, pyrrolidine (0.2 ml), triethylamine (0.7 ml) and diethyl cyanophosphate (0.5 ml), the title compound (0.4 g) was obtained as pale-yellow crystals, melting point 104–106° C.
$^1$H-NMR(CD$_3$OD)δ: 0.79–0.81(m, 7H), 1.91–2.14(m, 9H), 3.00–3.40(m, 4H), 3.60–3.80(m, 6H), 4.15–4.25(m, 4H), 4.57(m, 1H), 6.61(d, J=7.8, 1H), 6.98(s, 1H), 7.08(d, J=8.3, 1H), 7.20(dd, J=7.8, 8.3 m, 1H), 7.42–7.69(m, 3H), 7.72–7.84(m, 4H)

Example 35

(S)-1-(2-(5-methyl-1,2,4-oxadiazol-3-yl)benzo(b)furan-4-yloxy)-3-(4-(naphthalen-2-yl)piperidino)-2-propanol By the reactions in the same manner as in Example 3 using (S)-3-(4-glycidyloxybenzo(b)furan-2-yl)-5-methyl-1,2,4-oxadiazole (0.45 g) obtained in Starting Material Synthesis Example 31 and 4-(naphthalen-2-yl)piperidine (0.35 g), the title compound (0.65 g) was obtained as white crystals, melting point 146–148° C.

Example 36

(S)-1-(2-(5-methyl-1,2,4-oxadiazol-3-yl)benzo(b)furan-7-yloxy)-3-(4-(naphthalen-2-yl)piperidino)-2-propanol By the reactions in the same manner as in Example 1 using (S)-3-(7-glycidyloxybenzo(b)furan-2-yl)-5-methyl-1,2,4-oxadiazole (1.7 g) obtained in Starting Material Synthesis Example 35 and 4-(naphthalen-2-yl)piperidine (1.3 g), the title compound (2.0 g) was obtained as white crystals, melting point 169–170° C.

Example 37

(S)-1-(2-(5-methyl-1,3,4-oxadiazol-2-yl)benzo(b)furan-4-yloxy)-3-(4-(naphthalen-2-yl)piperidino)-2-propanol hydrochloride By the reactions in the same manner as in Example 1 using (S)-2-(4-glycidyloxybenzo(b)furan-2-yl)-5-methyl-1,3,4-oxadiazole (0.33 g) obtained in Starting Material Synthesis Example 39 and 4-(naphthalen-2-yl)piperidine (0.26 g), a brown oil (0.5 g) was obtained. This was dissolved in ethyl acetate and 1N solution of hydrochloric acid in ether was added. The precipitated crystals were collected by filtration and dried to give the title compound (0.30 g) as pale-yellow crystals, melting point 158–160° C.

Example 38

(S)-1-(2-(5-trifluoromethyl-1,3,4-oxadiazol-2-yl) benzo(b)furan-4-yloxy)-3-(4-(naphthalen-2-yl)piperidino)-2-propanol By the reactions in the same manner as in Example 1 using (S)-2-(4-glycidyloxybenzo(b)furan-2-yl)-5-trifluoromethyl-1,3,4-oxadiazole (1.0 g) obtained in Starting Material Synthesis Example 51 and 4-(naphthalen-2-yl)piperidine (0.75 g), the title compound (0.5 g) was obtained as a brown oil.

$^1$H-NMR(CDCl$_3$)δ: 1.87–2.00(m, 4H), 2.23(t, J=11.7, 1H), 2.51–2.58(m, 1H), 2.63–2.76(m, 3H), 3.05(brd, J=10.3, 1H), 3.23(brd, J=10.3, 1H), 4.15–4.26(m, 3H), 6.79(d, J=8.3, 1H), 7.26(d, J=8.3, 1H), 7.39–7.48(m, 4H), 7.64(s, 1H), 7.80(d, J=8.3, 4H)

Example 39

(S)-1-(2-(5-methyl-1,3,4-oxadiazol-2-yl)benzo(b) furan-7-yloxy)-3-(4-(naphthalen-2-yl)piperidino)-2-propanol To a solution of 2-(7-methoxybenzo(b)furan-2-yl)-5-methyl-1,3,4-oxadiazole (8.0 g) obtained in Starting Material Synthesis Example 40 in methylene chloride (100 ml) was added dropwise boron tribromide (10 ml) at −8° C. The mixture was stirred under ice-cooling for 1 hr. The reaction mixture was poured into ice water and the mixture was extracted with chloroform. The organic layer was dried over anhydrous sodium sulfate and concentrated under reduced pressure to give red crystals (6.0 g) of 7-hydroxy-2-(5-methyl-1,3,4-oxadiazol-2-yl)benzo(b)furan. This compound and (S)-glycidyl nosylate (7.25 g) were dissolved in dimethylformamide (100 ml) and potassium carbonate (11 g) was added. The mixture was heated at 50° C. for 2 hr. The reaction mixture was poured into ice water and the mixture was extracted with ethyl acetate. The organic layer was washed with saturated aqueous ammonium chloride solution, dried over anhydrous sodium sulfate and concentrated under reduced pressure to give an oily product (6.0 g). The oily product and 4-(naphthalen-2-yl)piperidine were dissolved in methanol (50 ml) and the mixture was refluxed under heating for 1 hr. After cooling, the solvent was evaporated under reduced pressure and the residue was purified by silica gel column chromatography (chloroform/methanol) to give the title compound (3.0 g) as pale-yellow crystals, melting point 140–142° C.

$^1$H-NMR(DMSO-d$_6$)δ: 1.77–1.83(m, 4H), 2.20–2.25(m, 2H), 2.47–2.66(m, 3H), 2.62(s, 3H), 3.04–3.13(m, 2H), 4.17(m, 2H), 4.30(m, 1H), 5.02(bs, 1H), 7.14(d, J=7.8, 1H), 7.29(t, J=7.8, 1H), 7.34(d, J=7.8, 1H), 7.41–7.48(m, 3H), 7.70(s, 1H), 7.72(s, 1H), 7.81–7.84(m, 3H)

Example 40

(S)-1-(2-(5-trifluoromethyl-1,3,4-oxadiazol-2-yl) benzo(b)furan-7-yloxy)-3-(4-(naphthalen-2-yl)piperidino)-2-propanol By the reactions in the same manner as in Example 1 using (S)-2-(7-glycidyloxybenzo(b)furan-2-yl)-5-trifluoromethyl-1,3,4-oxadiazole (1.0 g) obtained in Starting Material Synthesis Example 55 and 4-(naphthalen-2-yl)piperidine (0.80 g), the title compound (0.35 g) was obtained as a brown oil.

$^1$H-NMR(CDCl$_3$)δ: 1.81–2.00(m, 4H), 2.21–2.25(m, 1H), 2.47–2.60(m, 1H), 2.60–2.79(m, 3H), 3.07(d, J=9.8, 1H), 3.21–3.30(m, 1H), 4.23–4.31(m, 3H), 7.02–7.09(m, 1H), 7.21–7.36(m, 3H), 7.40–7.54(m, 3H), 7.68(s, 1H), 7.81(d, J=7.8, 1H)

The structural formulas of the compounds obtained in Examples 31 to 40 are shown in the following.

31

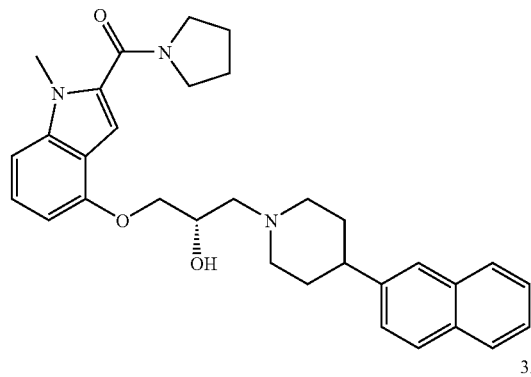

32

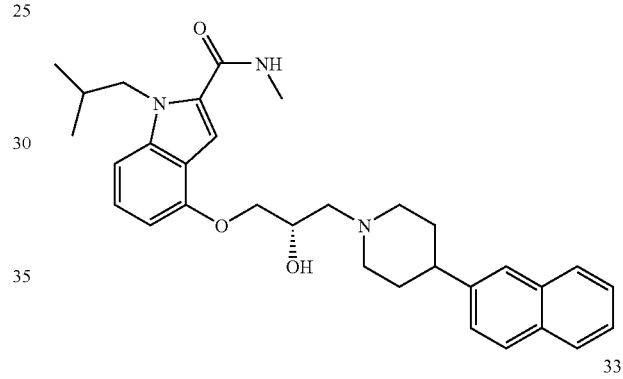

33

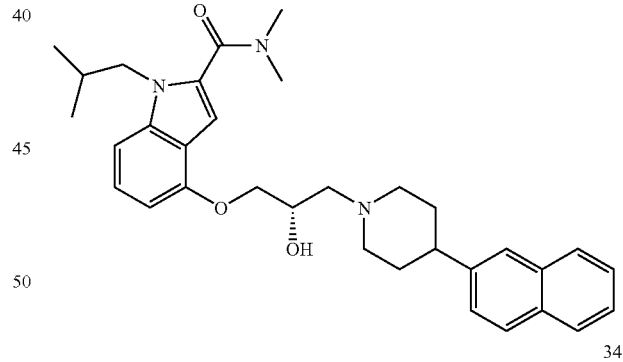

34

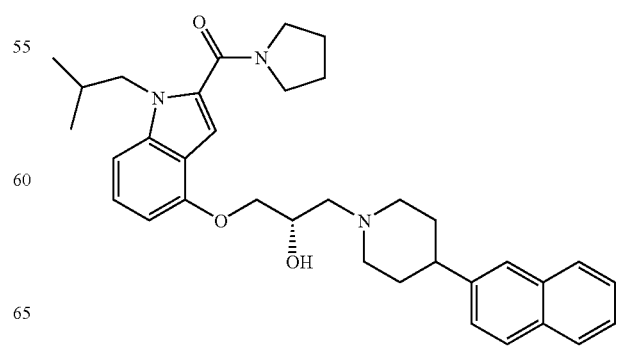

35
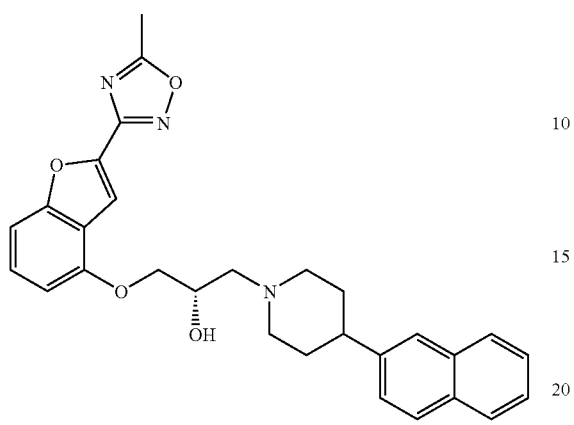
36
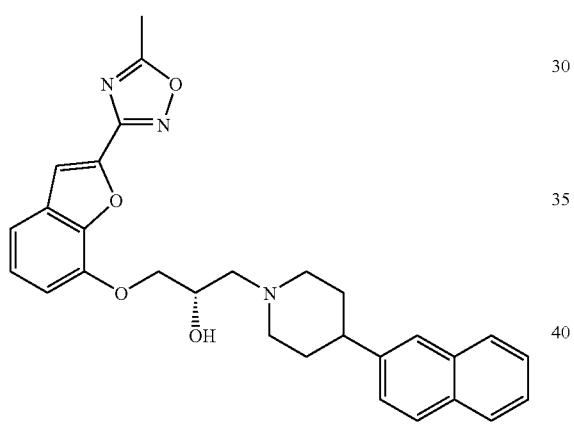
37
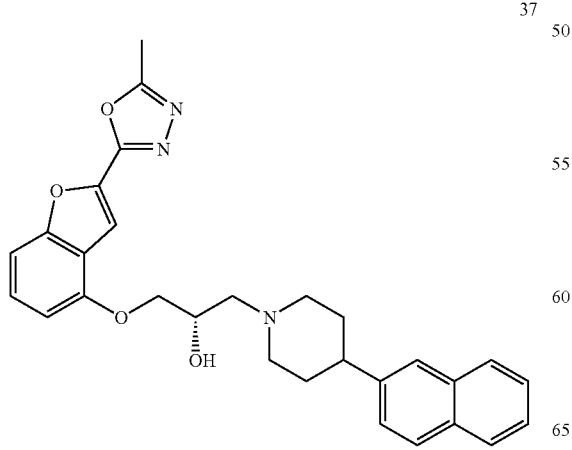
38
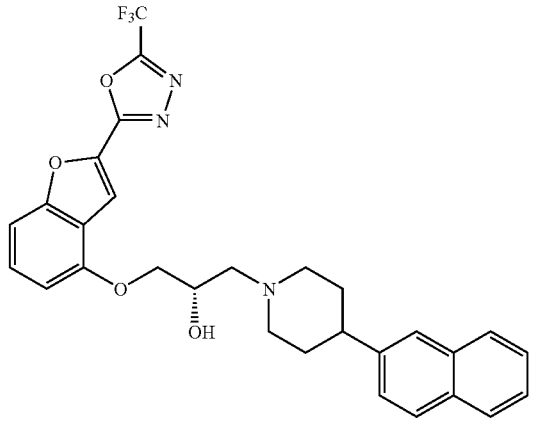
39
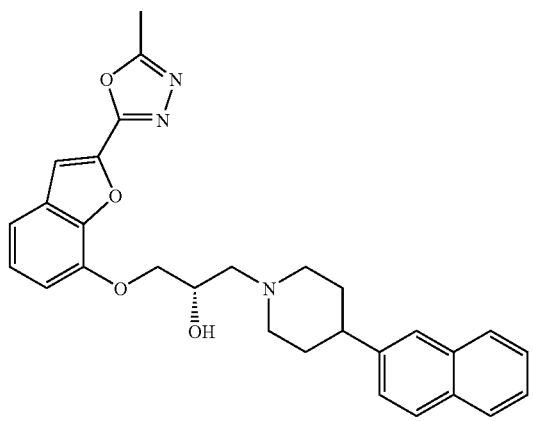
40
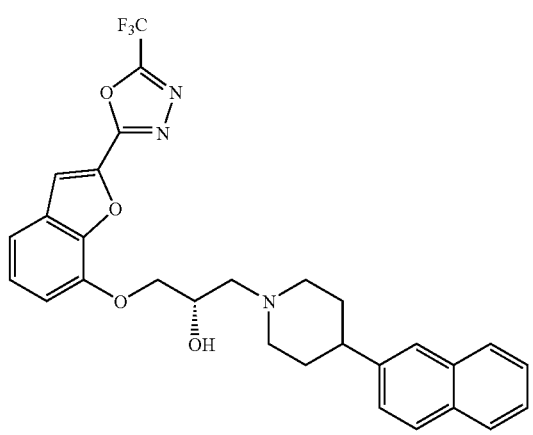

Example 41

(S)-1-(2-(5-methyl-1,3,4-oxadiazol-2-yl)benzo(b)thiophen-4-yloxy)-3-(4-(naphthalen-2-yl)piperidino)-2-propanol 2-(4-Hydroxybenzo(b)thiophen-2-yl)-5-methyl-1,3,4-oxadiazole (1.4 g) obtained in Starting Material Synthesis Example 43 and (S)-glycidyl nosylate (1.3 g) were dissolved in dimethylformamide (15 ml) and potassium carbonate (1.5 g) was added. The mixture was heated at 50° C. for 2 hr. The reaction mixture was poured into ice water and the mixture was extracted with ethyl acetate. The organic layer was washed with saturated aqueous ammonium chloride solution, dried over anhydrous sodium sulfate and concentrated under reduced pressure to give an oil (1.7 g). The oil and 4-(naphthalen-2-yl)piperidine were dissolved in methanol (20 ml) and the mixture was refluxed under heating for 1 hr. After cooling, the solvent was evaporated under reduced pressure and the residue was purified by silica gel column chromatography (chloroform/methanol) to give the title compound (0.36 g) as a brown oil.

$^1$H-NMR(DMSO-$d_6$)δ: 1.77–1.85(m, 4H), 2.18–2.25(m, 2H), 2.49–2.68(m, 3H), 2.61(s, 3H), 3.05–3.15(m, 2H), 4.18(m, 2H), 4.36(m, 1H), 5.02(bs, 1H), 7.01(d, J=7.8, 1H), 7.32(t, J=7.8, 1H), 7.34(d, J=7.8, 1H), 7.41–7.48(m, 3H), 7.74(s, 1H), 7.81–7.84(m, 3H), 8.07(s, 1H)

Example 42

(S)-1-(2-(5-methyl-1,3,4-oxadiazol-2-yl)-1H-indol-4-yloxy)-3-(4-(naphthalen-2-yl)piperidino)-2-propanol 4-Benzyloxy-2-(5-methyl-1,3,4-oxadiazol-2-yl)-1H-indole (5.0 g) obtained in Starting Material Synthesis Example 45 was dissolved in a mixed solvent (500 ml) of methanol-dimethylformamide (3:2) and 5% palladium-carbon (0.5 g) was added. The mixture was stirred for 5 hr under a hydrogen flow. The catalyst was removed by filtration through celite and the filtrate was concentrated under reduced pressure. To a solution of the obtained 4-hydroxy-2-(5-methyl-1,3,4-oxadiazol-2-yl)indole in dimethylformamide were added (S)-glycidyl nosylate (4 g) and potassium carbonate (4.2 g), and the mixture was heated at 50° C. for 5 hr. The reaction mixture was poured into ice water and the mixture was extracted with ethyl acetate. The organic layer was washed with saturated aqueous ammonium chloride solution, dried over anhydrous sodium sulfate and concentrated under reduced pressure. The residue was purified by silica gel column chromatography (chloroform/methanol) to give yellow crystals (1 g). The yellow crystals and 4-(naphthalen-2-yl)piperidine were dissolved in methanol (10 ml) and the mixture was refluxed under heating for 2 hr. After cooling, the solvent was evaporated under reduced pressure and the residue was purified by silica gel column chromatography (chloroform/methanol) to give the title compound (0.54 g) as yellow crystals, melting point 215–217° C.

$^1$H-NMR(DMSO-$d_6$)δ: 1.78–1.83(m, 4H), 2.22–2.25(m, 2H), 2.51–2.63(m, 3H), 2.58(s, 3H), 3.05–3.13(m, 2H), 4.05(m, 1H), 4.16(m, 2H), 4.89(bs, 1H), 6.58(d, J=7.8, 1H), 7.04(d, J=7.8, 1H), 7.13–7.19(m, 2H), 7.42(m, 3H), 7.70(s, 1H), 7.82(m, 3H), 12.16(s, 1H)

Example 43

(S)-3-(4-(naphthalen-2-yl)piperidino)-1-(2-(5-phenyl-1,3,4-oxadiazol-2-yl)benzo(b)furan-7-yloxy)-2-propanol To a solution of 2-(7-methoxybenzo(b)furan-2-yl)-5-phenyl-1,3,4-oxadiazole (3.7 g), obtained in Starting Material Synthesis Example 47, in methylene chloride (100 ml) was added dropwise boron tribromide (4 ml) with stirring at −8° C. The mixture was then stirred for 1 hr under ice-cooling, and the reaction mixture was poured into ice water and extracted with chloroform. The organic layer was dried over anhydrous sodium sulfate and concentrated under reduced pressure to give yellow crystals (2.7 g) of 7-hydroxy-2-(5-phenyl-1,3,4-oxadiazol-2-yl)benzo(b)furan. This compound and (S)-glycidyl nosylate (2.6 g) were dissolved in dimethylformamide (50 ml) and potassium carbonate (2.8 g) was added. The mixture was heated at 50° C. for 2 hr. The reaction mixture was poured into ice water and the mixture was extracted with ethyl acetate. The organic layer was washed with saturated aqueous ammonium chloride solution, dried over anhydrous sodium sulfate and concentrated under reduced pressure to give an oily product (1.7 g). The oily product and 4-(naphthalen-2-yl)piperidine were dissolved in methanol (20 ml) and the mixture was refluxed under heating for 1 hr. After cooling, the solvent was evaporated under reduced pressure and the residue was purified by silica gel column chromatography (chloroform/methanol) to give the title compound (2.3 g) as pale-yellow crystals, melting point 78–80° C.

$^1$H-NMR(DMSO-$d_6$)δ: 1.77–1.83(m, 4H), 2.21–2.23(m, 2H), 2.51–2.66(m, 3H), 3.05–3.14(m, 2H), 4.18(m, 2H), 4.33(m, 1H), 5.05(bs, 1H), 7.18(d, J=7.8, 1H), 7.32(t, J=7.8, 1H), 7.38–7.44(m, 4H), 7.65–7.70(m, 4H), 7.80–7.84(m, 3H), 7.90(s, 1H), 8.18(m, 2H)

Example 44

(S)-1-(2-(3-methyl-1,2,4-oxadiazol-5-yl)benzo(b)furan-4-yloxy)-3-(4-(naphthalen-2-yl)piperidino)-2-propanol hydrochloride By the reactions in the same manner as in Example 1 using (S)-5-(4-glycidyloxybenzo(b)furan-2-yl)-3-methyl-1,2,4-oxadiazole (0.46 g) obtained in Starting Material Synthesis Example 58 and 4-(naphthalen-2-yl)piperidine (0.43 g), a brown oil (1.0 g) was obtained. This compound was dissolved in ethyl acetate and 1N solution of hydrochloric acid in ether was added. The precipitated crystals were collected by filtration and dried to give the title compound (0.33 g) as brown crystals, melting point 216–218° C. (decomposition).

Example 45

(S)-1-(2-(3-methyl-1,2,4-oxadiazol-5-yl)benzo(b)thiophen-4-yloxy)-3-(4-(naphthalen-2-yl)piperidino)-2-propanol By the reactions in the same manner as in Example 1 using (S)-5-(4-glycidyloxybenzo(b)thiophen-2-yl)-3-methyl-1,2,4-oxadiazole (1.5 g) obtained in Starting Material Synthesis Example 61 and 4-(naphthalen-2-yl)piperidine (1.0 g), the title compound (1.5 g) was obtained as brown crystals, melting point 180–182° C.

Example 46

(S)-1-(2-(3-methyl-1,2,4-oxadiazol-5-yl)benzo(b)thiophen-4-yloxy)-3-(4-(naphthalen-1-yl)piperidino)-2-propanol hydrochloride By the reactions in the same manner as in Example 1 using (S)-5-(4-glycidyloxybenzo(b)thiophen-2-yl)-3-methyl-1,2,4-oxadiazole (0.73 g) obtained in Starting Material Synthesis Example 61 and 4-(naphthalen-1-yl)piperidine (1.0 g), a brown oil (1.5 g) was obtained as brown crystals. This compound was dissolved in ethyl acetate and 1N solution of hydrochloric acid in ether was added. The precipitated crystals were collected by filtration and dried to give the title compound (0.5 g) as pale-yellow crystals, melting point 235° C. or higher (decomposition).

Example 47

(S)-1-(2-(1,5-dimethylpyrazol-3-yl)benzo(b)furan-4-yloxy)-3-(4-(naphthalen-2-yl)piperidino)-2-propanol 1/4 hydrate By the reactions in the same manner as in Example 1 using (S)-3-(4-glycidyloxybenzo(b)furan-2-yl)-1,5-dimethylpyrazole (0.2 g) obtained in Starting Material Synthesis Example 63 and 4-(naphthalen-2-yl)piperidine (0.15 g), the title compound (0.16 g) was obtained, melting point 155–157° C.

Example 48

(S)-1-(2-(5-methyloxazol-2-yl)benzo(b)furan-7-yloxy)-3-(4-(naphthalen-2-yl)piperidino)-2-propanol By the reactions in the same manner as in Starting Material Synthesis Example 1 using 2-(7-hydroxybenzo(b)furan-2-yl)-5-methyloxazole (2.0 g) obtained in Starting Material Synthesis Example 65 and (S)-glycidyl nosylate (1.8 g), (S)-7-glycidyloxy-2-(5-methyloxazol-2-yl)benzo(b)furan (1.5 g) was obtained. Then, by the reactions in the same manner as in Example 1 using 4-(naphthalen-2-yl)piperidine (0.7 g), the title compound (0.26 g) was obtained, melting point 147–149° C.

The structural formulas of the compounds obtained in Examples 41 to 48 are shown in the following.

42

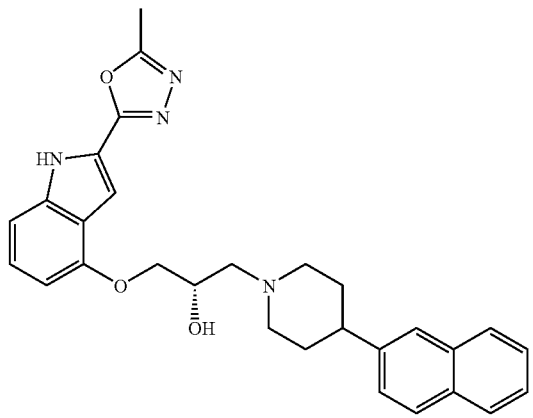

43

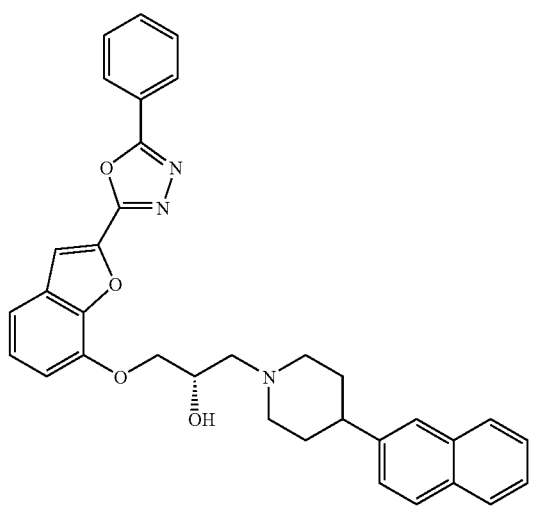

41

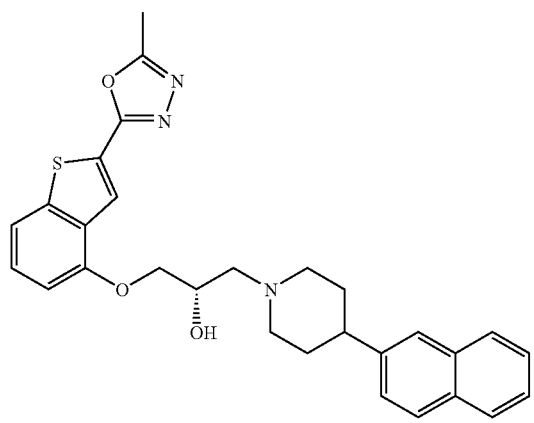

44

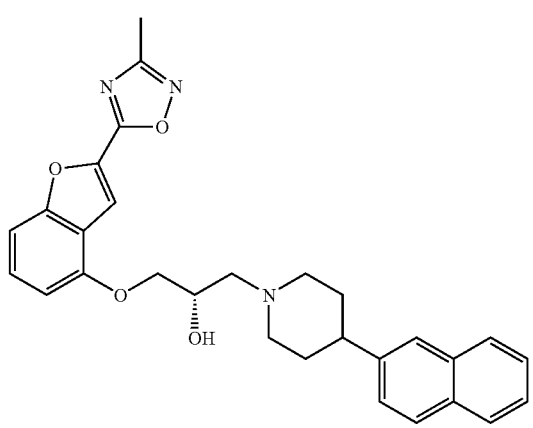

-continued

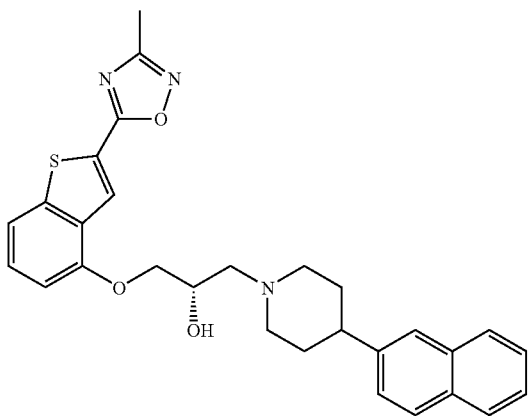
45

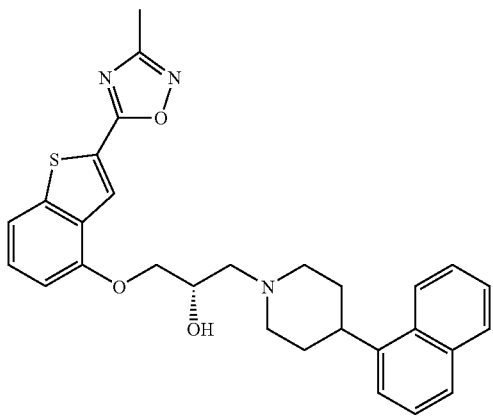
46

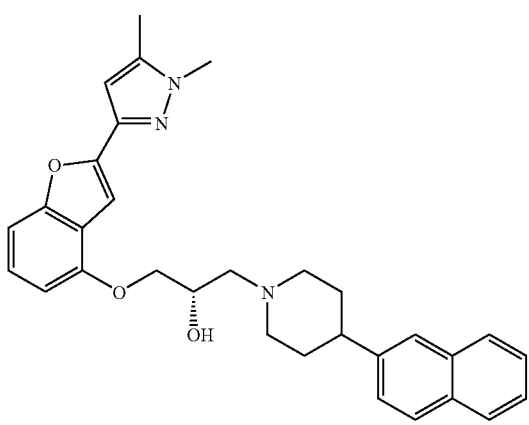
47

-continued

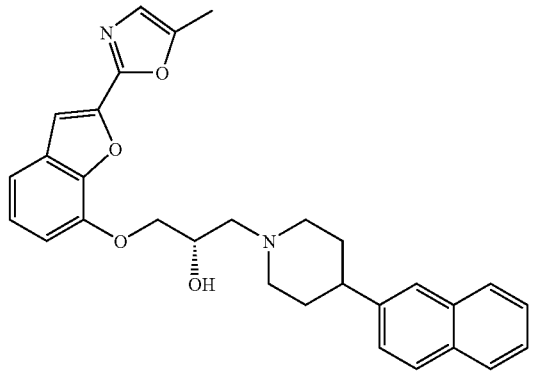
48

Example 49

(S)-1-(2-(3-methylisoxazol-5-yl)benzo(b)furan-7-yloxy)-3-(4-(naphthalen-2-yl)piperidino)-2-propanol 5-(7-Methoxybenzo(b)furan-2-yl)-3-methylisoxazole (2.04 g) obtained in Starting Material Synthesis Example 66 was dissolved in dichloromethane (30 ml) and boron tribromide (3 ml) was added dropwise with stirring at −40° C. The mixture was then stirred for 4 hr under ice-cooling and the reaction mixture was poured into ice water and extracted with chloroform. The organic layer was dried over anhydrous sodium sulfate and concentrated under reduced pressure to give red crystals (1.96 g) of 5-(7-hydroxybenzo(b)furan-2-yl)-3-methylisoxazole. This compound and (S)-glycidyl nosylate (2.5 g) were dissolved in dimethylformamide (20 ml) and potassium carbonate (2.48 g) was added. The mixture was heated at 50° C. for 3 hr. The reaction mixture was poured into ice water and the mixture was extracted with ethyl acetate. The organic layer was washed with saturated aqueous ammonium chloride solution, dried over anhydrous sodium sulfate and concentrated under reduced pressure to give an oily product (2.38 g). The oily product and 4-(naphthalen-2-yl)piperidine were dissolved in methanol (20 ml) and the solution was refluxed under heating for 1 hr. After cooling, the solvent was evaporated under reduced pressure and the residue was purified by silica gel column chromatography (chloroform/methanol) to give the title compound (2.93 g) as an oil.

$^1$H-NMR(DMSO-$d_6$)δ: 1.93–2.25(m, 4H), 2.33(s, 3H), 2.75–3.35(m, 5H), 3.65(m, 2H), 4.27(m, 2H), 4.48(m, 1H), 5.00(bs, 1H), 6.91(s, 1H), 7.11(d, J=7.8, 1H), 7.27(t, J=7.8, 1H), 7.34(d, J=7.8, 1H), 7.45–7.54(m, 4H), 7.74(s, 1H), 7.88(m, 3H)

Example 50

(S)-1-(2-(2-methylthiazol-4-yl)benzo(b)furan-4-yloxy)-3-(4-(naphthalen-2-yl)piperidino)-2-propanol By the reactions in the same manner as in Starting Material Synthesis Example 5 using 4-(4-methoxybenzo(b)furan-2-yl)-2-methylthiazole (2.7 g) obtained in Starting Material Synthesis Example 67 and boron tribromide (7.5 g), 4-(4-hydroxybenzo(b)furan-2-yl)-2-methylthiazole (2.0 g) was obtained as yellow crystals. By the reactions in the same manner as in Starting Material Synthesis Example 2 using this compound, (S)-glycidyl nosylate (2.9 g) and potassium carbonate (3.1 g), (S)-4-(4-glycidyloxybenzo(b)furan-2-yl)-2-methylthiazole (2.1 g) was obtained as a brown oil. By the reactions in the same manner as in Example 1 using the brown oil and 4-(naphthalen-2-yl)piperidine (1.5 g), the title compound (0.3 g) was obtained as white crystals, melting point 148–150° C.

Example 51

(S)-1-(2-(2-(5-methyl-1,3,4-oxadiazol-2-yl)vinyl)phenyloxy)-3-(4-(naphthalen-2-yl)piperidino)-2-propanol To a solution (20 ml) of 2-(2'-hydroxystyryl)-5-methyl-1,3,4-oxadiazole (1.5 g) obtained in Starting Material Synthesis Example 68 in DMF was added potassium carbonate (2.0 g), and then (S)-glycidyl nosylate (1.9 g) was added. The mixture was stirred at 40° C. for 3 hr. The reaction mixture was concentrated under reduced pressure and water was added. The mixture was extracted with ethyl acetate, and the organic layer was dried over anhydrous sodium sulfate and concentrated under reduced pressure to give an oil (1.3 g). To the oil (1.3 g) was added methanol (50 ml), and then 4-(naphthalen-2-yl)piperidine (1.0 g) was added. The mixture was refluxed under heating for 3 hr. After concentration, the residue was purified by silica gel column chromatography (chloroform/methanol) to give the title compound (1.0 g) as white crystals, melting point 105–106° C.

Example 52

(S)-1-(2-(2-(benzothiazol-2-yl)vinyl)phenyloxy)-3-(4-(naphthalen-2-yl)piperidino)-2-propanol To a solution (50 ml) of 2-(2'-hydroxystyryl)benzothiazole (2.5 g) obtained in Starting Material Synthesis Example 69 in DMF was added potassium carbonate (5.0 g), and then (S)-glycidyl nosylate (2.4 g) was added. The mixture was stirred at 50° C. for 2 hr. The reaction mixture was concentrated under reduced pressure and water was added. The mixture was extracted with ethyl acetate, and the organic layer was dried over anhydrous sodium sulfate and concentrated under reduced pressure to give yellow crystals of (S)-2-(2'-glycidyloxy)styrylbenzothiazole (2.7 g). To the yellow crystals (1.5 g) was added methanol (50 ml), and then 4-(naphthalen-2-yl)piperidine (1.0 g) was added. The mixture was refluxed under heating for 3 hr. After concentration, the residue was purified by silica gel column chromatography (chloroform/methanol) to give white crystals (1.3 g), melting point 125–127° C.

Example 53

(S)-1-(2-(2-(benzothiazol-2-yl)vinyl)phenyloxy)-3-(4-(naphthalen-1-yl)piperidino)-2-propanol By the reactions in the same manner as in Example 53 using (S)-2-(2'-glycidyloxystyryl)benzothiazole (0.9 g) and 4-(naphthalen-1-yl)piperidine (0.6 g), the title compound (0.98 g) was obtained as white crystals, melting point 146–148° C.

Example 54

(S)-1-(2-(2-(3-methyl-1,2,4-oxadiazol-5-yl)vinyl)phenyloxy)-3-(4-(naphthalen-2-yl)piperidino)-2-propanol hydrochloride To a solution (50 ml) of 5-(2'-hydroxystyryl)-3-methyl-1,2,4-oxadiazole (2.0 g) obtained in Starting Material Synthesis Example 70 in DMF was added potassium carbonate (3.0 g), and then (S)-glycidyl nosylate (2.6 g) was added. The mixture was stirred at 50° C. for 2 hr. The reaction mixture was concentrated under reduced pressure and water was added. The mixture was extracted with ethyl acetate and the organic layer was dried over anhydrous sodium sulfate. The solvent was evaporated under reduced pressure to give oily (S)-5-(2'-glycidyloxystyryl)-3-methyl-1,2,4-oxadiazole (2.2 g). This compound (1.2 g) was dissolved in methanol (50 ml), and 4-(naphthalen-2-yl)piperidine (1.0 g) was added. The mixture was refluxed under heating for 3 hr. After concentration, the concentrate was purified by silica gel column chromatography (chloroform/methanol), and 1 M solution of hydrochloric acid in methanol was added to the residue obtained. The precipitated crystals were collected by filtration and dried to give the title compound (1.2 g) as white crystals, melting point 184–186° C.

Example 55

(S)-1-(2-(2-(3-methyl-1,2,4-oxadiazol-5-yl)vinyl)phenyloxy)-3-(4-(naphthalen-1-yl)piperidino)-2-propanol hydrochloride By the reactions in the same manner as in Example 3 using 5-(2'-hydroxystyryl)-3-methyl-1,2,4-oxadiazole (1.0 g) obtained in Starting Material Synthesis Example 70 and 4-(naphthalen-1-yl)piperidine (1.0 g), the title compound (0.62 g) was obtained as white crystals, melting point 227–229° C. (decomposition)

Example 56

(S)-4-(2-hydroxy-3-(4-(naphthalen-2-yl)piperidino)propyloxy)benzo(b)furan-2-yl methyl ketone maleate By the reactions in the same manner as in Example 3 using (S)-4-glycidyloxybenzo(b)furan-2-yl methyl ketone (0.52 g) obtained in Starting Material Synthesis Example 71 and 4-(naphthalen-2-yl)piperidine (0.47 g), (S)-4-(2-hydroxy-3-(4-naphthalen-2-yl)piperidino)propyloxy)benzo(b)furan-2-yl methyl ketone (0.87 g) was obtained as a brown oil. This was dissolved in ethyl acetate and maleic acid (0.22 g) was added. The precipitated crystals were recrystallized from a mixed solvent of isopropanol-ethyl acetate to give the title compound (0.76 g) as pale-yellow crystals, melting point 153–155° C.

Example 57

(S)-4-(2-hydroxy-3-(4-(naphthalen-2-yl)piperidino)propyloxy)-3-methylbenzo(b)furan-2-yl methyl ketone maleate By the reactions in the same manner as in Example 3 using (S)-4-glycidyloxy-3-methylbenzo(b)furan-2-yl methyl ketone (0.60 g) obtained in Starting Material Synthesis Example 72 and 4-(naphthalen-2-yl)piperidine (0.51 g), (S)-4-(2-hydroxy-3-(4-naphthalen-2-yl)piperidino)propyloxy)-3-methylbenzo(b)furan-2-yl methyl ketone (1.1 g) was obtained as a brown oil. This was dissolved in ethyl acetate and maleic acid (0.25 g) was added. The precipitated crystals were recrystallized from a mixed solvent of isopropanol-ethyl acetate to give the title compound (0.82 g) as pale-yellow crystals, melting point 163–164° C.

Example 58

1-(4-(2-hydroxy-3-(4-(naphthalen-2-yl)piperidino)propyloxy)benzo(b)furan-2-yl)ethanol (S)-4-(2-Hydroxy-3-(4-(naphthalen-2-yl)piperidino)propyloxy)benzo(b)furan-2-yl methyl ketone (0.30 g) obtained in Example 56 was dissolved in methanol and sodium borohydride (30 mg) was added at room temperature. The mixture was stirred for 20 min. To the reaction mixture was added saturated aqueous ammonium chloride solution and the solvent was evaporated under reduced pressure. The obtained residue was dissolved in ethyl acetate, and the mixture was washed with water and dried over anhydrous magnesium sulfate. The solvent was evaporated under reduced pressure to give the title compound (0.24 g) as brown crystals, melting point 143–144° C.

The structural formulas of the compounds obtained in Examples 49 to 58 are shown in the following.

49

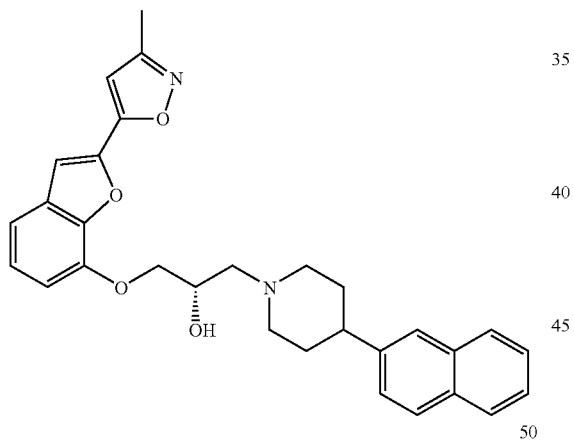

50

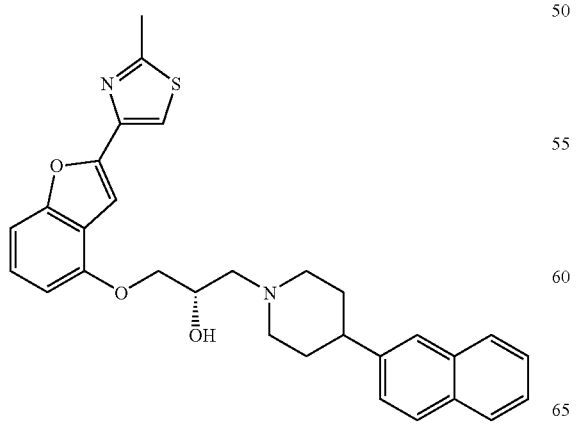

51

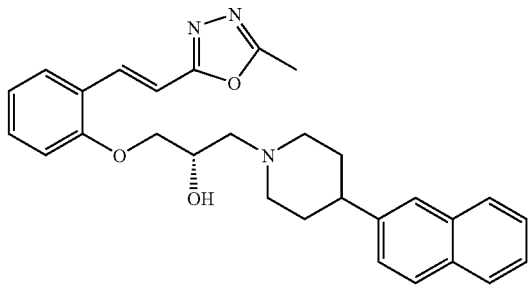

52

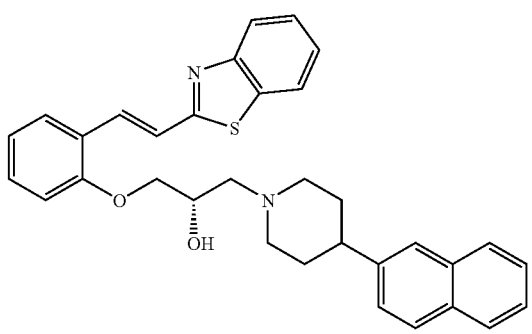

53

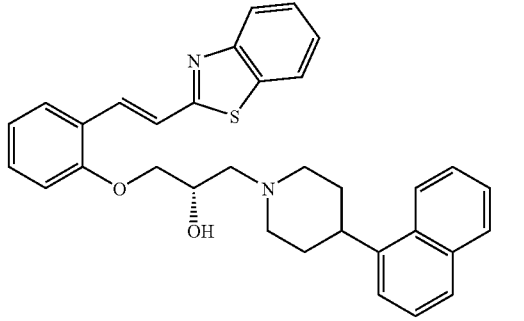

54

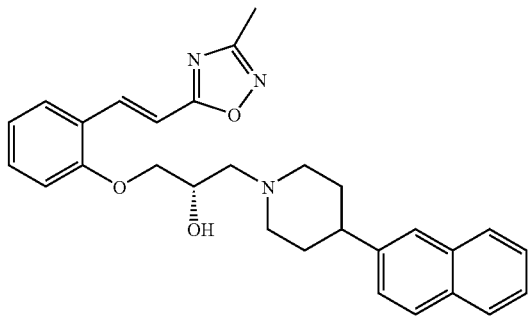

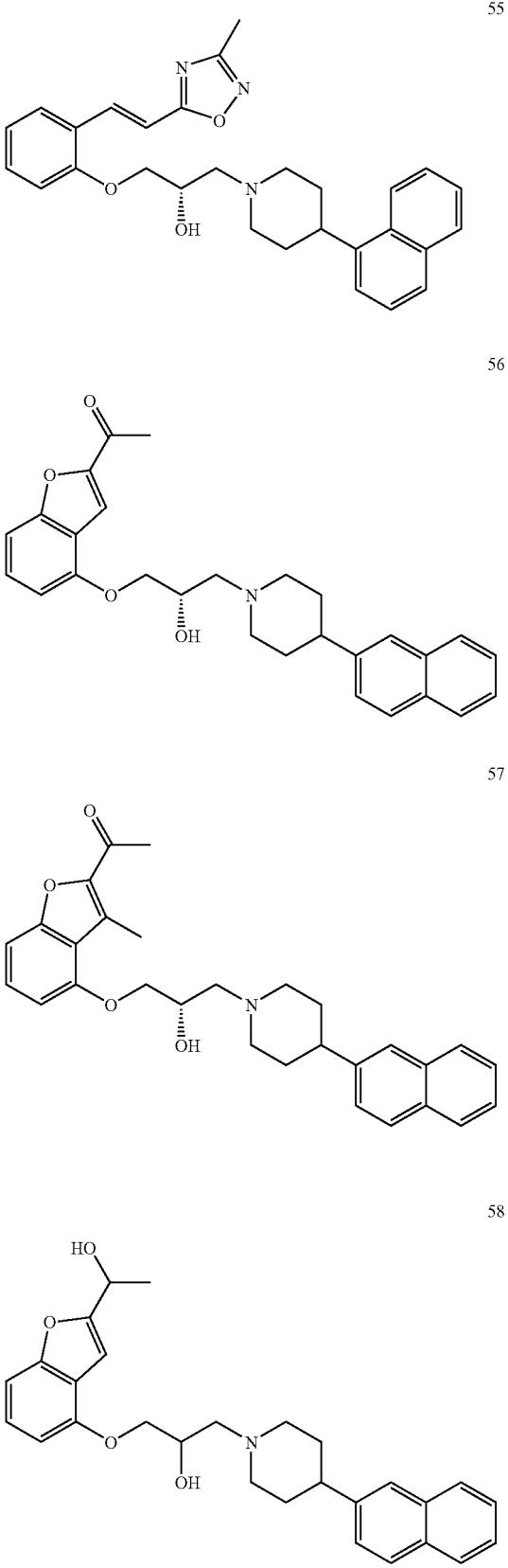

Example 59

(S)-5-(2-hydroxy-3-(4-(naphthalen-2-yl)piperidino)propyloxy)-3-morpholinomethyl-2-chromenone Red crystals (2 g) of 5-hydroxy-3-morpholinomethyl-2-chromenone and (S)-glycidyl nosylate (2 g) were dissolved in dimethylformamide (20 ml) and potassium carbonate (3 g) was added. The mixture was heated at 50° C. for 5 hr. The reaction mixture was poured into ice water and extracted with ethyl acetate. The organic layer was washed with saturated aqueous ammonium chloride solution, dried over anhydrous sodium sulfate and concentrated under reduced pressure to give an oily product (1.10 g). The oily product and 4-(naphthalen-2-yl)piperidine were dissolved in methanol (20 ml) and the mixture was refluxed under heating for 3 hr. After cooling, the solvent was evaporated under reduced pressure and the residue was purified by silica gel column chromatography (chloroform/methanol) to give the title compound (0.63 g) as an oil.

$^1$H-NMR(DMSO-$d_6$)δ: 2.09–2.22(m, 4H), 2.58(m, 2H), 2.75–3.35(m, 5H), 3.64(m, 8H), 4.01(s, 2H), 4.15(m, 2H), 4.46(m, 1H), 5.00(bs, 1H), 6.99(m, 2H), 7.46–7.57(m, 4H), 7.75(s, 1H), 7.88(m, 3H), 8.31(s, 1H)

Example 60

(S)-1-(2-(5-methyl-1,3,4-oxadiazol-2-yl)benzo(b)furan-7-yloxy)-3-(4-(naphthalen-1-yl)piperidino)-2-propanol 7-Methoxy-2-(5-methyl-1,3,4-oxadiazol-2-yl)benzo(b)furan (2 g) was dissolved in dichloromethane (50 ml) and boron tribromide (2 ml) was added dropwise with stirring at −8° C. The mixture was then stirred for 1 hr under ice-cooling and the reaction mixture was poured into ice water and extracted with chloroform. The organic layer was dried over anhydrous sodium sulfate and concentrated under reduced pressure to give red crystals (1.5 g) of 7-hydroxy-2-(5-methyl-1,3,4-oxadiazol-2-yl)benzo(b)furan. This compound and (S)-glycidyl nosylate (2 g) were dissolved in DMF (100 ml) and potassium carbonate (11 g) was added. The mixture was stirred at 50° C. for 2 hr. The reaction mixture was poured into ice water and extracted with ethyl acetate. The organic layer was washed with saturated aqueous chloride solution, dried over anhydrous sodium sulfate and concentrated under reduced pressure to give an oily product (2 g). The oily product and 4-(naphthalen-1-yl)piperidine were dissolved in methanol (20 ml) and the mixture was refluxed under heating for 1 hr. After cooling, the solvent was evaporated under reduced pressure and the residue was purified by silica gel column chromatography (chloroform/methanol) to give the title compound (1.0 g) as a pale-yellow oil.

$^1$H-NMR(DMSO-$d_6$)δ: 1.77–1.83(m, 4H), 2.20–2.25(m, 2H), 2.47–2.66(m, 3H), 2.62(s, 3H), 3.04–3.13(m, 2H), 4.17(m, 2H), 4.30(m, 1H), 5.02(bs, 1H), 7.17(d, J=7.8, 1H), 7.32(t, J=7.8, 1H), 7.40(d, J=7.8, 1H), 7.50–7.58(m, 4H), 7.74(s, 1H), 7.81(d, J=7.8, 1H), 7.93(d, J=7.8, 1H), 8.23(d, J=7.8, 1H)

Example 61

(S)-1-(2-(5-methyl-1,3,4-oxadiazol-2-yl)1H-indol-4-yloxy)-3-(4-(naphthalen-1-yl)piperidino)-2-propanol To a solution of 4-hydroxy-2-(5-methyl-1,3,4-oxadiazol-2-yl)-1H-indole in dimethylformamide were added (S)-glycidyl nosylate (2 g) and potassium carbonate (2 g), and the mixture was heated at 50° C. for 5 hr. The reaction mixture was poured into ice water and extracted with ethyl acetate. The organic layer was washed with saturated aqueous ammonium chloride solution, dried over anhydrous sodium sulfate and concentrated under reduced pressure. The residue was purified by silica gel column chromatography (chloroform/methanol) to give yellow crystals (0.5 g). The yellow crystals and 4-(naphthalen-1-yl)piperidine were dissolved in methanol (10 ml) and the mixture was refluxed under heating for 2 hr. After cooling, the solvent was evaporated under reduced pressure and the residue was purified by silica gel column chromatography (chloroform/methanol) to give the title compound (0.36 g) as yellow crystals, melting point 203–205° C.

$^1$H-NMR(DMSO-d$_6$)δ: 1.81–1.86(m, 4H), 2.33–2.39(m, 2H), 2.51–2.66(m, 3H), 2.58(s, 3H), 3.08–3.16(m, 2H), 4.05(m, 1H), 4.16(m, 2H), 4.92(bs, 1H), 6.58(d, J=7.8, 1H), 7.05(d, J=7.8, 1H), 7.13–7.19(m, 2H), 7.41–7.56(m, 4H), 7.75(d, J=7.8, 1H), 7.90(d, J=7.8, 1H), 8.14(d, J=7.8, 1H), 12.16(s, 1H)

Example 62

(S)-4-(2-acetoxy-3-(4-(naphthalen-2-yl)piperidino) propyloxy)-N-methoxy-N-methylbenzo(b)furan-2-carboxamide maleate (S)-4-(2-Hydroxy-3-(4-(naphthalen-2-yl)piperidino)propyloxy)-N-methoxy-N-methylbenzo(b)furan-2-carboxamide (0.40 g) obtained in Example 6 was dissolved in pyridine (20 ml) and acetic anhydride (10 ml) was added at room temperature. The mixture was stood for one day. The solvent was evaporated under reduced pressure and the obtained residue was purified by silica gel column chromatography (chloroform/methanol) to give (S)-4-(2-acetoxy-3-(4-(naphthalen-2-yl)piperidino)propyloxy)-N-methoxy-N-methylbenzo(b)furan-2-carboxamide (0.34 g) as a brown oil. This was dissolved in ethanol and maleic acid (0.10 g) was added. The precipitated crystals were collected by filtration and dried to give the title compound (0.25 g) as pale-yellow crystals, melting point 125–127° C.

Example 63 ethyl (S)-4-(2-hydroxy-3-(4-(naphthalen-2-yl)piperidino)propyloxy)benzo(b)furan-2-carboxylate By the reactions in the same manner as in Example 1 using ethyl (S)-4-glycidyloxybenzo(b)furan-2-carboxylate (3.3 g) and 4-(naphthalen-2-yl)piperidine (2.7 g), the title compound (5.1 g) was obtained as a brown oil.

$^1$H-NMR(CDCl$_3$)δ: 1.42(t, J=7.3, 3H), 1.87–1.99(m, 4H), 2.20(t, J=3.1, 1H), 2.50–2.54(m, 1H), 2.63–2.74(m, 3H), 3.05(brd, J=10.7, 1H), 3.23(brd, J=11.2, 1H), 4.13–4.25(m, 3H), 4.45(q, J=7.3, 2H), 6.72(d, J=8.3, 1H), 7.21(d, J=8.3, 1H), 7.35–7.49(m, 4H), 7.67(s, 1H), 7.68(d, J=6.3, 1H), 7.81(d, J=8.3, 3H)

Example 64

4-(2-hydroxy-3-(4-(naphthalen-2-yl)piperidino)propyloxy)-1H-indole-2-carboxamide By the reactions in the same manner as in Example 1 using 4-glycidyloxy-1H-indole-2-carboxamide (1.8 g) and 4-(naphthalen-2-ylpiperidine (1.4 g), the title compound (1.8 g) was obtained as white crystals, melting point 200–202° C.

Example 65

(S)-4-(2-hydroxy-3-(4-(naphthalen-2-yl)piperidino) propyloxy)-N,N-dimethylbenzo(b)thiophene-2-carboxamide L-tartaric acid By the reactions in the same manner as in Example 1 using 4-(glycidyloxy)benzo(b)thiophene-N,N-dimethylcarboxamide (3.5 g) and 4-(naphthalen-2-yl)piperidine (2.0 g), an oil (2.5 g) was obtained. This was dissolved in a solution of L-tartaric acid (2.0 g) in ethanol. The precipitated crystals were collected by filtration and dried to give the title compound (1.4 g) as white crystals, melting point 173–175° C.

Example 66

(S)-1-(7-(2-hydroxy-3-(5,6-dihydro-4-(naphthalen-2-yl)-2H-pyridin-1-yl)propyloxy)benzo(b)furan-2-ylcarbonyl)pyrrolidine By the reactions in the same manner as in Example 1 using (S)-1-(7-glycidyloxybenzo(b)furan-2-ylcarbonyl)pyrrolidine (2.1 g) and 5,6-dihydro-4-(naphthalen-2-yl)-2H-pyridine (1.8 g), the title compound (2.8 g) was obtained as white crystals, melting point 114–116° C.

Example 67

(S)-4-(2-hydroxy-3-(4-(naphthalen-2-yl)piperidino) propyloxy)-1-isopropyl-N,N-dimethylindole-2-carboxamide By the reactions in the same manner as in Example 3 using (S)-4-(2-hydroxy-3-(4-(naphthalen-2-yl)piperidino) propyloxy)-1-isopropylindole-2-carboxylic acid (2.5 g), dimethylamine hydrochloride (0.63 g), triethylamine (2.1 ml) and diethyl cyanophosphate (0.93 ml), the title compound (2.0 g) was obtained as a yellow oil.

$^1$H-NMR(CDCl$_3$)δ: 1.62(d, J=6.8, 6H), 1.94–1.97(m, 4H), 2.24(t, J=3.1, 1H), 2.44–2.54(m, 1H), 2.61–2.76(m, 3H), 3.05(brd, J=10.7, 1H), 3.15(s, 6H), 3.23(brd, J=11.2, 1H), 4.13–4.29(m, 3H), 4.79(q, J=6.8, 1H), 6.54(d, J=6.8, 1H), 6.67(s, 1H), 7.13–7.15(m, 2H), 7.38–7.46(m, 3H), 7.66(s, 1H), 7.79(d, J=8.3, 3H)

Example 68

(S)-1-(4-(2-hydroxy-3-(4-(naphthalen-2-yl)piperidino)propyloxy)-1-isopropylindole-2-carbonyl)pyrrolidine maleate By the reactions in the same manner as in Example 3 using (S)-4-(2-hydroxy-3-(4-(naphthalen-2-yl)piperidino) propyloxy)-1-isopropylindole-2-carboxylic acid (2.5 g), pyrrolidine (0.44 g), triethylamine (2.1 ml) and diethyl cyanophosphate (0.93 ml), a brown oil (2.1 g) was obtained. This was dissolved in ethanol and maleic acid (0.4 g) was added. The precipitated crystals were collected by filtration and dried to give the title compound (1.2 g) as pale-yellow crystals, melting point 154–155° C.

The structural formulas of the compounds obtained in Examples 59 to 68 are shown in the following.

59
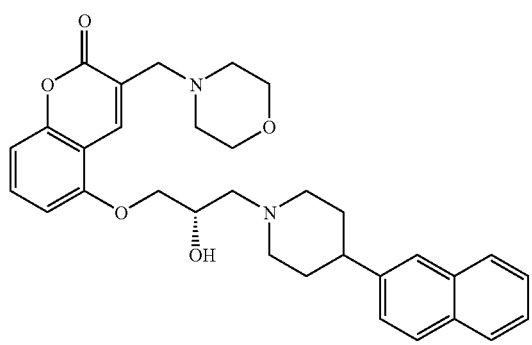
60
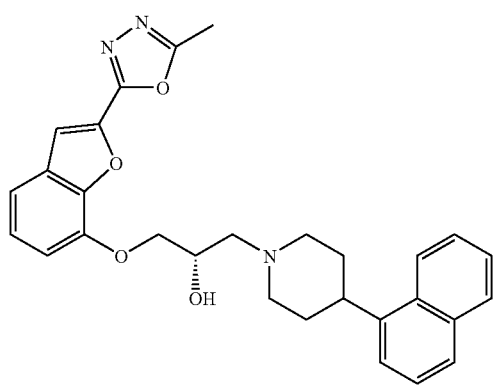
61
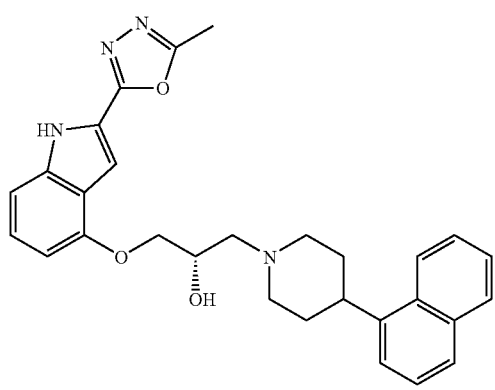
62
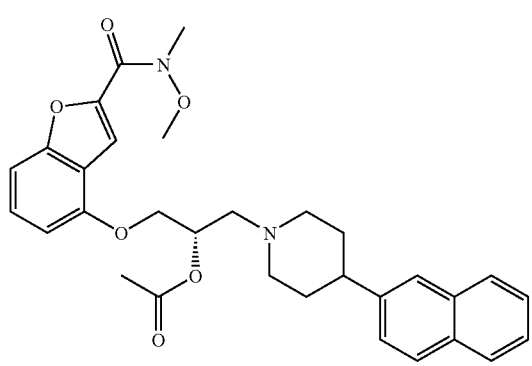
-continued
63
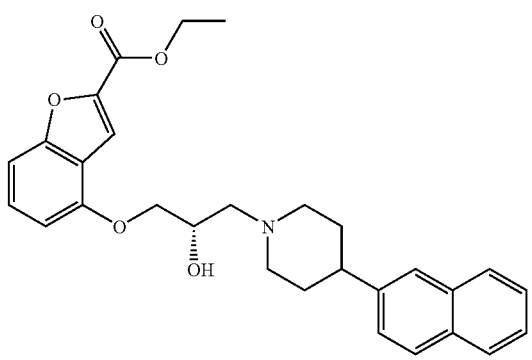
64
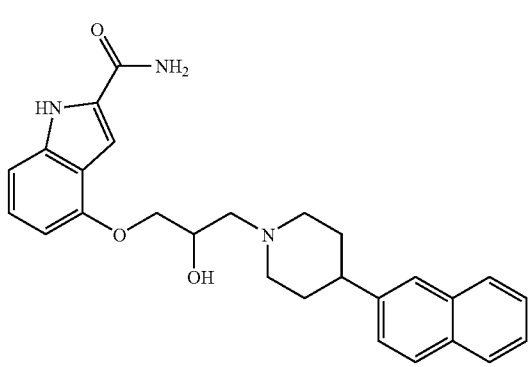
65
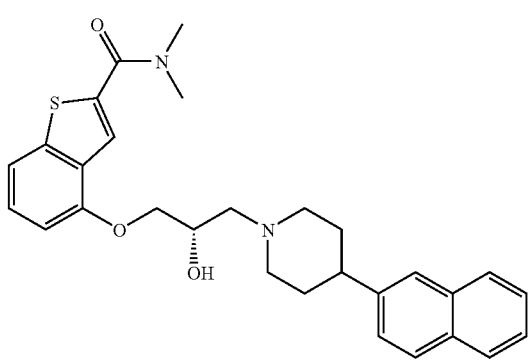
66
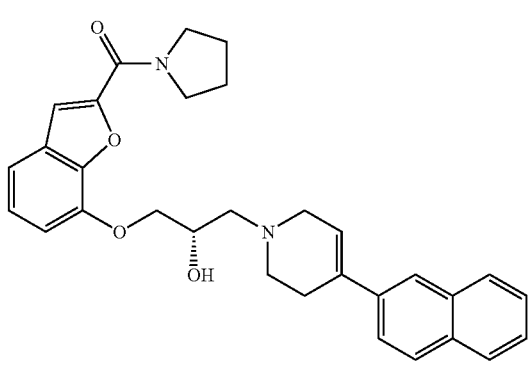

-continued

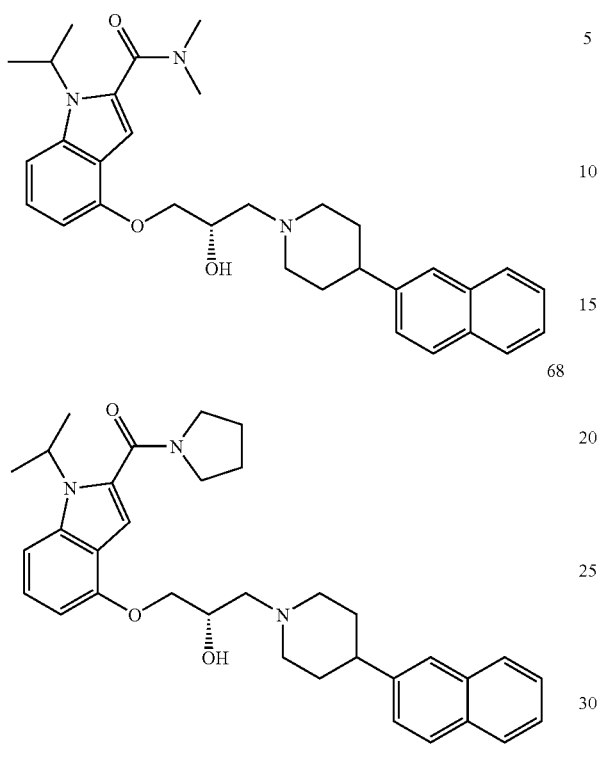

67

68

Example 69

(S)-1-(5-(2-hydroxy-3-(4-(naphthalen-2-yl)piperidin-1-yl)propyloxy)-2H-chromen-3-ylcarbonyl)pyrrolidine Red crystals (2.0 g) of 1-(5-hydroxy-2H-chromen-3-ylcarbonyl)pyrrolidine and (S)-glycidyl nosylate (2.0 g) were dissolved in dimethylformamide (20 ml), and potassium carbonate (3 g) was added. The mixture was heated at 50° C. for 3 hr. The reaction mixture was poured into ice water and extracted with ethyl acetate. The organic layer was washed with saturated aqueous ammonium chloride solution, dried over anhydrous sodium sulfate and concentrated under reduced pressure to give an oily product (3.27 g). The oily product and 4-(naphthalen-2-yl)piperidine were dissolved in methanol (20 ml) and the mixture was refluxed under heating for 3 hr. After cooling, the solvent was evaporated under reduced pressure and the residue was purified by silica gel column chromatography (chloroform/methanol) to give the title compound (0.12 g) as a brown oil.

$^1$H-NMR(CDCl$_3$)δ: 1.91–2.02(m, 8H), 2.17(m, 2H), 2.48–2.70(m, 3H), 2.96(m, 1H), 3.15(m, 1H), 3.54(m, 4H), 3.73(bs, 1H), 4.00–4.13(m, 3H), 4.87(s, 2H), 6.47(d, J=7.8 Hz, 1H), 6.50(d, J=7.8 Hz, 1H), 7.11(t, J=7.8 Hz, 1H), 7.16(s, 1H), 7.37(m, 3H), 7.64(s, 1H), 7.78(m, 3H)

By the same manner as in the above-mentioned Example, the following compounds can be synthesized.

Example 70

(S)-1-(2-(5-methyloxazol-2-yl)-1H-indol-4-yloxy)-3-(4-(naphthalen-2-yl)piperidino)-2-propanol

Example 71

(S)-1-(2-(5-methyloxazol-2-yl)-1H-indol-4-yloxy)-3-(4-(4-chlorophenyl)piperidino)-2-propanol

Example 72

(S)-1-(2-(5-methyloxazol-2-yl)-1H-indol-4-yloxy)-3-(4-(3,4-dichlorophenyl)piperidino)-2-propanol

Example 73

(S)-1-(2-(5-methyl-1,3,4-oxadiazol-2-yl)-1H-indol-4-yloxy)-3-(4-(4-chlorophenyl)piperidino)-2-propanol

Example 74

(S)-1-(2-(5-methyl-1,3,4-oxadiazol-2-yl)-1H-indol-4-yloxy)-3-(4-(3,4-dichlorophenyl)piperidino)-2-propanol

Example 75

(S)-1-(2-(5-methyl-1H-imidazol-2-yl)-1H-indol-4-yloxy)-3-(4-(3,4-dichlorophenyl)piperidino)-2-propanol

Example 76

(S)-1-(2-(3-methyl-1H-pyrazol-5-yl)-1H-indol-4-yloxy)-3-(4-(3,4-dichlorophenyl)piperidino)-2-propanol

Example 77

(S)-1-(2-(3-methylisoxazol-5-yl)-1H-indol-4-yloxy)-3-(4-(naphthalen-2-yl)piperidino)-2-propanol

Example 78

(S)-1-(2-(5-methyloxazol-2-yl)-1H-indol-4-yloxy)-3-(4-(4-methylphenyl)piperidino)-2-propanol The structural formulas of the compounds obtained in Examples 69 to 78 are shown in the following.

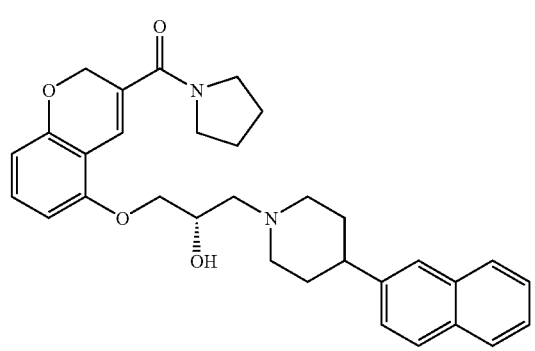

69

-continued
70
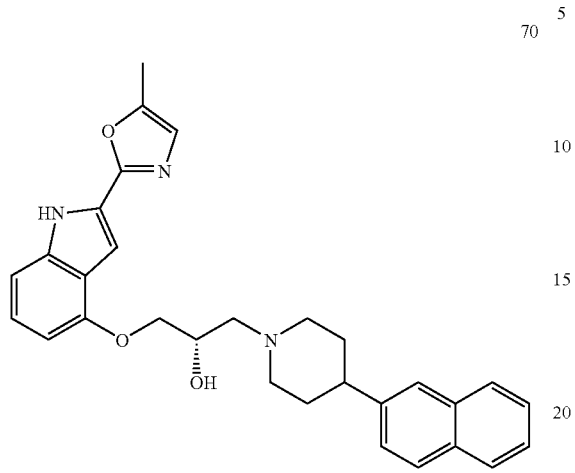
71
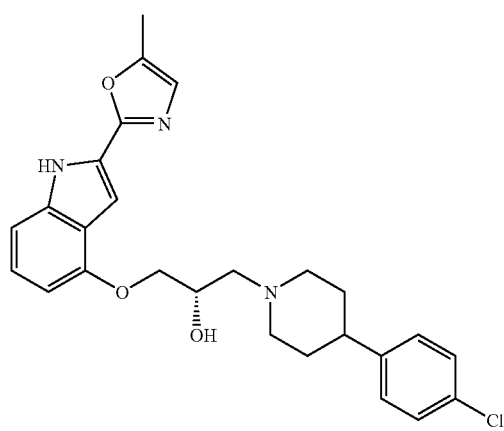
72
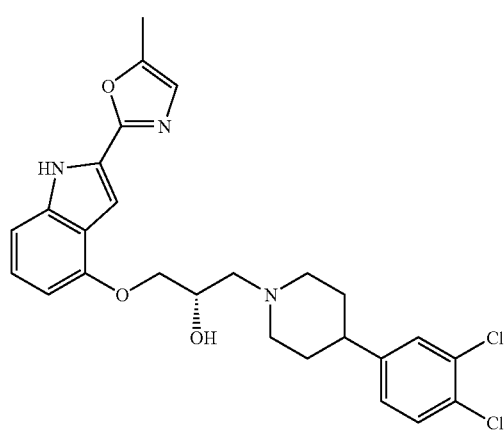
-continued
73
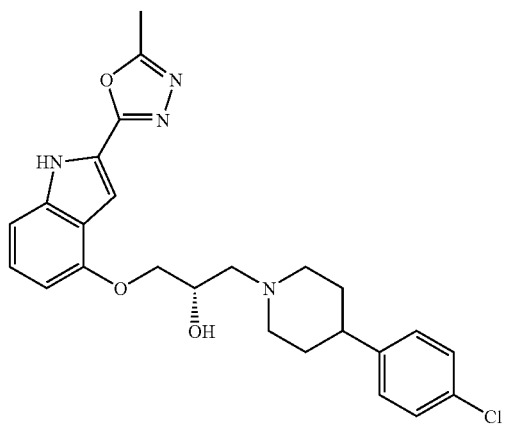
74
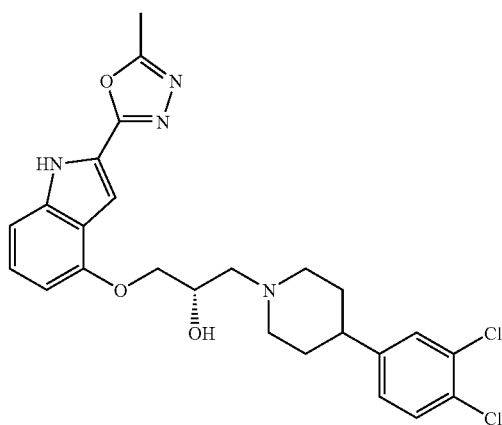
75
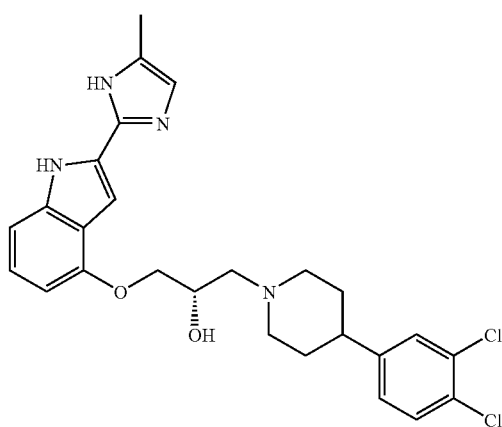

-continued

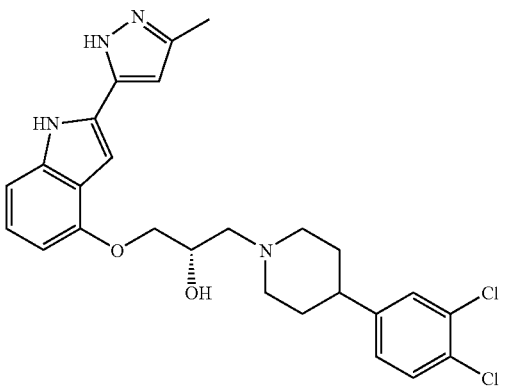

76

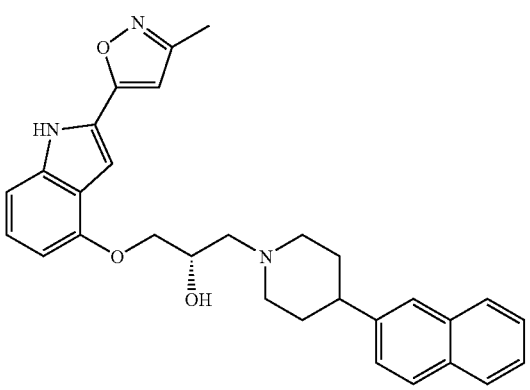

77

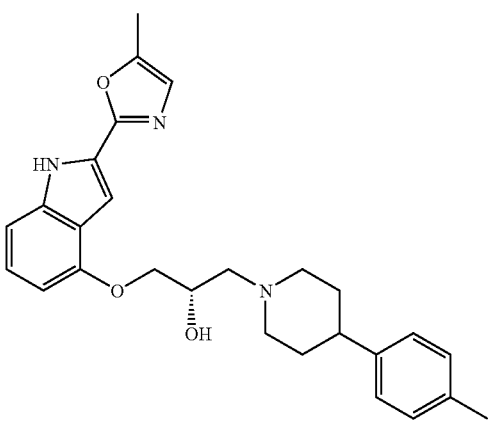

78

Example 79

(R)-1-(2-(5-methyl-1,3,4-oxadiazol-2-yl)-1H-indol-4-yloxy)-3-(4-(naphthalen-2-yl)piperidino)-2-propanol Example 80

(S)-1-(2-(5-methyloxazol-2-yl)benzo(b)furan-4-yloxy)-3-(4-(naphthalen-2-yl)piperidino)-2-propanol Example 81

(S)-3-(4-(3,4-dichlorophenyl)piperidino)-1-(2-(5-methyloxazol-2-yl)benzo(b)furan-4-yloxy)-2-propanol dihydrochloride 2-(4-Hydroxybenzo(b)furan)-5-methyloxazole (11.0 g) and (S)-glycidyl nosylate (13.0 g) were dissolved in dimethylformamide (100 ml) and potassium carbonate (15.0 g) was added. The mixture was stirred at room temperature for 10 hr. The reaction mixture was poured into ice water and extracted with ethyl acetate. The organic layer was washed with saturated aqueous ammonium chloride solution, dried over anhydrous sodium sulfate and concentrated under reduced pressure to give an oil (10.0 g). The oil and 4-(3,4-dichlorophenyl)piperidine were dissolved in methanol (100 ml) and the mixture was refluxed under heating for 2 hr. After cooling, the solvent was evaporated under reduced pressure and the residue was purified by silica gel column chromatography (chloroform/methanol). The obtained yellow oil (10 g) was dissolved in acetone and hydrochloric acid was added to give a hydrochloride. Recrystallization from ethanol gave the title compound (7.0 g) as pale-yellow crystals, melting point 190° C. (decomposition).

$^1$H-NMR(DMSO-d$_6$)δ: 2.02–2.24(m, 4H), 2.43(s, 3H), 2.92(m, 1H) 3.20(m, 2H), 3.35–3.48(m, 2H), 3.71–3.81(m, 2H), 4.13–4.23(m, 2H), 4.57(m, 1H), 6.89(d, J=7.8, 1H), 7.08(s, 1H), 7.26–7.31(m, 2H), 7.37(t, J=7.8, 1H), 7.50(s, 1H), 7.56–7.67(m, 2H), 10.37(bs, 1H)

Example 82

(S)-1-(2-(5-methyloxazol-2-yl)benzo(b)furan-4-yloxy)-3-(4-(4-chlorophenyl)piperidino)-2-propanol Example 83

(S)-1-(2-(5-methyl-1,3,4-oxadiazol-2-yl)benzo(b)furan-4-yloxy)-3-(4-(4-chlorophenyl)piperidino)-2-propanol Example 84

(R)-1-(2-(5-methyloxazol-2-yl)benzo(b)furan-4-yloxy)-3-(4-(naphthalen-2-yl)piperidino)-2-propanol Example 85

(S)-1-(2-(3-methylisoxazol-5-yl)benzo(b)furan-4-yloxy)-3-(4-(naphthalen-2-yl)piperidino)-2-propanol Example 86

(S)-1-(2-(5-methylthiazol-2-yl)benzo(b)furan-4-yloxy)-3-(4-(4-chlorophenyl)piperidino)-2-propanol Example 87

(S)-1-(2-(5-methylthiazol-2-yl)-1H-indol-4-yloxy)-3-(4-(naphthalen-2-yl)piperidino)-2-propanol The structural formulas of the compounds obtained in Examples 79 to 87 are shown in the following.

79
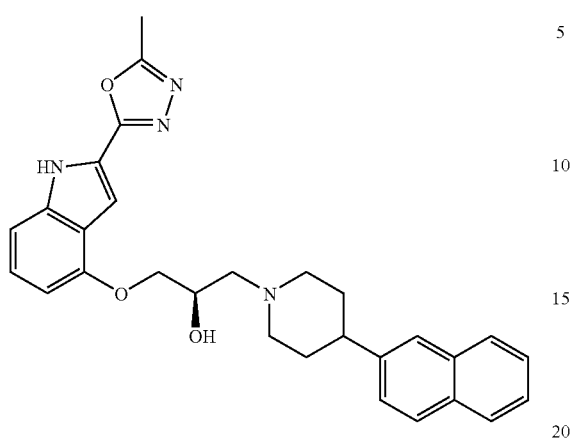
80
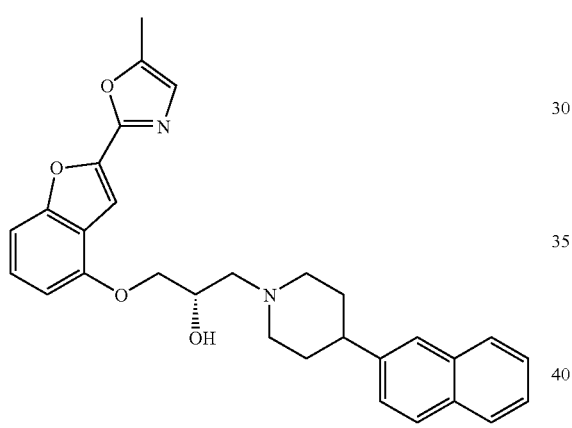
81
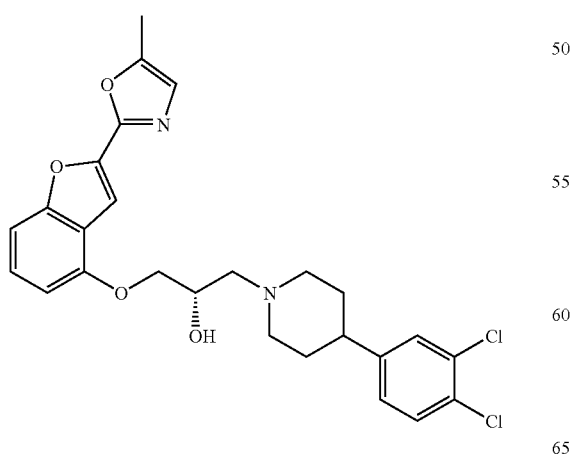
82
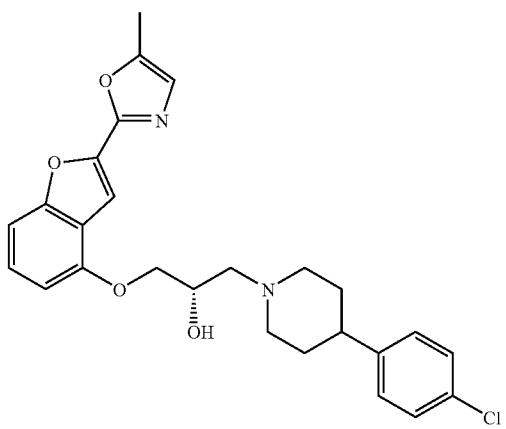
83
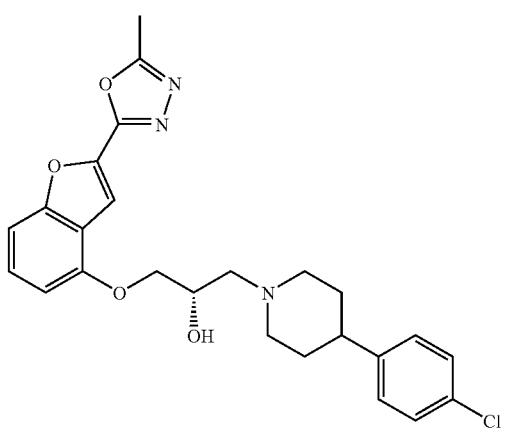
84
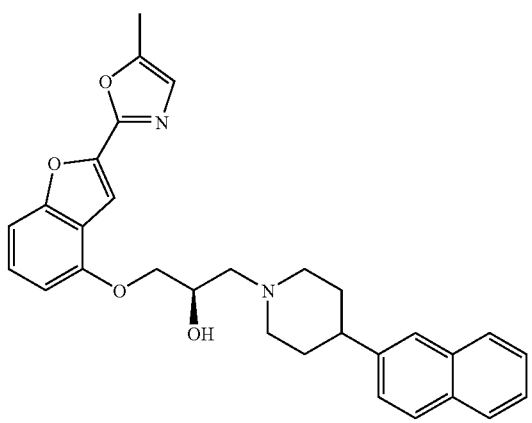

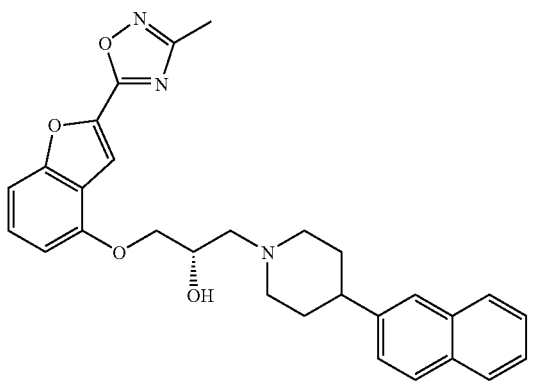

85

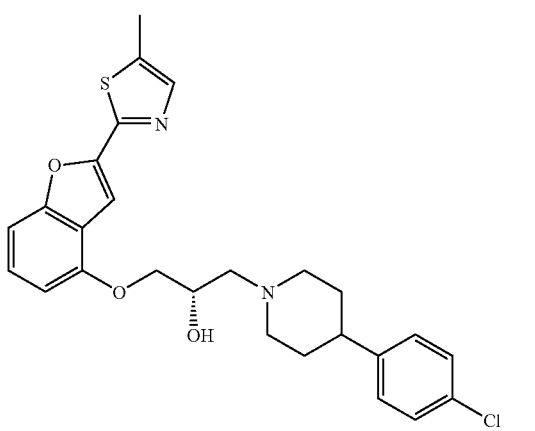

86

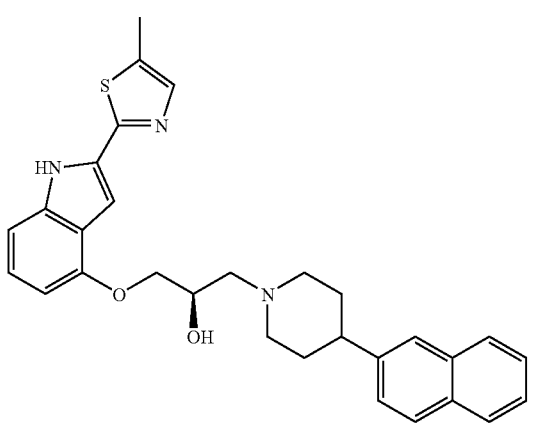

87

Example 88

(S)-1-(4-(3,4-dichlorophenyl)piperidino)-3-(2-(5-methyl-1,3,4-oxadiazol-2-yl)benzo(b)furan-4-yloxy)-2-propanol hydrochloride 1/4 hydrate By the reactions in the same manner as in Example 1 using (S)-2-(4-glycidyloxybenzo(b)furan-2-yl)-5-methyl-1,3,4-oxadiazole (23.0 g) obtained in the same manner as in Starting Material Synthesis Example 39 and 4-(3,4-dichlorophenyl)piperidine (18.6 g), a brown oil (39.0 g) was obtained. This was dissolved in ethanol. A solution of hydrochloric acid in ether was added and the mixture was allowed to stand. The precipitated crystals were collected by filtration and dried to give the title compound (23.5 g) as pale-yellow crystals, melting point 230–231° C.

Example 89

(S)-1-(4-(6-methoxynaphthalen-2-yl)piperidino)-3-(2-(5-methyl-1,3,4-oxadiazol-2-yl)benzo(b)furan-4-yloxy)-2-propanol By the reactions in the same manner as in Example 1 using (S)-2-(4-glycidyloxybenzo(b)furan-2-yl)-5-methyl-1,3,4-oxadiazole (1.4 g) obtained in Starting Material Synthesis Example 39 and 4-(6-methoxynaphthalen-2-yl)piperidine (1.2 g), crude crystals were obtained. This was recrystallized from ethyl acetate to give the title compound (1.2 g) as white crystals, melting point 156–158° C.

Example 90

(S)-1-(4-(3,4-methylenedioxyphenyl)piperidino)-3-(2-(5-methyl-1,3,4-oxadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-methyl-1,3,4-oxadiazole (0.50 g) obtained in Starting Material Synthesis Example 39 and 4-(3,4-methylenedioxyphenyl)piperidine (0.36 g), a brown oil (0.42 g) was obtained. This was dissolved in acetone and a solution of hydrochloric acid in ether was added. The solvent was evaporated under reduced pressure and the resulting crude crystals were recrystallized from a mixed solvent of isopropanol-ethyl acetate (2:1) to give the title compound (0.27 g) as pale-yellow crystals, melting point 200–202° C.

Example 91

(S)-1-(4-(3,4-dimethylphenyl)piperidino)-3-(2-(5-methyl-1,3,4-oxadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-methyl-1,3,4-oxadiazole (0.50 g) obtained in Starting Material Synthesis Example 39 and 4-(3,4-dimethylphenyl)piperidine (0.33 g), a brown oil (0.64 g) was obtained. This was dissolved in acetone and a solution of hydrochloric acid in ether was added. The solvent was evaporated under reduced pressure and the resulting crude crystals were recrystallized from a mixed solvent of isopropanol-isopropyl ether (2:1) to give the title compound (0.33 g) as pale-yellow crystals, melting point 150–152° C.

Example 92

(S)-3-(4-(3,4-dichlorophenyl)piperidino)-1-(2-(5-ethyl-1,3,4-oxadiazol-2-yl)benzo(b)furan-4-yloxy)-2-propanol hydrochloride 1/2 hydrate The yellow oil (0.90 g) obtained by the reactions in the same manner as in Example 1 using (S)-2-(4-glycidyloxybenzo(b)furan-2-yl)-5-ethyl-1,3,4-oxadiazole (0.50 g) obtained in Starting Material Synthesis Example 76 and 4-(3,4-dichlorophenyl)piperidine (0.40 g) was dissolved in acetone and absolution of hydrochloric acid in ether was added to give a hydrochloride. Recrystallization from a mixed solvent of isopropanol-isopropyl ether gave the title compound (0.34 g) as white crystals, melting point 148–150° C.

Example 93

(S)-3-(4-(3,4-dimethylphenyl)piperidino)-1-(2-(5-ethyl-1,3,4-oxadiazol-2-yl)benzo(b)furan-4-yloxy)-2-propanol hydrochloride 1/2 hydrate A yellow oil (5.0 g) obtained by the reactions in the same manner as in Example 1 using (S)-2-(4-glycidyloxybenzo(b)furan-2-yl)-5-ethyl-1,3,4-oxadiazole (3.0 g) obtained in Starting Material Synthesis Example 76 and 4-(3,4-dimethylphenyl)piperidine (2.0 g) was dissolved in a mixed solvent of acetone-ethyl acetate, and a solution of hydrochloric acid in ether was added to give a hydrochloride. Recrystallization from a mixed solvent of acetone-ethyl acetate gave the title compound (2.0 g) as pale-yellow crystals, melting point 178–180° C.

Example 94

(S)-1-(2-(3-methylisoxazol-5-yl)benzo(b)furan-4-yloxy)-3-(4-(naphthalen-2-yl)piperidino)-2-propanol hydrochloride 1/4 hydrate By the reactions in the same manner as in Example 1 using (S)-5-(4-glycidyloxybenzo(b)furan-2-yl)-3-methylisoxazole (0.50 g) obtained in Starting Material Synthesis Example 79 and 4-(naphthalen-2-yl)piperidine (0.37 g), a brown oil (0.69 g) was obtained. This was dissolved in ethyl acetate and a solution of hydrochloric acid in ether was added. The precipitated crystals were collected by filtration and dried to give the title compound (0.36 g) as white crystals, melting point 152–154° C.

Example 95

(S)-1-(4-(3,4-dichlorophenyl)piperazin-1-yl)-3-(2-(3-methylisoxazol-5-yl)benzo(b)furan-4-yloxy)-2-propanol hydrochloride 1/4 hydrate By the reactions in the same manner as in Example 1 using (S)-5-(4-glycidyloxybenzo(b)furan-2-yl)-3-methylisoxazole (0.50 g) obtained in Starting Material Synthesis Example 79 and 4-(3,4-dichlorophenyl)piperazine (0.40 g), a brown oil (0.60 g) was obtained. This was dissolved in isopropanol and a solution of hydrochloric acid in ether was added. The precipitated crystals were collected by filtration and dried to give the title compound (0.36 g) as brown crystals, melting point 250° C. or higher.

The structural formulas of the compounds obtained in Examples 88 to 95 are shown in the following.

88

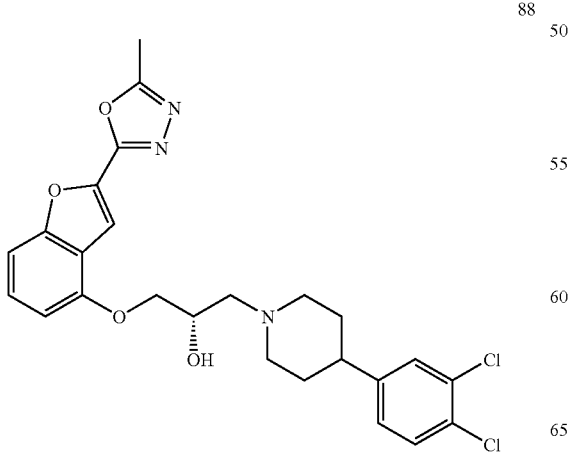

89

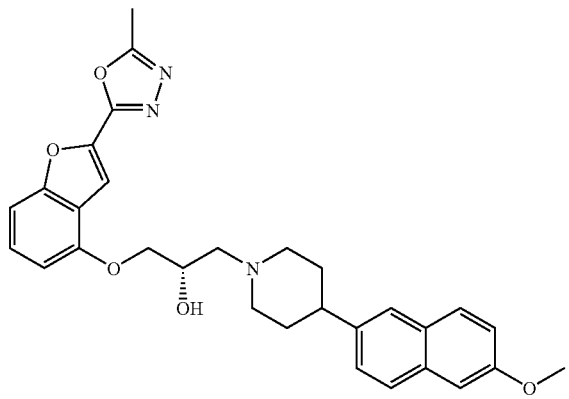

90

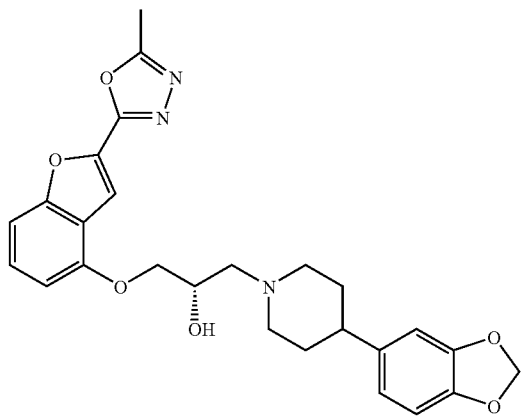

91

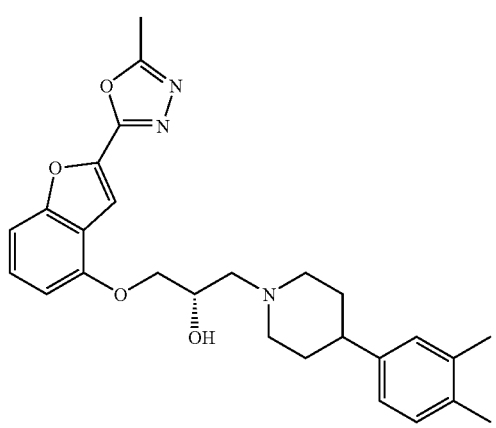

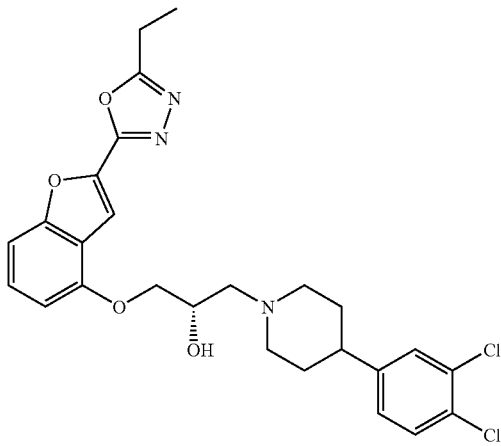

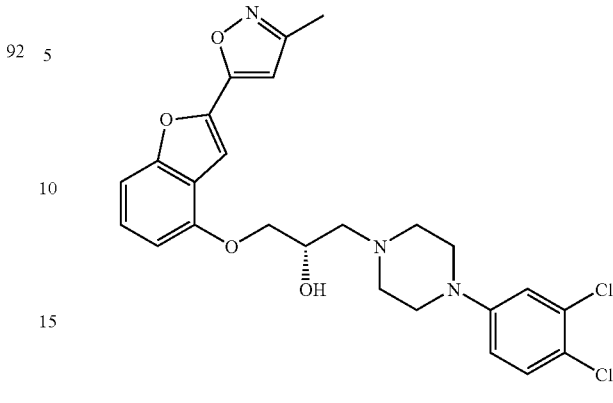

Example 96

(S)-1-(4-(3,4-dichlorophenyl)piperidino)-3-(2-(5-methyl-1,3,4-thiadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-methyl-1, 3,4-thiadiazole (0.35 g) obtained in Starting Material Synthesis Example 82 and 4-(3,4-dichlorophenyl)piperidine (0.28 g), a brown oil (0.60 g) was obtained. This was dissolved in isopropanol and a solution of hydrochloric acid in ether was added. The precipitated crystals were collected by filtration and dried to give the title compound (0.19 g) as pale-yellow crystals, melting point 220–222° C.

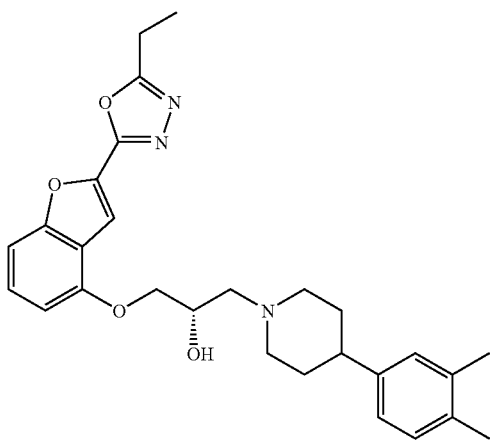

Example 97

(S)-1-(4-(3,4-dimethylphenyl)piperidino)-3-(2-(5-methyl-1,3,4-thiadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-methyl-1, 3,4-thiadiazole (0.35 g) obtained in Starting Material Synthesis Example 82 and 4-(3,4-dimethylphenyl)piperidine (0.32 g), a brown oil (0.50 g) was obtained. This was dissolved in isopropanol and a solution of hydrochloric acid in ether was added. The precipitated crystals were collected by filtration and dried to give the title compound (0.21 g) as pale-yellow crystals, melting point 191–194° C.

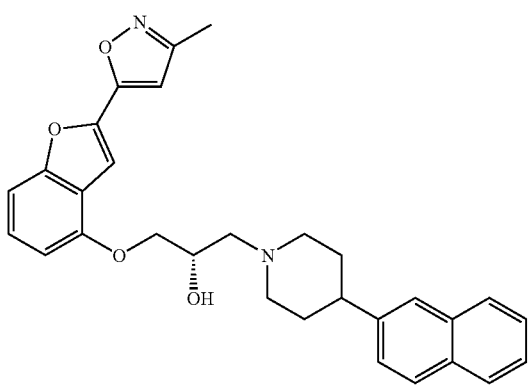

Example 98

(R)-1-(4-(3,4-dichlorophenyl)piperidino)-3-(2-(5-methyl-1,3,4-oxadiazol-2-yl)benzo(b)furan-4-yloxy)-2-propanol hydrochloride monohydrate By the reactions in the same manner as in Example 1 using (R)-2-(4-glycidyloxybenzo(b)furan-2-yl)-5-methyl-1, 3,4-oxadiazole (0.43 g), obtained by the reactions in the same manner as in Starting Material Synthesis Example 1 using (R)-glycidyl nosylate and 2-(4-hydroxybenzo(b)furan-2-yl)-5-methyl-1,3,4-oxadiazole, and 4-(3,4-dichlorophenyl)piperidine (0.35 g), a brown oil (0.70 g) was obtained. This was dissolved in ethanol and a solution of hydrochloric acid in ether was added. The mixture was allowed to stand and the precipitated crystals were collected by filtration and dried to give the title compound (0.28 g) as pale-yellow crystals, melting point 230–231° C.

Example 99

(S)-1-(4-(3-chlorophenyl)piperidino)-3-(2-(5-methyl-1,3,4-oxadiazol-2-yl)benzo(b)furan-4-yloxy)-2-propanol hydrochloride 1/2 hydrate By the reactions in the same manner as in Example 1 using (S)-2-(4-glycidyloxybenzo(b)furan-2-yl)-5-methyl-1,3,4-oxadiazole (0.50 g) obtained in Starting Material Synthesis Example 39 and 4-(3-chlorophenyl)piperidine (0.32 g), a brown oil (0.70 g) was obtained. This was dissolved in ethanol and a solution of hydrochloric acid in ether was added. The mixture was allowed to stand and the precipitated crystals were collected by filtration and dried to give the title compound (0.09 g) as yellow crystals, melting point 170–172° C.

Example 100

(S)-1-(4-(4-chlorophenyl)piperidino)-3-(2-(5-methyl-1,3,4-oxadiazol-2-yl)benzo(b)furan-4-yloxy)-2-propanol hydrochloride 3/2 hydrate By the reactions in the same manner as in Example 1 using (S)-2-(4-glycidyloxybenzo(b)furan-2-yl)-5-methyl 1,3,4-oxadiazole (0.50 g) obtained in Starting Material Synthesis Example 39 and 4-(4-chlorophenyl)piperidine (0.32 g), a brown oil (0.62 g) was obtained. This was dissolved in ethanol and a solution of hydrochloric acid in ether was added. The mixture was allowed to stand and the precipitated crystals were collected by filtration and dried to give the title compound (0.32 g) as pale-yellow crystals, melting point 200–202° C.

Example 101

(S)-1-(4-(3,4-methylenedioxyphenyl)piperidino)-3-(2-(5-ethyl-1,3,4-oxadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-ethyl-1,3,4-oxadiazole (0.80 g) obtained in Starting Material Synthesis Example 76 and 4-(3,4-methylenedioxyphenyl)piperidine (0.57 g), a brown oil (1.02 g) was obtained. This was dissolved in isopropanol and a solution of hydrochloric acid in ether was added. The mixture was allowed to stand and the precipitated crystals were collected by filtration and dried to give the title compound (0.36 g) as brown crystals, melting point 170–173° C.

Example 102

(S)-1-(4-(2,4-dimethylphenyl)piperidino)-3-(2-(5-methyl-1,3,4-oxadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-methyl-1,3,4-oxadiazole (0.60 g) obtained in Starting Material Synthesis Example 39 and 4-(2,4-dimethylphenyl)piperidine (0.38 g), a brown oil (0.68 g) was obtained. This was dissolved in a mixed solvent of isopropanol-isopropyl ether (1:1) and a solution of hydrochloric acid in ether was added. The mixture was allowed to stand and the precipitated crystals were collected by filtration and dried to give the title compound (0.31 g) as white crystals, melting point 190–194° C.

Example 103

(S)-1-(4-phenylpiperidino)-3-(2-(5-methyl-1,3,4-oxadiazol-2-yl)benzo(b)furan-4-yloxy)-2-propanol hydrobromide monohydrate By the reactions in the same manner as in Example 1 using (S)-2-(4-glycidyloxybenzo(b)furan-2-yl)-5-methyl-1,3,4-oxadiazole (1.80 g) obtained in Starting Material Synthesis Example 39 and 4-phenylpiperidine (1.00 g), a brown oil (1.02 g) was obtained. This was dissolved in ethanol and hydrobromic acid was added. The mixture was allowed to stand and the precipitated crystals were collected by filtration and dried to give the title compound (1.84 g) as brown crystals, melting point 158–160° C.

The structural formulas of the compounds obtained in Examples 96 to 103 are shown in the following.

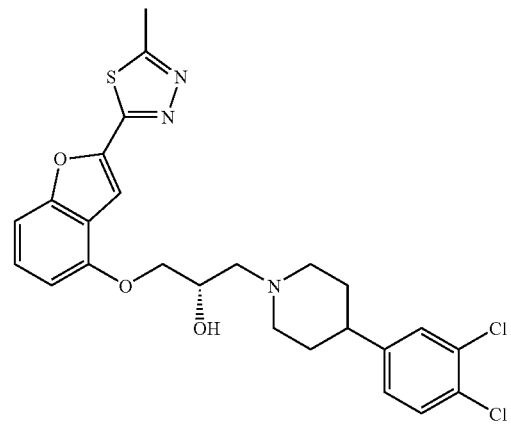

96

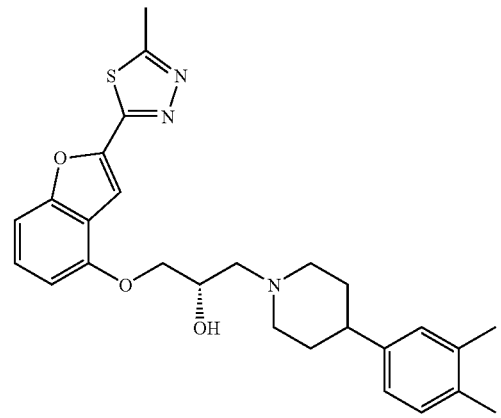

97

98
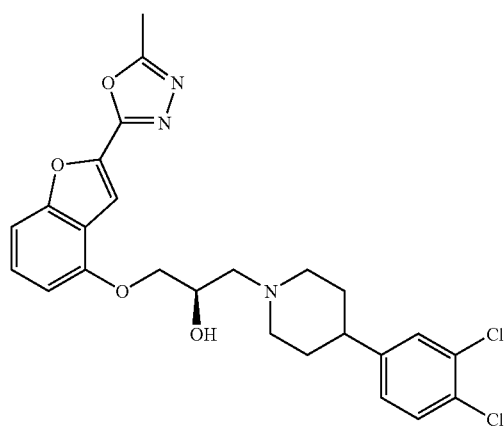
99
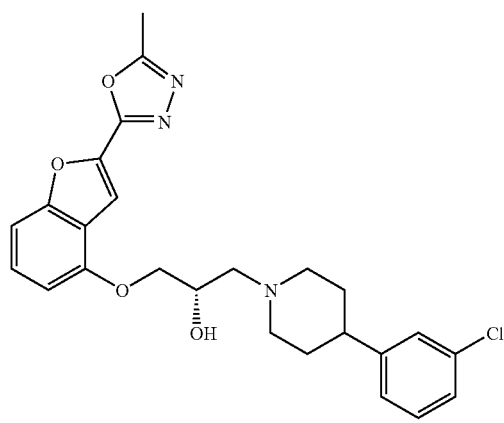
100
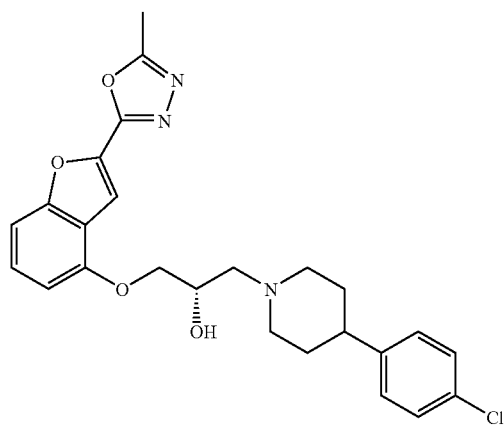
101
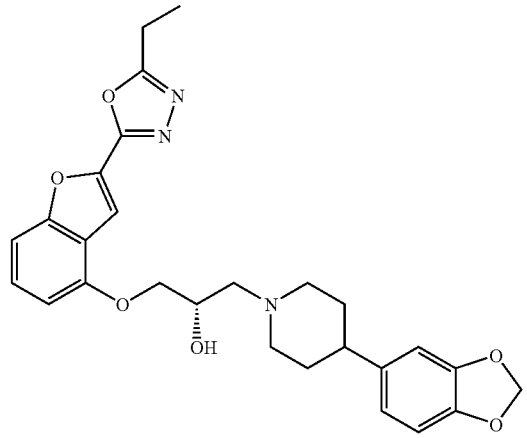
102
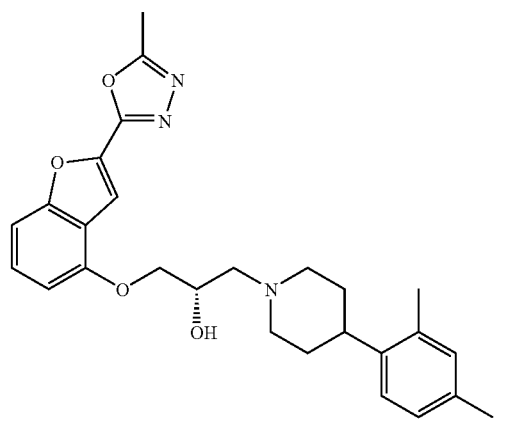
103
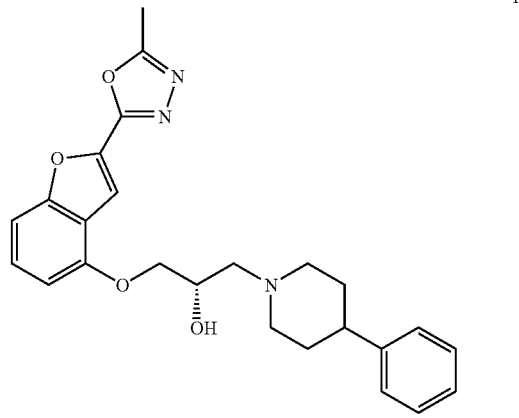

Example 104

(S)-1-(2-(5-ethyl-1,3,4-oxadiazol-2-yl)benzo(b)furan-4-yloxy)-3-(4-(naphthalen-2-yl)piperidino)-2-propanol hydrochloride 4/5 hydrate By the reactions in the same manner as in Example 1 using (S)-2-(4-glycidyloxybenzo(b)furan-2-yl)-5-ethyl-1,3,4-oxadiazole (0.43 g) obtained in Starting Material Synthesis Example 76 and 4-(naphthalen-2-yl)piperidine (0.40 g), a brown oil (0.63 g) was obtained. This was dissolved in ethanol and a solution of hydrogen chloride in ether was added. The mixture was allowed to stand and the precipitated crystals were collected by filtration and dried to give the title compound (0.16 g) as brown crystals, melting point 113–115° C.

Example 105

(S)-1-(4-hydroxy-4-(naphthalen-2-yl)piperidino)-3-(2-(5-methyl-1,3,4-oxadiazol-2-yl)benzo(b)furan-4-yloxy)-2-propanol hydrochloride By the reactions in the same manner as in Example 1 using (S)-2-(4-glycidyloxybenzo(b)furan-2-yl)-5-methyl-1,3,4-oxadiazole (1.0 g) obtained in Starting Material Synthesis Example 39 and 4-hydroxy-4-(naphthalen-2-yl)piperidine (0.77 g), a brown oil (1.6 g) was obtained. This was dissolved in ethanol and a solution of hydrogen chloride in ether was added. The mixture was allowed to stand and the precipitated crystals were collected by filtration and dried to give the title compound (1.2 g) as white crystals, melting point 227–228° C.

Example 106

(S)-1-(4-(3,4-dichlorophenyl)piperazin-1-yl)-3-(2-(5-methyl-1,3,4-oxadiazol-2-yl)benzo(b)furan-4-yloxy)-2-propanol hydrochloride By the reactions in the same manner as in Example 1 using (S)-2-(4-glycidyloxybenzo(b)furan-2-yl)-5-methyl-1,3,4-oxadiazole (0.80 g) obtained in Starting Material Synthesis Example 39 and 4-(3,4-dichlorophenyl)piperazine (0.65 g), a brown oil (1.2 g) was obtained. This was dissolved in acetone and a solution of hydrogen chloride in ether was added. The mixture was allowed to stand and the precipitated crystals were collected by filtration and dried to give the title compound (0.4 g) as white crystals, melting point 232–233° C.

Example 107

(S)-1-(4-(3,4-dichlorophenyl)-3,6-dihydro-2H-pyridin-1-yl)-3-(2-(5-methyl-1,3,4-oxadiazol-2-yl)benzo(b)furan-4-yloxy)-2-propanol hydrochloride By the reactions in the same manner as in Example 1 using (S)-2-(4-glycidyloxybenzo(b)furan-2-yl)-5-methyl-1,3,4-oxadiazole (1.7 g) obtained in Starting Material Synthesis Example 39 and 4-(3,4-dichlorophenyl)-3,6-dihydro-2H-pyridine (1.4 g), a brown oil (2.2 g) was obtained. This was dissolved in ethanol and a solution of hydrogen chloride in ether was added. The mixture was allowed to stand and the precipitated crystals were collected by filtration and dried to give the title compound (1.5 g) as white crystals, melting point 204–207° C.

Example 108

(S)-1-(4-(3,4-dichlorophenyl)piperidino)-3-(2-(5-ethylthiophen-2-yl)benzo(b)furan-4-yloxy)-2-propanol hydrochloride 1/2 hydrate By the reactions in the same manner as in Example 1 using (S)-2-(5-ethylthiophen-2-yl)-4-glycidyloxybenzo(b)furan (921 mg) obtained in Starting Material Synthesis Example 89 and 4-(3,4-dichlorophenyl)piperidine (777 mg), a colorless oil (1.51 g) was obtained. This was dissolved in methanol and 1 equivalent of hydrochloric acid was added. The mixture was stirred for 15 min and the solvent was evaporated under reduced pressure. The residue was recrystallized from a mixed solvent of methanol-water and the precipitated crystals were collected by filtration and dried to give the title compound (691 mg) as colorless crystals, melting point 183–185° C.

Example 109

(S)-1-(4-(3,4-dichlorophenyl)piperidino)-3-(2-(1-methylimidazol-2-yl)benzo(b)furan-4-yloxy)-2-propanol dihydrochloride 5/2 hydrate By the reactions in the same manner as in Example 1 using (S)-4-glycidyloxy-2-(1-methylimidazol-2-yl)benzo(b)furan (649 mg) obtained in Starting Material Synthesis Example 92 and 4-(3,4-dichlorophenyl)piperidine (591 mg), a colorless amorphous solid (521 mg) was obtained. This was dissolved in methanol and 2 equivalents of hydrochloric acid were added. The mixture was stirred for 15 min and the solvent was evaporated under reduced pressure. The residue was recrystallized twice from a mixed solvent of methanol-ethyl acetate, and the precipitated crystals were collected by filtration and dried to give the title compound (397 mg) as colorless crystals, melting point >155° C.

Example 110

(S)-1-(2-(1-methylimidazol-2-yl)benzo(b)furan-4-yloxy)-3-(4-(naphthalen-2-yl)piperidino)-2-propanol dihydrochloride 5/2 hydrate By the reactions in the same manner as in Example 1 using (S)-4-glycidyloxy-2-(1-methylimidazol-2-yl)benzo(b)furan (649 mg) obtained in Starting Material Synthesis Example 92 and 4-(naphthalen-2-yl)piperidine (542 mg), a colorless amorphous solid (547 mg) was obtained. This was dissolved in methanol and 2 equivalents of hydrochloric acid were added. The mixture was stirred for 15 min and the solvent was evaporated under reduced pressure. The residue was recrystallized from a mixed solvent of methanol-ethyl acetate, and the precipitated crystals were collected by filtration and dried to give the title compound (295 mg) as colorless crystals, melting point >160° C.

Example 111

(S)-1-(4-(3,4-dichlorophenyl)piperidino)-3-(2-(5-methyloxazol-2-yl)benzo(b)thiophen-4-yloxy)-2-propanol hydrochloride By the reactions in the same manner as in Example 1 using (S)-4-glycidyloxy-2-(5-methyloxazol-2-yl)benzo(b)thiophene (735 mg) obtained in Starting Material Synthesis Example 95 and 4-(3,4-dichlorophenyl)piperidine (589 mg), a colorless amorphous solid (963 mg) was obtained. This was dissolved in methanol and 2 equivalents of hydrochloric acid were added. The mixture was stirred for 15 min and the solvent was evaporated under reduced pressure. The residue was recrystallized from methanol and the precipitated crystals were collected by filtration and dried to give the title compound (528 mg) as pale-yellow crystals, melting point >225° C. (decomposition).

The structural formulas of the compounds obtained in Examples 104 to 111 are shown in the following.

104

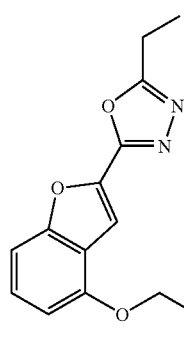

105

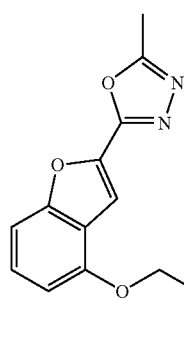

106

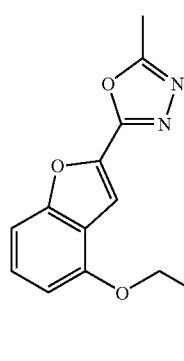

-continued

107

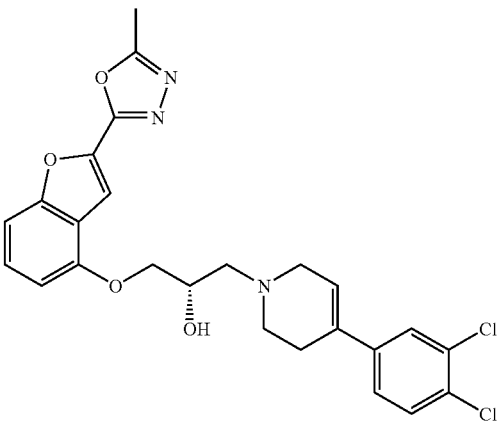

108

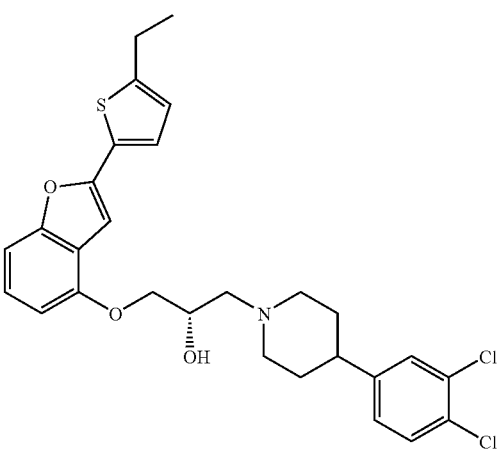

109

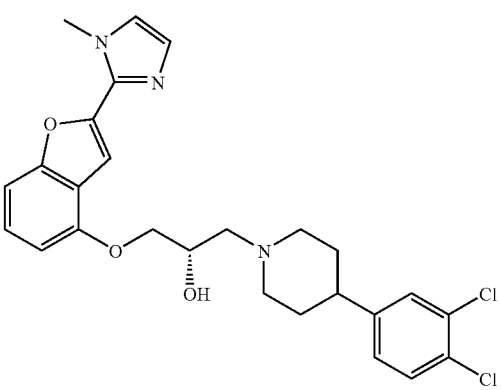

-continued

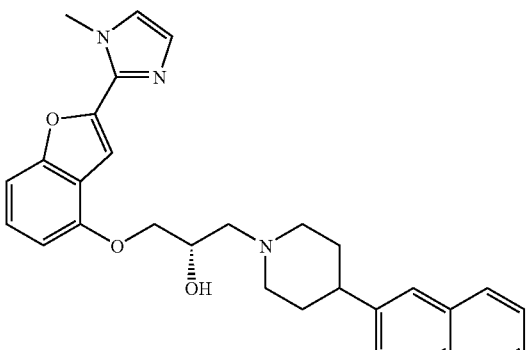

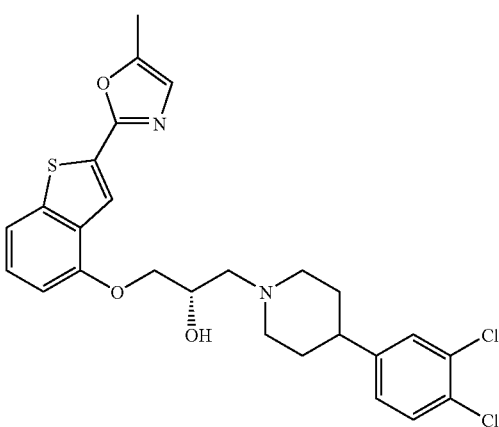

Example 112

(S)-1-(2-(5-methyloxazol-2-yl)benzo(b)thiophen-4-yloxy)-3-(4-(naphthalen-2-yl)piperidino)-2-propanol By the reactions in the same manner as in Example 1 using (S)-4-glycidyloxy-2-(5-methyloxazol-2-yl)benzo(b)thiophene (735 mg) obtained in Starting Material Synthesis Example 95 and 4-(naphthalen-2-yl)piperidine (540 mg), a colorless amorphous solid (1.04 g) was obtained. This was recrystallized from ethyl acetate and the precipitated crystals were collected by filtration and dried to give the title compound (793 mg) as pale-yellow crystals, melting point 138–139° C.

Example 113

(S)-1-(4-(6-methoxynaphthalen-2-yl)piperidino)-3-(2-(5-methyloxazol-2-yl)benzo(b)thiophen-4-yloxy)-2-propanol By the reactions in the same manner as in Example 1 using (S)-4-glycidyloxy-2-(5-methyloxazol-2-yl)benzo(b)thiophene (735 mg) obtained in Starting Material Synthesis Example 95 and 4-(6-methoxynaphthalen-2-yl)piperidine (617 mg), a colorless amorphous solid (981 mg) was obtained. This was recrystallized from a mixed solvent of chloroform-hexane and the precipitated crystals were collected by filtration and dried to give the title compound (714 mg) as pale-yellow crystals, melting point 163–165.5° C.

Example 114

(S)-1-(4-(3,4-dichlorophenyl)piperidino)-3-(2-(4,4-dimethyloxazolin-2-yl)benzo(b)furan-4-yloxy)-2-propanol By the reactions in the same manner as in Example 1 using (S)-4-glycidyloxy-2-(4,4-dimethyloxazolin-2-yl)benzo(b)furan (933 mg) obtained in Starting Material Synthesis Example 98 and 4-(3,4-dichlorophenyl)piperidine (748 mg), the title compound (1.12 g)) was obtained as a pale yellow amorphous solid.
$^1$H-NMR(CDCl$_3$)δ: 1.41(s, 6H), 1.45–1.90(m, 5H), 2.12 (br.t, J=12.0, 1H), 2.41(br.t, J=12.0, 1H), 2.45–2.65(m, 3H), 2.98(br.d, J=12.0, 1H), 3.14(br.d, J=12.0, 1H), 4.05–4.20(m, 3H), 4.14(s, 2H), 6.68(d, J=8.0, 1H), 7.05(dd, J=8.0, 1.0, 1H), 7.17(d, J=8.0, 1H), 7.25–7.40(m, 3H)

Example 115

(S)-1-(2-(4,4-dimethyloxazolin-2-yl)benzo(b)furan-4-yloxy)-3-(4-(naphthalen-2-yl)piperidino)-2-propanol By the reactions in the same manner as in Example 1 using (S)-4-glycidyloxy-2-(4,4-dimethyloxazolin-2-yl)benzo(b)furan (1.25 g) obtained in Starting Material Synthesis Example 98 and 4-(naphthalen-2-yl)piperidine (914 mg), the title compound (1.28 g) was obtained as a colorless amorphous solid.
$^1$H-NMR(CDCl$_3$)δ: 1.41(s, 6H), 1.80–2.00(m, 4H), 2.19 (br.t, J=12.0, 1H), 2.40–2.55(m, 1H), 2.60–2.80(m, 3H), 3.00(br.d, J=11.0, 1H), 3.19(br.d, J=11.0, 1H), 4.05–4.25(m, 3H), 4.13(s, 2H), 6.69(d, J=8.0, 1H), 7.17(d, J=8.0, 1H), 7.28(t, J=8.0, 1H)7.35–7.45(m, 3H), 7.65(s, 1H), 7.75–7.85 (m, 2H)

Example 116

(S)-1-(2-(4,4-dimethyloxazolin-2-yl)benzo(b)furan-4-yloxy)-3-(4-(6-methoxynaphthalen-2-yl)piperidino)-2-propanol By the reactions in the same manner as in Example 1 using (S)-4-glycidyloxy-2-(4,4-dimethyloxazolin-2-yl)benzo(b)furan (933 mg) obtained in Starting Material Synthesis Example 98 and 4-(6-methoxynaphthalen-2-yl)piperidine (783 mg), a colorless amorphous solid was obtained. This was recrystallized from ethyl acetate, and the precipitated crystals were collected by filtration and dried to give the title compound (871 mg) as colorless crystals, melting point 133–134° C.

Example 117

(S)-1-(4-(3,4-dichlorophenyl)piperidino)-3-(2-ethylsulfonylbenzo(b)furan-4-yloxy)-2-propanol hydrochloride 1/4 hydrate By the reactions in the same manner as in Example 1 using (S)-2-(ethylsulfonyl)-4-glycidyloxybenzo(b)furan (1.15 g) obtained in Starting Material Synthesis Example 101 and 4-(3,4-dichlorophenyl)piperidine (936 mg), a colorless amorphous solid (1.11 g) was obtained. This was dissolved in methanol and 1 equivalent of hydrochloric acid was added. The mixture was stirred for 15 min and the solvent was evaporated under reduced pressure. The residue was recrystallized from a mixed solvent of acetone-ether, and the precipitated crystals were collected by filtration and dried to give the title compound (734 mg) as colorless crystals, melting point 135–140° C.

Example 118

(S)-1-(4-(3,4-dimethylphenyl)piperidino)-3-(2-ethyl-sulfonylbenzo(b)furan-4-yloxy)-2-propanol By the reactions in the same manner as in Example 1 using (S)-2-(ethylsulfonyl)-4-glycidyloxybenzo(b)furan (1.15 g) obtained in Starting Material Synthesis Example 101 and 4-(3,4-dimethylphenyl)piperidine (761 mg), the title compound (827 mg) was obtained as a yellowish brown oil.

$^1$H-NMR(CDCl$_3$)δ: 1.34(t, J=8.0, 3H), 1.40–1.95(m, 5H), 2.13(br.t, J=12.0, 1H), 2.22(s, 3H), 2.24(s, 3H), 2.40–2.70 (m, 4H), 2.96(br.d, J=12.0, 1H), 3.14(br.d, J=12.0, 1H), 3.30(q, J=8.0, 2H), 4.05–4.20(m, 3H), 6.75(d, J=8.0, 1H), 6.96(d, J=8.0, 1H), 6.99(d, J=12.0, 1H), 7.17(d, J=8.0, 1H), 7.39(t, J=8.0, 1H), 7.66(s, 1H)

Example 119

(S)-1-(4-(3,4-dichlorophenyl)piperidino)-3-(2-(N,N-dimethylsulfamoyl)benzo(b)furan-4-yloxy)-2-propanol hydrochloride 3/2 hydrate By the reactions in the same manner as in Example 1 using (S)-2-(N,N-dimethylsulfamoyl)-4-glycidyloxybenzo (b)furan (677 mg) obtained in Starting Material Synthesis Example 104 and 4-(3,4-dichlorophenyl)piperidine (524 mg), a colorless amorphous solid (1.01 g) was obtained. This was dissolved in methanol and 2 equivalents of hydrochloric acid were added. The mixture was stirred for 15 min and the solvent was evaporated under reduced pressure. The residue was recrystallized from methanol, and the precipitated crystals were collected by filtration and dried to give the title compound (213 mg) as colorless crystals, melting point 222–225° C.

The structural formulas of the compounds obtained in Examples 112 to 119 are shown in the following.

113

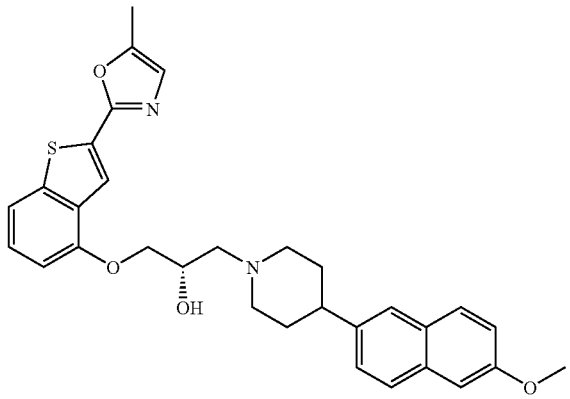

-continued

114

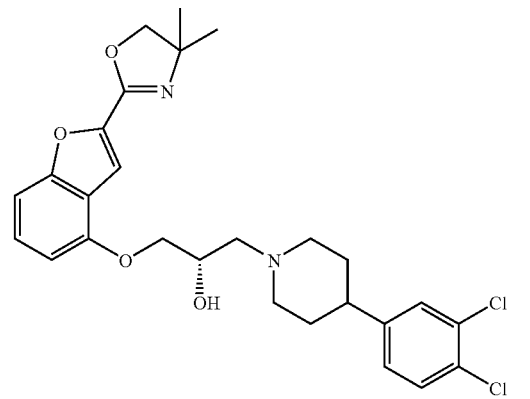

112

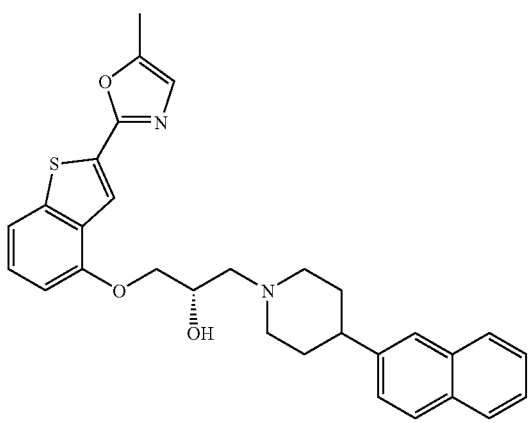

115

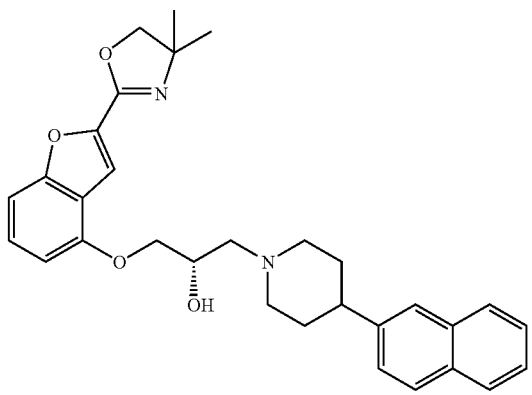

-continued

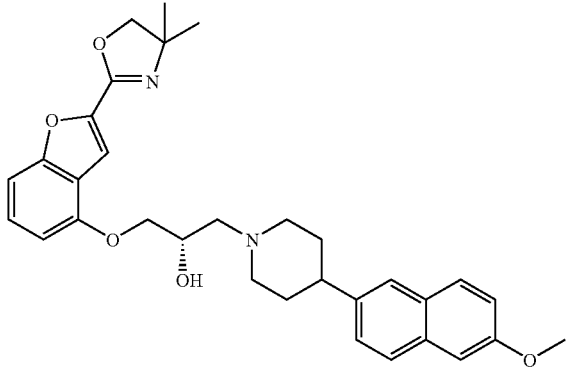

116

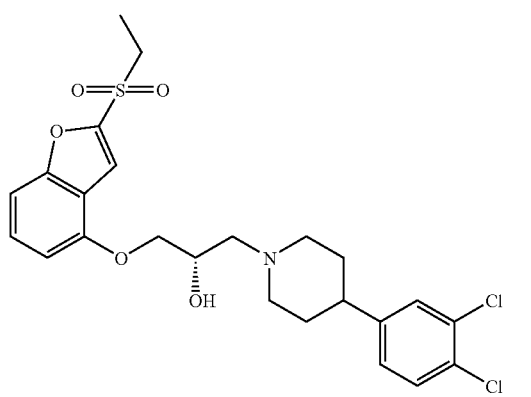

117

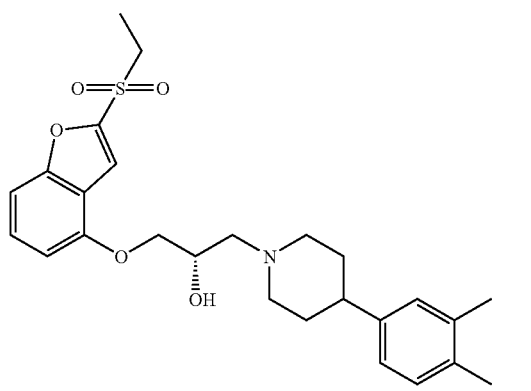

118

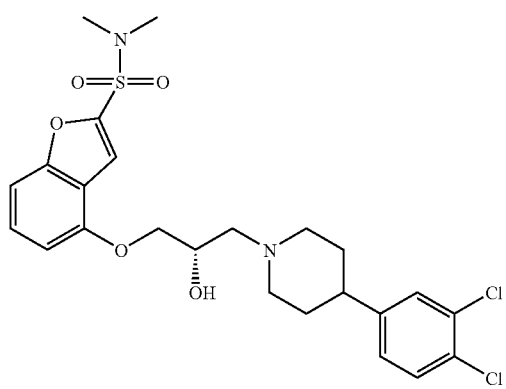

119

Example 120

(S)-1-(4-(3,4-dimethylphenyl)piperidino)-3-(2-(N,N-dimethylsulfamoyl)benzo(b)furan-4-yloxy)-2-propanol By the reactions in the same manner as in Example 1 using (S)-2-(N,N-dimethylsulfamoyl)-4-glycidyloxybenzo(b)furan (677 mg) obtained in Starting Material Synthesis Example 104 and 4-(3,4-dimethylphenyl)piperidine (431 mg), a colorless amorphous solid was obtained. This was recrystallized from a mixed solvent of ethyl acetate-hexane, and the precipitated crystals were collected by filtration and dried to give the title compound (677 mg) as colorless crystals, melting point 146–148° C.

Example 121

(S)-1-(4-(3,4-dichlorophenyl)piperidino)-3-(2-(5-ethyloxazol-2-yl)benzo(b)furan-4-yloxy)-2-propanol hydrochloride By the reactions in the same manner as in Example 1 using (S)-2-(5-ethyloxazol-2-yl)-4-glycidyloxybenzo(b)furan (500 mg) obtained in Starting Material Synthesis Example 108 and 4-(3,4-dichlorophenyl)piperidine (403 mg), a colorless amorphous solid (854 mg) was obtained. This was dissolved in methanol and 2 equivalents of hydrochloric acid were added. The mixture was stirred for 15 min and the solvent was evaporated under reduced pressure. The residue was recrystallized from methanol, and the precipitated crystals were collected by filtration and dried to give the title compound (441 mg) as colorless crystals, melting point 232–234° C.

Example 122

(S)-1-(4-(3,4-dimethylphenyl)piperidino)-3-(2-(5-ethyloxazol-2-yl)benzo(b)furan-4-yloxy)-2-propanol dihydrochloride By the reactions in the same manner as in Example 1 using (S)-2-(5-ethyloxazol-2-yl)-4-glycidyloxybenzo(b)furan (500 mg) obtained in Starting Material Synthesis Example 108 and 4-(3,4-dimethylphenyl)piperidine (531 mg), a colorless amorphous solid (1.03 g) was obtained. This was dissolved in methanol and 2 equivalents of hydrochloric acid were added. The mixture was stirred for 15 min and the solvent was evaporated under reduced pressure. The residue was recrystallized from a mixed solvent of methanol-ethyl acetate-diisopropyl ether (2:1:1), and the precipitated crystals were collected by filtration and dried to give the title compound (468 mg) as pale-yellow crystals, melting point 86–89° C.

Example 123

(S)-1-(4-(3,4-dichlorophenyl)piperidino)-3-(2-(5-isopropyl-1,3,4-oxadiazol-2-yl)benzo(b)furan-4-yloxy)-2-propanol hydrochloride monohydrate By the reactions in the same manner as in Example 1 using (S)-2-(4-glycidyloxybenzo(b)furan-2-yl)-5-isopropyl-1,3,4-oxadiazole (0.6 g) and 4-(3,4-dichlorophenyl)piperidine (0.46 g), an oil (0.75 g) was obtained. This was dissolved in ethanol and a solution of hydrogen chloride in dioxane was added. The precipitated crystals were collected by filtration and dried to give the title compound (0.48 g) as white crystals, melting point 142–144° C.

Example 124

(S)-1-(4-(3,4-dichlorophenyl)piperidino)-3-(2-(5-phenyl-1,3,4-oxadiazol-2-yl)benzo(b)furan-4-yloxy)-2-propanol hydrochloride By the reactions in the same manner as in Example 1 using (S)-2-(4-glycidyloxybenzo(b)furan-2-yl)-5-phenyl-1,3,4-oxadiazole (0.60 g) and 4-(3,4-dichlorophenyl)piperidine (0.50 g), an oil (0.85 g) was obtained. This was dissolved in ethanol and a solution of hydrogen chloride in dioxane was added. The precipitated crystals were collected by filtration and dried to give the title compound (0.65 g) as white crystals, melting point 220–222° C.

Example 125

(S)-1-(4-(benzo(b)thiophen-2-yl)piperidino)-3-(2-(5-methyl-1,3,4-oxadiazol-2-yl)benzo(b)furan-4-yloxy)-2-propanol hydrochloride 1/2 hydrate By the reactions in the same manner as in Example 1 using (S)-5-(4-glycidyloxybenzo(b)furan-2-yl)-2-methyl-1,3,4-oxadiazole (0.4 g) and 4-(benzo(b)thiophen-2-yl)piperidine (0.35 g), an oil (0.65 g) was obtained. This was dissolved in ethanol and a solution of hydrogen chloride in dioxane was added. The precipitated crystals were collected by filtration and dried to give the title compound (0.40 g) as white crystals, melting point 190–192° C.

Example 126

(S)-2-(4-(3,4-dimethylphenyl)piperidino)-1-(2-(2-methyloxazol-5-yl)benzo(b)furan-4-yloxy)-2-propanol dihydrochloride 1/2 hydrate By the reactions in the same manner as in Example 1 using (S)-5-(4-glycidyloxybenzo(b)furan-2-yl)-2-methyloxazole (0.60 g) and 4-(3,4-dimethylphenyl)piperidine (0.35 g), an oil (0.55 g) was obtained. This was dissolved in ethanol and a solution of hydrogen chloride in dioxane was added. The precipitated crystals were collected by filtration and dried to give the title compound (0.19 g) as white crystals, melting point 79–81° C.

Example 127

(S)-1-(4-(2,3-dihydro-2-oxobenzimidazol-1-yl)piperidino)-3-(2-(5-methyl-1,3,4-oxadiazol-2-yl)benzo(b)furan-4-yloxy)-2-propanol maleate By the reactions in the same manner as in Example 1 using (S)-5-(4-glycidyloxybenzo(b)furan-2-yl)-2-methyl-1,3,4-oxadiazole (1.0 g) and 4-(2,3-dihydro-2-oxobenzimidazol-1-yl)piperidine (1.0 g), an oil (1.4 g) was obtained. This was dissolved in acetone and maleic acid was added. The precipitated crystals were collected by filtration and dried to give the title compound (1.68 g) as pale-yellow crystals, melting point 178–180° C.

The structural formulas of the compounds obtained in Examples 120 to 127 are shown in the following.

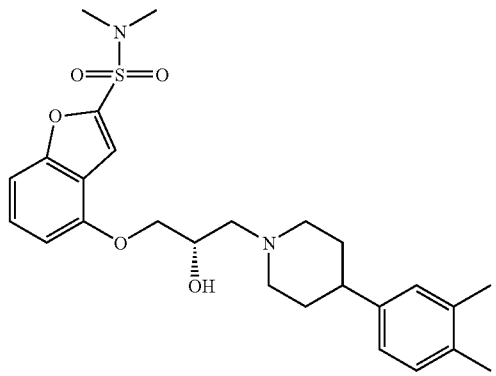

120

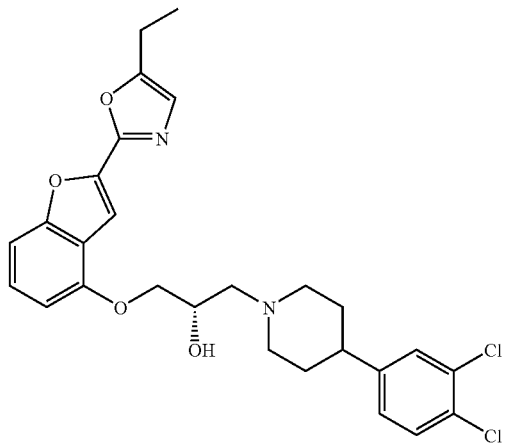

121

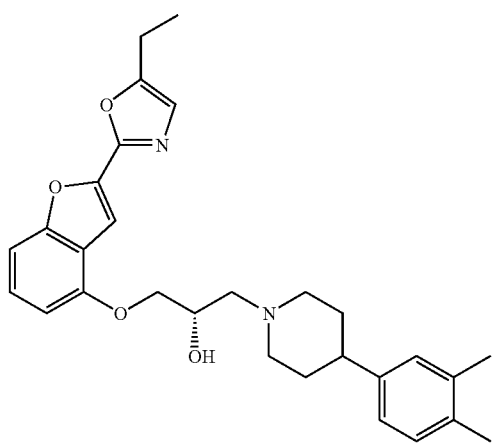

122

123

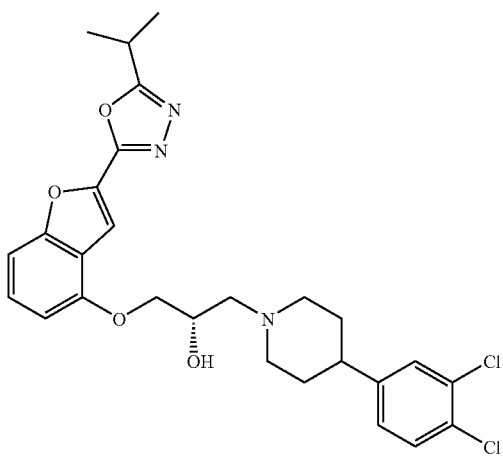

124

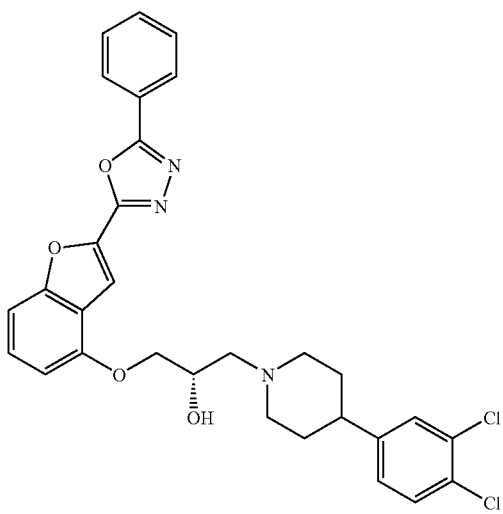

125

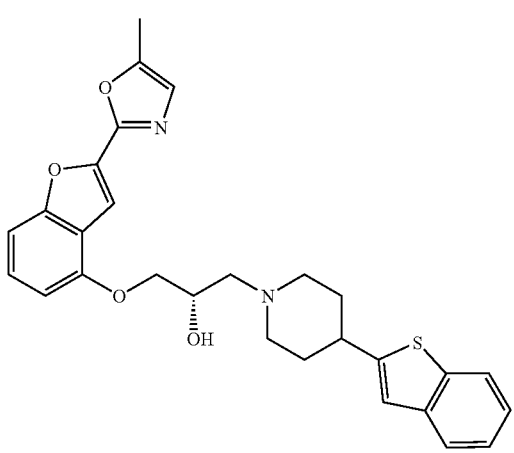

126

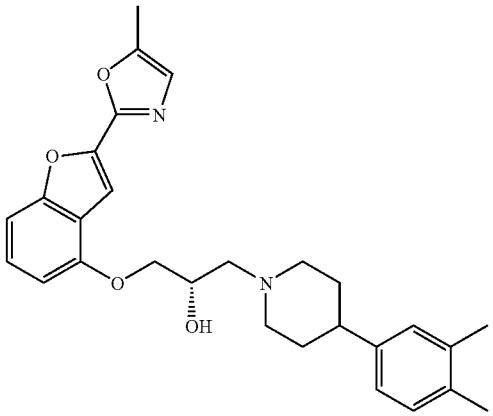

127

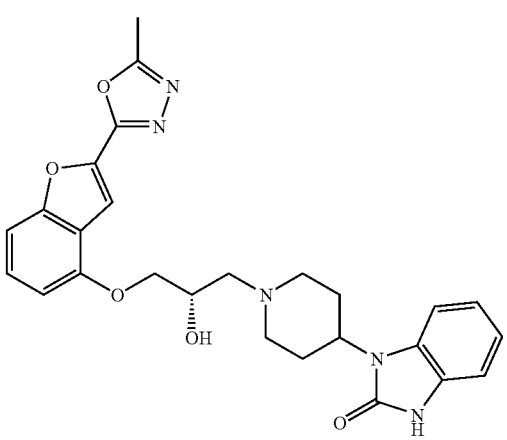

Example 128

(S)-1-(4-(3,4-difluorophenyl)piperidino)-3-(2-(5-methyl-1,3,4-oxadiazol-2-yl)benzo(b)furan-4-yloxy)-2-propanol p-toluenesulfonate 1/2 hydrate By the reactions in the same manner as in Example 1 using (S)-5-(4-glycidyloxybenzo(b)furan-2-yl)-2-methyl-1,3,4-oxadiazole (1.0 g) and 4-(3,4-difluoro)piperidine (1.0 g), an oil (1.7 g) was obtained. This was dissolved in acetone and p-toluenesulfonic acid was added. The precipitated crystals were collected by filtration and dried to give the title compound (0.97 g) as pale-yellow crystals, melting point 80–82° C.

Example 129

(S)-1-(4-(3,4-dimethoxyphenyl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1, 3,4-oxadiazole (0.90 g) and 4-(3,4-dimethoxyphenyl)piperidine (0.90 g); the title compound (0.80 g) was obtained as a brown oil.

$^1$H-NMR(CDCl$_3$): 1.78–1.95(m, 4H), 2.16(t, 1H, J=1.8), 2.41–2.60(m, 2H), 2.62–2.49(m, 5H), 3.00(d, 1H, J=11.2), 3.17(d, 1H, J=11.2), 3.86(s, 3H), 3.90(s, 3H), 4.15–4.30(m, 3H), 6.70–6.83(m, 4H), 7.22(d, 1H, J=8.3), 7.34(t, 1H, J=8.3), 7.61(s, 1H)

Example 130

(S)-3-(2-(5-methyl-1,3,4-oxadiazol-2-yl)benzo(b)furan-4-yloxy)-1-(4-(1,2,3,4-tetrahydronaphthalen-6-yl)piperidino)-2-propanol hydrochloride 1/4 hydrate By the reactions in the same manner as in Example 1 using (S)-5-(4-glycidyloxybenzo(b)furan-2-yl)-2-methyl-1,3,4-oxadiazole (1.0 g) and 4-(1,2,3,4-tetrahydronaphthalen-6-yl)piperidine (1.0 g), an oil (0.95 g) was obtained. This was dissolved in isopropanol and a solution of hydrogen chloride in dioxane was added. The precipitated crystals were collected by filtration and dried to give the title compound (0.36 g) as pale-yellow crystals, melting point 119–121° C.

Example 131

(S)-3-(4-(1,4-benzodioxan-6-yl)piperidino)-1-(2-(5-methyl-1,3,4-oxadiazol-2-yl)benzo(b)furan-4-yloxy)-2-propanol hydrochloride 1/2 hydrate By the reactions in the same manner as in Example 1 using (S)-5-(4-glycidyloxybenzo(b)furan-2-yl)-2-methyl-1,3,4-oxadiazole (1.0 g) and 4-(1,4-benzodioxan-6-yl)piperidine (1.0 g), an oil (1.45 g) was obtained. This was dissolved in isopropanol and a solution of hydrogen chloride in dioxane was added. The precipitated crystals were collected by filtration and dried to give the title compound (0.95 g) as white crystals, melting point 164–166° C.

Example 132

(S)-3-(4-(1,4-benzodioxan-6-yl)piperidino)-1-(2-(5-ethyl-1,3,4-oxadiazol-2-yl)benzo(b)furan-4-yloxy)-2-propanol hydrochloride 1/2 hydrate By the reactions in the same manner as in Example 1 using (S)-2-ethyl-5-(4-glycidyloxybenzo(b)furan-2-yl)-1,3,4-oxadiazole (1.0 g) and 4-(1,4-benzodioxan-6-yl)piperidine (1.0 g), an oil (1.55 g) was obtained. This was dissolved in a mixed solution of isopropanol-isopropyl ether (1:1) and a solution of hydrogen chloride in dioxane was added. The precipitated crystals were collected by filtration and dried to give the title compound (0.71 g) as brown crystals, melting point 238–240° C.

Example 133

(S)-1-(4-(3,4-dichlorophenyl)piperidino)-3-(2-(5-dimethylamino-1,3,4-oxadiazol-2-yl)benzo(b)furan-4-yloxy)-2-propanol By the reactions in the same manner as in Example 1 using (S)-2-(dimethylamino)-5-(4-glycidyloxybenzo(b)furan-2-yl)-1,3,4-oxadiazole (0.65 g) and 4-(3,4-dichlorophenyl)piperidine (0.65 g), the title compound (0.38 g) was obtained as brown crystals, melting point 209–211° C.

Example 134

(S)-3-(4-(3,4-dichlorophenyl)piperidino)-1-(2-(acetohydrazinocarbonyl)benzo(b)furan-4-yloxy)-2-propanol N'-(4-Hydroxybenzo(b)furan-2-ylcarbonyl)acetohydrazide (2.5 g) obtained in Starting Material Synthesis Example 109 and (S)-glycidyl nosylate (2.3 g) were dissolved in dimethylformamide (30 ml), and potassium carbonate (3.3 g) was added. The mixture was stirred at room temperature for 15 hr. The reaction mixture was poured into ice water and extracted with ethyl acetate. The organic layer was washed with saturated aqueous ammonium chloride solution, dried over anhydrous sodium sulfate and concentrated under reduced pressure to give a yellow oil (0.7 g). This oil and 4-(3,4-dichlorophenyl)piperidine were dissolved in methanol (10 ml) and the mixture was refluxed under heating for 3 hr. After cooling, the solvent was evaporated under reduced pressure and the residue was purified by silica gel column chromatography (chloroform/methanol) to give the title compound (0.48 g) as pale-yellow crystals, melting point 180° C. (decomposition).

$^1$H-NMR(DMSO-d$_6$)δ: 1.72–1.88(m, 4H), 2.02(s, 3H), 2.14–2.17(m, 1H), 2.39–2.55(m, 2H), 2.64–2.66(m, 2H), 3.02(m, 1H), 3.18(m, 1H), 4.13–4.20(m, 2H), 4.54(m, 1H), 6.05(bs, 1H), 6.87(d, J=7.8, 1H), 7.06–7.09(m, 1H), 7.24(d, J=7.8, 1H), 7.32–7.39(m, 3H), 7.79(s, 1H), 9.92(s, 1H), 10.50(s, 1H)

Example 135

(S)-3-(4-(3,4-dichlorophenyl)piperidino)-1-(2-(5-methoxycarbonyl-1,3,4-oxadiazol-2-yl)benzo(b)furan-4-yloxy)-2-propanol 5-Ethoxycarbonyl-2-(4-hydroxybenzo(b)furan-2-yl)-1,3,4-oxadiazole (2.5 g) and (S)-glycidyl nosylate (2.3 g) were dissolved in dimethylformamide (30 ml) and potassium carbonate (2.45 g) was added. The mixture was stirred at room temperature for 14 hr. The reaction mixture was poured into ice water and extracted with ethyl acetate. The organic layer was washed with saturated aqueous ammonium chloride solution, dried over anhydrous sodium sulfate and concentrated under reduced pressure to give yellow crystals (1.7 g). This was dissolved in methanol (20 ml) and 4-(3,4-dichlorophenyl)piperidine (1.2 g) was added. The mixture was refluxed under heating for 2 hr. After cooling, the solvent was evaporated under reduced pressure and the residue was purified by silica gel column chromatography (chloroform/methanol) to give the title compound (1.5 g) as pale-yellow crystals (ethyl ester was converted to methyl ester in methanol), melting point 160° C. (decomposition).

$^1$H-NMR(CDCl$_3$)δ: 1.71–1.89(m, 4H), 2.14–2.20(m, 1H), 2.45–2.57(m, 2H), 2.64–2.66(m, 2H), 3.02(m, 1H), 3.18(m, 1H), 4.11(s, 3H), 5.05(bs, 1H), 6.77(d, J=7.8, 1H), 7.06–7.09(m, 1H), 7.24(d, J=7.8, 1H), 7.32–7.43(m, 3H), 7.85(s, 1H)

The structural formulas of the compounds obtained in Examples 128 to 135 are shown in the following.

128
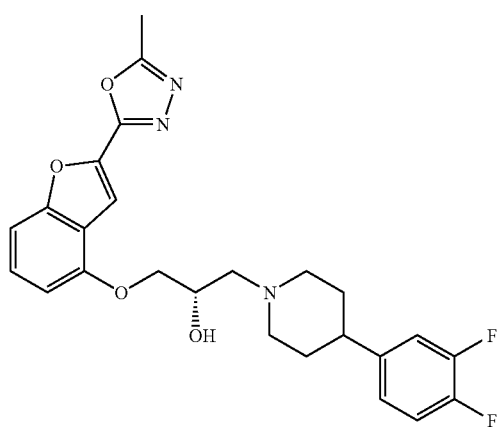
129
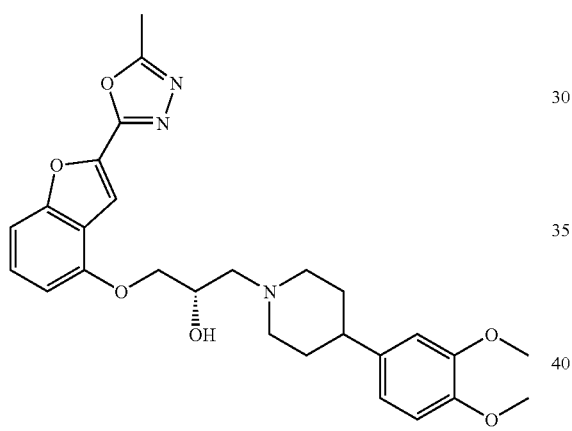
130
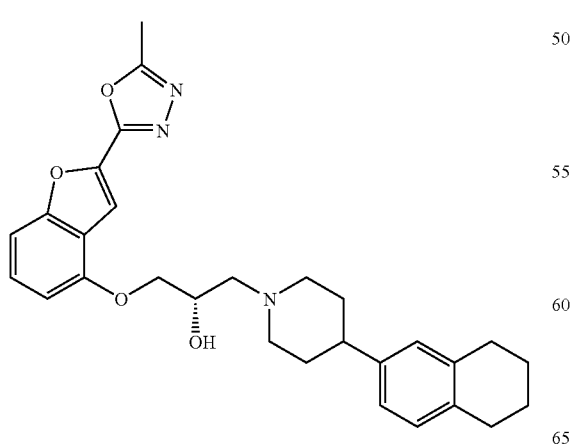
131
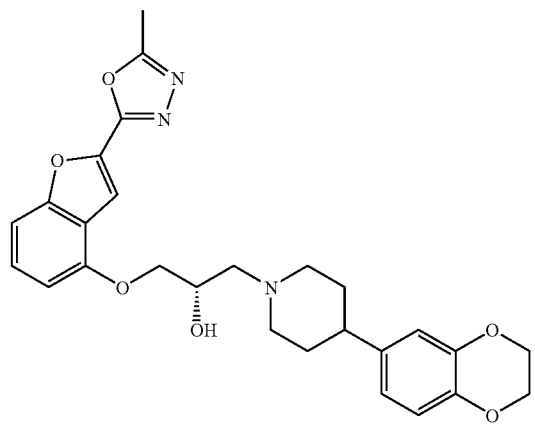
132
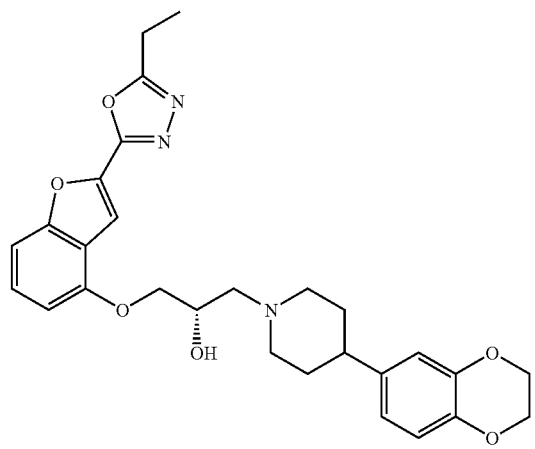
133
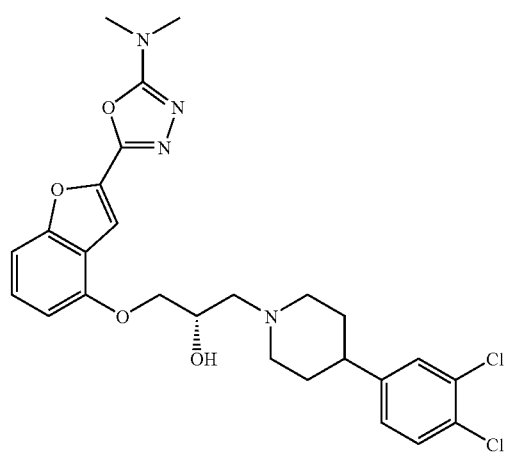

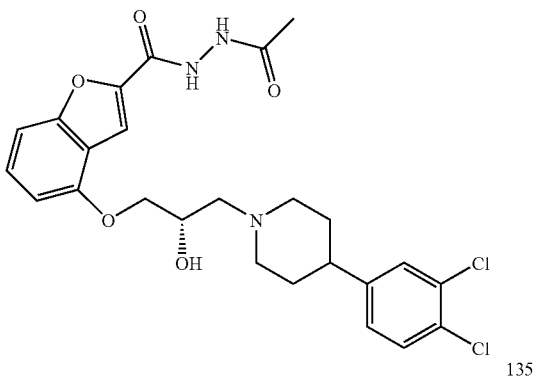

Example 136

(S)-3-(4-(3,4-dichlorophenyl)piperidino)-1-(2-(5-hydroxymethyl-1,3,4-oxadiazol-2-yl)benzo(b)furan-4-yloxy)-2-propanol (S)-3-(4-(3,4-Dichlorophenyl)piperidino)-1-(2-(5-ethoxycarbonyl-1,3,4-oxadiazol-2-yl)benzo(b)furan-4-yloxy)-2-propanol (1.3 g) obtained in Example 135 was dissolved in THF (20 ml) and lithium borohydride (60 mg) was added with stirring under ice-cooling. The mixture was stirred for 1 hr at room temperature, then poured into ice-water, and extracted with chloroform. The organic layer was dried over anhydrous sodium sulfate and concentrated under reduced pressure to give yellow crystals (1.2 g). The crystals were purified by silica gel column chromatography (chloroform/methanol) to give the title compound (100 mg) as pale-yellow crystals, melting point 158–160° C.

$^1$H-NMR(DMSO-d$_6$)δ: 1.62–1.72(m, 4H), 2.09–2.15(m, 2H), 2.50–2.55(m, 2H), 2.99–3.08(m, 2H), 4.08(m, 2H), 4.21(m, 1H), 4.75(d, J=8.0, 1H), 4.96(bs, 1H), 6.01(t, J=8.0, 1H), 6.92(d, J=7.8, 1H), 7.25(d, J=7.8, 1H), 7.33(d, J=7.8, 1H), 7.42–7.53(m, 3H), 7.80(s, 1H)

Example 137

(S)-2-(4-(2-acetoxy-3-(4-(3,4-dichlorophenyl)piperidino)propyloxy)benzo(b)furan-2-yl)-5-methyl-1,3,4-oxadiazole hydrochloride (S)-1-(4-(3,4-Dichlorophenyl)piperidino)-3-(2-(5-methyl-1,3,4-oxadiazol-2-yl)benzo(b)furan-4-yloxy)-2-propanol (1.0 g) was dissolved in pyridine (20 ml) and acetic anhydride (10 ml), and the mixture was left standing at room temperature for 12 hr. The solvent was evaporated under reduced pressure and the residue was purified by silica gel column chromatography (chloroform/methanol). The obtained oil was dissolved in ethanol and a solution of hydrogen chloride in ether was added. The precipitated crystals were collected by filtration and dried to give the title compound (0.58 g) as pale-yellow crystals, melting point 163–166° C. (decomposition)

Example 138

(S)-1-(2-(5-(1-methylethyl)-1,3,4-oxadiazol-2-yl)benzo(b)furan-4-yloxy)-3-(4-(3,4-methylenedioxyphenyl)piperidino)-2-propanol hydrochloride By the reactions in the same manner as in Example 1 using (S)-5-(4-glycidyloxybenzo(b)furan-2-yl)-2-(1-methylethyl)-1,3,4-oxadiazole (0.8 g) and 4-(3,4-methylenedioxyphenyl)piperidine (0.7 g), an oil was obtained. This was dissolved in acetone and a hydrochloric acid-ethanol solution was added. The precipitated crystals were collected by filtration and dried to give the title compound (0.81 g) as white crystals, melting point 211–213° C.

Example 139

(R)-1-(2-(5-(1-methylethyl)-1,3,4-oxadiazol-2-yl)benzo(b)furan-4-yloxy)-3-(4-(3,4-methylenedioxyphenyl)piperidino)-2-propanol hydrochloride By the reactions in the same manner as in Example 1 using (R)-5-(4-glycidyloxybenzo(b)furan-2-yl)-2-(1-methylethyl)-1,3,4-oxadiazole (1.0 g) and 4-(3,4-methylenedioxyphenyl)piperidine (0.75 g), an oil was obtained. This was dissolved in acetone and a hydrogen chloride-dioxane solution was added. The precipitated crystals were collected by filtration and dried to give the title compound (0.61 g) as white crystals, melting point 209–211° C.

Example 140

(S)-1-(2-(5-(1-methylethyl)-1,3,4-oxadiazol-2-yl)benzo(b)furan-4-yloxy)-3-(4-(naphthalen-2-yl)piperidino)-2-propanol hydrochloride 3/4 hydrate By the reactions in the same manner as in Example 1 using (S)-5-(4-glycidyloxybenzo(b)furan-2-yl)-2-(1-methylethyl)-1,3,4-oxadiazole (0.5 g) and 4-(naphthalen-2-yl)piperidine (0.5 g), an oil was obtained. This was dissolved in acetone and hydrochloric acid was added. The precipitated crystals were collected by filtration and dried to give the title compound (0.26 g) as white crystals, melting point 124–126° C.

Example 141

(S)-1-(4-(3,4-dimethylphenyl)piperidino)-3-(2-(5-(1-methylethyl)-1,3,4oxadiazol-2-yl)benzo(b)furan-4-yloxy)-2-propanol hydrobromide By the reactions in the same manner as in Example 1 using (S)-5-(4-glycidyloxybenzo(b)furan-2-yl)-2-(1-methylethyl)-1,3,4-oxadiazole (0.6 g) and 4-(3,4-dimethylphenyl)piperidine (0.6 g), an oil was obtained. This was dissolved in isopropanol, and 48% hydrobromic acid was added. The precipitated crystals were collected by filtration and dried to give the title compound (0.48 g) as pale-yellow crystals, melting point 159–161° C.

Example 142

(S)-1-(2-(5-(1,1-dimethylethyl)-1,3,4-oxadiazol-2-yl)benzo(b)furan-4-yloxy)-3-(4-(1,4-benzodioxan-6-yl)piperidino)-2-propanol hydrochloride By the reactions in the same manner as in Example 1 using (S)-5-(4-glycidyloxybenzo(b)furan-2-yl)-2-(1,1-dimethylethyl)-1,3,4-oxadiazole (0.8 g) and 4-(1,4-benzodioxan-6-yl)piperidine (0.70 g), an oil was obtained. This was dissolved in acetone and hydrochloric acid was added. The precipitated crystals were collected by filtration and dried to give the title compound (0.55 g) as white crystals, melting point 197–199° C.

Example 143

(S)-1-(2-(5-(1,1-dimethylethyl)-1,3,4-oxadiazol-2-yl)benzo(b)furan-4-yloxy)-3-(4-(3,4-dichlorophenyl)piperidino)-2-propanol hydrochloride 1/2 hydrate By the reactions in the same manner as in Example 1 using (S)-5-(4-glycidyloxybenzo(b)furan-2-yl)-2-(1,1-dimethylethyl)-1,3,4-oxadiazole (1.0 g) and 4-(3,4-dichlorophenyl)piperidine (0.80 g), an oil was obtained. This was dissolved in acetone and hydrochloric acid was added. The precipitated crystals were collected by filtration and dried to give the title compound (0.55 g) as white crystals, melting point 207–209° C.

The structural formulas of the compounds obtained in Examples 136 to 143 are shown in the following.

136

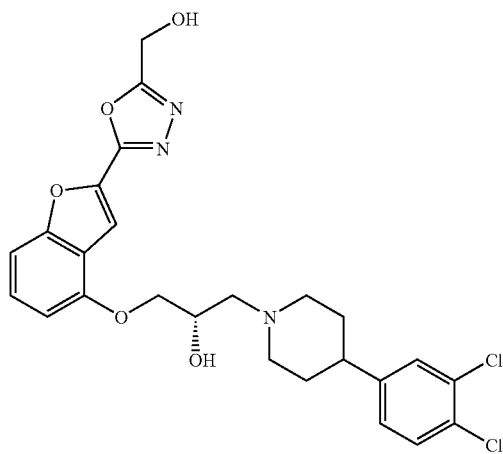

137

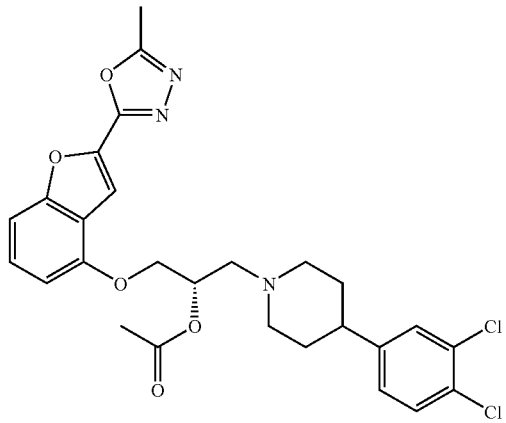

138

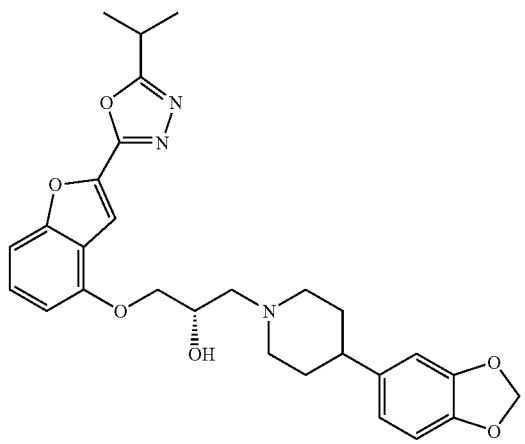

139

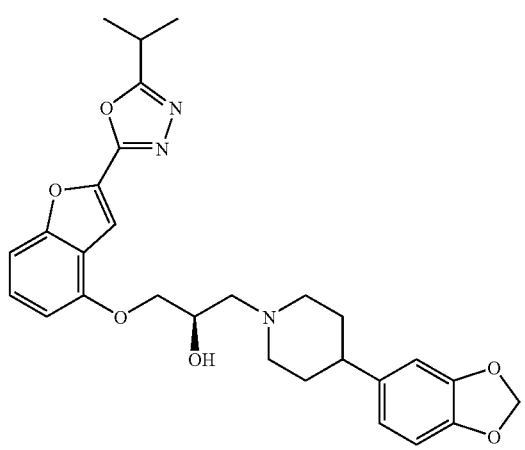

140

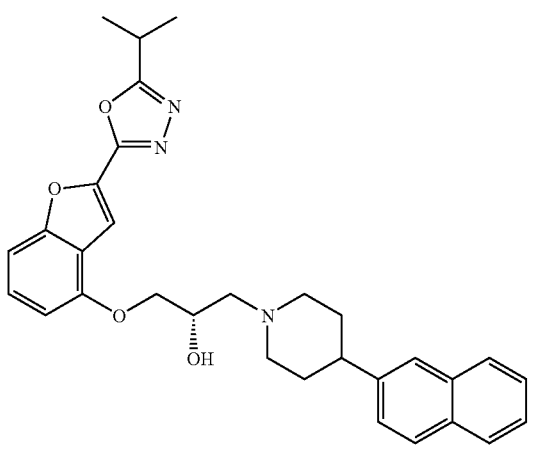

141

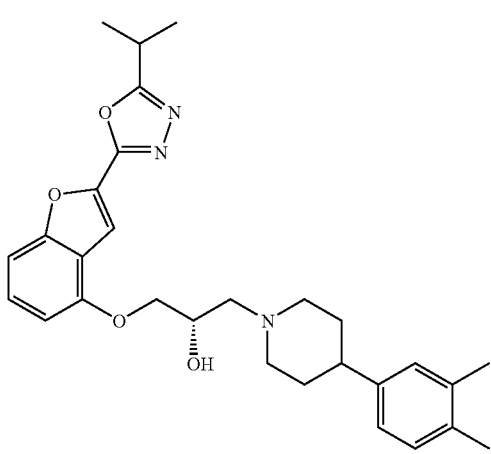

142

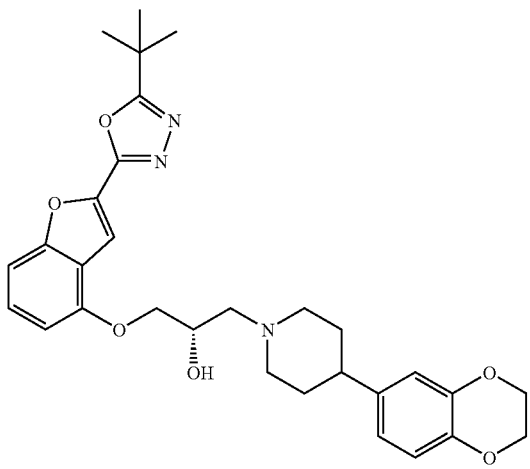

143

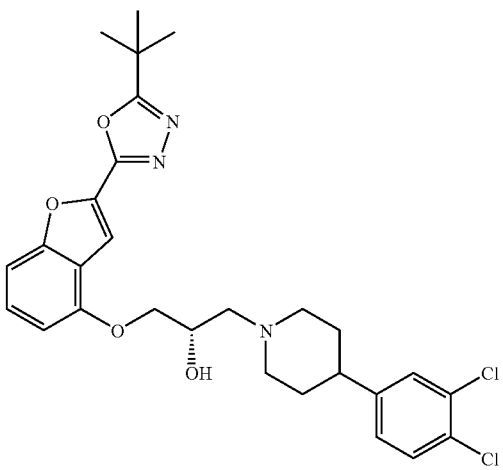

Example 144

(S)-1-(2-(5-(1,1-dimethylethyl)-1,3,4-oxadiazol-2-yl)benzo(b)furan-4-yloxy)-3-(4-(3,4-methylenedioxyphenyl)piperidino)-2-propanol hydrochloride 1/2 hydrate By the reactions in the same manner as in Example 1 using (S)-5-(4-glycidyloxybenzo(b)furan-2-yl)-2-(1,1-dimethylethyl)-1,3,4-oxadiazole (1.5 g) and 4-(3,4-methylenedioxyphenyl)piperidine (1.2 g), an oil was obtained. This was dissolved in acetone and hydrochloric acid was added. The precipitated crystals were collected by filtration and dried to give the title compound (1.33 g) as white crystals, melting point 204–206° C.

Example 145

(S)-1-(2-(5-(2-methylpropyl)-1,3,4-oxadiazol-2-yl)benzo-(b)furan-4-yloxy)-3-(4-(3,4-methylenedioxyphenyl)piperidino)-2-propanol hydrochloride By the reactions in the same manner as in Example 1 using (S)-5-(4-glycidyloxybenzo(b)furan-2-yl)-2-(2-methylpropyl)-1,3,4-oxadiazole (0.62 g) and 4-(3,4-methylenedioxyphenyl)piperidine (0.4 g), an oil was obtained. This was dissolved in acetone and hydrochloric acid was added. The precipitated crystals were collected by filtration and dried to give the title compound (0.51 g) as pale-yellow crystals, melting point 185–187° C.

Example 146

(S)-1-(2-(5-(2-methylpropyl)-1,3,4-oxadiazol-2-yl)benzo-(b)furan-4-yloxy)-3-(4-(naphthalen-2-yl)piperidino)-2-propanol hydrochloride By the reactions in the same manner as in Example 1 using (S)-5-(4-glycidyloxy)benzo(b)furan-2-yl)-2-(2-methylpropyl)-1,3,4-oxadiazole (0.62 g) and 4-(naphthalen-2-yl)piperidine (0.4 g), an oil was obtained. This was dissolved in acetone and hydrochloric acid was added. The precipitated crystals were collected by filtration and dried to give the title compound (0.35 g) as pale-yellow crystals, melting point 78–80° C.

Example 147

(S)-1-(4-(3,4-dimethylphenyl)piperidino)-3-(2-(5-(2-methylpropyl)-1,3,4-oxadiazol-2-yl)benzo(b)furan-4-yloxy)-2-propanol hydrochloride By the reactions in the same manner as in Example 1 using (S)-5-(4-glycidyloxy)benzo(b)furan-2-yl)-2-(2-methylpropyl)-1,3,4-oxadiazole (0.6 g) and 4-(3,4-dimethylphenyl)piperidine (0.4 g), an oil was obtained. This was dissolved in acetone and hydrochloric acid was added. The precipitated crystals were collected by filtration and dried to give the title compound (0.45 g) as white crystals, melting point 156–158° C.

Example 148

(S)-1-(2-(5-(2-methylpropyl)-1,3,4-oxadiazol-2-yl)benzo(b)furan-4-yloxy)-3-(4-(3,4-dichlorophenyl)piperidino)-2-propanol hydrochloride By the reactions in the same manner as in Example 1 using (S)-5-(4-glycidyloxy)benzo(b)furan-2-yl)-2-(2-methylpropyl)-1,3,4-oxadiazole (0.62 g) and 4-(3,4-dichlorophenyl)piperidine (0.46 g), an oil was obtained. This was dissolved in acetone and hydrochloric acid was added. The precipitated crystals were collected by filtration and dried to give the title compound (0.23 g) as white crystals, melting point 98–100° C.

Example 149

(S)-1-((1-benzylpiperidin-4-yl)amino)-3-(2-(5-methyl-1,3,4-oxadiazol-2-yl)benzo(b)furan-4-yloxy)-2-propanol dihydrochloride monohydrate By the reactions in the same manner as in Example 1 using (S)-5-(4-glycidyloxybenzo(b)furan-2-yl)-2-methyl-1,3,4-oxadiazole (1.5 g) and 4-amino-1-benzylpiperidine (1.0 g), an oil was obtained. This was dissolved in acetone and hydrochloric acid-ethanol solution was added. The precipitated crystals were collected by filtration and dried to give the title compound (1.2 g) as white crystals, melting point 260–262° C.

Example 150

(S)-1-(2-(5-methyl-1,3,4-oxadiazol-2-yl)benzo(b)furan-4-yloxy)-3-(4-(4-methylphenyl)piperidino)-2-propanol hydrochloride 1/4 hydrate By the reactions in the same manner as in Example 1 using (S)-5-(4-glycidyloxybenzo(b)furan-2-yl)-2-methyl-1,3,4-oxadiazole (1.0 g) and 4-(4-methylphenyl)piperidine (0.75 g), an oil was obtained. This was dissolved in acetone and hydrochloric acid-ethanol solution was added. The precipitated crystals were collected by filtration and dried to give the title compound (0.95 g) as white crystals, melting point 203–205° C.

Example 151

(S)-1-(4-(2,3-dihydrobenzo(b)furan-5-yl)piperidino)-3-(2-(5-methyl-1,3,4-oxadiazol-2-yl)benzo(b)furan-4-yloxy)-2-propanol hydrochloride By the reactions in the same manner as in Example 1 using (S)-5-(4-glycidyloxybenzo(b)furan-2-yl)-2-methyl-1,3,4-oxadiazole (0.50 g) and 4-(2,3-dihydrobenzo(b)furan-5-yl)piperidine (0.35 g), an oil was obtained. This was dissolved in ethanol and hydrochloric acid was added. The precipitated crystals were collected by filtration and dried to give the title compound (0.55 g) as white crystals, melting point 198–200° C.

The structural formulas of the compounds obtained in Examples 144 to 151 are shown in the following.

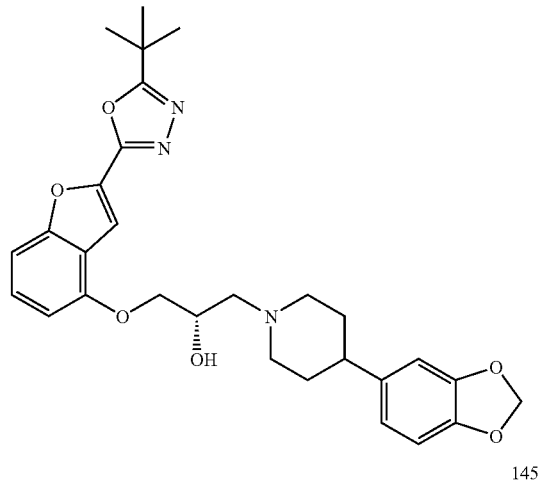

144

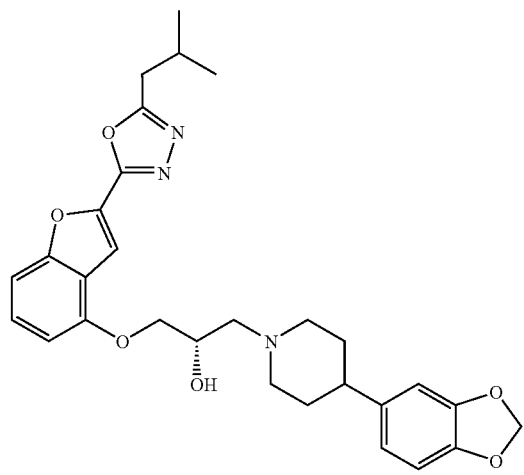

145

146
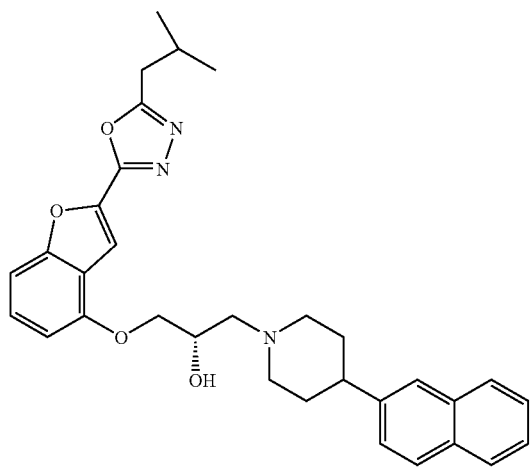
147
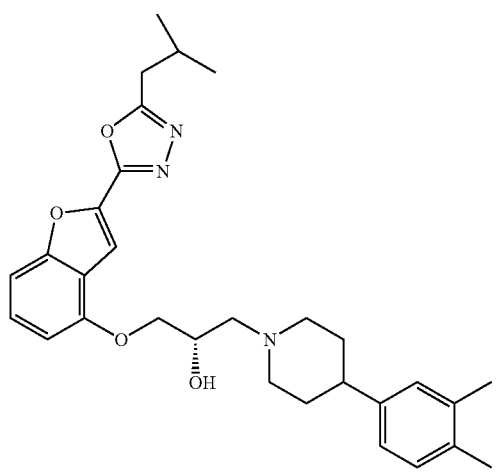
148
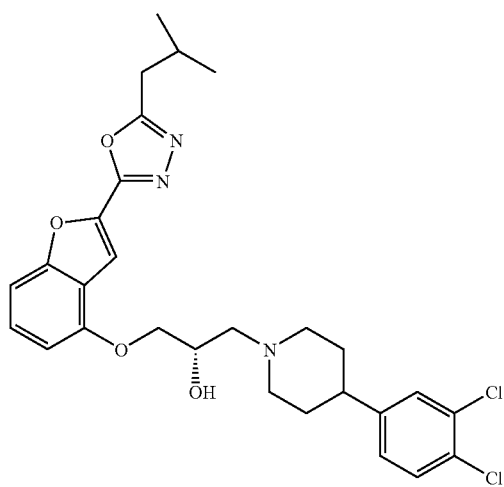
149
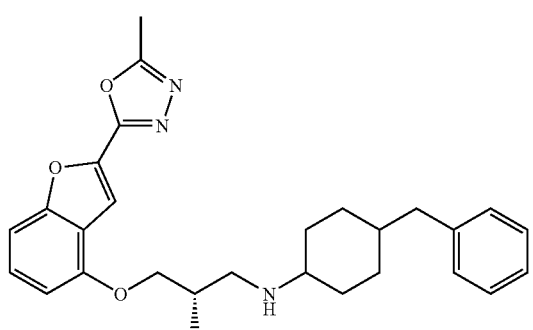
150
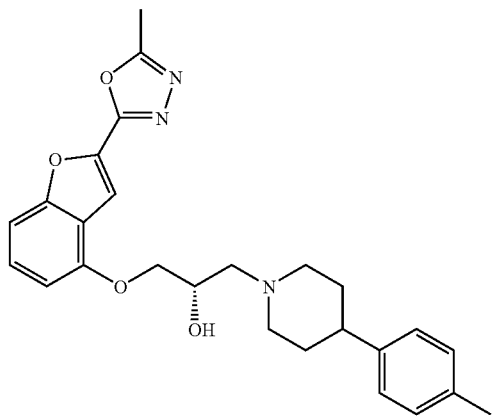
151
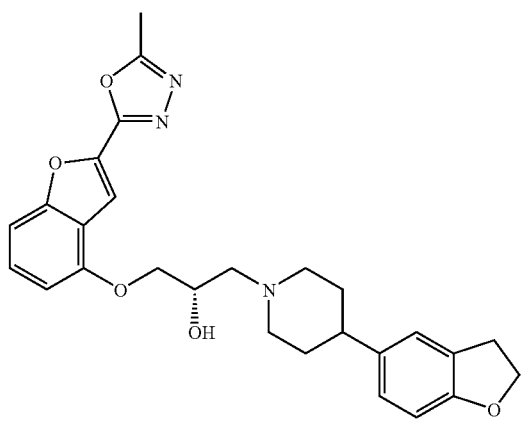
Example 152
(S)-1-(4-(2,3-dihydrobenzo(b)furan-5-yl)piperidino)-3-(2-(5-hydroxymethyl-1,3,4-oxadiazol-2-yl)benzo(b)furan-4-yloxy)-2-propanol
By the reactions in the same manner as in Example 1 using (S)-5-(4-glycidyloxybenzo(b)furan-2-yl)-2-hydroxymethyl-1,3,4-oxadiazole (0.58 g) and 4-(2,3-dihy-

Example 153

(R)-1-(4-(2,3-dihydrobenzo(b)furan-5-yl)piperidino)-3-(2-(5-methyl-1,3,4-oxadiazol-2-yl)benzo(b)furan-4-yloxy)-2-propanol hydrobromide By the reactions in the same manner as in Example 1 using (R)-5-(4-glycidyloxybenzo(b)furan-2-yl)-2-methyl-1,3,4-oxadiazole (0.25 g) and 4-(2,3-dihydrobenzo(b)furan-5-yl)piperidine (0.18 g), an oil was obtained. This was dissolved in isopropanol and hydrogen chloride-ether solution was added. The precipitated crystals were collected by filtration and dried to give the title compound (0.32 g) as white crystals, melting point 176–179° C.

Example 154

(S)-1-(4-(2,3-dihydrobenzo(b)furan-5-yl)piperidino)-3-(2-(5-ethyl-1,3,4-oxadiazol-2-yl)benzo(b)furan-4-yloxy)-2-propanol hydrochloride 1/2 hydrate By the reactions in the same manner as in Example 1 using (S)-2-ethyl-5-(4-glycidyloxybenzo(b)furan-2-yl)-1,3,4-oxadiazole (0.50 g) and 4-(2,3-dihydrobenzo(b)furan-5-yl)piperidine (0.35 g), an oil was obtained. This was dissolved in a mixed solution of isopropanol-ethyl acetate (1:1) and a hydrogen chloride-ether solution was added. The precipitated crystals were collected by filtration and dried to give the title compound (0.25 g) as white crystals, melting point 180–182° C.

Example 155

(S)-1-(4-(2,3-dihydrobenzo(b)furan-5-yl)piperidino)-3-(2-(5-(1-methylethyl)-1,3,4-oxadiazol-2-yl)benzo(b)furan-4-yloxy)-2-propanol dihydrobromide 3/2 hydrate By the reactions in the same manner as in Example 1 using (S)-5-(4-glycidyloxybenzo(b)furan-2-yl)-2-(1-methylethyl)-1,3,4-oxadiazole (0.50 g) and 4-(2,3-dihydrobenzo(b)furan-5-yl)piperidine (0.35 g), an oil was obtained. This was dissolved in isopropanol and 48% hydrobromic acid was added. The precipitated crystals were collected by filtration and dried to give the title compound (0.38 g) as yellow crystals, melting point 131–136° C. (decomposition).

Example 156

(S)-1-(4-(chroman-6-yl)piperidino)-3-(2-(5-methyl-1,3,4-oxadiazol-2-yl)benzo(b)furan-4-yloxy)-2-propanol hydrochloride By the reactions in the same manner as in Example 1 using (S)-5-(4-glycidyloxybenzo(b)furan-2-yl)-2-methyl-1,3,4-oxadiazole (1.0 g) and 4-(chroman-6-yl)piperidine (0.90 g), an oil was obtained. This was dissolved in isopropanol and hydrogen chloride-ethanol solution was added. The precipitated crystals were collected by filtration and dried to give the title compound (1.3 g) as white crystals, melting point 202–204° C.

Example 157

(S)-1-(4-(chroman-6-yl)piperidino)-3-(2-(5-ethyl-1,3,4-oxadiazol-2-yl)benzo(b)furan-4-yloxy)-2-propanol (L)-tartrate By the reactions in the same manner as in Example 1 using (S)-2-ethyl-5-(4-glycidyloxybenzo(b)furan-2-yl)-1,3,4-oxadiazole (1.0 g) and 4-(chroman-6-yl)piperidine (0.90 g), an oil was obtained. This was dissolved in ethanol and (L)-tartaric acid-ethanol solution was added. The precipitated crystals were collected by filtration and dried to give the title compound (1.4 g) as white crystals, melting point 176–178° C.

Example 158

(S)-1-(4-(chroman-6-yl)piperidino)-3-(2-(5-(1-methylethyl)-1,3,4-oxadiazol-2-yl)benzo(b)furan-4-yloxy)-2-propanol hydrochloride By the reactions in the same manner as in Example 1 using (S)-5-(4-glycidyloxybenzo(b)furan-2-yl)-2-(1-methylethyl)-1,3,4-oxadiazole (1.0 g) and 4-(chroman-6-yl)piperidine (0.90 g), an oil was obtained. This was dissolved in isopropanol and hydrogen chloride-ethanol solution was added. The precipitated crystals were collected by filtration and dried to give the title compound (1.3 g) as white crystals, melting point 183–185° C.

Example 159 ethyl (S)-4-(4-fluorophenyl)-1-(2-hydroxy-3-(2-(5-methyl-1,3,4-oxadiazol-2-yl)benzo(b)furan-4-yloxy)propyl)piperidine-4-carboxylate hydrobromide monohydrate By the reactions in the same manner as in Example 1 using (S)-5-(4-glycidyloxybenzo(b)furan-2-yl)-2-methyl-1,3,4-oxadiazole (1.0 g) and ethyl 4-(4-fluorophenyl)piperidine-4-carboxylate (0.82 g), an oil was obtained. This was dissolved in acetone, hydrobromic acid was added. The precipitated crystals were collected by filtration and dried to give the title compound (0.66 g) as white crystals, melting point 132–135° C.

The structural formulas of the compounds obtained in Examples 152 to 159 are shown in the following.

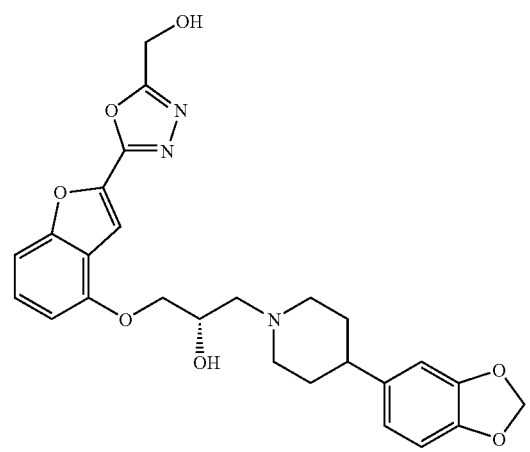

152

209
-continued
153
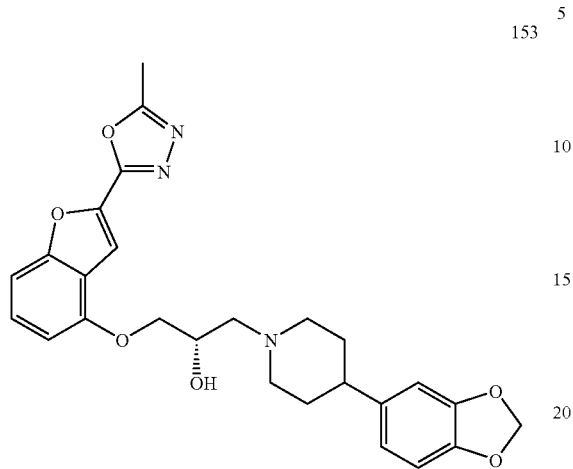
154
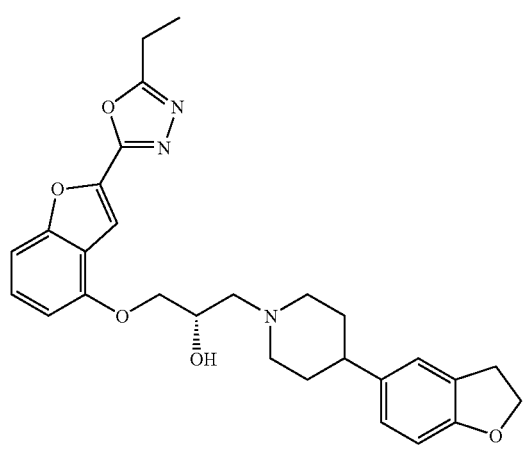
155
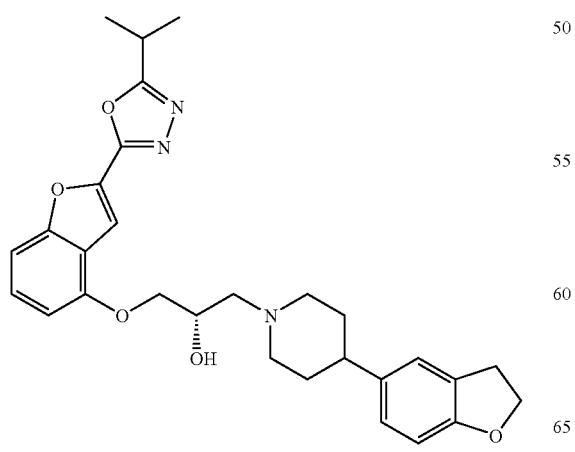
210
-continued
156
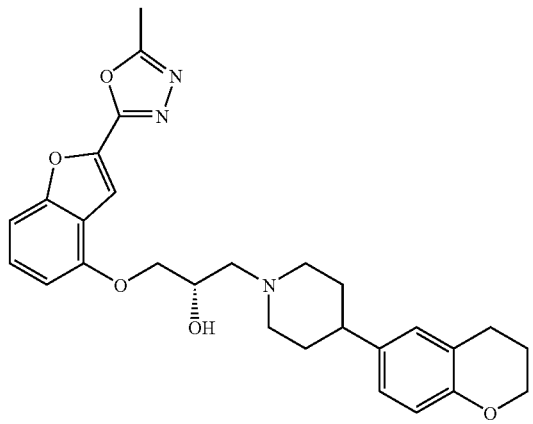
157
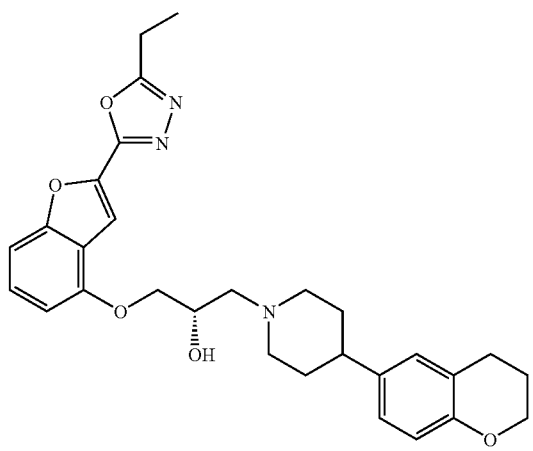
158
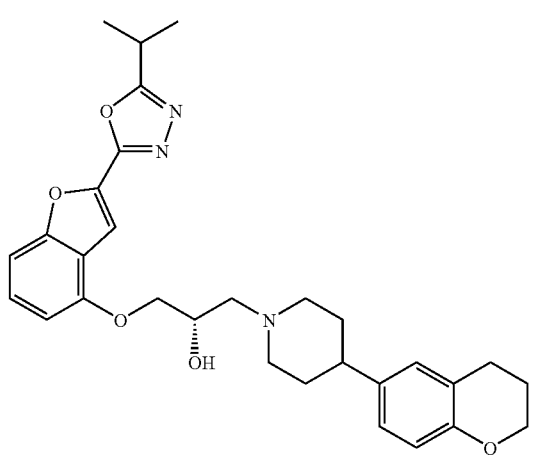

-continued

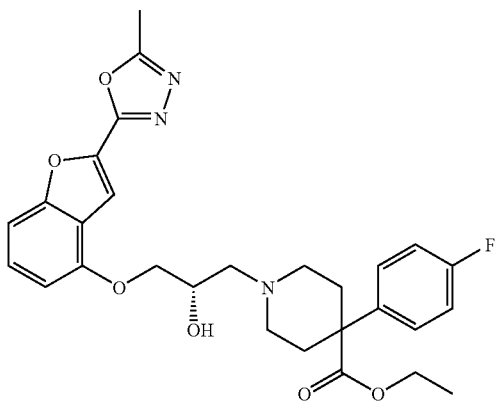

159

Example 160

(S)-4-(3,4-dichlorophenyl)-1-(2-hydroxy-3-(2-(5-methyl-1,3,4-oxadiazol-2-yl)benzo(b)furan-4-yloxy) propyl)piperidine-4-carbonitrile hydrobromide monohydrate By the reactions in the same manner as in Example 1 using (S)-5-(4-glycidyloxybenzo(b)furan-2-yl)-2-methyl-1,3,4-oxadiazole (0.22 g) and 4-(3,4-dichlorophenyl)piperidine-4-carbonitrile (0.20 g), an oil was obtained. This was dissolved in acetone and hydrobromic acid was added. The precipitated crystals were collected by filtration and dried to give the title compound (0.12 g) as brown crystals, melting point 265–268° C. (decomposition).

Example 161

(S)-1-(4-hydroxy-4-(3,4-methylenedioxyphenyl) piperidino)-3-(2-(5-methyl-1,3,4-oxadiazol-2-yl) benzo(b)furan-4-yloxy)-2-propanol hydrochloride 1/2 hydrate By the reactions in the same manner as in Example 1 using (S)-5-(4-glycidyloxybenzo(b)furan-2-yl)-2-methyl-1,3,4-oxadiazole (0.51 g) and 4-hydroxy-4-(3,4-methylenedioxyphenyl)piperidine (0.42 g), an oil was obtained. This was dissolved in isopropanol and hydrochloric acid-ether solution was added. The precipitated crystals were collected by filtration and dried to give the title compound (0.51 g) as white crystals, melting point 184–186° C.

Example 162

(S)-1-(2-(5-methylthio-1,3,4-oxadiazol-2-yl)benzo (b)furan-4-yloxy)-3-(4-(naphthalen-2-yl)piperidino)-2-propanol hydrochloride 1/4 hydrate By the reactions in the same manner as in Example 1 using 5-(4-hydroxybenzo(b)furan-2-yl)-2-methylthio-1,3,4-oxadiazole (0.62 g) obtained in Starting Material Synthesis Example 115, (S)-glycidyl nosylate (0.71 g) and potassium carbonate (0.41 g), (S)-5-(4-glycidyloxybenzo(b)furan-2-yl)-2-methylthio-1,3,4-oxadiazole (0.54 g) was obtained. This was dissolved in methanol and 4-(naphthalen-2-yl)piperidine (0.5 g) was added. The mixture was refluxed under heating for 5 hr. The reaction solvent was evaporated under reduced pressure and the residue was purified by silica gel column chromatography (chloroform/methanol) to give an oil. This was dissolved in ethyl acetate and a hydrochloric acid-ether solution was added. The precipitated crystals were collected by filtration and dried to give the title compound (0.34 g) as brown crystals, melting point 121–126° C.

Example 163

(S)-1-(2-(5-methoxy-1,3,4-oxadiazol-2-yl)benzo(b) furan-4-yloxy)-3-(4-(naphthalen-2-yl)piperidino)-2-propanol hydrochloride 1/4 hydrate By the reactions in the same manner as in Example 1 using (S)-5-(4-glycidyloxybenzo(b)furan-2-yl)-2-methoxy-1,3,4-oxadiazole (0.18 g) obtained in Starting Material Synthesis Example 118 and 4-(naphthalen-2-yl)piperidine (0.12 g), an oil was obtained. This was dissolved in acetone and a hydrochloric acid-ether solution was added. The precipitated crystals were collected by filtration and dried to give the title compound (0.11 g) as white crystals, melting point 250–251° C.

Example 164

(S)-1-(2-(5-methoxy-1,3,4-oxadiazol-2-yl)benzo(b) furan-4-yloxy)-3-(4-(3,4-methylenedioxyphenyl) piperidino)-2-propanol hydrochloride 1/4 hydrate By the reactions in the same manner as in Example 1 using (S)-5-(4-glycidyloxybenzo(b)furan-2-yl)-2-methoxy-1,3,4-oxadiazole (0.30 g) and 4-(3,4-methylenedioxyphenyl)piperidine (0.20 g), an oil was obtained. This was dissolved in acetone and a hydrochloric acid-ether solution was added. The precipitated crystals were collected by filtration and dried to give the title compound (0.17 g) as white crystals, melting point 242–246° C. (decomposition)

Example 165

(S)-1-(2-(5-ethoxy-1,3,4-oxadiazol-2-yl)benzo(b) furan-4-yloxy)-3-(4-(3,4-methylenedioxyphenyl) piperidino)-2-propanol By the reactions in the same manner as in Example 1 using (S)-2-ethoxy-5-(4-glycidyloxybenzo(b)furan-2-yl)-1,3,4-oxadiazole (1.0 g) and 4-(3,4-methylenedioxyphenyl) piperidine (0.65 g), crude crystals were obtained. The crystals were recrystallized from ethanol and purified to give the title compound (1.2 g) as white crystals, melting point 117–118° C.

Example 166

(S)-1-(2-(5-(1-methylethyloxy)-1,3,4-oxadiazol-2-yl) benzo(b)furan-4-yloxy)-3-(4-(naphthalen-2-yl)piperidino)-2-propanol hydrobromide 1/2 hydrate By the reactions in the same manner as in Example 1 using (S)-2-(1-methylethyloxy)-5-(4-glycidyloxybenzo(b) furan-2-yl)-1,3,4-oxadiazole (0.50 g) and 4-(naphthalen-2-yl)piperidine (0.35 g), an oil was obtained. This was dissolved in isopropanol and 48% hydrobromic acid was added. The precipitated crystals were collected by filtration and dried to give the title compound (0.52 g) as yellow crystals, melting point 123–135° C.

Example 167

(S)-1-(2-(5-(1-methylethyloxy)-1,3,4-oxadiazol-2-yl)benzo(b)furan-4-yloxy)-3-(4-(3,4-methylenedioxyphenyl)piperidino)-2-propanol hydrobromide By the reactions in the same manner as in Example 1 using (S)-2-(1-methylethyloxy)-5-(4-glycidyloxybenzo(b)furan-2-yl)-1,3,4-oxadiazole (0.50 g) and 4-(3,4-methylenedioxyphenyl)piperidine (0.35 g), an oil was obtained. This was dissolved in isopropanol and 48% hydrobromic acid was added. The precipitated crystals were collected by filtration and dried to give the title compound (0.58 g) as yellow crystals, melting point 196–198° C.

The structural formulas of the compounds obtained in Examples 160 to 167 are shown in the following.

-continued

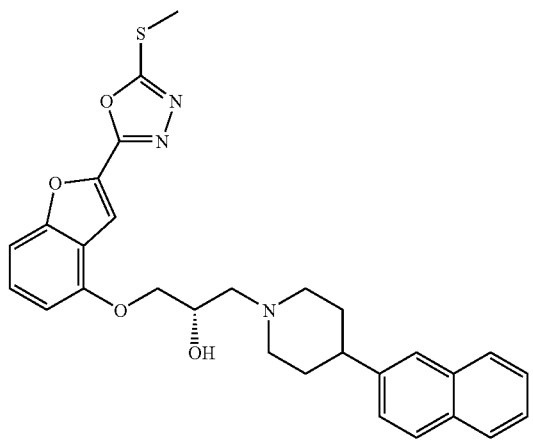

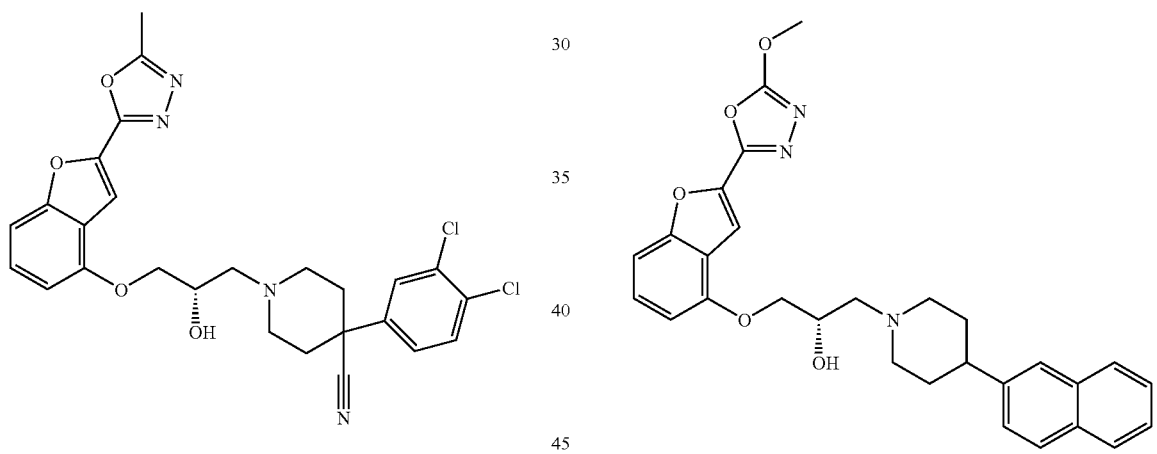

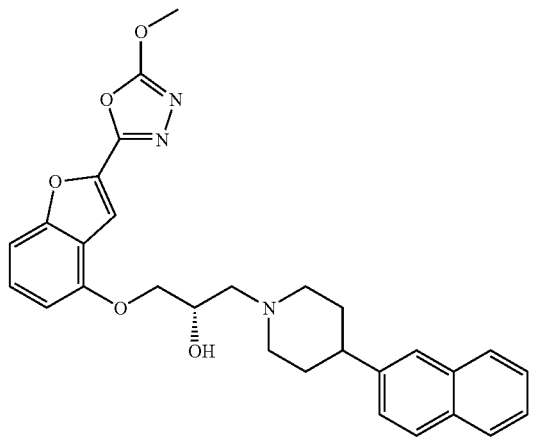

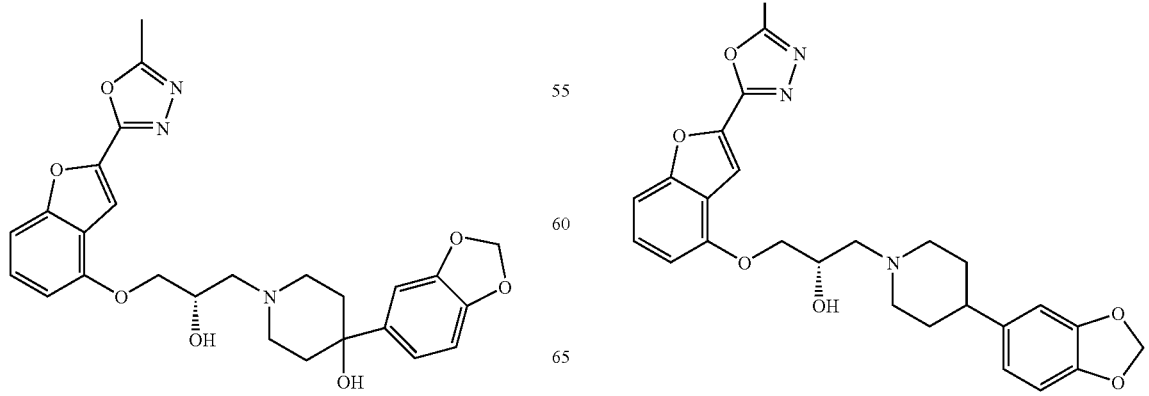

-continued

165

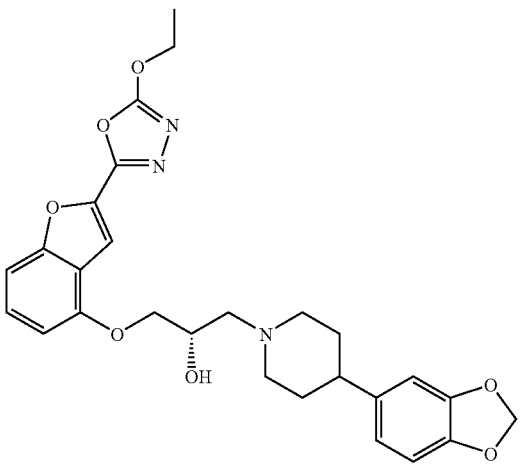

166

167

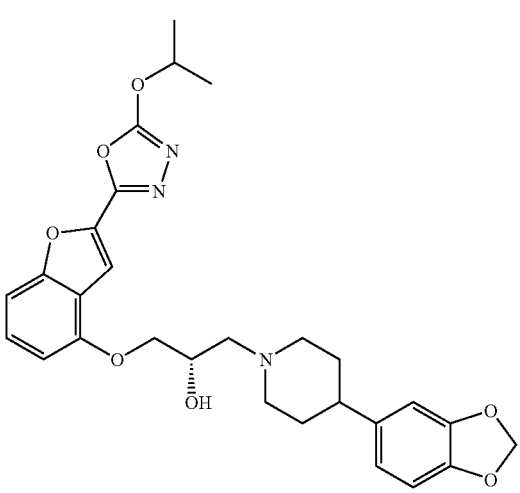

Example 168

(S)-1-(2-(5-methyloxazol-2-yl)benzo(b)furan-4-yloxy)-3-(4-(3,4-methylenedioxyphenyl)piperidino)-2-propanol hydrochloride By the reactions in the same manner as in Example 1 using (S)-2-(4-glycidyloxybenzo(b)furan-2-yl)-5-methyloxazole (2.0 g) and 4-(3,4-methylenedioxyphenyl)piperidine (1.4 g), an oil was obtained. This was dissolved in ethanol and hydrochloric acid was added. The precipitated crystals were collected by filtration and dried to give the title compound (1.2 g) as pale-yellow crystals, melting point 239–241° C.
$^1$H-NMR(DMSO-$d_6$)δ:1.93–2.00(m, 4H), 2.42(s, 3H), 2.78(m, 1H), 3.20(m, 2H), 3.35–3.42(m, 2H), 3.69–3.73(m, 2H), 4.12–4.20(m, 2H), 4.53(m, 1H), 5.98(s, 2H), 6.05(m, 1H), 6.72(d, J=7.8, 1H), 6.79–6.90(m, 3H), 7.08(s, 1H), 7.31–7.38(m, 2H), 7.61(s, 1H), 10.05(bs, 1H)

Example 169

(S)-1-(4-(2,3-dihydrobenzo(b)furan-5-yl)piperidino)-3-(2-(5-methyloxazol-2-yl)benzo(b)furan-4-yloxy)-2-propanol hydrochloride By the reactions in the same manner as in Example 1 using (S)-2-(4-glycidyloxybenzo(b)furan-2-yl)-5-methyloxazole (1.4 g) and 4-(2,3-dihydrobenzo(b)furan-5-yl)piperidine (1.0 g), an oil was obtained. This was dissolved in ethanol and hydrochloric acid was added. The precipitated crystals were collected by filtration and dried to give the title compound (0.81 g) as white crystals, melting point 230–233° C.
$^1$H-NMR(CDCl$_3$)δ:2.01–2.08(m, 2H), 2.45(s, 3H), 2.59–2.74(m, 3H) 2.90–3.02(m, 2H), 3.18(t, J=8.0, 2H), 3.32(m, 2H), 3.80–3.92(m, 2H), 4.02(m, 1H), 4.35(m, 1H), 4.56(t, J=8.0, 2H), 4.79(m, 1H), 5.68(bs, 1H), 6.72(m, 2H), 6.93(s, 1H), 6.98(d, J=7.8, 1H) 7.16(s, 1H), 7.23–7.35(m, 2H), 7.42(s, 1H), 11.85(bs, 1H)

Example 170

(S)-1-(2-(5-ethyloxazol-2-yl)benzo(b)furan-4-yloxy)-3-(4-(3,4-methylenedioxyphenyl)piperidino)-2-propanol dihydrochloride 1/2 hydrate By the reactions in the same manner as in Example 1 using (S)-5-ethyl-2-(4-glycidyloxybenzo(b)furan-2-yl)oxazole (1.0 g) and 4-(3,4-methylenedioxyphenyl)piperidine (0.8 g), an oil was obtained. This was dissolved in acetone and hydrochloric acid was added. The precipitated crystals were collected by filtration and dried to give the title compound (1.05 g) as white crystals, melting point 145–147° C.

Example 171

(S)-1-(2-(5-ethyloxazol-2-yl)benzo(b)furan-4-yloxy)-3-(4-(1,4-benzodioxan-6-yl)piperidino)-2-propanol hydrochloride 5/4 hydrate By the reactions in the same manner as in Example 1 using (S)-5-ethyl-2-(4-glycidyloxybenzo(b)furan-2-yl)oxazole (0.6 g) and 4-(1,4-benzodioxan-6-yl)piperidine (0.6 g), an oil was obtained. This was dissolved in acetone and hydrochloric acid was added. The precipitated crystals were collected by filtration and dried to give the title compound (0.5 g) as white crystals, melting point 89–91° C.

Example 172

(S)-1-(2-(5-ethyloxazol-2-yl)benzo(b)furan-4-yloxy)-3-(4-(naphthalen-2-yl)piperidino)-2-propanol hydrochloride 1/2 hydrate By the reactions in the same manner as in Example 1 using (S)-5-ethyl-2-(4-glycidyloxybenzo(b)furan-2-yl)oxazole (0.7 g) and 4-(naphthalen-2-yl)piperidine (0.6 g), an oil was obtained. This was dissolved in acetone, and hydrochloric acid was added. The precipitated crystals were collected by filtration and dried to give the title compound (0.6 g) as white crystals, melting point 114–116° C.

Example 173

(S)-1-(2-(5-(1-methylethyl)oxazol-2-yl)benzo(b)furan-4-yloxy)-3-(4-(3,4-methylenedioxyphenyl)piperidino)-2-propanol dihydrochloride 1/2 hydrate By the reactions in the same manner as in Example 1 using (S)-2-(4-glycidyloxybenzo(b)furan-2-yl)-5-(1-methylethyl)oxazole (1.0 g) and 4-(3,4-methylenedioxyphenyl)piperidine (0.8 g), an oil was obtained. This was dissolved in acetone and hydrochloric acid was added. The precipitated crystals were collected by filtration and dried to give the title compound (0.97 g) as white crystals, melting point 139–141° C.

Example 174

(S)-1-(2-(5-(1-methylethyl)oxazol-2-yl)benzo(b)furan-4-yloxy)-3-(4-(3,4-dimethylphenyl)piperidino)-2-propanol hydrochloride 1/2 hydrate By the reactions in the same manner as in Example 1 using (S)-2-(4-glycidyloxybenzo(b)furan-2-yl)-5-(1-methylethyl)oxazole (0.8 g) and 4-(3,4-dimethylphenyl)piperidine (0.6 g), an oil was obtained. This was dissolved in acetone and hydrochloric acid was added. The precipitated crystals were collected by filtration and dried to give the title compound (0.59 g) as white crystals, melting point 119–121° C.

Example 175

(S)-1-(2-(5-(1-methylethyl)oxazol-2-yl)benzo(b)furan-4-yloxy)-3-(4-(3,4-dichlorophenyl)piperidino)-2-propanol hydrochloride 1/2 hydrate By the reactions in the same manner as in Example 1 using (S)-2-(4-glycidyloxybenzo(b)furan-2-yl)-5-(1-methylethyl)oxazole (0.95 g) and 4-(3,4-dichlorophenyl)piperidine (0.85 g), an oil was obtained. This was dissolved in acetone and hydrochloric acid was added. The precipitated crystals were collected by filtration and dried to give the title compound (0.98 g) as white crystals, melting point 202–204° C.

The structural formulas of the compounds obtained in Examples 168 to 175 are shown in the following.

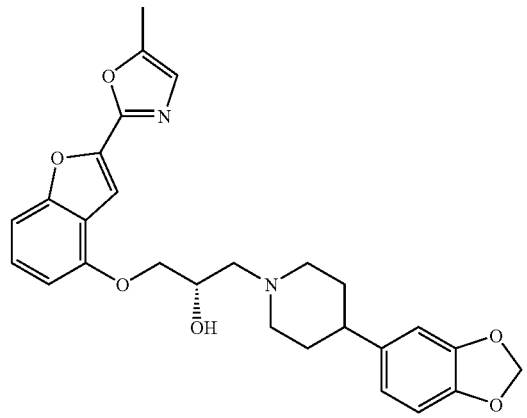

168

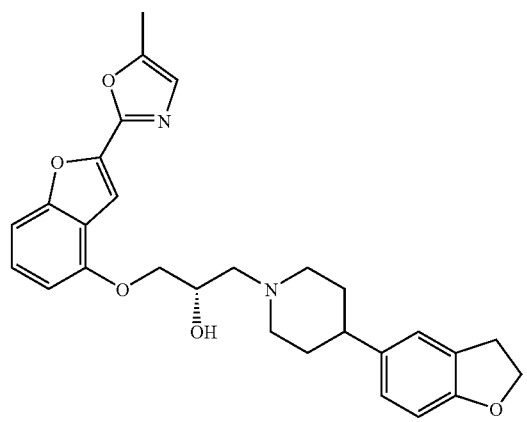

169

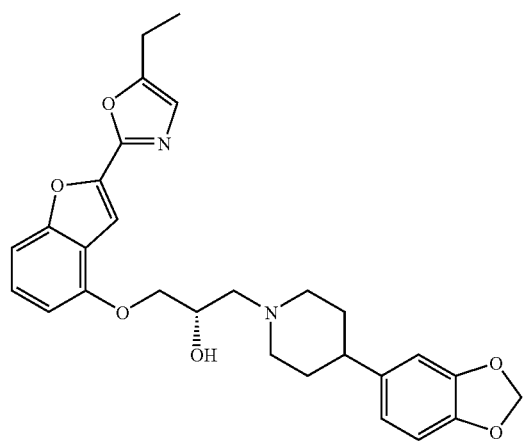

170

171

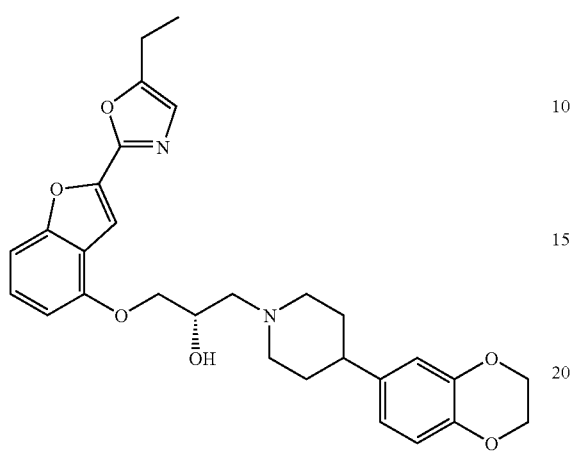

172

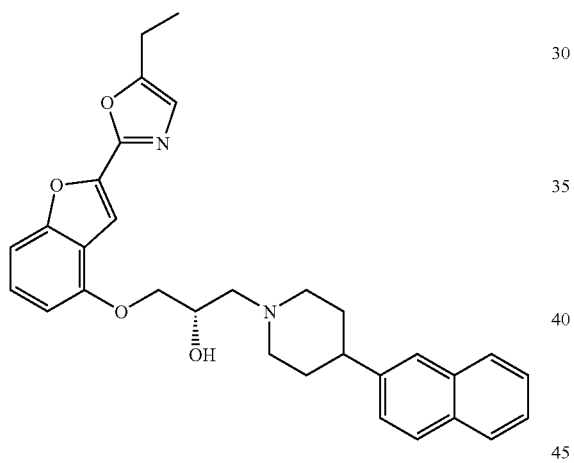

173

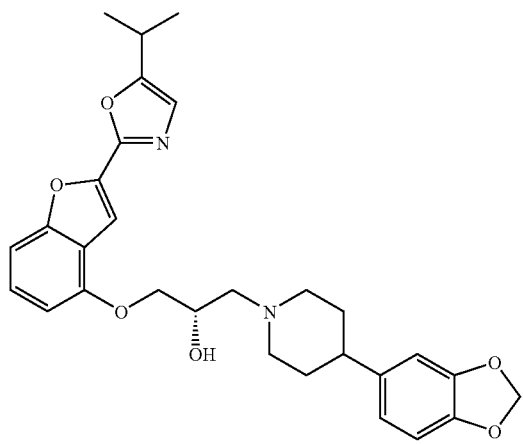

174

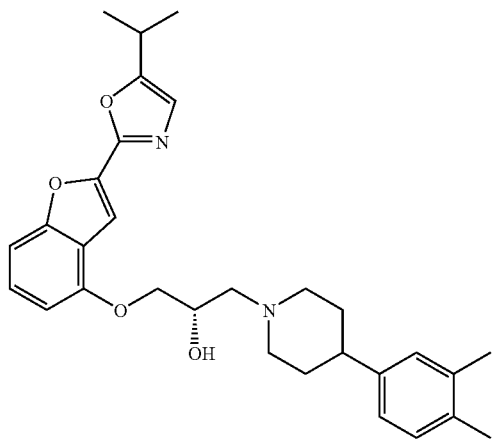

175

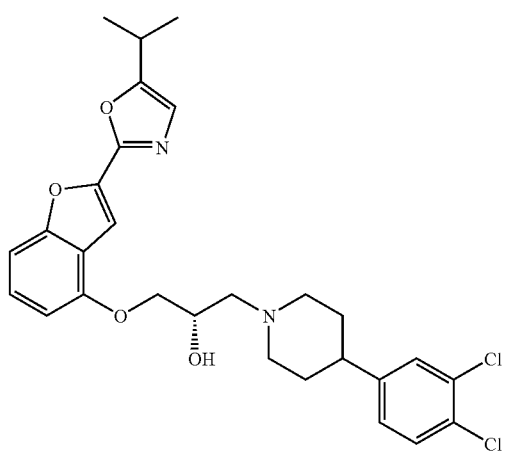

Example 176

5-methyl-2-(4-(3-(4-(3,4-methylenedioxyphenyl) piperidino)propyloxy)benzo(b)furan-2-yl)-1,3,4-oxadiazole 5-Methyl-2-(4-(3-chloropropyloxy)benzo(b)furan-2-yl)-1,3,4-oxadiazole (1.0 g), 4-(3,4-methylenedioxyphenyl)piperidine (0.7 g), potassium carbonate (1.5 g) and potassium iodide (1.0 g) were dissolved in a mixed solvent (50 ml) of DMF-toluene (2:1) and the solution was stirred with refluxing under heating at 80° C. for 4 hr. The reaction mixture was poured into water, extracted with ethyl acetate and dried. The solvent was evaporated under reduced pressure and the residue was purified by silica gel column chromatography (chloroform/methanol) to give the title compound (0.99 g) as white crystals, melting point 125–127° C.

Example 177

5-methyl-2-(4-(3-(4-(naphthalen-2-yl)piperidino) propyloxy)benzo(b)furan-2-yl)-1,3,4-oxadiazole hydrochloride By the reactions in the same manner as in Example 176 using 5-methyl-2-(4-(3-chloropropyloxy)benzo(b)furan-2-yl)-1,3,4-oxadiazole (1.0 g), 4-(naphthalen-2-yl)piperidine (0.7 g), potassium carbonate (1.5 g) and potassium iodide (1.0 g), an oil was obtained. This was dissolved in acetone and a hydrochloric acid-ethanol solution was added. The precipitated crystals were collected by filtration and dried to give the title compound (1.2 g) as white crystals, melting point 205–207° C.

Example 178

2-(4-(3-((1-benzylpiperidin-4-yl)amino)propyloxy) benzo(b)furan-2-yl)-5-methyl-1,3,4-oxadiazole dihydrochloride 1/2 hydrate By the reactions in the same manner as in Example 176 using 2-(4-(3-bromopropyloxy)benzo(b)-2-yl)furan-5-methyl-1,3,4-oxadiazole (0.8 g), 4-amino-1-benzylpiperidine (0.7 g), potassium carbonate (1.5 g) and potassium iodide (1.0 g), an oil was obtained. This was dissolved in acetone and a hydrochloric acid-ethanol solution was added. The precipitated crystals were collected by filtration and dried to give the title compound (0.51 g) as white crystals, melting point 265° C. or higher.

Example 179

5-ethyl-2-(4-(3-(4-(naphthalen-2-yl)piperidino)propyloxy)benzo(b)furan-2-yl)-1,3,4-oxadiazole hydrochloride By the reactions in the same manner as in Example 176 using 5-ethyl-2-(4-(3-chloropropyloxy)benzo(b)furan-2-yl)-1,3,4-oxadiazole (0.7 g), 4-(naphthalen-2-yl)piperidine (0.5 g), potassium carbonate (1.5 g) and potassium iodide (1.0 g), an oil was obtained. This was dissolved in acetone and a hydrochloric acid-ethanol solution was added. The precipitated crystals were collected by filtration and dried to give the title compound (0.16 g) as white crystals, melting point 198–200° C.

Example 180

5-ethyl-2-(4-(3-(4-(3,4-methylenedioxyphenyl)piperidino)propyloxy)benzo(b)furan-2-yl)-1,3,4-oxadiazole hydrochloride 1/4 hydrate By the reactions in the same manner as in Example 176 using 5-ethyl-2-(4-(3-chloropropyloxy)benzo(b)furan-2-yl)-1,3,4-oxadiazole (1.0 g), 4-(3,4-methylenedioxyphenyl)piperidine (0.8 g), potassium carbonate (0.68 g) and potassium iodide (0.57 g), an oil was obtained. This was dissolved in ethanol and a hydrochloric acid-ethanol solution was added. The precipitated crystals were collected by filtration and dried to give the title compound (0.92 g) as white crystals, melting point 192–193° C.

Example 181

5-ethyl-2-(4-(3-(4-(3,4-dichlorophenyl)piperidino) propyloxy)benzo(b)furan-2-yl)-1,3,4-oxadiazole hydrochloride 1/4 hydrate By the reactions in the same manner as in Example 176 using 5-ethyl-2-(4-(3-chloropropyloxy)benzo(b)furan-2-yl)-1,3,4-oxadiazole (1.0 g), 4-(3,4-dichlorophenyl)piperidine (0.79 g), potassium carbonate (0.68 g) and potassium iodide (0.57 g), an oil was obtained. This was dissolved in ethanol and a hydrochloric acid-ethanol solution was added. The precipitated crystals were collected by filtration and dried to give the title compound (1.1 g) as white crystals, melting point 225–227° C.

Example 182

2-(4-(3-(4-(1,4-benzodioxan-6-yl)piperidino)propyloxy)benzo(b)furan-2-yl)-5-(1-methylethyl)-1,3,4-oxadiazole hydrochloride By the reactions in the same manner as in Example 176 using 5-(1-methylethyl)-2-(4-(3-chloropropyloxy)benzo(b)furan-2-yl)-1,3,4-oxadiazole (0.9 g), 4-(1,4-benzodioxan-6-yl)piperidine (0.7 g), potassium carbonate (1.5 g) and potassium iodide (1.0 g), an oil was obtained. This was dissolved in acetone and hydrochloric acid was added. The precipitated crystals were collected by filtration and dried to give the title compound (0.68 g) as white crystals, melting point 203–205° C.

Example 183

2-(4-(3-(4-(3,4-dimethylphenyl)piperidino)propyloxy)benzo(b)furan-2-yl)-5-(1-methylethyl)-1,3,4-oxadiazole hydrochloride By the reactions in the same manner as in Example 176 using 5-(1-methylethyl)-2-(4-(3-chloropropyloxy)benzo(b)furan-2-yl)-1,3,4-oxadiazole (1.0 g), 4-(3,4-dimethylphenyl)piperidine (0.8 g), potassium carbonate (1.5 g) and potassium iodide (1.0 g), an oil was obtained. This was dissolved in acetone and hydrochloric acid was added. The precipitated crystals were collected by filtration and dried to give the title compound (0.9 g) as white crystals, melting point 217–219° C.

The structural formulas of the compounds obtained in Examples 176 to 183 are shown in the following.

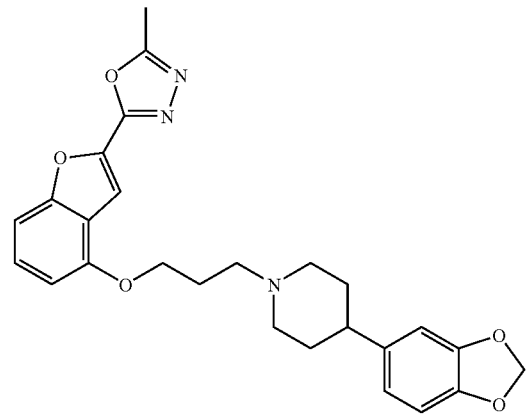

176

177
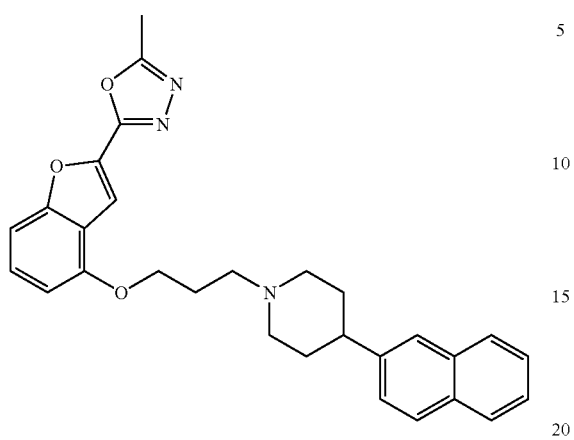
178
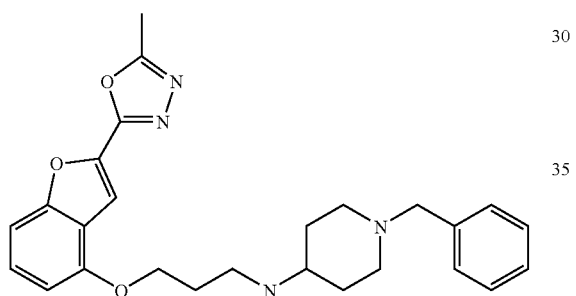
179
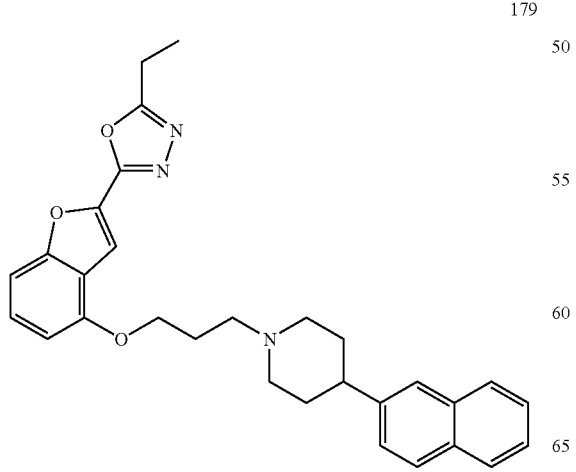
180
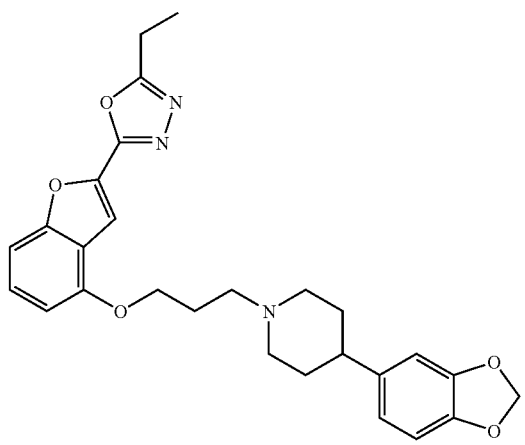
181
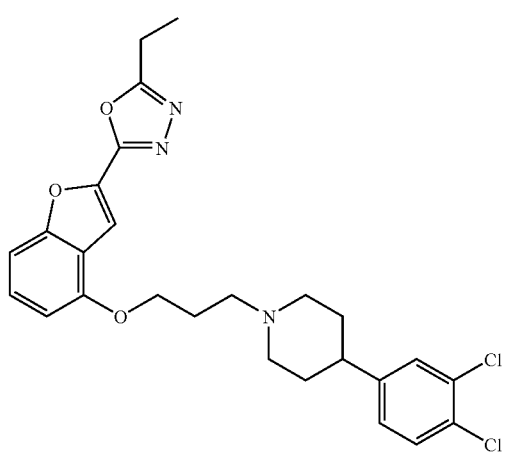
182
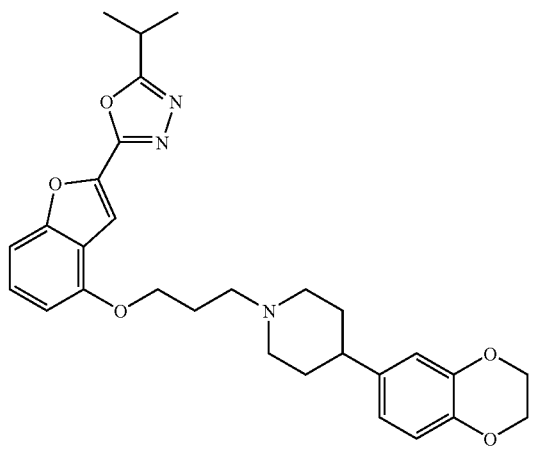

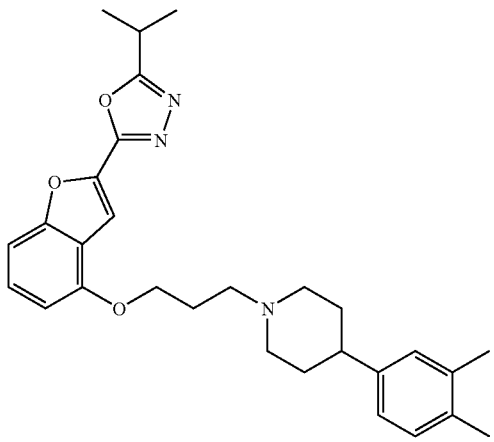

Example 184

2-(4-(3-(4-(3,4-dichlorophenyl)piperidino)propyloxy)benzo(b)furan-2-yl)-5-(1-methylethyl)-1,3,4-oxadiazole hydrochloride By the reactions in the same manner as in Example 176 using 5-(1-methylethyl)-2-(4-(3-chloropropyloxy)benzo(b)furan-2-yl)-1,3,4-oxadiazole (1.0 g), 4-(3,4-dichlorophenyl)piperidine (0.8 g), potassium carbonate (1.5 g) and potassium iodide (1.0 g), an oil was obtained. This was dissolved in acetone and hydrochloric acid was added. The precipitated crystals were collected by filtration and dried to give the title compound (0.9 g) as white crystals, melting point 247–249° C.

Example 185

2-(4-(3-(4-(naphthalen-2-yl)piperidino)propyloxy)benzo(b)furan-2-yl)-5-(1-methylethyl)-1,3,4-oxadiazole hydrochloride By the reactions in the same manner as in Example 176 using 5-(1-methylethyl)-2-(4-(3-chloropropyloxy)benzo(b)furan-2-yl)-1,3,4-oxadiazole (1.0 g), 4-(naphthalen-2-yl)piperidine (0.9 g), potassium carbonate (1.5 g) and potassium iodide (1.0 g), an oil was obtained. This was dissolved in acetone and hydrochloric acid was added. The precipitated crystals were collected by filtration and dried to give the title compound (1.15 g) as white crystals, melting point 215–217° C.

Example 186

2-(4-(3-(4-(3,4-methylenedioxyphenyl)piperidino)propyloxy)benzo(b)furan-2-yl)-5-(1-methylethyl)-1,3,4-oxadiazole hydrochloride By the reactions in the same manner as in Example 176 using 5-(1-methylethyl)-2-(4-(3-chloropropyloxy)benzo(b)furan-2-yl)-1,3,4-oxadiazole (1.0 g), 4-(3,4-methylenedioxyphenyl)piperidine (1.0 g), potassium carbonate (1.5 g) and potassium iodide (1.0 g), an oil was obtained. This was dissolved in acetone and hydrochloric acid was added. The precipitated crystals were collected by filtration and dried to give the title compound (1.07 g) as white crystals, melting point 193–195° C.

Example 187

2-(4-(3-(4-(3,4-dimethylphenyl)piperidino)propyloxy)benzo(b)furan-2-yl)-5-(1,1-dimethylethyl)-1,3,4-oxadiazole hydrochloride By the reactions in the same manner as in Example 176 using 5-(1,1-dimethylethyl)-2-(4-(3-chloropropyloxy)benzo(b)furan-2-yl)-1,3,4-oxadiazole (0.8 g), 4-(3,4-dimethylphenyl)piperidine (0.7 g), potassium carbonate (1.5 g) and potassium iodide (1.0 g), an oil was obtained. This was dissolved in acetone and hydrochloric acid was added. The precipitated crystals were collected by filtration and dried to give the title compound (0.68 g) as white crystals, melting point 226–228° C.

Example 188

2-(4-(3-(4-(3,4-dichlorophenyl)piperidino)propyloxy)benzo(b)furan-2-yl)-5-(1,1-dimethylethyl)-1,3,4-oxadiazole hydrochloride By the reactions in the same manner as in Example 176 using 5-(1,1-dimethylethyl)-2-(4-(3-chloropropyloxy)benzo(b)furan-2-yl)-1,3,4-oxadiazole (1.0 g), 4-(3,4-dichlorophenyl)piperidine (0.8 g), potassium carbonate (1.5 g) and potassium iodide (1.0 g), an oil was obtained. This was dissolved in acetone and hydrochloric acid was added. The precipitated crystals were collected by filtration and dried to give the title compound (0.75 g) as white crystals, melting point 249–251° C.

Example 189

2-(4-(3-(4-(3,4-methylenedioxyphenyl)piperidino)propyloxy)benzo(b)furan-2-yl)-5-(1,1-dimethylethyl)-1,3,4-oxadiazole hydrochloride By the reactions in the same manner as in Example 176 using 5-(1,1-dimethylethyl)-2-(4-(3-chloropropyloxy)benzo(b)furan-2-yl)-1,3,4-oxadiazole (1.0 g), 4-(3,4-methylenedioxyphenyl)piperidine (0.8 g), potassium carbonate (1.5 g) and potassium iodide (1.0 g), an oil was obtained. This was dissolved in acetone and hydrochloric acid was added. The precipitated crystals were collected by filtration and dried to give the title compound (1.1 g) as white crystals, melting point 211–213° C.

Example 190

5-(2-methylpropyl)-2-(4-(3-(4-(3,4-methylenedioxyphenyl)piperidin-1-yl)propyloxy)benzo(b)furan-2-yl)-1,3,4-oxadiazole By the reactions in the same manner as in Example 176 using 5-(2-methylpropyl)-2-(4-(3-chloropropyloxy)benzo(b)furan-2-yl)-1,3,4-oxadiazole (0.5 g), 4-(3,4-methylenedioxyphenyl)piperidine (0.37 g), potassium carbonate (0.2 g) and potassium iodide (0.25 g), the title compound (0.32 g) was obtained as brown crystals, melting point 103–105° C.

Example 191

2-(4-(3-(4-(3,4-dimethylphenyl)piperidin-1-yl)propyloxy)benzo(b)furan-2-yl)-5-(2-methylpropyl)-1,3,4-oxadiazole hydrochloride By the reactions in the same manner as in Example 176 using 5-(2-methylpropyl)-2-(4-(3-chloropropyloxy)benzo(b)furan-2-yl)-1,3,4-oxadiazole (0.67 g), 4-(3,4-dimethylphenyl)piperidine (0.4 g), potassium carbonate (0.33 g) and potassium iodide (0.33 g), an oil was obtained. This was dissolved in ethanol and hydrochloric acid was added. The precipitated crystals were collected by filtration and dried to give the title compound (0.28 g) as white crystals, melting point 200–203° C.

The structural formulas of the compounds obtained in Examples 184 to 191 are shown in the following.

184

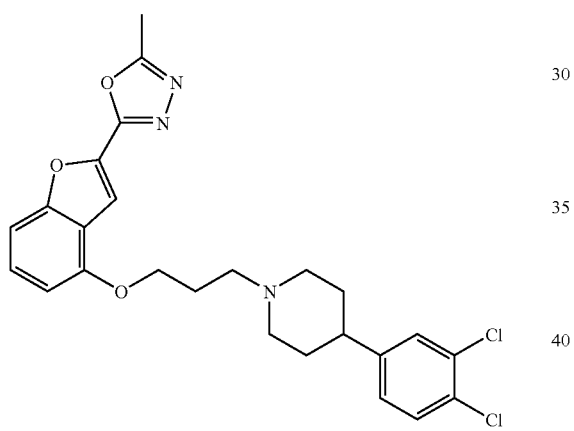

185

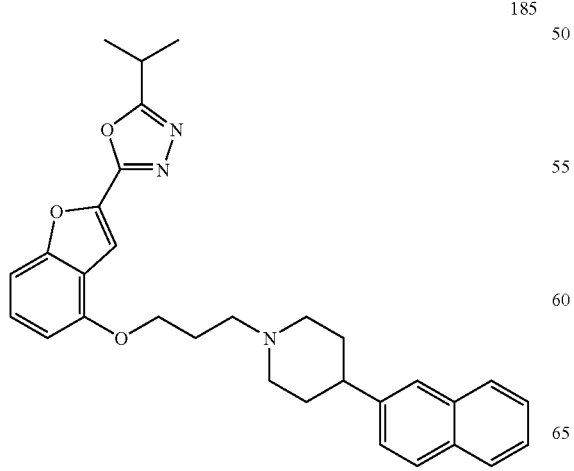

186

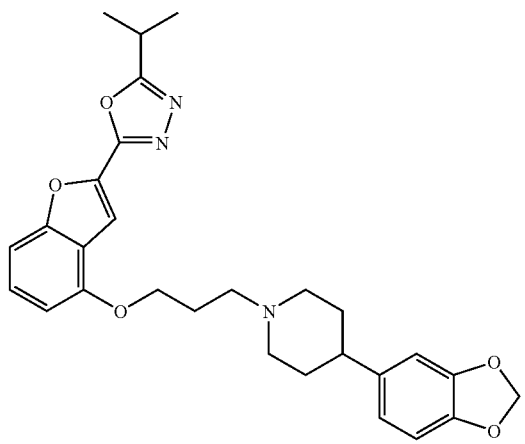

187

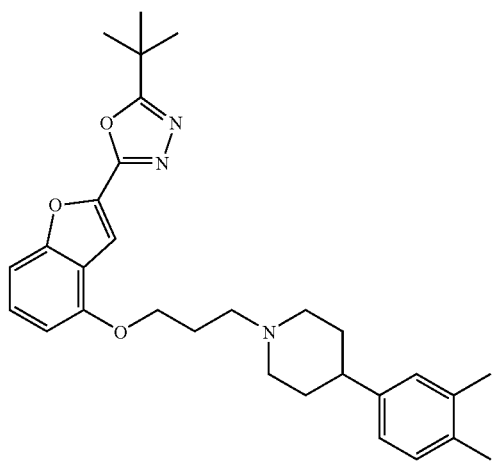

188

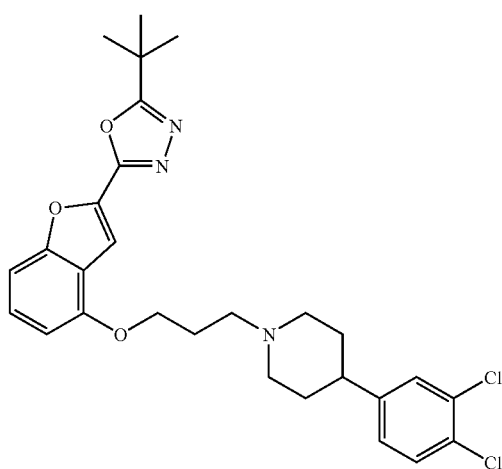

-continued

189

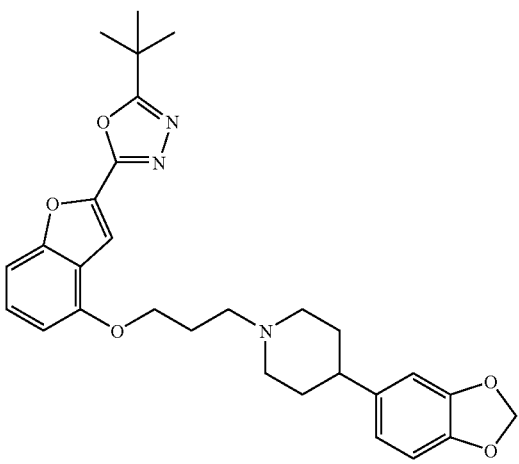

190

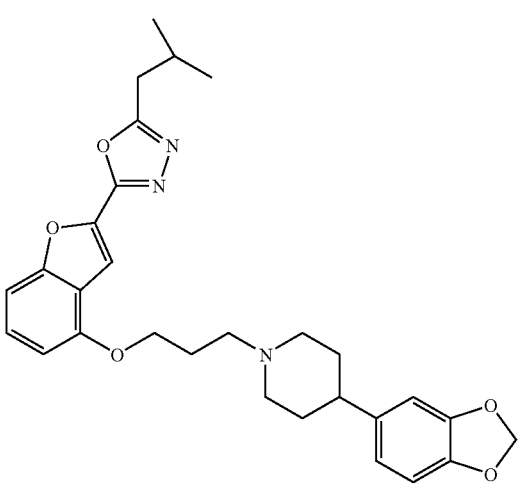

191

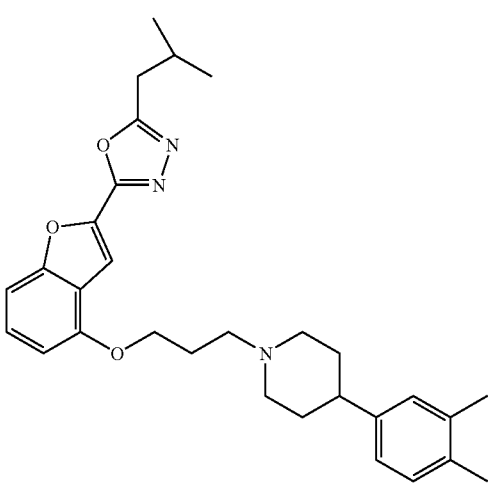

Example 192

2-(4-(3-(4-(3,4-dichlorophenyl)piperidin-1-yl)propyloxy)benzo(b)furan-2-yl)-5-(2-methylpropyl)-1,3,4-oxadiazole hydrochloride By the reactions in the same manner as in Example 176 using 5-(2-methylpropyl)-2-(4-(3-chloropropyloxy)benzo(b)furan-2-yl)-1,3,4-oxadiazole (0.43 g), 4-(3,4-dichlorophenyl)piperidine (0.3 g), potassium carbonate (0.2 g) and potassium iodide (0.25 g), an oil was obtained. This was dissolved in ethanol and hydrochloric acid was added. The precipitated crystals were collected by filtration and dried to give the title compound (0.3 g) as white crystals, melting point 212–215° C.

Example 193

2-(4-(3-(4-(naphthalen-2-yl)piperidin-1-yl)propyloxy)benzo(b)furan-2-yl)-5-(2-methylpropyl)-1,3,4-oxadiazole hydrochloride By the reactions in the same manner as in Example 176 using 5-(2-methylpropyl)-2-(4-(3-chloropropyloxy)benzo(b)furan-2-yl)-1,3,4-oxadiazole (0.67 g), 4-(naphthalen-2-yl)piperidine (0.4 g), potassium carbonate (0.33 g) and potassium iodide (0.33 g), an oil was obtained. This was dissolved in ethanol and hydrochloric acid was added. The precipitated crystals were collected by filtration and dried to give the title compound (0.48 g) as pale-yellow crystals, melting point 183–185° C.

Example 194

(S)-3-(4-(3,4-dichlorophenyl)piperidino)-1-(2-(5-methyl-1,3,4-oxadiazol-2-yl)benzo(b)furan-4-yloxy)-2-propanone To a solution of (S)-3-(4-(3,4-dichlorophenyl)piperidino)-1-(2-(5-methyl-1,3,4-oxadiazol-2-yl)benzo(b)furan-4-yloxy)-2-propanol (1.0 g) in a mixed solvent (20 ml) of DMSO-toluene (1:1) were added WSC (1.9 g) and trifluoroacetic acid (0.60 ml), and the mixture was further stirred under ice-cooling for 1 hr and then at room temperature for 1 hr. The reaction mixture was poured into ice water and extracted with ethyl acetate. The organic layer was washed with saturated aqueous sodium hydrogencarbonate solution and dried over anhydrous sodium sulfate. The solvent was evaporated under reduced pressure and the obtained crude crystals were washed with ethanol and ethyl acetate to give the title compound (0.28 g) as white crystals, melting point 128° C. (decomposition).

$^1$H-NMR(CDCl$_3$)δ:1.83(m, 4H), 2.05(m, 2H), 2.31(m, 1H), 2.67(s, 3H), 3.05(m, 2H), 3.54(s, 2H), 4.90(s, 2H), 6.62(d, J=7.8, 1H), 7.07(m, 1H), 7.26–7.38(m, 4H), 7.64(s, 1H)

The following compounds can be also synthesized by similar reactions.

Example 195

(S)-1-(2-(2-(5-methyl-1,3,4-oxadiazol-2-yl)vinyl)phenyloxy)-3-(4-(3,4-methylenedioxyphenyl)piperidino)-2-propanol By the reactions in the same manner as in Example 1 using (S)-5-(2'-glycidyloxystyryl)-2-methyl-1,3,4-oxadiazole and 4-(2,3-dihydrobenzo(b)furan-6-yl)piperidine, the title compound can be obtained.

Example 196

(S)-1-(2-(2-(3-methyl-1,2,4-oxadiazol-5-yl)vinyl)phenyloxy)-3-(4-(3,4-dichlorophenyl)piperidino)-2-propanol By the reactions in the same manner as in Example 1 using (S)-5-(2'-glycidyloxystyryl)-3-methyl-1,2,4-oxadiazole and 4-(3,4-dichlorophenyl)piperidine, the title compound can be obtained.

Example 197

(S)-4-(2-hydroxy-3-(4-(chroman-6-yl)piperidino)propyloxy)-N,N-dimethylbenzo(b)thiophene-2-carboxamide By the reactions in the same manner as in Example 1 using (S)-4-(glycidyloxy)benzo(b)thiophen-2-yl-N,N-dimethylcarboxamide and 4-(chroman-6-yl)piperidine, the title compound can be obtained.

Example 198

(S)-1-(4-(2,3-dihydrobenzo(b)furan-6-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(2,3-dihydrobenzo(b)furan-6-yl)piperidine, the title compound was obtained as white crystals, melting point 133–135° C.

Example 199

(S)-1-(4-(2,3-dihydrobenzo(b)furan-6-yl)piperidino)-3-(2-(5-methyloxazol-2-yl)benzo(b)thiophen-4-yloxy)-2-propanol By the reactions in the same manner as in Example 1 using (S)-2-(4-glycidyloxybenzo(b)furan-2-yl)-5-methyloxazole and 4-(2,3-dihydrobenzo(b)furan-6-yl)piperidine, the title compound can be obtained.

The structural formulas of the compounds obtained in Examples 192 to 199 are shown in the following.

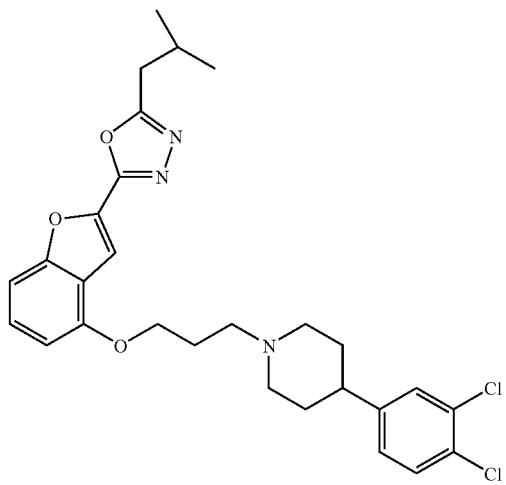

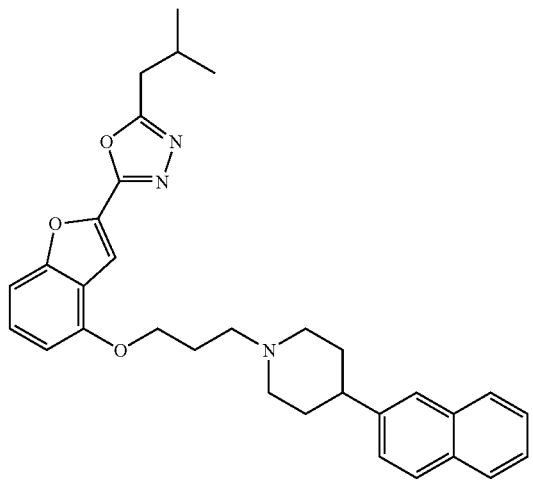

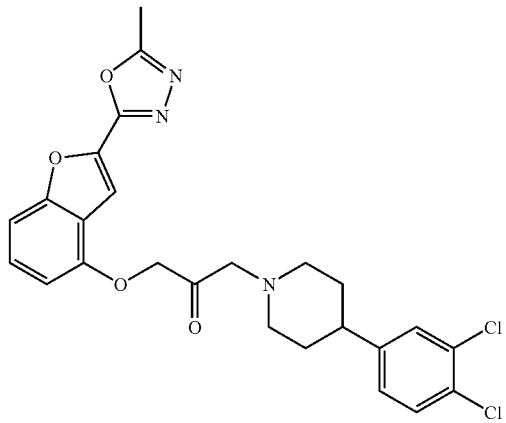

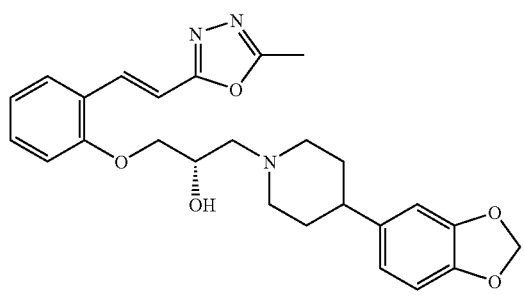

195

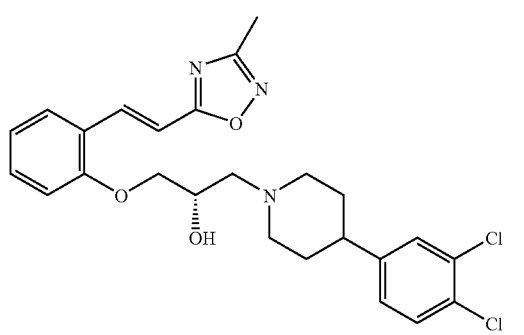

196

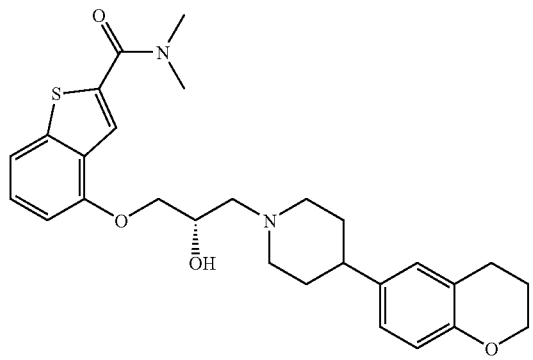

197

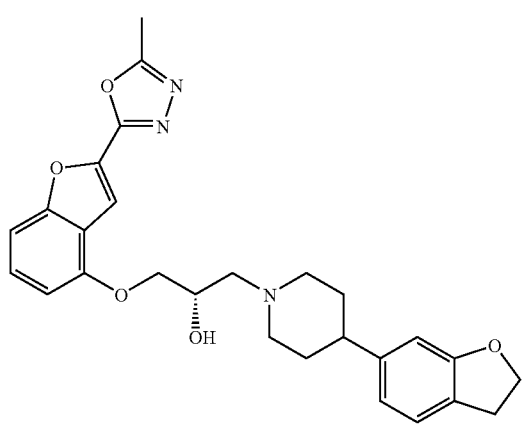

198

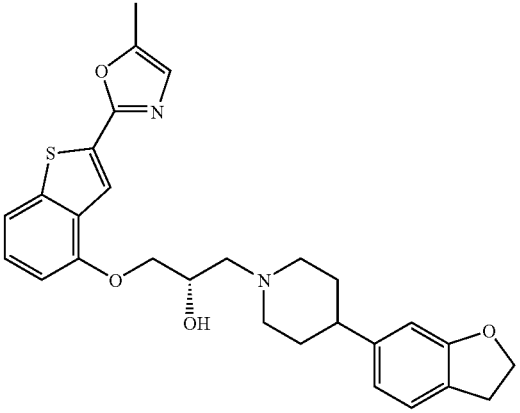

199

Example 200

(S)-1-(4-(4-methoxy-3-methylphenyl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(4-methoxy-3-methylphenyl)piperidine, the title compound was obtained as white crystals, melting point 128–130° C.

Example 201

(S)-1-(4-(2,3-dihydrobenzo(b)thiophen-5-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(2,3-dihydrobenzo(b)thiophen-5-yl)piperidine, the title compound can be obtained.

Example 202

(S)-1-(4-(indan-5-yl)piperidino)-3-(2-(5-methyl-1,3,4-oxadiazol-2-yl)benzo(b)furan-4-yloxy)-2-propanol hydrochloride By the reactions in the same manner as in Example 1 using (S)-5-(4-glycidyloxybenzo(b)furan-2-yl)-2-methyl-1,3,4-oxadiazole and 4-(indan-5-yl)piperidine, the title compound was obtained as white crystals, melting point 202–205° C.

Example 203

(S)-1-(4-(inden-5-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(inden-5-yl)piperidine, the title compound can be obtained.

Example 204

(S)-1-(4-(1-methylindolin-5-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(1-methylindolin-5-yl)piperidine, the title compound can be obtained.

Example 205

(S)-1-(2-(5-methyl-1,3,4-oxadiazol-2-yl)benzo(b)furan-4-yloxy)-3-(1,3-dihydrobenzo(c)furan-1-spiro-4'-piperidin-1'-yl)-2-propanol 1/4 hydrate By the reactions in the same manner as in Example 1 using (S)-5-(4-glycidyloxybenzo(b)furan-2-yl)-2-methyl-1,3,4-oxadiazole and 1,3-dihydrobenzo(c)furan-1-spiro-4'-piperidine, the title compound was obtained as white crystals, melting point 198–199° C.

Example 206

(S)-1-(2-(5-ethyl-1,3,4-oxadiazol-2-yl)benzo(b)furan-4-yloxy)-3-(1,3-dihydrobenzo(c)furan-1-spiro-4'-piperidin-1'-yl)-2-propanol By the reactions in the same manner as in Example 1 using (S)-2-ethyl-5-(4-glycidyloxybenzo(b)furan-2-yl)-2-methyl-1,3,4-oxadiazole and 1,3-dihydrobenzo(c)furan-1-spiro-4'-piperidine, the title compound can be obtained.

Example 207

(S)-1-(2-(5-(1-methylethyl)-1,3,4-oxadiazol-2-yl)benzo(b)furan-4-yloxy)-3-(1,3-dihydrobenzo(c)furan-1-spiro-4'-piperidin-1'-yl)-2-propanol By the reactions in the same manner as in Example 1 using (S)-2-(1-methylethyl)-5-(4-glycidyloxybenzo(b)furan-2-yl)-1,3,4-oxadiazole and 1,3-dihydrobenzo(c)furan-1-spiro-4'-piperidine, the title compound can be obtained.

The structural formulas of the compounds obtained in Examples 200 to 207 are shown in the following.

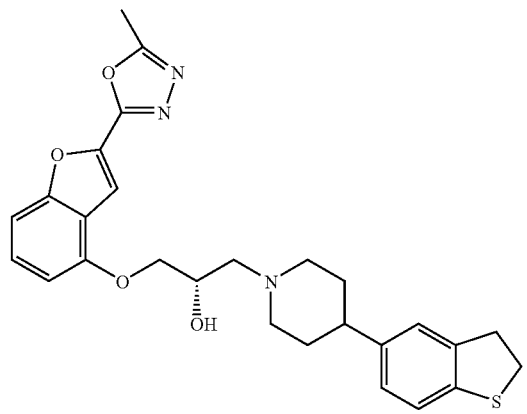

201

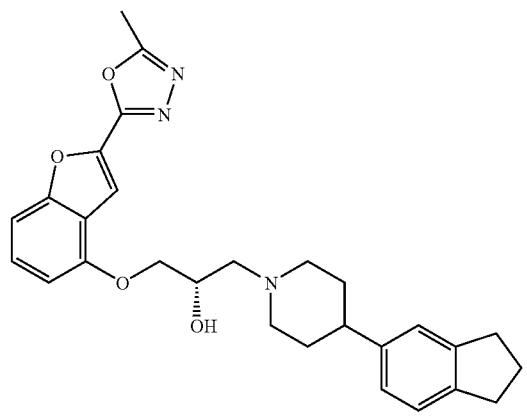

202

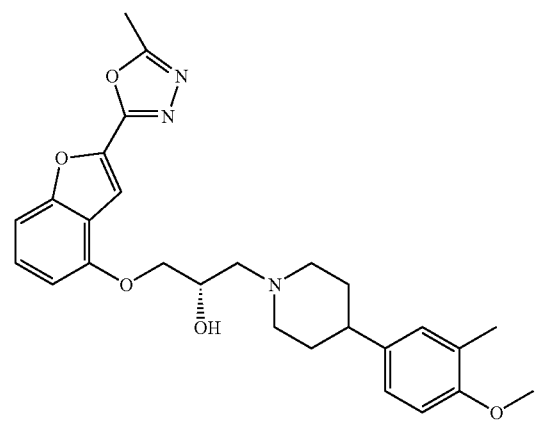

200

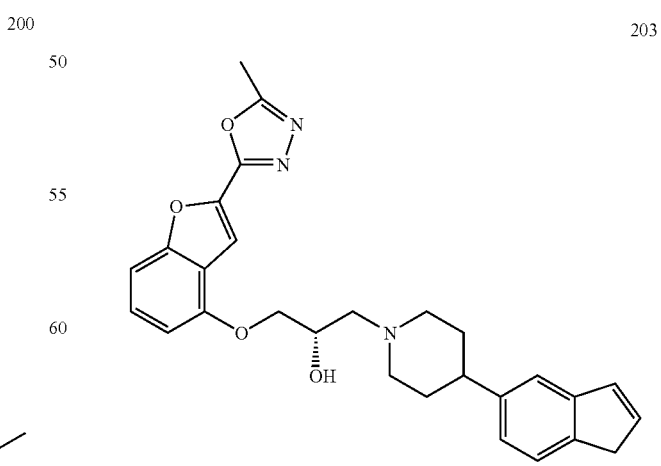

203

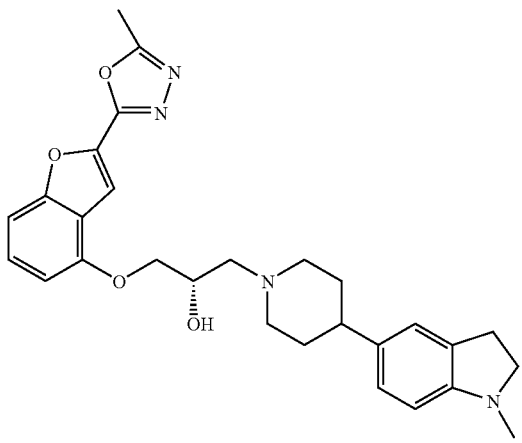

204

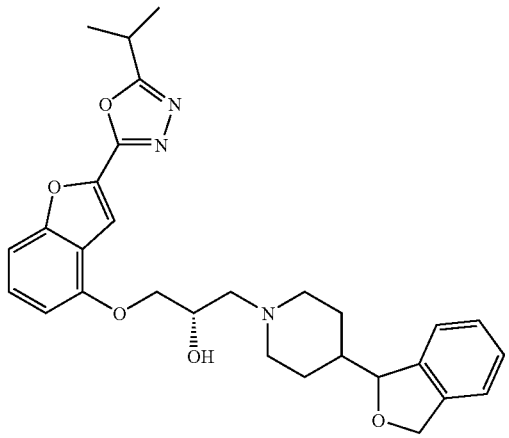

207

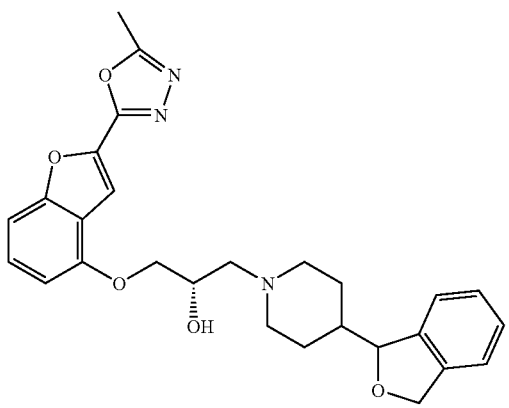

205

Example 208

(S)-1-(4-benzylpiperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-benzylpiperidine, the title compound can be obtained.

Example 209

(S)-1-(4-(2,3-dihydrobenzo(b)furan-5-yl)piperidino)-3-(2-(5-methyl-1,3,4-oxadiazol-2-yl)benzo(b)thiophen-4-yloxy)-2-propanol By the reactions in the same manner as in Example 1 using (S)-5-(4-glycidyloxybenzo(b)thiophen-2-yl)-2-methyl-1,3,4-oxadiazole and 4-(2,3-dihydrobenzo(b)furan-5-yl)piperidine, the title compound can be obtained.

Example 210

(S)-1-(4-(benzo(b)furan-5-yl)piperidino)-3-(2-(5-methyl-1,3,4-oxadiazol-2-yl)benzo(b)furan-4-yloxy)-2-propanol hydrochloride 1/2 hydrate By the reactions in the same manner as in Example 1 using (S)-5-(4-glycidyloxybenzo(b)furan-2-yl)-2-methyl-1,3,4-oxadiazole and 4-(benzo(b)furan-5-yl)piperidine, the title compound could be obtained, melting point 182–184° C.

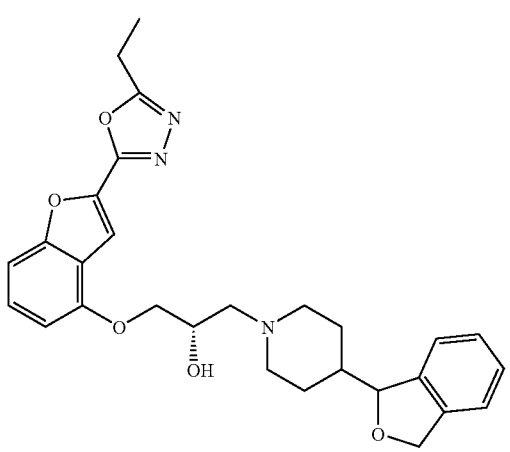

206

Example 211

(S)-1-(4-(2,3-dihydrobenzo(b)furan-5-yl)piperidino)-3-(2-(5-methyl-1,2,4-oxadiazol-3-yl)benzo(b)furan-4-yloxy)-2-propanol By the reactions in the same manner as in Example 1 using (S)-3-(4-glycidyloxybenzo(b)furan-2-yl)-5-methyl-1,2,4-oxadiazole and 4-(2,3-dihydrobenzo(b)furan-5-yl)piperidine, the title compound can be obtained.

Example 212

(S)-1-(3-(3,4-dichlorophenyl)propylamino)-3-(2-(5-methyl-1,2,4-oxadiazol-3-yl)benzo(b)furan-4-yloxy)-2-propanol By the reactions in the same manner as in Example 1 using (S)-3-(4-glycidyloxybenzo(b)furan-2-yl)-5-methyl-1,2,4-oxadiazole and 3-(3,4-dichlorophenyl)propylamine, the title compound can be obtained.

Example 213

(S)-1-(4-(naphthalen-2-yl)piperidino)-3-(2-(5-methyl-1,3,4-thiadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-thiadiazole and 4-(naphthalen-2-yl)piperidine, the title compound can be obtained.

Example 214

(S)-1-(4-(2,3-dihydrobenzo(b)thiophen-6-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(2,3-dihydrobenzo(b)thiophen-6-yl)piperidine, the title compound can be obtained.

Example 215

(S)-1-(4-(chroman-7-yl)piperidino)-3-(2-(5-methyl-1,3,4-oxadiazol-2-yl)benzo(b)furan-4-yloxy)-2-propanol hydrochloride 1/2 hydrate By the reactions in the same manner as in Example 1 using (S)-5-(4-glycidyloxybenzo(b)furan-2-yl)-2-methyl-1,3,4-oxadiazole and 4-(chroman-7-yl)piperidine, the title compound was obtained as white crystals, melting point 210–212° C.

The structural formulas of the compounds obtained in Examples 208 to 215 are shown in the following.

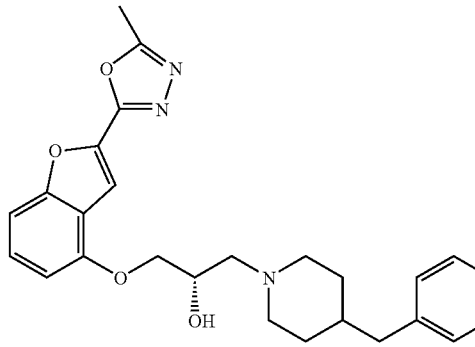

208

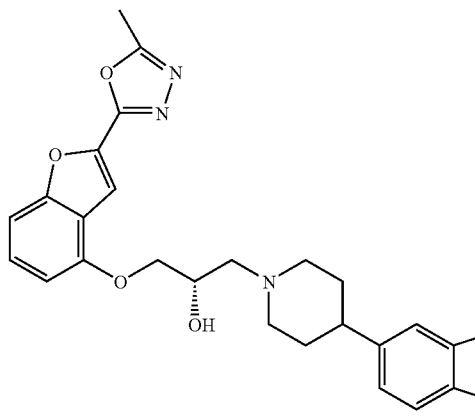

209

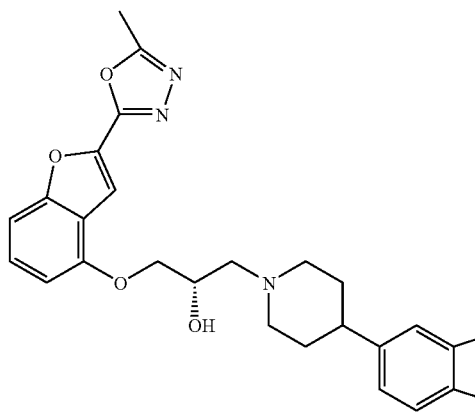

210

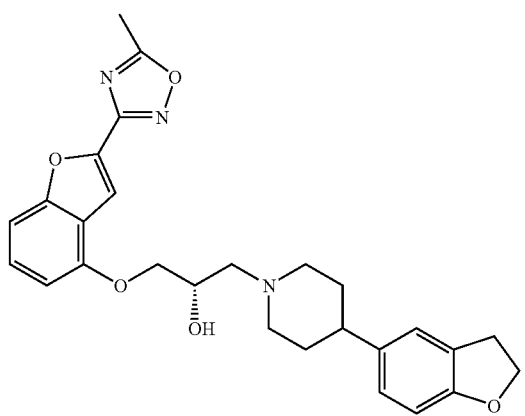

211

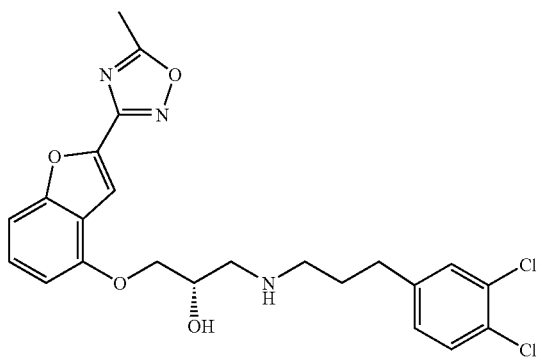

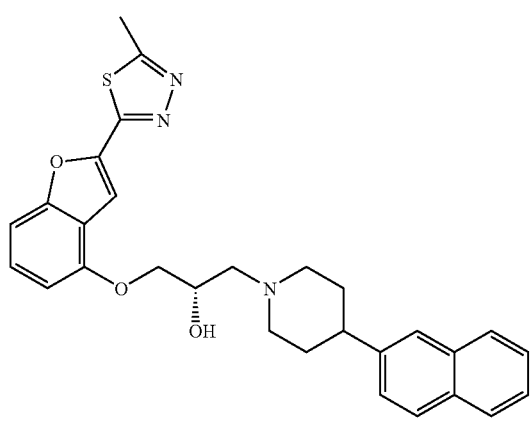

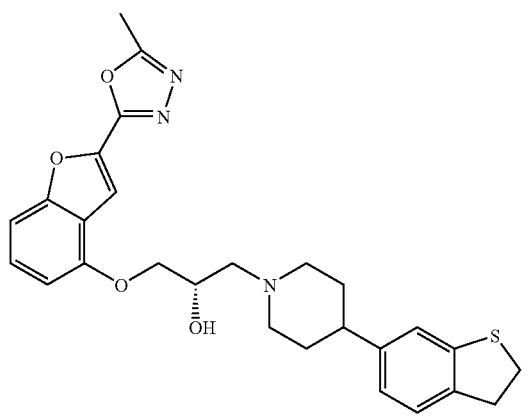

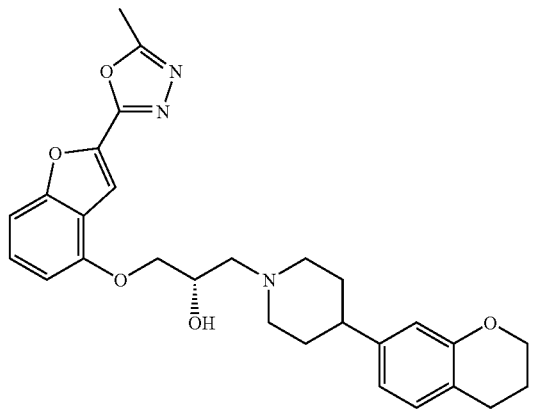

Example 216

(S)-1-(4-(benzo(b)thiophen-5-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(benzo(b)thiophen-5-yl)piperidine, the title compound can be obtained.

Example 217

(S)-1-(4-(2H-chromen-6-yl)piperidino)-3-(2-(5-methyl-1,3,4-oxadiazol-2-yl)benzo(b)furan-4-yloxy)-2-propanol By the reactions in the same manner as in Example 1 using (S)-5-(4-glycidyloxybenzo(b)furan-2-yl)-2-methyl-1,3,4-oxadiazole and 4-(2H-chromen-6-yl)piperidine, the title compound can be obtained.

Example 218

(S)-1-(4-(3,4-dihydro-2H-benzo(b)thiin-7-yl)piperidino)-3-(2-(5-methyl-1,3,4-oxadiazol-2-yl)benzo(b)furan-4-yloxy)-2-propanol

Example 219

(S)-1-(4-(3-chloro-4-methoxyphenyl)piperidino)-3-(2-(5-methyl-1,3,4-oxadiazol-2-yl)benzo(b)furan-4-yloxy)-2-propanol hydrochloride white crystals, melting point 218–220° C.

Example 220

(S)-1-(4-(4-chloro-3-methoxyphenyl)piperidino)-3-(2-(5-methyl-1,3,4-oxadiazol-2-yl)benzo(b)furan-4-yloxy)-2-propanol

Example 221

(S)-1-(4-(benzo(d)isoxazol-5-yl)piperidino)-3-(2-(5-methyl-1,3,4-oxadiazol-2-yl)benzo(b)furan-4-yloxy)-2-propanol

Example 222

(S)-1-(4-(4-chloro-3-methylphenyl)piperidino)-3-(2-(5-methyl-1,3,4-oxadiazol-2-yl)benzo(b)furan-4-yloxy)-2-propanol hydrochloride melting point 184–186° C.

Example 223

(S)-1-(4-(3-chloro-4-methylphenyl)piperidino)-3-(2-(5-methyl-1,3,4-oxadiazol-2-yl)benzo(b)furan-4-yloxy)-2-propanol hydrochloride white crystals, melting point 188–190° C.

The structural formulas of the compounds obtained in Examples 216 to 223 are shown in the following.

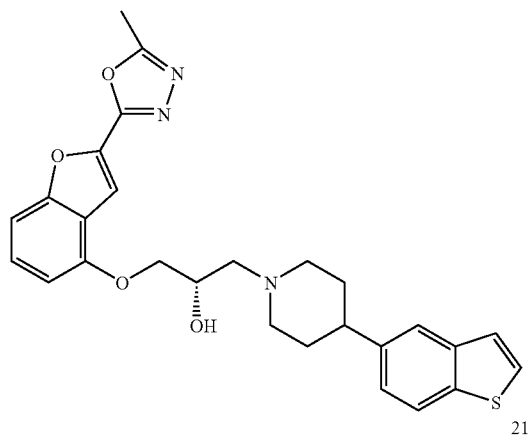

216

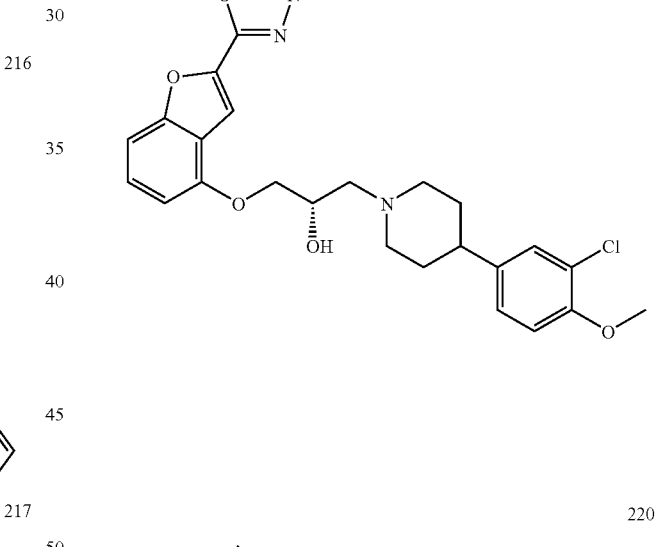

218

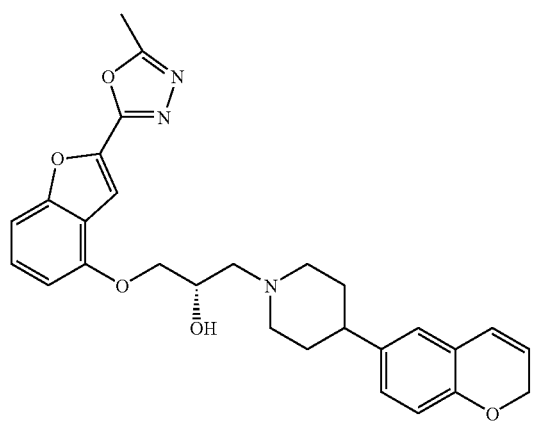

217

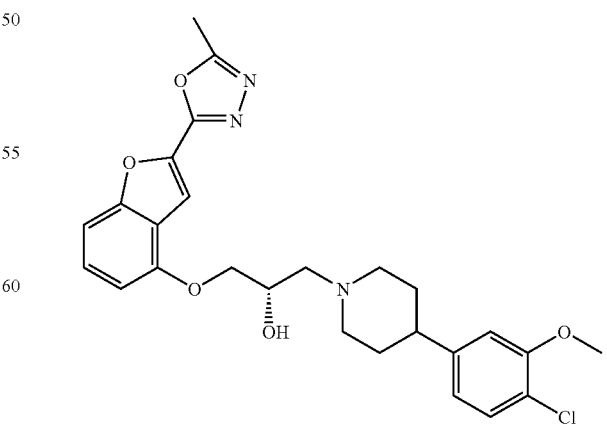

219

220

221

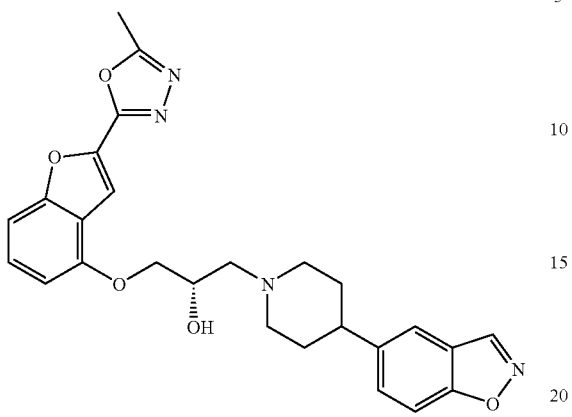

222

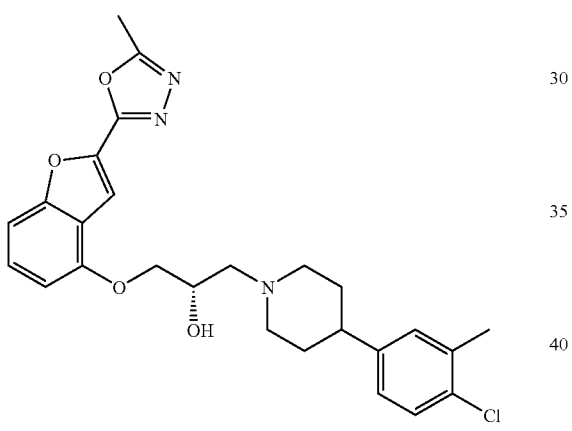

223

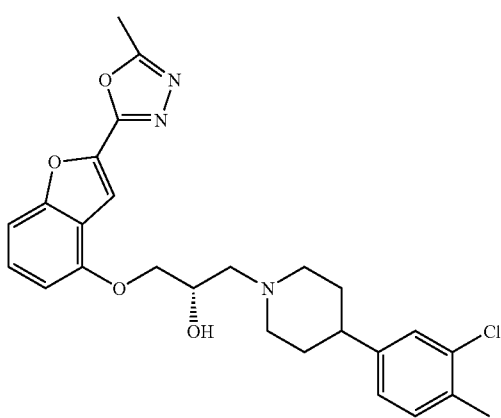

Example 224

(S)-1-(4-(benzo(b)furan-6-yl)piperidino)-3-(2-(5-methyl-1,3,4-oxadiazol-2-yl)benzo(b)furan-4-yloxy)-2-propanol

Example 225

(S)-1-(4-(2H-chromen-7-yl)piperidino)-3-(2-(5-methyl-1,3,4-oxadiazol-2-yl)benzo(b)furan-4-yloxy)-2-propanol

Example 226

(S)-1-(4-(1H-indol-6-yl)piperidino)-3-(2-(5-methyl-1,3,4-oxadiazol-2-yl)benzo(b)furan-4-yloxy)-2-propanol

Example 227

(S)-1-(4-(1-methylindol-6-yl)piperidino)-3-(2-(5-methyl-1,3,4-oxadiazol-2-yl)benzo(b)furan-4-yloxy)-2-propanol

Example 228

(S)-1-(4-(1,3-dihydrobenzo(c)furan-5-yl)piperidino)-3-(2-(5-methyl-1,3,4-oxadiazol-2-yl)benzo(b)furan-4-yloxy)-2-propanol

Example 229

(S)-1-(4-(isochroman-7-yl)piperidino)-3-(2-(5-methyl-1,3,4-oxadiazol-2-yl)benzo(b)furan-4-yloxy)-2-propanol

Example 230

(S)-1-(4-(isochroman-6-yl)piperidino)-3-(2-(5-methyl-1,3,4-oxadiazol-2-yl)benzo(b)furan-4-yloxy)-2-propanol

Example 231

(S)-1-(4-(2,3-dihydrobenzo(b)furan-4-yl)piperidino)-3-(2-(5-methyl-1,3,4-oxadiazol-2-yl)benzo(b)furan-4-yloxy)-2-propanol

Example 232

(S)-1-(4-(2,2-dimethyl-2,3-dihydrobenzo(b)furan-5-yl)piperidino)-3-(2-(5-methyl-1,3,4-oxadiazol-2-yl)benzo(b)furan-4-yloxy)-2-propanol 1/2 terephthalate melting point 159–162° C.

Example 233

(S)-1-(4-(3,4-dihydro-2H-benzo(b)thiin-6-yl)piperidino)-3-(2-(5-methyl-1,3,4-oxadiazol-2-yl)benzo(b)furan-4-yloxy)-2-propanol hydrochloride white crystals, melting point 223–225° C.

The structural formulas of the compounds obtained in Examples 224 to 233 are shown in the following.
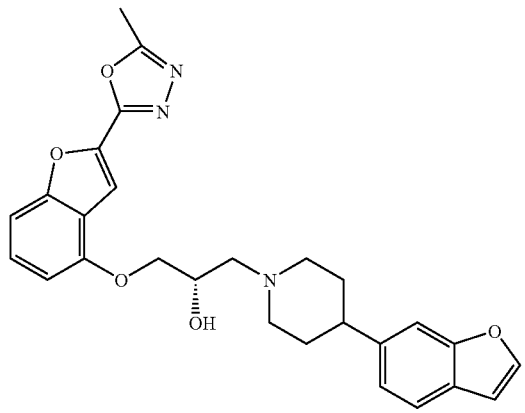
224
225
226
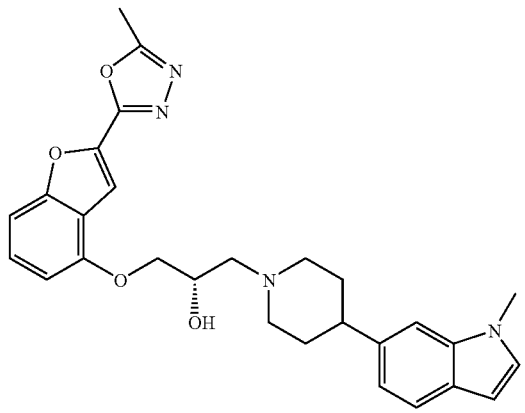
227
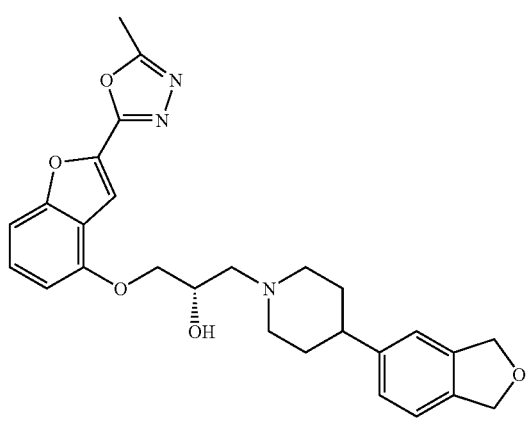
228
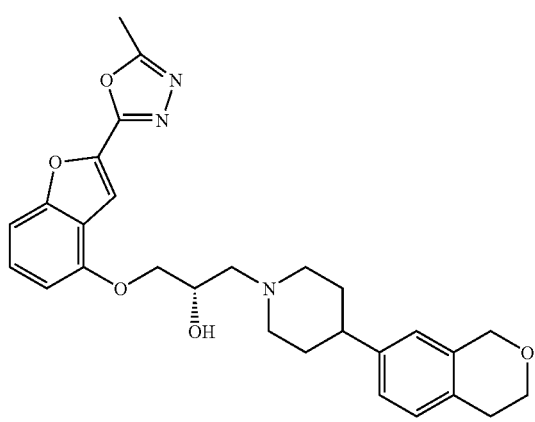
229

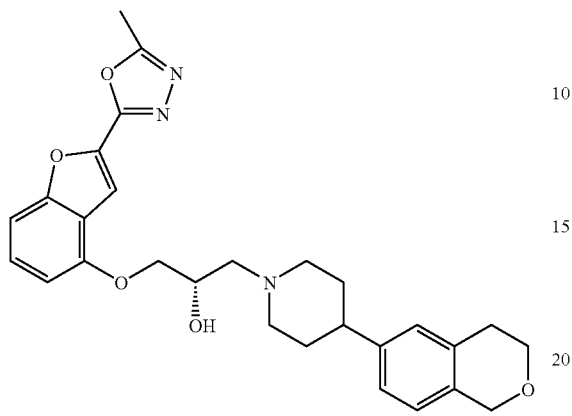

230

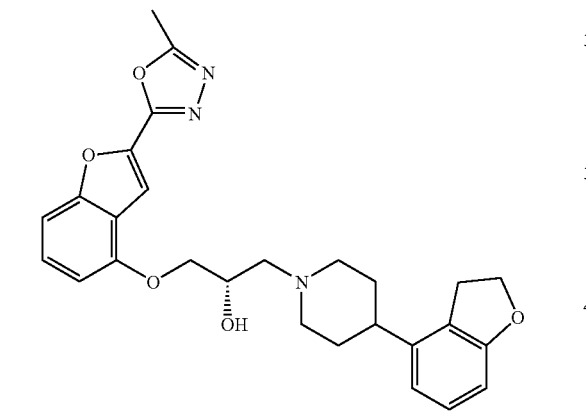

231

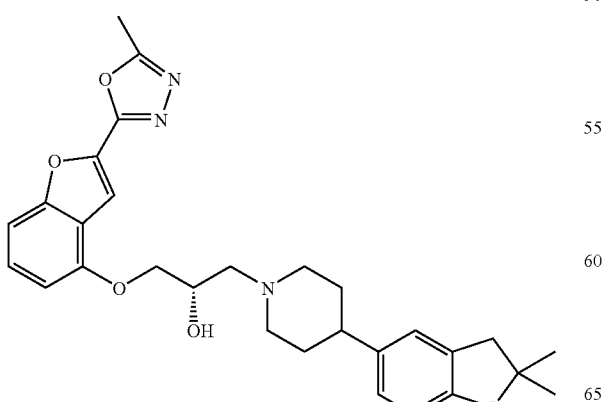

232

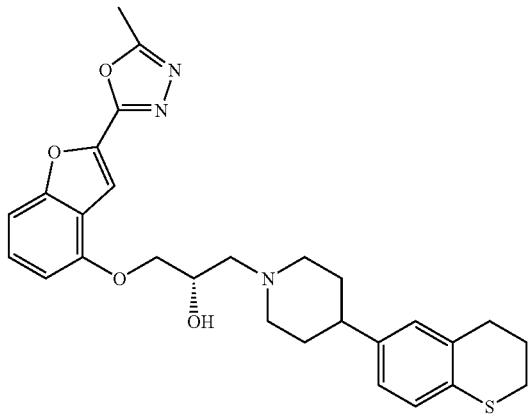

233

Example 234

(S)-1-(4-(4-chloro-3-trifluoromethylphenyl)piperidino)-3-(2-(5-methyl-1,3,4-oxadiazol-2-yl)benzo(b)furan-4-yloxy)-2-propanol hydrochloride white crystals, melting point 222–224° C.

Example 235

(S)-1-(4-(4-chloro-3-fluorophenyl)piperidino)-3-(2-(5-methyl-1,3,4-oxadiazol-2-yl)benzo(b)furan-4-yloxy)-2-propanol hydrochloride white crystals, melting point 139–141° C.

Example 236

(S)-1-(4-(benzo(b)furan-6-yl)-5,6-dihydro-2H-pyridin-1-yl)-3-(2-(5-methyl-1,3,4-oxadiazol-2-yl)benzo(b)furan-4-yloxy)-2-propanol hydrochloride white crystals, melting point 135–138° C.

Example 237

(S)-1-(2-(5-isopropenyl-1,3,4-oxadiazol-2-yl)benzo(b)furan-4-yloxy)-3-(4-(3,4-methylenedioxyphenyl)piperidino)-2-propanol hydrochloride white crystals, melting point 128–130° C.

Example 238

(S)-1-(4-(benzo(b)furan-5-yl)-5,6-dihydro-2H-pyridin-1-yl)-3-(2-(5-methyl-1,3,4-oxadiazol-2-yl)benzo(b)furan-4-yloxy)-2-propanol white crystals, melting point 168–170° C.

The structural formulas of the compounds obtained in Examples 234 to 238 are shown in the following.

234

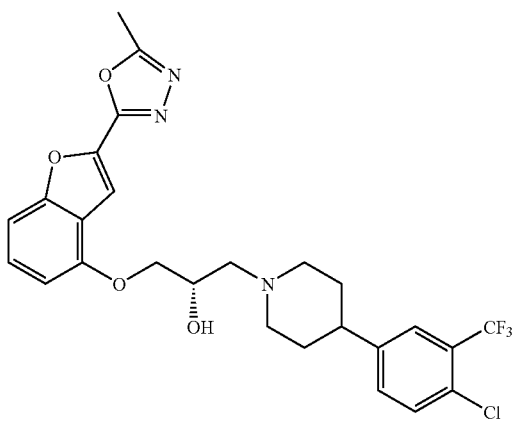

235

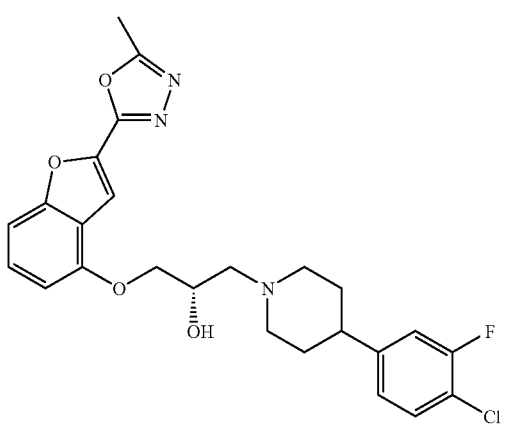

236

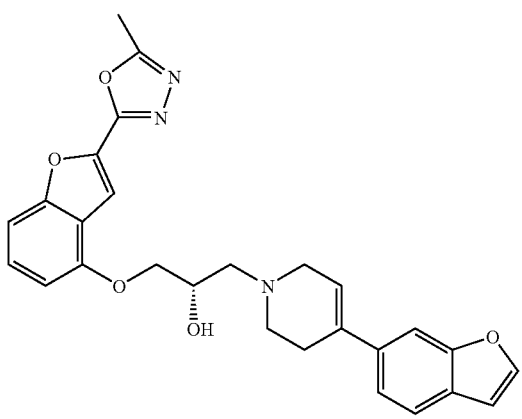

237

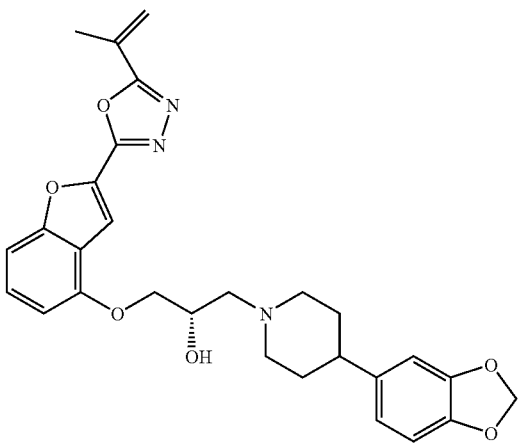

238

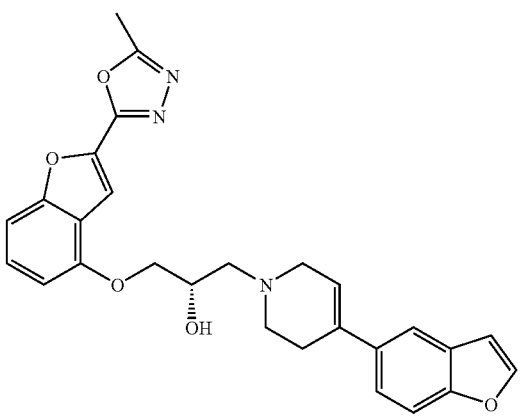

Example 301

(1) 3,5-dihydro-5-(2'-methoxybenzylidene)-2-methylimidazol-4-one 4-(2'-Methoxybenzylidene)-2-methyl-4H-oxazol-5-one (2.4 g) was dissolved in ethanol (50 ml) and aqueous ammonia (20 ml) and potassium carbonate (3 g) were added. The mixture was heated at 80° C. for 10 hr. After cooling, the solvent was evaporated under reduced pressure and water was added to the residue. The mixture was extracted with ethyl acetate. The organic layer was dried over anhydrous sodium sulfate and concentrated under reduced pressure. The precipitated yellow crystals were collected by filtration to give the title compound (2 g).

¹H-NMR(DMSO-d₆)δ:2.23(s, 3H), 3.87(s, 3H), 7.00(t, J=7.8, 1H) 7.02(d, J=8.3, 1H), 7.18(s, 1H), 7.35(t, J=7.8, 1H), 8.71(d, J=8.3, 1H)

(2) (S)-3,5-dihydro-5-(2'-(2-hydroxy-3-(4-(naphthalen-2-yl)piperidin-1-yl)propyloxy)benzylidene)-2-methylimidazol-4-one 3,5-Dihydro-5-(2'-methoxybenzylidene)-2-methylimidazol-4-one (1.28 g) was dissolved in dichloromethane (20 ml) and boron tribromide (4.5 g) was added dropwise while stirring at −40° C. Thereafter, the mixture was stirred for 2 hr under ice-cooling and the reaction mixture was poured into ice water and extracted with chloroform. The organic layer was dried over anhydrous sodium sulfate and concentrated under reduced pressure to give 3,5-dihydro-5-(2'-hydroxybenzylidene)-2-methylimidazol-4-one (1 g) as red crystals. The crystals and (S)-glycidyl nosylate (1.3 g) were dissolved in dimethylformamide (20 ml) and potassium carbonate (1.38 g) was added. The mixture was heated at 50° C. for 2 hr. The reaction mixture was poured into ice water and extracted with ethyl acetate. The organic layer was washed with saturated aqueous ammonium chloride solution, dried over anhydrous sodium sulfate and concentrated under reduced pressure to give an oily product (1.12 g). This oily product and 4-(naphthalen-2-yl)piperidine were dissolved in methanol (15 ml) and the mixture was refluxed under heating for 2 hr. After cooling, the solvent was evaporated under reduced pressure and the residue was purified by silica gel column chromatography (chloroform/methanol) to give the title compound (0.23 g) as an oil.

¹H-NMR(DMSO-d₆)δ:1.91–2.20(m, 4H), 2.45(s, 3H), 2.90–3.05(m, 4H), 3.16(m, 1H), 3.54(m, 2H), 4.17(m, 2H), 4.31(m, 1H), 5.01(bs, 1H), 6.87(t, J=7.8, 1H), 6.91(d, J=8.3, 1H), 7.30(s, 1H), 7.42–7.54(m, 5H), 7.72(s, 1H), 7.84(m, 2H), 8.78(d, J=8.3, 1H)

Example 302

(1) 3,5-dihydro-2,3-dimethyl-5-(2'-methoxybenzylidene) imidazol-4-one 4-(2'-Methoxybenzylidene)-2-methyl-4H-oxazol-5-one (5 g) was dissolved in ethanol (100 ml) and aqueous methylamine solution (20 ml) and potassium carbonate (7 g) were added. The mixture was heated at 80° C. for 7 hr. After cooling, the solvent was evaporated under reduced pressure and the precipitated yellow crystals were collected by filtration to give the title compound (2 g).

¹H-NMR(DMSO-d₆)δ:2.35(s, 3H), 3.10(s, 3H), 3.89(s, 3H), 7.00(t, J=7.8, 1H), 7.05(d, J=8.3, 1H), 7.33(s, 1H), 7.39(t, J=7.8, 1H), 8.73(d, J=8.3, 1H)

(2) (S)-3,5-dihydro-2,3-dimethyl-5-(2'-(2-hydroxy-3-(4-(naphthalen-2-yl)piperidin-1-yl)propyloxy)benzylidene) imidazol-4-one 3,5-Dihydro-2,3-dimethyl-5-(2'-methoxybenzylidene) imidazol-4-one (2 g) was dissolved in dichloromethane (30 ml) and boron tribromide (2 ml) was added dropwise while stirring the mixture at −40° C. Thereafter, the reaction mixture was stirred under ice-cooling for 1 hr, and the reaction mixture was poured into ice water and extracted with chloroform. The organic layer was dried over anhydrous sodium sulfate and concentrated under reduced pressure to give 3,5-dihydro-2,3-dimethyl-5-(2'-hydroxybenzylidene)imidazol-4-one (1.72 g) as red crystals. The crystals and (S)-glycidyl nosylate (2 g) were dissolved in dimethylformamide (20 ml) and potassium carbonate (2.2 g) was added. The mixture was heated at 50° C. for 3 hr, and the reaction mixture was poured into ice water and extracted with ethyl acetate. The organic layer was washed with saturated aqueous ammonium chloride solution, dried over anhydrous sodium sulfate and concentrated under reduced pressure to give an oily product (2.27 g). This oily product and 4-(naphthalen-2-yl)piperidine were dissolved in methanol (20 ml) and the mixture was refluxed under heating for 2 hr. After cooling, the solvent was evaporated under reduced pressure and the residue was purified by silica gel column chromatography (chloroform/methanol) to give the title compound (1.25 g) as an oil.

¹H-NMR(DMSO-d₆)δ:2.03–2.20(m, 4H), 2.37(s, 3H), 2.99(m, 1H), 3.11(s, 3H), 3.10–3.23(m, 3H), 3.31(m, 1H), 3.63(m, 2H), 4.13(m, 2H), 4.34(m, 1H), 5.05(bs, 1H), 7.06(t, J=7.8, 1H), 7.12(d, J=8.3, 1H), 7.38–7.52(m, 6H), 7.74(s, 1H), 7.88(m, 2H), 8.78(d, J=8.3, 1H)

Example 303

(1) 3,5-dihydro-5-(2'-methoxybenzylidene)-2-methyl-3-phenylimidazol-4-one 4-(2'-Methoxybenzylidene)-2-methyl-4H-oxazol-5-one (5 g) was dissolved in acetic acid (100 ml), and aniline (2.33 g) and sodium acetate (1.8 g) were added. The mixture was heated at 100° C. for 5 hr. The reaction mixture was poured into ice-water, neutralized with potassium carbonate and extracted with ethyl acetate. The organic layer was washed with water, dried over anhydrous sodium sulfate and concentrated under reduced pressure. The residue was purified by silica gel column chromatography (hexane/ethyl acetate) to give the title compound (1.85 g) as yellow crystals.

¹H-NMR(CDCl₃)δ:2.27(s, 3H), 3.90(s, 3H), 6.92(d, J=8.3, 1H), 7.06(t, J=7.8, 1H), 7.26(m, 2H), 7.35–7.53(m, 4H), 7.78(s, 1H), 8.78(d, J=8.3, 1H)

(2) (S)-3,5-dihydro-5-(2'-(2-hydroxy-3-(4-(naphthalen-2-yl)piperidin-1-yl)propyloxy)benzylidene)-2-methyl-3-phenylimidazol-4-one 3,5-Dihydro-5-(2'-methoxybenzylidene)-2-methyl-3-phenylimidazol-4-one (1.85 g) was dissolved in dichloromethane (30 ml) and boron tribromide (2 ml) was added dropwise while stirring the mixture at −40° C. Thereafter, the mixture was stirred under ice-cooling for 1 hr, poured into ice water and extracted with chloroform. The organic layer was dried over anhydrous sodium sulfate and concentrated under reduced pressure to give 3,5-dihydro-5-(2'-hydroxybenzylidene)-2-methyl-3-phenylimidazol-4-one (1.76 g) as red crystals. The crystals and (S)-glycidyl nosylate (1.63 g) were dissolved in dimethylformamide (20 ml) and potassium carbonate (1.74 g) was added. The mixture was heated at 50° C. for 2 hr. The reaction mixture was poured into ice water and extracted with ethyl acetate. The organic layer was washed with saturated aqueous ammonium chloride solution, dried over anhydrous sodium sulfate and concentrated under reduced pressure to give an oily product (2.13 g). This oily product and 4-(naphthalen-2-yl)piperidine were dissolved in methanol (20 ml) and refluxed under heating for 2 hr. After cooling, the solvent was evaporated under reduced pressure and the residue was purified by silica gel column chromatography (chloroform/methanol) to give the title compound (0.45 g) as an oil.

¹H-NMR(DMSO-d₆)δ:2.09–2.20(m, 4H), 2.23(s, 3H), 3.00(m, 1H), 3.15–3.29(m, 3H), 3.37(m, 1H), 3.66(m, 2H), 4.14(m, 2H), 4.39(m, 1H), 5.02(bs, 1H), 7.10(t, J=7.8, 1H), 7.14(d, J=8.3, 1H), 7.38–7.56(m, 10H), 7.73(s, 1H), 7.88(m, 3H), 8.84(d, J=8.3, 1H)

Example 304

(1) 3-ethyl-3,5-dihydro-5-(2'-methoxybenzylidene)-2-methylimidazol-4-one 4-(2'-Methoxybenzylidene)-2-methyl-4H-oxazol-5-one (5 g) was dissolved in ethanol (100 ml) and an aqueous ethylamine solution (15 ml) and potassium carbonate (7 g) were added thereto. The mixture was heated at 80° C. for 5 hr. After cooling, the solvent was evaporated under reduced pressure and the precipitated yellow crystals were collected by filtration to give the title compound (1.2 g).
¹H-NMR(CDCl₃)δ:1.25(t, J=7.3, 3H), 2.39(s, 3H), 3.67 (q, J=7.3, 2H), 3.88(s, 3H), 6.89(d, J=8.3, 1H), 7.02(t, J=7.8, 1H), 7.34(t, J=7.8, 1H), 7.67(s, 1H), 8.72(d, J=8.3, 1H)

(2) (S)-3-ethyl-3,5-dihydro-5-(2'-(2-hydroxy-3-(4-(naphthalen-2-yl)piperidin-1-yl)propyloxy)benzylidene)-2-methylimidazol-4-one 3-Ethyl-3,5-dihydro-5-(2'-methoxybenzylidene)-2-methylimidazol-4-one (1.2 g) was dissolved in dichloromethane (20 ml) and boron tribromide (1.5 ml) was added dropwise while stirring the mixture at −40° C. Thereafter, the mixture was stirred under ice-cooling for 1 hr, poured into ice water and extracted with chloroform. The organic layer was dried over anhydrous sodium sulfate and concentrated under reduced pressure to give 3-ethyl-3,5-dihydro-5-(2'-hydroxybenzylidene)-2-methylimidazol-4-one (1 g) as red crystals. The crystals and (S)-glycidyl nosylate (1.3 g) were dissolved in dimethylformamide (20 ml) and potassium carbonate (1.38 g) was added. The mixture was heated at 50° C. for 2 hr, poured into ice water and extracted with ethyl acetate. The organic layer was washed with saturated aqueous ammonium chloride solution, dried over anhydrous sodium sulfate and concentrated under reduced pressure to give an oily product (1.02 g). This oily product and 4-(naphthalen-2-yl)piperidine were dissolved in methanol (10 ml) and the mixture was refluxed under heating for 2 hr. After cooling, the solvent was evaporated under reduced pressure and the residue was purified by silica gel column chromatography (chloroform/methanol) to give the title compound (0.52 g) as an oil.
¹H-NMR(DMSO-d₆)δ:1.27(t, J=7.3, 3H), 2.03–2.20(m, 4H), 2.42(s, 3H), 2.99(m, 1H), 3.68(q, J=7.3, 2H), 3.10–3.23 (m, 3H), 3.31(m, 1H), 3.63(m, 2H), 4.13(m, 2H), 4.34(m, 1H), 5.05(bs, 1H), 7.06(t, J=7.8, 1H), 7.12(d, J=8.3, 1H), 7.38–7.52(m, 6H), 7.74(s, 1H), 7.88(m, 2H), 8.78(d, J=8.3, 1H)

Example 305

(1) 3-benzyl-3,5-dihydro-5-(2'-methoxybenzylidene)-2-methylimidazol-4-one 4-(2'-Methoxybenzylidene)-2-methyl-4H-oxazol-5-one (5 g) was dissolved in acetic acid (50 ml) and benzylamine (2.68 g) and sodium acetate (2 g) were added. The mixture was heated at 100° C. for 2 hr, poured into ice-water, neutralized with potassium carbonate and extracted with ethyl acetate. The organic layer was washed with water, dried over anhydrous sodium sulfate and concentrated under reduced pressure. The residue was purified by silica gel column chromatography (hexane/ethyl acetate) to give the title compound (1.38 g) as yellow crystals.
¹H-NMR(CDCl₃)δ:2.2.5 (s, 3H), 3.89(s, 3H), 4.83(s, 2H), 6.90(d, J=8.3, 1H), 7.02(t, J=7.8, 1H), 7.22–7.35(m, 6H), 7.77(s, 1H), 8.73(d, J=8.3, 1H)

(2) (S)-3-benzyl-3,5-dihydro-5-(2'-(2-hydroxy-3-(4-(naphthalen-2-yl)piperidin-1-yl)propyloxy)benzylidene)-2-methylimidazol-4-one 3-Benzyl-3,5-dihydro-5-(2'-methoxybenzylidene)-2-methylimidazol-4-one (1.38 g) was dissolved in dichloromethane (20 ml) and boron tribromide (1.3 ml) was added dropwise while stirring the mixture at −40° C. Thereafter, the mixture was stirred under ice-cooling for 1 hr, poured into ice water and extracted with chloroform. The organic layer was dried over anhydrous sodium sulfate and concentrated under reduced pressure to give 3-benzyl-3,5-dihydro-5-(2'-hydroxybenzylidene)-2-methylimidazol-4-one (1.14 g) as red crystals. The crystals and (S)-glycidyl nosylate (1 g) were dissolved in dimethylformamide (20 ml) and potassium carbonate (1.1 g) was added. The mixture was heated at 50° C. for 2 hr, poured into ice water and extracted with ethyl acetate. The organic layer was washed with saturated aqueous ammonium chloride solution, dried over anhydrous sodium sulfate and concentrated under reduced pressure to give an oily product (1.05 g). This oily product and 4-(naphthalen-2-yl)piperidine were dissolved in methanol (10 ml) and refluxed under heating for 2 hr. After cooling, the solvent was evaporated under reduced pressure and the residue was purified by silica gel column chromatography (chloroform/methanol) to give the title compound (0.25 g) as an oil.
¹H-NMR(DMSO-d₆)δ:2.09–2.20(m, 4H), 2.23(s, 3H), 3.00(m, 1H), 3.15–3.29(m, 3H), 3.37(m, 1H), 3.66(m, 2H), 4.14(m, 2H), 4.39(m, 1H), 4.89(s, 2H), 5.02(bs, 1H), 7.12(t, J=7.8, 1H), 7.15(d, J=8.3, 1H), 7.40–7.58(m, 10H), 7.75(s, 1H), 7.85(m, 3H), 8.85(d, J=8.3, 1H)

Example 306

(S)-5-(2'-(2-hydroxy-3-(4-(naphthalen-2-yl)piperidino)propyloxy)benzylidene)-1,3-dimethylimidazolidine-2,4-dione 2-(Methoxymethyloxy)benzaldehyde (10 g) and hydantoin (8.2 g) were dissolved in piperidine (20 ml). Benzylamine (2.68 g) and sodium acetate (2 g) were added thereto and the mixture was heated at 130° C. for 5 hr. The reaction mixture was poured into ice water, neutrized with hydrochloric acid and extracted with ethyl acetate to give a reaction concentrate (10 g). Thereto were added dimethylformamide (100 ml) and potassium carbonate (13.5 g), and then methyl iodide (3.7 ml) was added. The mixture was stirred while refluxing under heating at 40° C. for 2 hr. The reaction mixture was concentrated under reduced pressure and water was added. The mixture was extracted with ethyl acetate. The organic layer was dried over anhydrous sodium sulfate and concentrated under reduced pressure. The residue was purified by silica gel column chromatography (hexane/acetone) to give an oily product (6.2 g). Acetic acid (50 ml) and water (50 ml) were poured into the oily product and the mixture was refluxed under heating for 1 hr. After completion of the reaction, the reaction mixture was poured into water, and extracted with chloroform/methanol. The organic layer was dried over anhydrous sodium sulfate and concentrated under reduced pressure to give an oily product (6.0 g). Thereto were added dimethylformamide (60 ml) and potassium carbonate (10.7 g), and (S)-glycidyl nosylate (6.7 g) was further added. The mixture was stirred with heating at 50° C. for 2 hr. The reaction mixture was concentrated under reduced pressure and water was added. The mixture was extracted with ethyl acetate. The organic layer was dried over anhydrous sodium sulfate, and concentrated under reduced pressure to give an oily product (2.4 g). This oil (1.0 g) and 4-(naphthalen-2-yl)piperidine (0.9 g) were dissolved in methanol (30 ml) and the mixture was refluxed under heating for 3 hr. After cooling, the solvent was evaporated under reduced pressure and the residue was purified by silica gel column chromatography (chloroform/methanol) to give an oily product.

$^1$H-NMR(CDCl$_3$)δ:1.85–1.95(m, 4H), 2.16(m, 1H), 2.47–2.70(m, 3H), 2.94(s, 3H), 2.99(bs, 1H), 3.13(s, 3H), 3.20(bs, 1H), 4.01–4.13(m, 3H), 6.63–6.99(m, 2H), 7.15(d, 1H, J=7.4), 7.28–7.44(m, 6H), 7.64(s, 1H), 7.77(m, 2H)

Example 307

(1) α-(2'-hydroxybenzylidene)-γ-butyrolactone

Salicylaldehyde (293 g) and γ-butyrolactone (413 g) were dissolved in toluene (2.4 L) and the solution was cooled to not more than 3° C. in an ice-salt bath. Thereto was added sodium methoxide (324 g) over 20 min. The temperature of the reaction mixture rose to 24° C. After stirring at room temperature for 3 hr, the mixture was stirred for 45 min under heating at 60–65° C. The reaction mixture was cooled again in an ice-bath and 10% sulfuric acid (2.51 ml) was added dropwise. The obtained white suspension was filtrated, washed with water and dried to give the title compound (324 g), melting point 162–164° C.

(2) (S)-α-(2'-(2,3-epoxypropan-1-yloxy)benzylidene)-γ-butyrolactone

To α-(2'-hydroxybenzylidene)-γ-butyrolactone (60 g) were added dimethylformamide (600 ml) and potassium carbonate (87 g) and (S)-glycidyl nosylate (82 g) was added. The reaction mixture was stirred for 2 days at room temperature. The reaction mixture was concentrated under reduced pressure and water was added. The mixture was extracted with ethyl acetate. The organic layer was dried over anhydrous sodium sulfate and concentrated under reduced pressure. The obtained crystals were recrystallized from ethyl acetate to give the title compound (55 g), melting point 68–70° C.

(3) (S)-α-(2'-(2-hydroxy-3-(4-(naphthalen-2-yl) piperidino) propyloxy) benzylidene)-γ-butyrolactone (S)-α-(2'-(2,3-epoxypropan-1-yloxy)benzylidene)-γ-butyrolactone (50 g) and 4-(naphthalen-2-yl)piperidine (43 g) were dissolved in ethanol (500 ml) and the mixture was refluxed under heating for 2 hr. After cooling, the solvent was evaporated under reduced pressure and the obtained crystals were collected by filtration. The crystals were recrystallized once from acetonitrile and once from a mixed solvent of ethyl acetate and ethanol to give the title compound (50 g), melting point 138–140° C.

Example 308

(1)(R)-α-(2'-(2,3-epoxypropan-1-yloxy)benzylidene)-γ-butyrolactone

To α-(2'-hydroxybenzylidene)-γ-butyrolactone (11 g) were added dimethylformamide (100 ml) and potassium carbonate (20 g) and (R)-glycidyl nosylate (15 g) was added. The mixture was stirred at 50° C. for 3 hr. Water was added and the mixture was extracted with ethyl acetate. The organic layer was dried over anhydrous sodium sulfate and concentrated under reduced pressure to give the title compound (10 g) as crystals, melting point 135–137° C.

(2) (R)-α-(2'-(2-hydroxy-3-(4-(naphthalen-2-yl)piperidino)propyloxy)benzylidene)-γ-butyrolactone 1/4 hydrate By the reactions in the same manner as in Example 307 using (R)-α-(2'-(2,3-epoxypropan-1-yloxy)benzylidene)-γ-butyrolactone (2.7 g) and 4-(naphthalen-2-yl)piperidine (2.5 g) in methanol (50 ml), the title compound (2.4 g) was obtained, melting point 136–138° C.

Example 309

α-(2'-(2-hydroxy-3-(4-(naphthalen-2-yl)piperidino) propyloxy)benzylidene)-γ-butyrolactone Dimethylformamide (30 ml) and potassium carbonate (4.4 g) were added to α-(2'-hydroxybenzylidene)-γ-butyrolactone (3 g), and a racemic compound of glycidyl nosylate (3.4 g) was added. The mixture was stirred at 50° C. for 3 hr. Water was added and the mixture was extracted with ethyl acetate. The organic layer was dried over anhydrous sodium sulfate and concentrated under reduced pressure to give oily α-(2'-(2,3-epoxypropan-1-yloxy)benzylidene)-γ-butyrolactone (3.2 g). This compound (0.4 g) was reacted in methanol with 4-(naphthalen-2-yl)piperidine (0.5 g) in the same manner as in Example 307 to give the title compound, melting point 127–128° C.

Example 310

(S)-α-(2'-(3-(4-(3-fluoro-4-methylphenyl)piperidino)-2-hydroxypropyloxy)benzylidene)-γ-butyrolactone 1/10 hydrate By the reactions in the same manner as in Example 307 using (S)-α-(2'-(2,3-epoxypropan-1-yloxy)benzylidene)-γ-butyrolactone (1.0 g) and 4-(3-fluoro-4-methylphenyl)piperidine (0.8 g) in methanol (50 ml), the title compound (1.24 g) was obtained, melting point 131–133° C.

The structural formulas of the compounds obtained in Examples 301 to 310 are shown in the following.

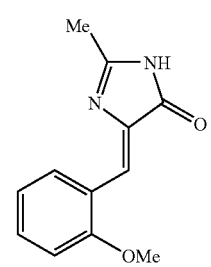

301-1

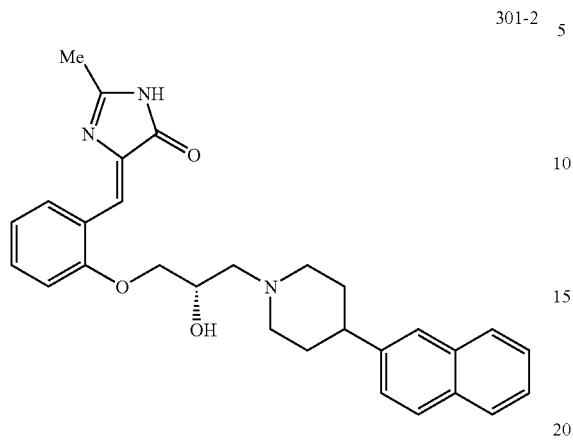
301-2
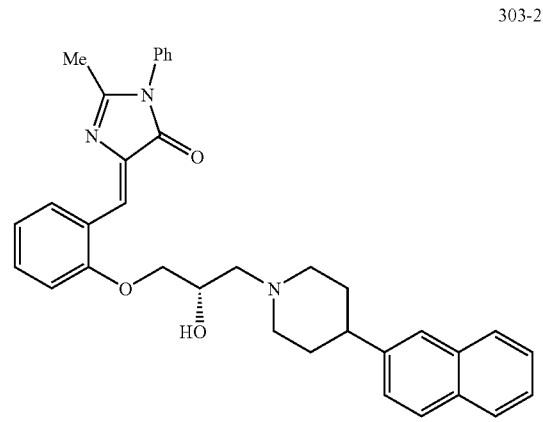
303-2
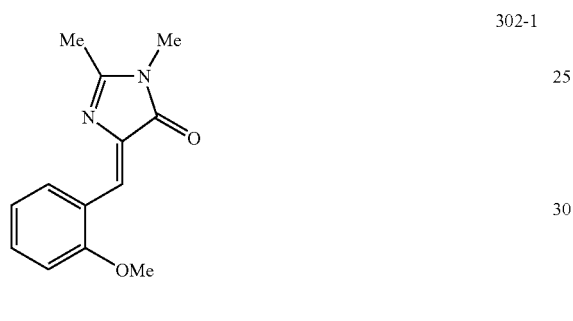
302-1
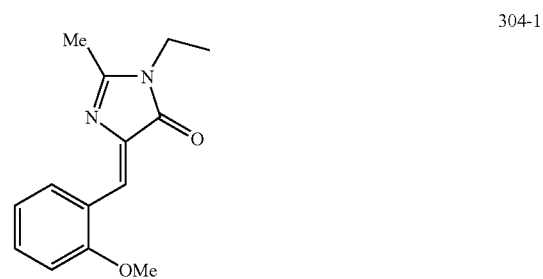
304-1
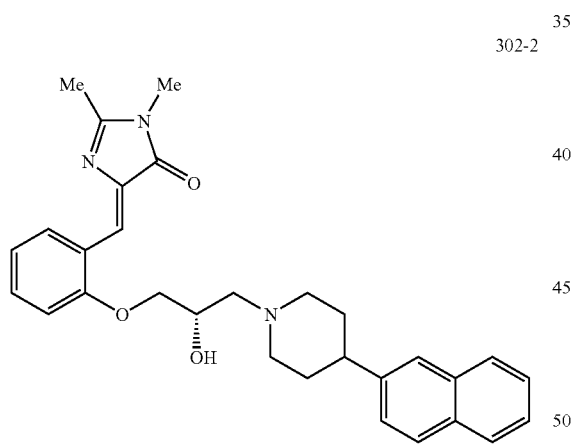
302-2
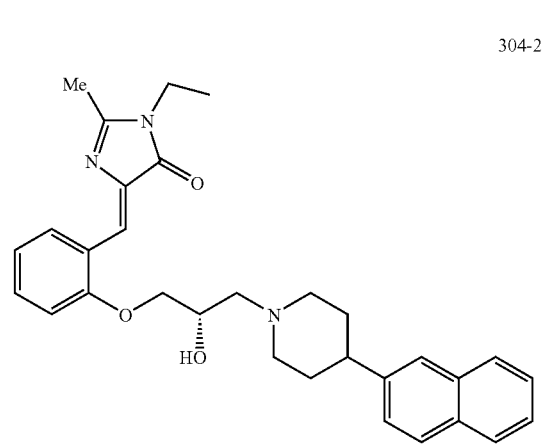
304-2
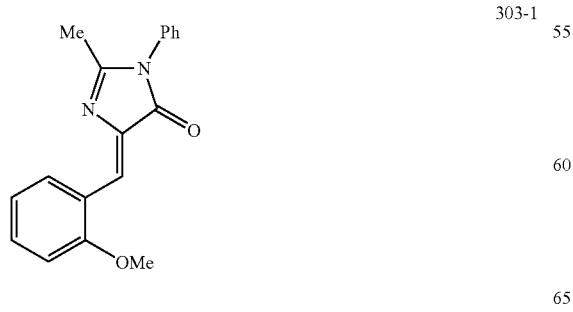
303-1
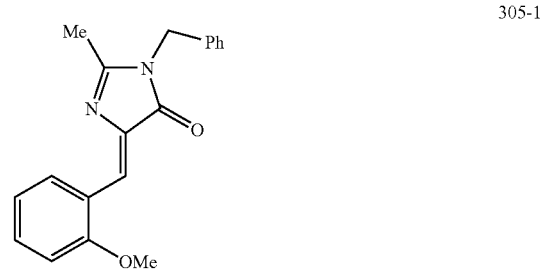
305-1

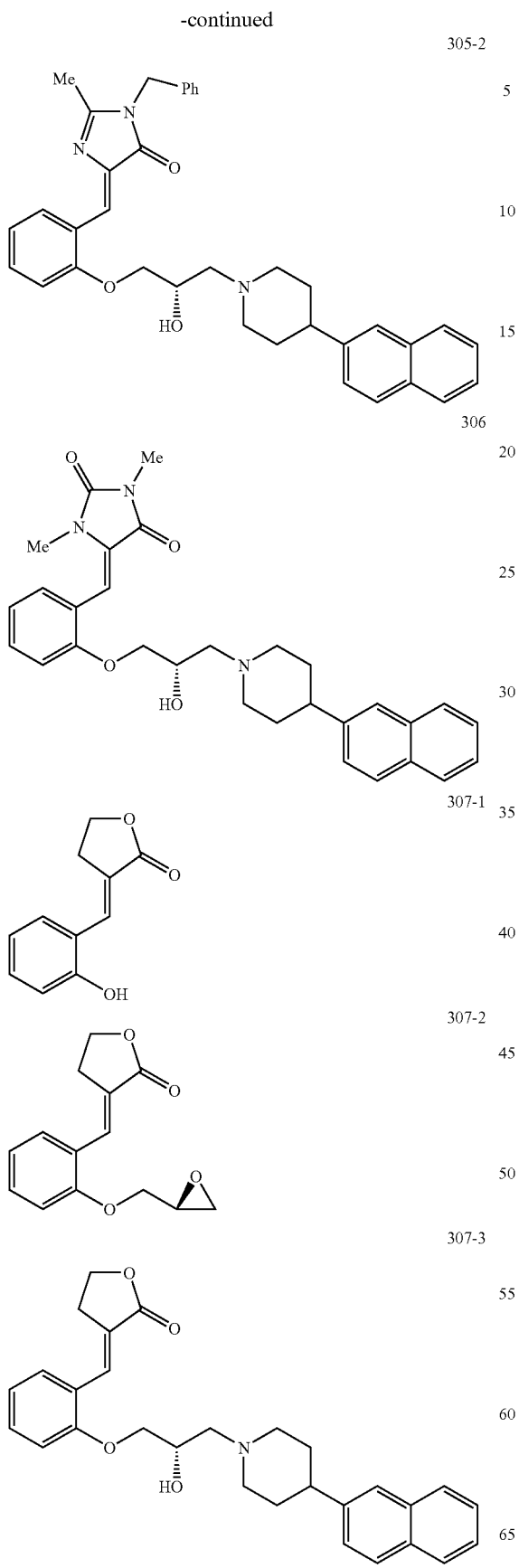
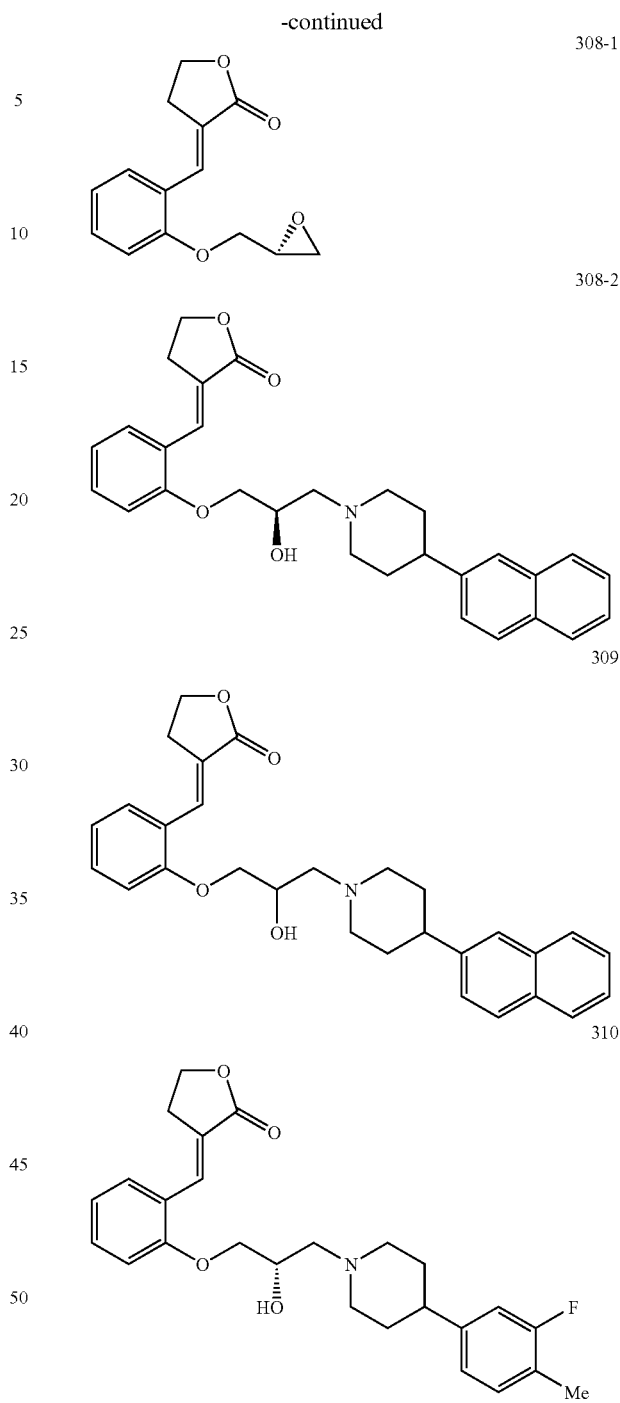
Example 311
(S)-α-(2'-(3-(4-(3,4-dimethylphenyl)piperidino)-2-hydroxypropyloxy)benzylidene)-γ-butyrolactone 1/5 hydrate
By the reactions in the same manner as in Example 307 using (S)-α-(2'-(2,3-epoxypropan-1-yloxy)benzylidene)-γ-butyrolactone (1.0 g) and 4-(3,4-dimethylphenyl)piperidine (0.8 g) in methanol (50 ml), the title compound (0.61 g) was obtained, melting point 125–126° C.

Example 312

(S)-α-(2'-(3-(4-(4-chloro-3-fluorophenyl)piperidino)-2-hydroxypropyloxy)benzylidene)-γ-butyrolactone 1/2 hydrate By the reaction in same manner as in Example 307 using (S)-α-(2'-(2,3-epoxypropan-1-yloxy)benzylidene)-γ-butyrolactone (1.0 g) and 4-(4-chloro-3-fluorophenyl)piperidine (0.8 g) in methanol (50 ml), the title compound (0.58 g), melting point 114–115° C.

Example 313

(S)-α-(2'-(3-(4-(4-chloro-3-trifluoromethylphenyl)piperidino)-2-hydroxypropyloxy) benzylidene)-γ-butyrolactone hydrochloride monohydrate The reaction was performed in same manner as in Example 307 using (S)-α-(2'-(2,3-epoxypropan-1-yloxy)benzylidene)-γ-butyrolactone (1.0 g) and 4-(4-chloro-3-trifluoromethylphenyl)piperidine (0.8 g) in methanol (50 ml), and the obtained oil was treated with methanol/hydrochloric acid to give the title compound (0.45 g), melting point 172–174° C.

Example 314

(S)-α-(2'-(2-hydroxy-3-(4-(naphthalen-1-yl)piperidino)propyloxy)benzylidene)-γ-butyrolactone p-toluenesulfonate The reaction was performed in same manner as in Example 307 using (S)-α-(2'-(2,3-epoxypropan-1-yloxy)benzylidene)-γ-butyrolactone (5.8 g) and 4-(naphthalen-1-yl)piperidine (5.0 g) in methanol (100 ml) and the obtained oil was treated with ethyl acetate/p-toluenesulfonic acid to give the title compound (7.8 g), melting point 119–121° C.

Example 315

(S)-α-(2'-(2-hydroxy-3-(4-(naphthalen-2-yl)piperidino)propyloxy)benzylidene)-δ-valerolactone 1/5 hydrate Salicylaldehyde (15.2 g) and δ-valerolactone (25 g) were dissolved in toluene (150 ml). By the reaction in the same manner as in Example 307, oily α-(2'-hydroxybenzylidene)-δ-valerolactone (7.0 g) was obtained. Dimethylformamide (70 ml) and potassium carbonate (9.5 g) were added hereto and (S)-glycidyl nosylate (8.9 g) was added. The mixture was stirred at 40° C. for 2 hr. The reaction mixture was concentrated under reduced pressure. Water was added and the mixture was extracted with ethyl acetate. The organic layer was dried over anhydrous sodium sulfate and concentrated under reduced pressure to give the oily title compound (7.8 g). The reaction in the same manner as in Example 307 using this product (1.0 g) and 4-(naphthalen-2-yl)piperidine (1.0 g) in methanol (50 ml) was performed and the obtained oil was recrystallized from ethyl acetate to give the title compound (0.38 g), melting point 142–144° C.

Example 316

(1) α-(2'-hydroxybenzylidene)-γ-valerolactone

Salicylaldehyde (15.2 g) and γ-valerolactone (25 g) were dissolved in toluene (150 ml). By the reactions as in the same manner as in Example 307, the title compound (17 g) was obtained, melting point 112–114° C.

(2) (S)-α-(2'-(2-hydroxy-3-(4-(naphthalen-2-yl)piperidino)propyloxy)benzylidene)-γ-valerolactone 1/5 hydrate Dimethylformamide (70 ml) and potassium carbonate (9.5 g) were added to α-(2'-hydroxybenzylidene)-γ-valerolactone (7 g) and (S)-glycidyl nosylate (8.9 g) was added. The mixture was stirred at 40° C. for 2 hr. The reaction mixture was concentrated under reduced pressure. Water was added and the mixture was extracted with ethyl acetate. The organic layer was dried over anhydrous sodium sulfate and concentrated under reduced pressure to give an oil. (7.5 g). By the reaction using this product (1.0 g) and 4-(naphthalen-2-yl)piperidine (1.0 g) in methanol (50 ml) in the same manner as in Example 307, an oily title compound (0.8 g) was obtained.

$^1$H-NMR(CDCl$_3$)δ:1.44(d, 3H, J=6.3), 1.83–2.00(m, 4H), 2.24(t, 1H, J=11.2), 2.48–2.60(m, 1H), 2.62–2.82(m, 4H), 3.02(d, 1H, J=12.2), 3.20(d, 1H, J=12.2), 3.30(dd, 1H, J=5.4, 11.7), 4.00–4.23(m, 3H), 4.68–4.73(m, 1H), 7.00(m, 2H), 7.33–7.45(m, 6H), 7.64(s, 1H), 7.77(d, 2H, J=8.3), 8.00(s, 1H)

Example 317

(S)-3-(2'-(2-hydroxy-3-(4-(5,6,7,8-tetrahydronaphthalen-2-yl)piperidino)propyloxy)benzylidene)-2-pyrrolidone 1/4 hydrate Sodium hydride (16 g) was suspended in tetrahydrofuran (100 ml) and a solution of N-acetylpyrrolidone (25 g) and o-anisaldehyde (26.8 g) in tetrahydrofuran (100 ml) was added dropwise under ice-cooling. After completion of the reaction, the reaction mixture was poured into water. The mixture was acidified with hydrochloric acid and extracted with ethyl acetate. The organic layer was dried over anhydrous magnesium sulfate. After filtration, the solvent was evaporated under reduced pressure to give oily 3-(2'-methoxybenzylidene)-2-pyrrolidone (4.7 g). The oil was dissolved in methylene chloride (60 ml). By demethylation using boron tribromide under ice-cooling, 3-(2'-hydroxybenzylidene)-2-pyrrolidone (4.0 g) was obtained as yellow crystals. To the crystals (1.5 g) were added dimethylformamide (50 ml) and potassium carbonate (2.2 g). (S)-Glycidyl nosylate (2.3 g) was added and the mixture was stirred at room temperature for 2 days. The reaction mixture was concentrated under reduced pressure and water was added. The mixture was extracted with chloroform. The organic layer was dried over anhydrous sodium sulfate to give an oily compound (1.8 g). By the reaction of the oil (0.5 g) and 4-(5,6,7,8-tetrahydronaphthalen-2-yl)piperidine (0.5 g) in methanol in the same manner as in Example 307, the title compound (0.4 g) was obtained, melting point 157–159° C.

Example 318

(S)-3-(2'-(3-(4-(3,4-dimethylphenyl)piperidino)-2-hydroxypropyloxy)benzylidene)-2-pyrrolidone 1/4 hydrate By the method in the same manner as in Example 317 using 4-(3,4-dimethylphenyl)piperidine (0.5 g), the title compound (0.52 g) was obtained, melting point 156–158° C.

Example 319

(S)-3-(2'-(2-hydroxy-3-(4-(naphthalen-2-yl)piperidino)propyloxy)benzylidene)-2-pyrrolidone By the method in the same manner as in Example 317 using 4-(naphthalen-2-yl)piperidine (0.5 g), the title compound (0.40 g) was obtained, melting point 172–174° C.

Example 320

(R)-3-(2'-(2-hydroxy-3-(4-(naphthalen-2-yl)piperidino)propyloxy)benzylidene)-2-pyrrolidone By the method in the same manner as in Example 317 using (R)-glycidyl nosylate and 4-(naphthalen-2-yl)piperidine, the title compound (0.55 g) was obtained, melting point 188–190° C.

The structural formulas of the compounds obtained in Examples 311 to 320 are shown in the following.

-continued

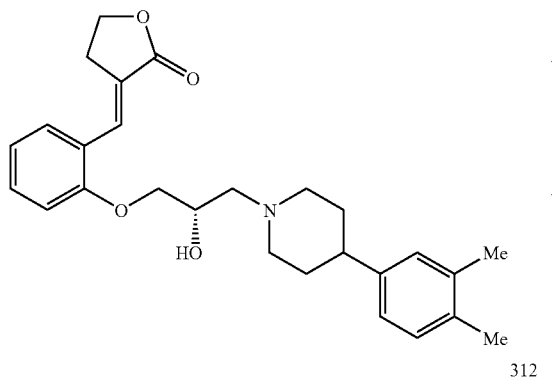

311

312

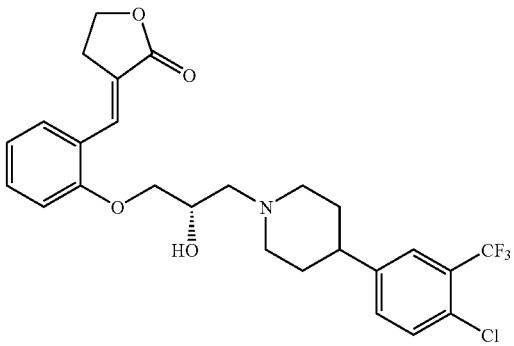

313

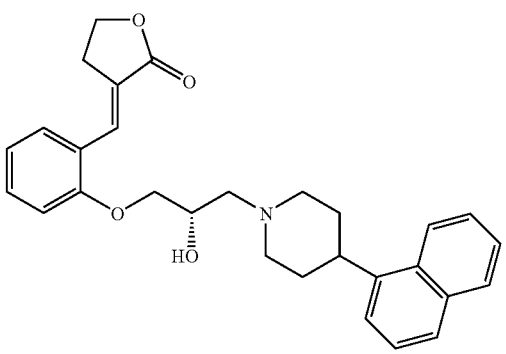

314

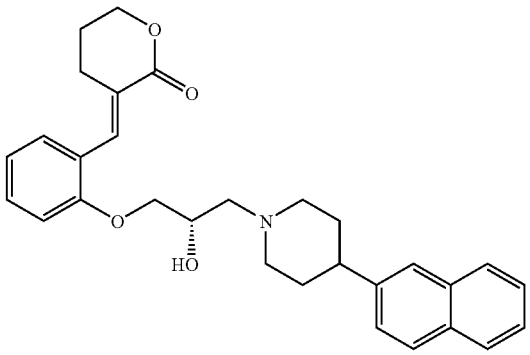

315

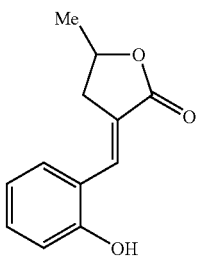

316-1

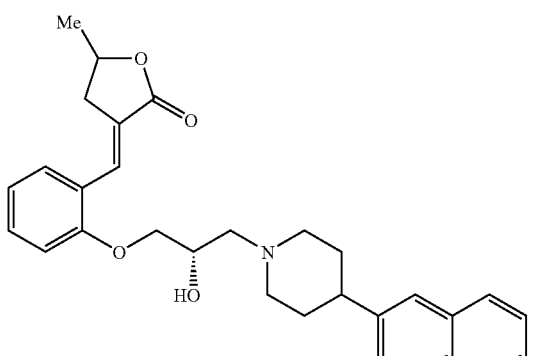

316-2

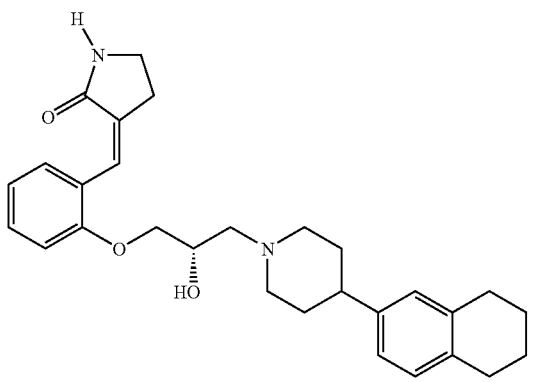

317

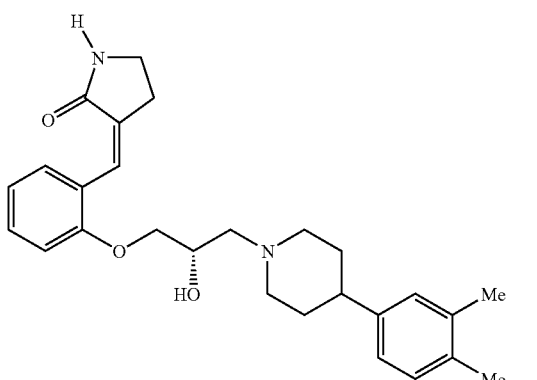

318

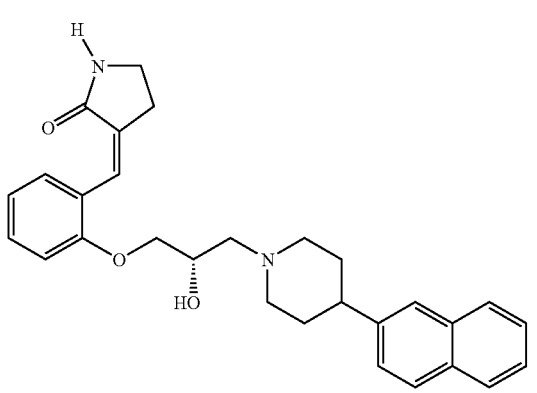

319

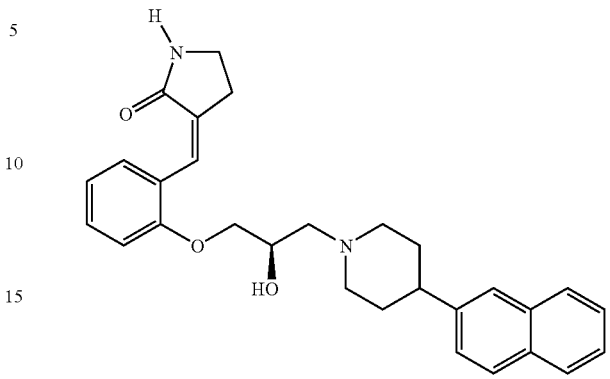

320

Example 321

(1) 3-(2'-methoxybenzylidene)-1-methyl-2-pyrrolidone

The intermediate 3-(2'-methoxybenzylidene)-2-pyrrolidone (5.0 g) obtained in Example 317 was dissolved in dimethylformamide (50 ml) and sodium hydride (0.99 g) was added thereto under ice-cooling. The mixture was stirred at room temperature for 30 min. Methyl iodide (1.72 ml) was added under ice-cooling and the mixture was stirred for 8 hr at room temperature. After completing of the reaction, the reaction mixture was poured into water and extracted with ethyl acetate. The organic layer was dried over anhydrous sodium sulfate and concentrated under reduced pressure to give the title compound (3.6 g).

$^1$H-NMR(CDCl$_3$):3.00(m, 5H), 3.46(t, 2H), 3.85(s, 3H), 6.91(d, J=8.2, 1H), 6.96(t, J=8.2, 1H), 7.20–7.30(m, 1H), 7.41(d, J=8.2, 1H), 7.70(m, 1H)

(2) (S)-3-(2'-(2-hydroxy-3-(4-(5,6,7,8-tetrahydronaphthalen-2-yl)piperidino)propyloxy)benzylidene)-1-methyl-2-pyrrolidone dihydrochloride 3-(2'-Methoxybenzylidene)-1-methyl-2-pyrrolidone (3.6 g) was dissolved in methylene chloride (50 ml). Demethylation was performed using boron tribromide (12.7 g) under ice-cooling to give white crystals (3.0 g). To the crystals (1.6 g) were added dimethylformamide (50 ml) and potassium carbonate (2.2 g), and (S)-glycidyl nosylate (2.3 g) was added. The reaction mixture was stirred at room temperature for 2 days. The reaction mixture was concentrated under reduced pressure. Water was added to the residue and the mixture was extracted with chloroform. The organic layer was dried over anhydrous sodium sulfate to give an oily compound (2.1 g). By the reaction of the oil (1.0 g) and 4-(5,6,7,8-tetrahydronaphthalen-2-yl)piperidine (0.5 g) in methanol in the same manner as in Example 317, the oily title compound was obtained. By the treatment of the oily compound in a mixed solvent of hydrochloric acid and methanol, the title compound (0.026 g) was obtained, melting point 227–230° C.

Example 322

(S)-3-(2'-(2-hydroxy-3-(4-(naphthalen-2-yl)piperidino)propyloxy)benzylidene)-1-methyl-2-pyrrolidone dihydrochloride By the methods in the same manner as in Example 317 using 4-(naphthalen-2-yl)piperidine (1.0 g), the title compound (0.33 g) was obtained, melting point 136–139° C.

Example 323

(R)-3-(2'-(2-hydroxy-3-(4-(naphthalen-2-yl)piperidino)propyloxy)benzylidene)-1-methyl-2-pyrrolidone monohydrochloride monohydrate By the methods in the same manner as in Example 317 using (R)-glycidyl nosylate and 4-(naphthalen-2-yl)piperidine (0.6 g), the title compound (0.40 g) was obtained, melting point 127–129° C.

Example 324

(1) 3-(2'-methoxybenzylidene)-1-(2-methoxyethyl)-2-pyrrolidone

The intermediate 3-(2'-methoxybenzylidene)-2-pyrrolidone (5.0 g) obtained in Example 317 was dissolved in dimethylformamide (50 ml) and sodium hydride (0.99 g) was added under ice-cooling. The mixture was stirred at room temperature for 30 min. To the reaction mixture was again added 2-methoxyethyl chloride (2.3 ml) under ice-cooling, and the mixture was stirred at room temperature for 1 hr and at 70° C. for 1 hr. After cooling, the reaction mixture was poured into water and extracted with ethyl acetate. The organic layer was dried over anhydrous sodium sulfate and concentrated under reduced pressure to give an oily title compound (2.8 g).

$^1$H-NMR(CDCl$_3$):2.98–3.02(m, 2H), 3.37–3.39(m, 2H), 3.42–3.65(m, 4H), 3.81(s, 3H), 3.85(s, 3H), 6.87–6.98(m, 2H), 7.22(t, J=8.2, 1H), 7.29(d, J=8.2, 1H), 7.71(bs, 1H)

(2) (S)-3-(2'-(2-hydroxy-3-(4-(naphthalen-2-yl)piperidino)propyloxy)benzylidene)-1-(2-methoxyethyl)-2-pyrrolidone hydrochloride 3-(2'-Methoxybenzylidene)-1-(2-methoxyethyl)-2-pyrrolidone (2.8 g) was dissolved in methylene chloride (30 ml) and demethylated with boron tribromide (8.7 g) under ice-cooling to give an oil (1.68 g). To the oil were added dimethylformamide (50 ml) and potassium carbonate (2.2 g). (S)-Glycidyl nosylate (2.3 g) was added and the mixture was stirred at room temperature for one day. The reaction mixture was concentrated under reduced pressure, and water was added. The reaction mixture was extracted with chloroform and the organic layer was dried over anhydrous sodium sulfate to give an oily compound (0.8 g). The oil (1.0 g) and 4-(naphthalen-2-yl)piperidine (0.8 g) were reacted in methanol in the same manner as in Example 317 to give an oily title compound. The oily compound was treated with a mixed solvent of hydrochloric acid and methanol to give the title compound (0.075 g), melting point 254–257° C.

Example 325

(S)-α-(2'-(2-hydroxy-3-(4-(6-methoxynaphthalen-2-yl) piperidino) propyloxy) benzylidene)-γ-butyrolactone (S)-α-(2'-(2,3-Epoxypropan-1-yloxy)benzylidene)-γ-butyrolactone (1.2 g) and 4-(6-methoxynaphthalen-2-yl)piperidine (1.2 g) were dissolved in methanol (50 ml), and the mixture was refluxed under heating for 2 hr. After cooling, the solvent was evaporated under reduced pressure and the residue was purified by silica gel column chromatography (chloroform/methanol) to give the title compound (1.0 g), melting point 148–150° C.

Example 326

(Z)-(S)-α-(2'-(2-hydroxy-3-(4-(naphthalen-2-yl)piperidino)propyloxy)benzylidene)-γ-butyrolactone (S)-α-(2'-(2-Hydroxy-3-(4-(naphthalen-2-yl)piperidino) propyloxy)benzylidene)-γ-butyrolactone (2.0 g) was dissolved in ethanol (300 ml) and exposed to the sunlight for 6 hr. The solvent was concentrated under reduced pressure and the obtained oil was purified by silica gel column chromatography (chloroform/methanol) to give the title compound (0.3 g).

$^1$H-NMR(CDCl$_3$):1.81–2.05(m, 4H), 2.17–2.25(m, 1H), 2.50–2.80(m, 4H), 3.06(d, 1H, J=10.7), 3.15(dt, 2H, J=2.0, 5.4), 3.24(d, 1H, J=10.7), 4.00–4.05(m, 2H), 4.18–4.28(m, 1H), 4.40(t, 2H, J=7.3), 6.90(d, 1H, J=8.3), 6.97(t, 1H, J=7.5), 7.30–7.558 (m, 4H), 7.66(s, 1H), 7.70–7.88(m, 3H), 7.90(d, 1H, J=7.8)

Example 327

(1) α-(2'-hydroxybenzyl)-γ-butyrolactone

α-(2'-Hydroxybenzylidene)-γ-butyrolactone (5.0 g) was dissolved in ethanol (400 ml) and 10% palladium carbon (0.5 g) was added. The reaction mixture was reduced for 6 hr at 50 atm. The reaction mixture was filtered and the organic solvent was concentrated to give the title compound (5.0 g).

$^1$H-NMR(CDCl$_3$):2.05–2.20(m, 1H), 2.12–2.39(m, 1H), 2.92–2.97(m, 1H), 2.97–3.01(m, 1H), 3.05–3.20(m, 1H), 4.18–4.23(m, 1H), 4.28–4.38(m, 1H), 6.80–6.92(m, 2H), 7.05–7.20(m, 2H)

(2) (2S)-α-(2'-(2,3-epoxypropan-1-yloxy)benzyl)-γ-butyrolactone

Dimethylformamide (100 ml) and potassium carbonate (10 g) were added to α-(2'-hydroxybenzyl)-γ-butyrolactone (5.0 g), and (S)-glycidyl nosylate (6 g) was added. The mixture was stirred at room temperature for 2 days. The reaction mixture was concentrated under reduced pressure and water was added. The reaction mixture was extracted with ethyl acetate. The organic layer was dried over anhydrous sodium sulfate and concentrated under reduced pressure to give the title compound (6.1 g).

$^1$H-NMR(CDCl$_3$):1.90–2.05(m, 1H), 2.06–2.30(m, 1H), 2.62–3.00(m, 5H), 3.28–3.40(m, 2H), 3.92–4.00(m, 1H), 4.06–4.20(m, 1H), 4.22–4.38(m, 1H), 6.82–6.90(m, 1H), 6.91–6.98(m, 1H), 7.03–7.18(m, 2H)

(3) (2S)-α-(2'-(2-hydroxy-3-(4-(naphthalen-2-yl)piperidino)propyloxy)benzyl)-γ-butyrolactone (2S)-α-(2'-(2,3-Epoxypropan-1-yloxy)benzyl)-γ-butyrolactone (1.5 g) and 4-(naphthalen-2-yl)piperidine (1.5 g) were dissolved in methanol (50 ml) and the reaction mixture was refluxed under heating for 2 hr. After cooling, the solvent was evaporated under reduced pressure and the obtained oil was purified by silica gel column chromatography (chloroform/methanol) to give the title compound (1.3 g).

$^1$H-NMR(CDCl$_3$):1.80–2.00(m, 5H), 2.10–2.22(m, 1H), 2.48–2.58(bs, 1H), 2.60–2.78(m, 4H), 2.98–3.05(m, 1H), 3.07–3.09(bs, 1H), 3.37–3.40(m, 1H), 4.00–4.04(m, 2H), 4.06–4.23(m, 2H), 4.25–4.32(m, 1H), 6.80–6.92(m, 2H), 7.15–7.20(m, 1H), 7.22–7.25(m, 1H), 7.37–7.43(m, 3H), 7.66(s, 1H), 7.77–7.82(m, 3H)

Example 328

(1) N-(2'-hydroxybenzyl)-2-oxazolidone

2-Oxazolidone (3.0 g) was dissolved in dimethylformamide (120 ml) and sodium hydride (2.5 g) was added under ice-cooling. The mixture was stirred at room temperature for 1 hr and 2-methoxybenzyl chloride (6.5 g) was again added under ice-cooling. The mixture was heated to 60° C. and stirred for 1 hr. The mixture was allowed to reach room temperature and poured into ice-water. The aqueous layer was extracted with ethyl acetate and the organic layer was dried over anhydrous magnesium sulfate. The organic solvent was concentrated under reduced pressure to give an oil (8.0 g). Methylene chloride (100) was added thereto, and boron tribromide (9 ml) was added dropwise under stirring at −78° C. Then, the reaction mixture was stirred for 2 hr under ice-cooling. The reaction mixture was poured into ice water and extracted with chloroform. The organic layer was dried over anhydrous sodium sulfate and concentrated under reduced pressure to give the title compound (5.5 g).

$^1$H-NMR(CDCl$_3$):3.43(t, 2H, J=8.3), 3.82(s, 3H), 4.28(t, 2H, J=8.3), 4.42(s, 2H), 6.81–6.97(m, 2H), 7.24–7.30(m, 2H)

(2) (S)-N-(2'-(2-hydroxy-3-(4-(naphthalen-2-yl)piperidino)propyloxy)benzyl)-2-oxazolidone Dimethylformamide (100 ml) and potassium carbonate (10 g) were added to N-(2'-hydroxybenzyl)-2-oxazolidone (5.0 g) and (S)-glycidyl nosylate (6 g) was added, and then the mixture was stirred at room temperature for 2 days. The reaction mixture was concentrated under reduced pressure and water was added. The reaction mixture was extracted with ethyl acetate. The organic layer was dried over anhydrous sodium sulfate and concentrated under reduced pressure. The residue was washed with hexane to give an oil (6.0 g). The oil (1.5 g) and 4-(naphthalen-2-yl)piperidine (1.5 g) were dissolved in methanol (50 ml), and the mixture was refluxed under heating for 2 hr. After cooling, the solvent was evaporated under reduced pressure and the obtained oil was purified by silica gel column chromatography (chloroform/methanol) to give the title compound (2.7 g)

$^1$H-NMR(CDCl$_3$):1.80–2.00(m, 4H), 2.20–2.25(m, 1H), 2.32–2.40(m, 1H), 2.58–2.75(m, 3H), 3.10(t, 2H, J=9.7), 3.39(t, 2H, J=8.3), 3.91–3.98(m, 1H), 4.04–4.10(m, 1H), 4.17–4.15(m, 3H), 4.42–4.60(m, 2H), 6.82–6.95(m, 2H), 7.19–7.30(m, 1H), 7.31–7.38(m, 1H), 7.39–7.50(m, 3H), 7.65(s, 1H), 7.77–7.82(m, 3H)

The structural formulas of the compounds obtained in Examples 321 to 328 are shown in the following.

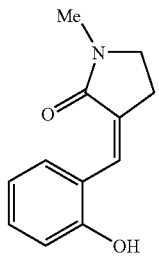

321-1

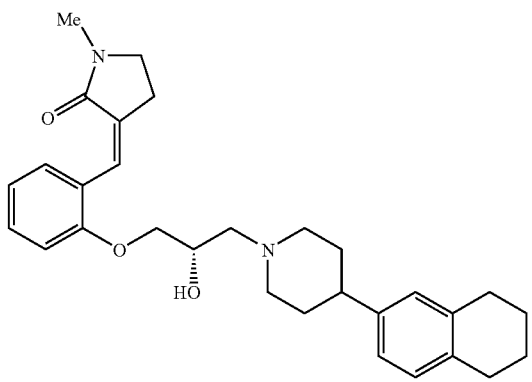

321-2

322

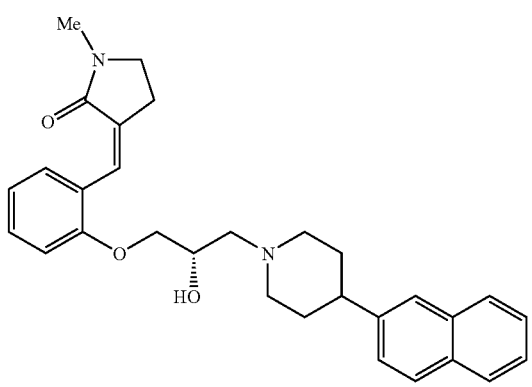

323

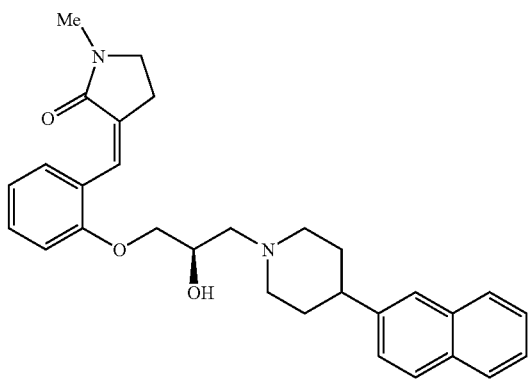

273
-continued
324-1
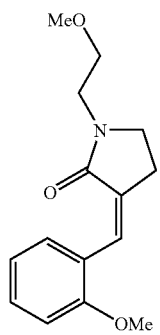
324-2
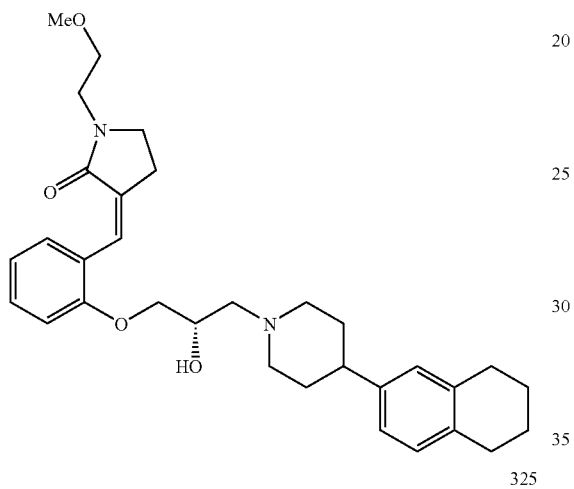
325
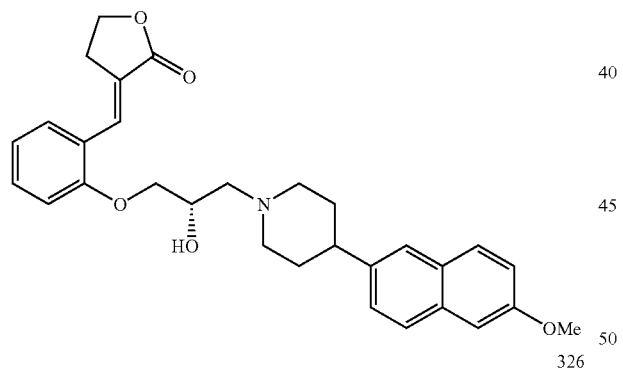
326
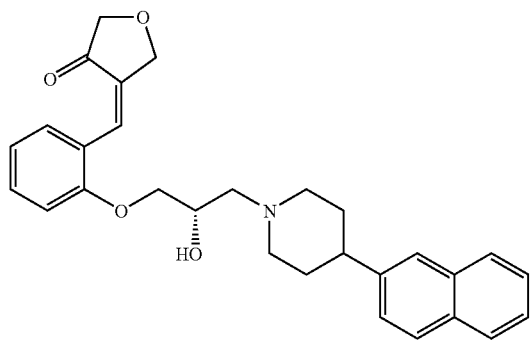
274
-continued
327-1
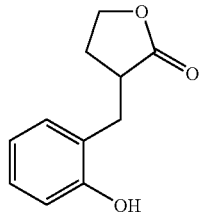
327-2
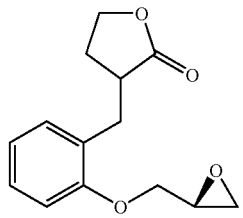
327-3
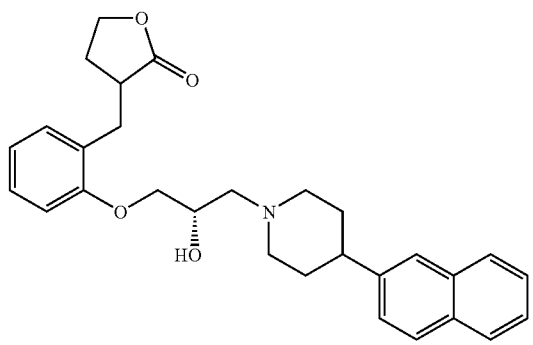
328-1
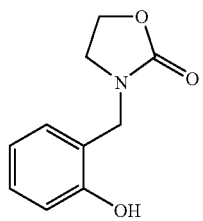
328-2
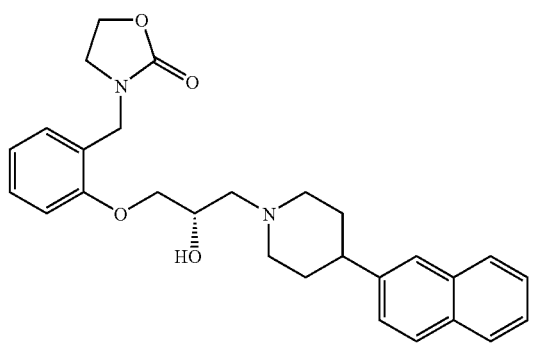

By the reactions in the same manner, the following compounds can be synthesized.

Example 401

(S)-1-(4-(1-methyl-2-oxoindolin-5-yl)piperidino)-3-(2-(5-methyl-1,3,4-oxadiazol-2-yl)benzo(b)furan-4-yloxy)-2-propanol

Example 402

(S)-1-(4-(1H-indol-5-yl)piperidino)-3-(2-(5-methyl-1,3,4-oxadiazol-2-yl)benzo(b)furan-4-yloxy)-2-propanol

Example 403

(S)-1-(4-(1-methylindol-5-yl)piperidino)-3-(2-(5-methyl-1,3,4-oxadiazol-2-yl)benzo(b)furan-4-yloxy)-2-propanol

Example 404

(S)-1-(4-(2,2-dimethyl-2,3-dihydrobenzo(b)furan-6-yl)piperidino)-3-(2-(5-methyl-1,3,4-oxadiazol-2-yl)benzo(b)furan-4-yloxy)-2-propanol

Example 405

(S)-1-(4-(4-chloro-2,2-dimethyl-2,3-dihydrobenzo(b)thiophen-6-yl)piperidino)-3-(2-(5-methyl-1,3,4-oxadiazol-2-yl)benzo(b)furan-4-yloxy)-2-propanol

Example 406

(S)-1-(4-(2-methyl-2,3-dihydrobenzo(b)furan-5-yl)piperidino)-3-(2-(5-methyl-1,3,4-oxadiazol-2-yl)benzo(b)furan-4-yloxy)-2-propanol

Example 407

(S)-1-(4-(2,4,6-trimethylphenyl)piperidino)-3-(2-(5-methyl-1,3,4-oxadiazol-2-yl)benzo(b)furan-4-yloxy)-2-propanol

Example 408

(S)-1-(4-(3,5-dichlorophenyl)piperidino)-3-(2-(5-methyl-1,3,4-oxadiazol-2-yl)benzo(b)furan-4-yloxy)-2-propanol

Example 409

(S)-1-(4-(2-methylbenzo(b)furan-6-yl)piperidino)-3-(2-(5-methyl-1,3,4-oxadiazol-2-yl)benzo(b)furan-4-yloxy)-2-propanol

Example 410

(S)-1-(4-(3-methylbenzo(d)isoxazol-5-yl)piperidino)-3-(2-(5-methyl-1,3,4-oxadiazol-2-yl)benzo(b)furan-4-yloxy)-2-propanol

Example 411

(S)-1-(4-(2H-1-oxoisoindolin-5-yl)piperidino)-3-(2-(5-methyl-1,3,4-oxadiazol-2-yl)benzo(b)furan-4-yloxy)-2-propanol

Example 412

(S)-1-(4-(2-methyl-1-oxoisoindolin-5-yl)piperidino)-3-(2-(5-methyl-1,3,4-oxadiazol-2-yl)benzo(b)furan-4-yloxy)-2-propanol The structural formulas of the compounds obtained in Examples 401 to 412 are shown in the following Table 1.

TABLE 1

| Ex. No. | Substituent R$^1$ |
|---|---|
| 401 | (4-(1-methyl-2-oxoindolin-5-yl)piperidino) |
| 402 | (4-(1H-indol-5-yl)piperidino) |
| 403 | (4-(1-methylindol-5-yl)piperidino) |
| 404 | (4-(2,2-dimethyl-2,3-dihydrobenzo(b)furan-6-yl)piperidino) |
| 405 | (4-(4-chloro-2,2-dimethyl-2,3-dihydrobenzo(b)thiophen-6-yl)piperidino) |

TABLE 1-continued

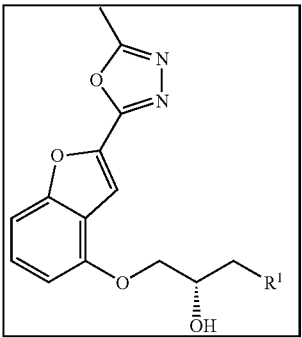

| Ex. No. | Substituent R¹ |
|---|---|
| 406 | 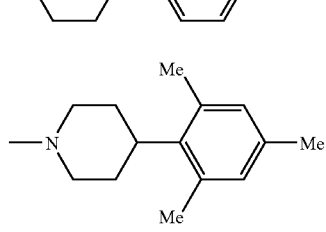 |
| 407 | 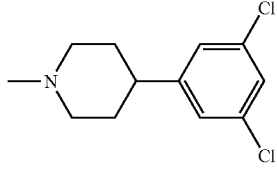 |
| 408 | 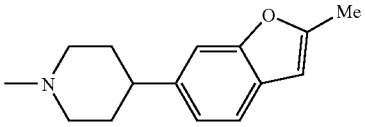 |
| 409 | 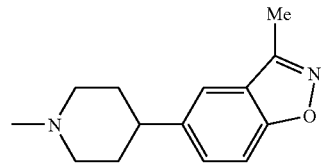 |
| 410 | 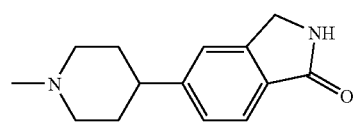 |
| 411 | 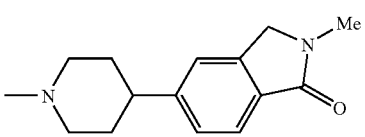 |
| 412 |  |

Example 413

(S)-1-(4-(quinolin-6-yl)piperidino)-3-(2-(5-methyl-1,3,4-oxadiazol-2-yl)benzo(b)furan-4-yloxy)-2-propanol Example 414

(S)-1-(4-(isoquinolin-6-yl)piperidino)-3-(2-(5-methyl-1,3,4-oxadiazol-2-yl)benzo(b)furan-4-yloxy)-2-propanol Example 415

(S)-1-(4-(quinolin-3-yl)piperidino)-3-(2-(5-methyl-1,3,4-oxadiazol-2-yl)benzo(b)furan-4-yloxy)-2-propanol Example 416

(S)-1-(4-(7-methyl-2,3-dihydrobenzo(b)furan-5-yl)piperidino)-3-(2-(5-methyl-1,3,4-oxadiazol-2-yl)benzo(b)furan-4-yloxy)-2-propanol Example 417

(S)-1-(4-(7-chloro-2,3-dihydrobenzo(b)furan-5-yl)piperidino)-3-(2-(5-methyl-1,3,4-oxadiazol-2-yl)benzo(b)furan-4-yloxy)-2-propanol Example 418

(S)-1-(4-(1H-2-oxoindolin-5-yl)piperidino)-3-(2-(5-methyl-1,3,4-oxadiazol-2-yl)benzo(b)furan-4-yloxy)-2-propanol Example 419

(S)-1-(4-(3-chloro-4-fluorophenyl)piperidino)-3-(2-(5-methyl-1,3,4-oxadiazol-2-yl)benzo(b)furan-4-yloxy)-2-propanol Example 420

(S)-1-(4-(4,5-dimethylthiophen-2-yl)piperidino)-3-(2-(5-methyl-1,3,4-oxadiazol-2-yl)benzo(b)furan-4-yloxy)-2-propanol Example 421

(S)-1-(4-(4,5-dichlorothiophen-2-yl)piperidino)-3-(2-(5-methyl-1,3,4-oxadiazol-2-yl)benzo(b)furan-4-yloxy)-2-propanol Example 422

(S)-1-(4-(2-methylpyridin-4-yl)piperidino)-3-(2-(5-methyl-1,3,4-oxadiazol-2-yl)benzo(b)furan-4-yloxy)-2-propanol Example 423

(S)-1-(4-(4,5-dimethylfuran-2-yl)piperidino)-3-(2-(5-methyl-1,3,4-oxadiazol-2-yl)benzo(b)furan-4-yloxy)-2-propanol

Example 424

(S)-1-(4-(4,5-dichlorofuran-2-yl)piperidino)-3-(2-(5-methyl-1,3,4-oxadiazol-2-yl)benzo(b)furan-4-yloxy)-2-propanol The structural formulas of the compounds obtained in Examples 413 to 424 are shown in the following Table 2.

TABLE 2

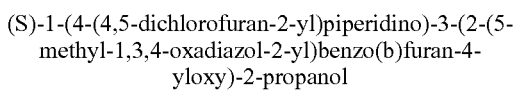

| Ex. No. | Substituent R¹ |
|---|---|
| 413 | ![piperidine-quinoline] |
| 414 | ![piperidine-isoquinoline] |
| 415 | ![piperidine-quinoline isomer] |
| 416 | ![piperidine-dihydrobenzofuran-Me] |
| 417 | ![piperidine-dihydrobenzofuran-Cl] |
| 418 | ![piperidine-oxindole] |
| 419 | ![piperidine-phenyl-Cl,F] |
| 420 | ![piperidine-dimethylthiophene] |
| 421 | ![piperidine-dichlorothiophene] |
| 422 | ![piperidine-methylpyridine] |
| 423 | ![piperidine-dimethylfuran] |
| 424 | ![piperidine-dichlorofuran] |

Example 425

(S)-1-(4-(4-chloro-2-methylphenyl)piperidino)-3-(2-(5-methyl-1,3,4-oxadiazol-2-yl)benzo(b)fran-4-yloxy)-2-propanol hydrochloride 1/2 hydrate (S)-2-(4-Glycidyloxybenzo(b)fran-2-yl)-5-methyl-1,3,4-oxadiazole (7.0 g) and 4-(4-chloro-2-methylphenyl)piperidine (6 g) were heated in methanol for 3 h with stirring. The solvent was evaporated and an oil was purified by silica gel column chromatography (chloroform/methanol). The obtained oil was dissolved in acetone and hydrochloric acid-ethanol was added to give the title compound (6.8 g), melting point 201–203° C.

Example 426

(S)-1-(4-(2,6-dimethoxyphenyl)piperidino)-3-(2-(5-methyl-1,3,4-oxadiazol-2-yl)benzo(b)fran-4-yloxy)-2-propanol 1/2 terephthalate 1/2 hydrate In the same manner as in Example 425, the title compound was synthesized from (S)-2-(4-glycidyloxybenzo(b)fran-2-yl)-5-methyl-1,3,4-oxadiazole and 4-(2,6-dimethoxyphenyl)piperidine, melting point 170–171° C.

Example 427

(S)-1-(4-(3-fluoro-4-methylphenyl)piperidino)-3-(2-(5-methyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-methyl-1,3,4-oxadiazole and 4-(3-fluoro-4-methylphenyl)piperidine, melting point 214–216° C.

Example 428

(S)-1-(4-(2,4,6-trimethoxyphenyl)piperidino)-3-(2-(5-methyl-1,3,4-oxadiazol-2-yl)benzo(b)fran-4-yloxy)-2-propanol 1/2 terephthalate 1/2 hydrate In the same manner as in Example 425, the title compound was synthesized from (S)-2-(4-glycidyloxybenzo(b)fran-2-yl)-5-methyl-1,3,4-oxadiazole and 4-(2,4,6-trimethoxyphenyl)piperidine, melting point 209–211° C.

Example 429

(S)-1-(4-(4-chloro-2,6-dimethoxyphenyl)piperidino)-3-(2-(5-methyl-1,3,4-oxadiazol-2-yl)benzo(b)fran-4-yloxy)-2-propanol 1/2 terephthalate dihydrate In the same manner as in Example 425, the title compound was synthesized from (S)-2-(4-glycidyloxybenzo(b)fran-2-yl)-5-methyl-1,3,4-oxadiazole and 4-(4-chloro-2,6-dimethoxyphenyl)piperidine, melting point 231–232° C.

Example 430

(S)-1-(4-(3-chloro-4-ethoxyphenyl)piperidino)-3-(2-(5-methyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-methyl-1,3,4-oxadiazole and 4-(3-chloro-4-ethoxyphenyl)piperidine, melting point 212–214° C.

Example 431

(S)-1-(4-(3-chloro-4-isopropoxyphenyl)piperidino)-3-(2-(5-methyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-methyl-1,3,4-oxadiazole and 4-(3-chloro-4-isopropoxyphenyl)piperidine, melting point 204–206° C.

Example 432

(S)-1-(4-(4-methoxy-2-methylphenyl)piperidino)-3-(2-(5-methyl-1,3,4-oxadiazol-2-yl)benzo(b)fran-4-yloxy)-2-propanol hydrochloride monohydrate In the same manner as in Example 425, the title compound was synthesized from (S)-2-(4-glycidyloxybenzo(b)fran-2-yl)-5-methyl-1,3,4-oxadiazole and 4-(4-methoxy-2-methylphenyl)piperidine, melting point 190–192° C.

Example 433

(S)-1-(4-(5-chloro-4-methoxy-2-methylphenyl)piperidino)-3-(2-(5-methyl-1,3,4-oxadiazol-2-yl)benzo(b)fran-4-yloxy)-2-propanol hydrochloride 1/2 hydrate In the same manner as in Example 425, the title compound was synthesized from (S)-2-(4-glycidyloxybenzo(b)fran-2-yl)-5-methyl-1,3,4-oxadiazole and 4-(5-chloro-4-methoxy-2-methylphenyl)piperidine, melting point 240–242° C.

Example 434

(S)-1-(4-(2,4-dimethoxyphenyl)piperidino)-3-(2-(5-methyl-1,3,4-oxadiazol-2-yl)benzo(b)fran-4-yloxy)-2-propanol terephthalate In the same manner as in Example 425, the title compound was synthesized from (S)-2-(4-glycidyloxybenzo(b)fran-2-yl)-5-methyl-1,3,4-oxadiazole and 4-(2,4-dimethoxyphenyl)piperidine, melting point 192–194° C.

Example 435

(S)-1-(4-(4-chloro-2-fluoro-3-methylphenyl)piperidino)-3-(2-(5-methyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-methyl-1,3,4-oxadiazole and 4-(4-chloro-2-fluoro-3-methylphenyl)piperidine, melting point 218–220° C.

Example 436

(S)-1-(4-(4-fluoro-2-methylphenyl)piperidino)-3-(2-(5-methyl-1,3,4-oxadiazol-2-yl)benzo(b)fran-4-yloxy)-2-propanol hydrochloride 1/2 hydrate In the same manner as in Example 425, the title compound was synthesized from (S)-2-(4-glycidyloxybenzo(b)fran-2-yl)-5-methyl-1,3,4-oxadiazole and 4-(4-fluoro-2-methylphenyl)piperidine, melting point 245–247° C.

Example 437

(S)-1-(4-(3-chloro-4-methoxy-5-methylphenyl)piperidino)-3-(2-(5-methyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-ethyl-1,3,4-oxadiazole and 4-(3-chloro-4-methoxy-5-methylphenyl)piperidine, melting point 222–224° C.

Example 438

(S)-1-(4-(1-methoxynaphthalen-2-yl)piperidino)-3-(2-(5-methyl-1,3,4-oxadiazol-2-yl)benzo(b)fran-4-yloxy)-2-propanol hydrochloride 1/2 hydrate In the same manner as in Example 425, the title compound was synthesized from (S)-2-(4-glycidyloxybenzo(b)fran-2-yl)-5-methyl-1,3,4-oxadiazole and 4-(1-methoxynaphthalen-2-yl)piperidine, melting point 149–151° C.

Example 439

(S)-1-(4-(3,4-dimethyl-2-methoxyphenyl)piperidino)-3-(2-(5-methyl-1,3,4-oxadiazol-2-yl)benzo(b)fran-4-yloxy)-2-propanol hydrochloride monohydrate In the same manner as in Example 425, the title compound was synthesized from (S)-2-(4-glycidyloxybenzo(b)fran-2-yl)-5-methyl-1,3,4-oxadiazole and 4-(3,4-dimethyl-2-methoxyphenyl)piperidine, melting point 214–216° C.

Example 440

(S)-1-(2-(5-methyl-1,3,4-oxadiazol-2-yl)benzo(b)fran-4-yloxy)-3-(4-(2,4,6-trimethylphenyl)piperidino)-2-propanol hydrochloride In the same manner as in Example 425, the title compound was synthesized from (S)-2-(4-glycidyloxybenzo(b)fran-2-yl)-5-methyl-1,3,4-oxadiazole and 4-(2,4,6-trimethylphenyl)piperidine, melting point 158–160° C.

Example 441

(S)-1-(2-(5-methyl-1,3,4-oxadiazol-2-yl)benzo(b)fran-4-yloxy)-3-(4-(3-methylthiophenyl)piperidino)-2-propanol hydrochloride In the same manner as in Example 425, the title compound was synthesized from (S)-2-(4-glycidyloxybenzo(b)fran-2-yl)-5-methyl-1,3,4-oxadiazole and 4-(3-methylthiophenyl)piperidine, melting point 176–178° C.

Example 442

(S)-1-(2-(5-methyl-1,3,4-oxadiazol-2-yl)benzo(b)fran-4-yloxy)-3-(4-(4-methylthiophenyl)piperidino)-2-propanol hydrochloride 1/2 hydrate In the same manner as in Example 425, the title compound was synthesized from (S)-2-(4-glycidyloxybenzo(b)fran-2-yl)-5-methyl-1,3,4-oxadiazole and 4-(4-methylthiophenyl)piperidine, melting point 180–182° C.

Example 443

(S)-1-(4-(indolin-1-yl)piperidino)-3-(2-(5-methyl-1,3,4-oxadiazol-2-yl)benzo(b)fran-4-yloxy)-2-propanol 3/2 terephthalate 1/2 hydrate In the same manner as in Example 425, the title compound was synthesized from (S)-2-(4-glycidyloxybenzo(b)fran-2-yl)-5-methyl-1,3,4-oxadiazole and 4-(indolin-1-yl)piperidine, melting point 182–184° C.

Example 444

(S)-1-(4-(indol-1-yl)piperidino)-3-(2-(5-methyl-1,3,4-oxadiazol-2-yl)benzo(b)fran-4-yloxy)-2-propanol monoterephthalate 1/2 hydrate In the same manner as in Example 425, the title compound was synthesized from (S)-2-(4-glycidyloxybenzo(b)fran-2-yl)-5-methyl-1,3,4-oxadiazole and 4-(indol-1-yl)piperidine, melting point 145–147° C.

Example 445

(S)-1-(4-(4-chloro-3-ethylphenyl)piperidino)-3-(2-(5-methyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-methyl-1,3,4-oxadiazole and 4-(4-chloro-3-ethylphenyl)piperidine, melting point 177–178° C.

Example 446

(S)-1-(4-(4-chloro-3-isopropylphenyl)piperidino)-3-(2-(5-ethyl-1,3,4-oxadiazol-2-yl)benzo(b)fran-4-yloxy)-2-propanol hydrochloride In the same manner as in Example 425, the title compound was synthesized from (S)-2-(4-glycidyloxybenzo(b)fran-2-yl)-5-ethyl-1,3,4-oxadiazole and 4-(4-chloro-3-isopropylphenyl)piperidine, melting point 154–156° C.

Example 447

(S)-3-(3-(3-(4-(3,4-dichlorophenyl)piperidino)-2-hydroxypropyloxy)benzyl)oxazolidin-2-one terephthalate In the same manner as in Example 425, the title compound was synthesized from (S)-3-(3-glycidyloxybenzyl)oxazolidin-2-one and 4-(3,4-dichlorophenyl)piperidine, melting point 157–159° C.

Example 448

(S)-1-(3-(3-(4-(3,4-dichlorophenyl)piperidino)-2-hydroxypropyloxy)benzyl)pyrrolidin-2-one terephthalate 1/2 hydrate In the same manner as in Example 425, the title compound was synthesized from (S)-1-(3-glycidyloxybenzyl)pyrrolidin-2-one and 4-(3,4-dichlorophenyl)piperidine, melting point 132–134° C.

Example 449

(S)-1-(3-(2-hydroxy-3-(4-(naphthalen-2-yl)piperidino)propyloxy)benzyl)pyrrolidin-2-one terephthalate In the same manner as in Example 425, the title compound was synthesized from (S)-1-(3-glycidyloxybenzyl)pyrrolidin-2-one and 4-(naphthalen-2-yl)piperidine, melting point 153–155° C.

Example 450

(S)-1-(2-(2-hydroxy-3-(4-(3,4-methylenedioxyphenyl)piperidino)propyloxy)benzyl)pyrrolidin-2-one terephthalate In the same manner as in Example 425, the title compound was synthesized from (S)-1-(2-glycidyloxybenzyl)pyrrolidin-2-one and 4-(3,4-methylenedioxyphenyl)piperidine, melting point 169–171° C.

Example 451

(S)-α-(3-(3-(4-(3,4-dichlorophenyl)piperidino)-2-hydroxypropyloxy)benzylidene)-γ-butyrolactone hydrochloride In the same manner as in Example 425, the title compound was synthesized from (S)-α-(3-glycidyloxybenzylidene)-γ-butyrolactone and 4-(3,4-dichlorophenyl)piperidine, melting point 147–149° C.

Example 452

(S)-α-(3-(2-hydroxy-3-(4-(naphthalen-2-yl)piperidino)propyloxy) benzylidene)-γ-butyrolactone hydrochloride In the same manner as in Example 425, the title compound was synthesized from (S)-α-(3-glycidyloxybenzylidene)-γ-butyrolactone and 4-(naphthalen-2-yl)piperidine, melting point 82–84° C.

The structural formulas of the compounds obtained in Examples 425–452 are shown in the following.

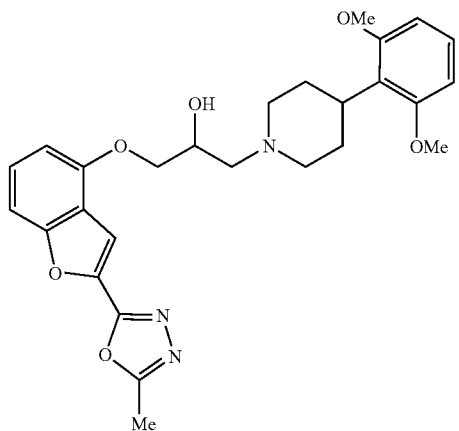

426

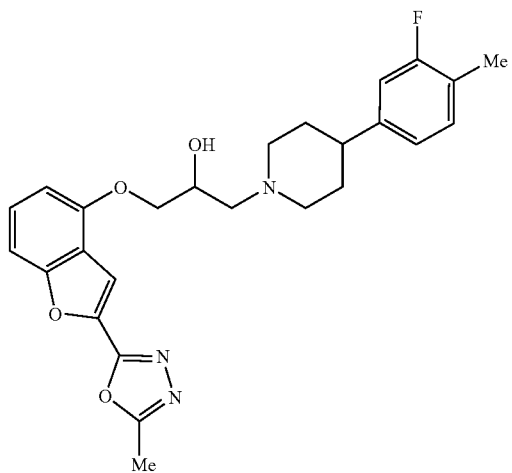

427

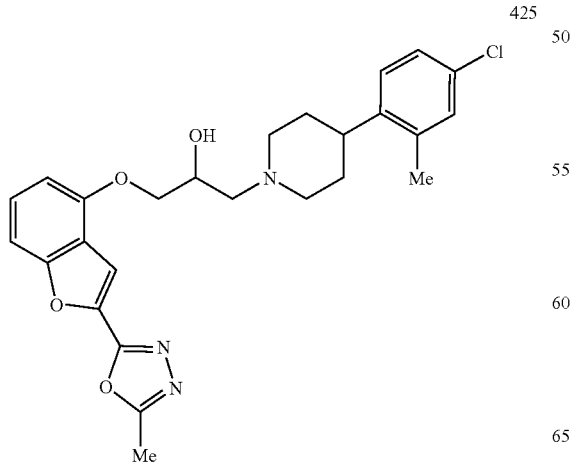

425

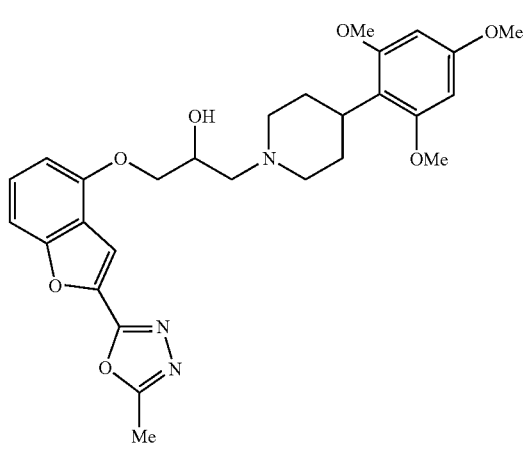

428

| 287 | 288 |
|---|---|
| 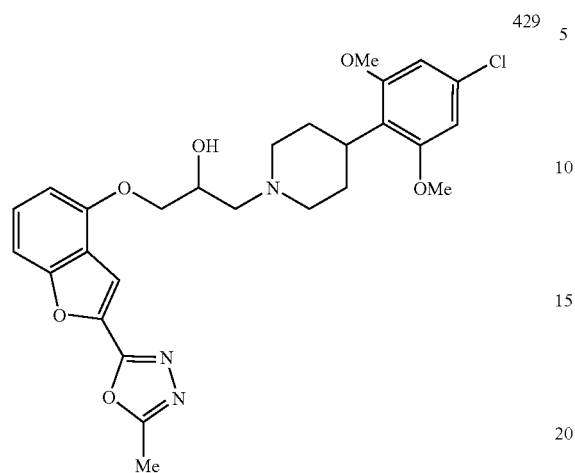 429 | 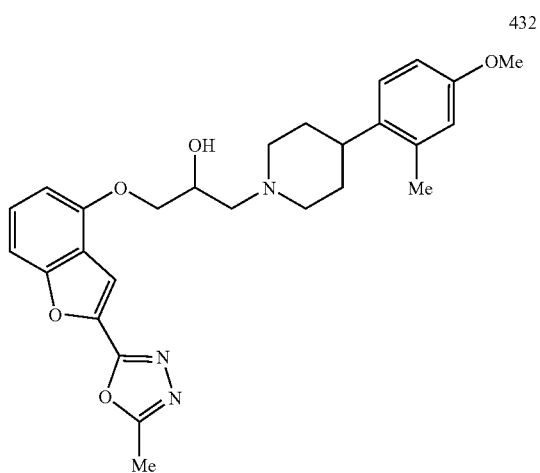 432 |
| 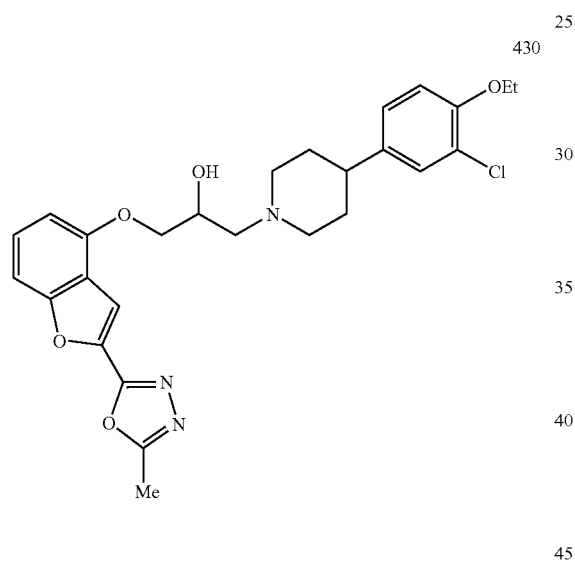 430 | 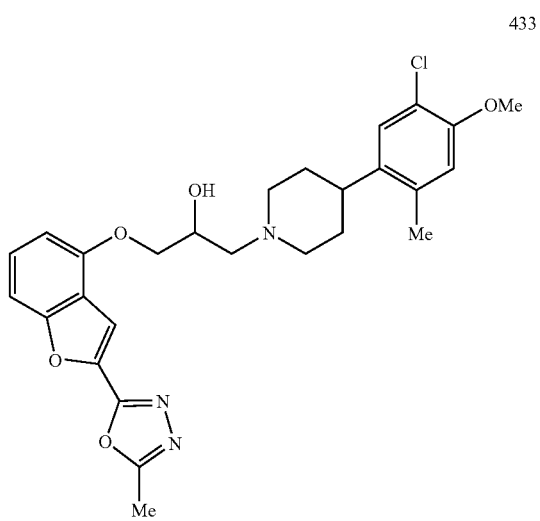 433 |
| 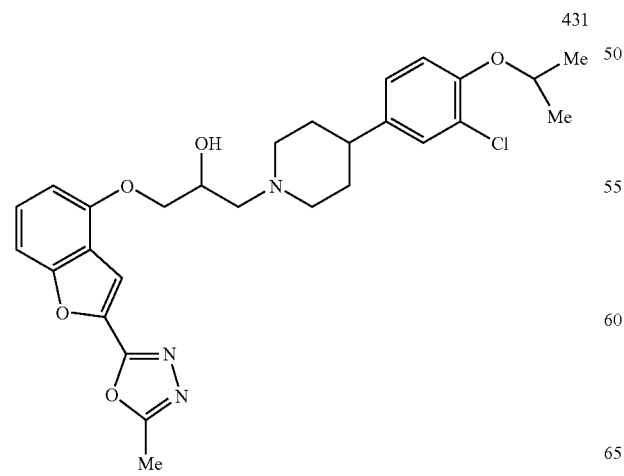 431 | 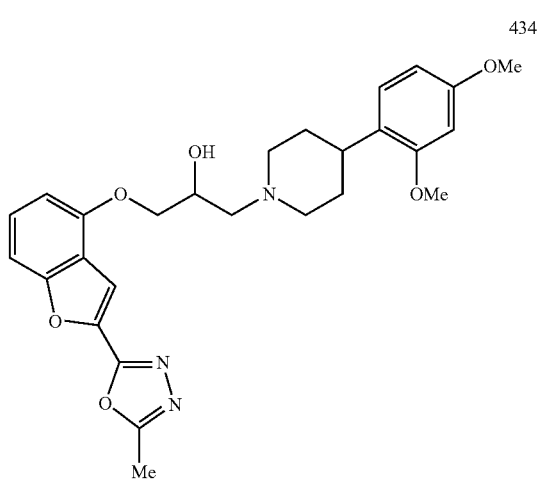 434 |

435
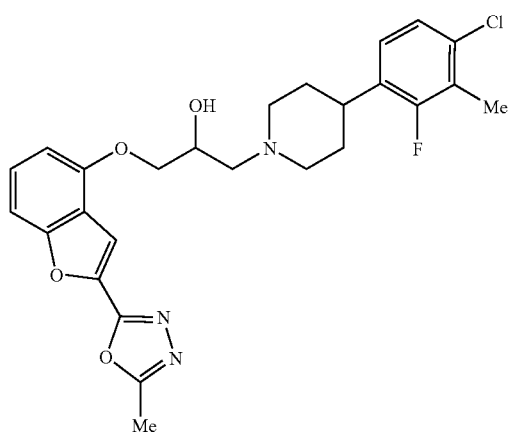
436
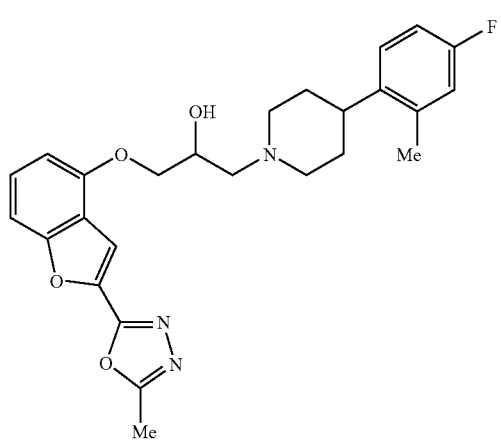
437
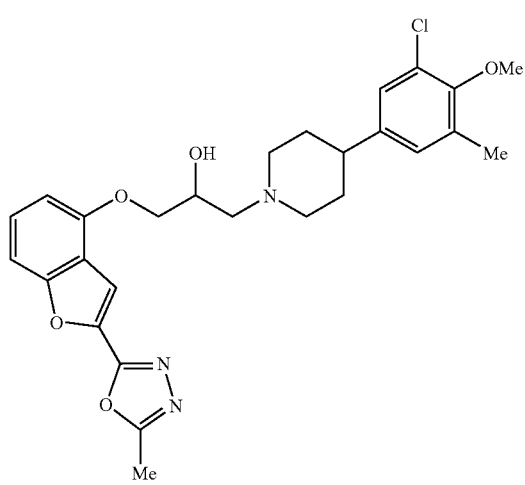
438
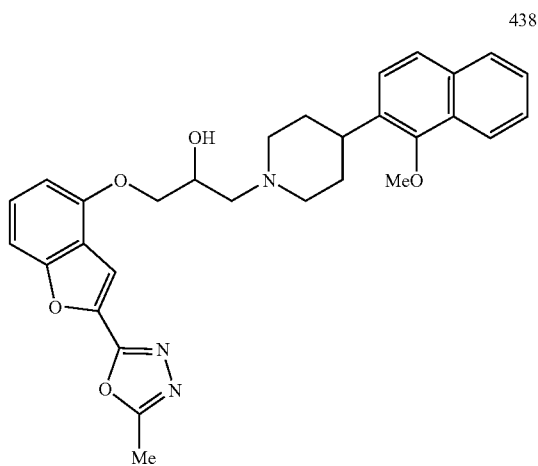
439
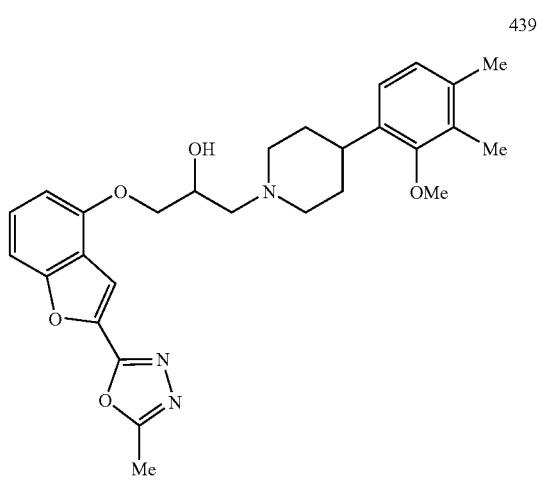
440
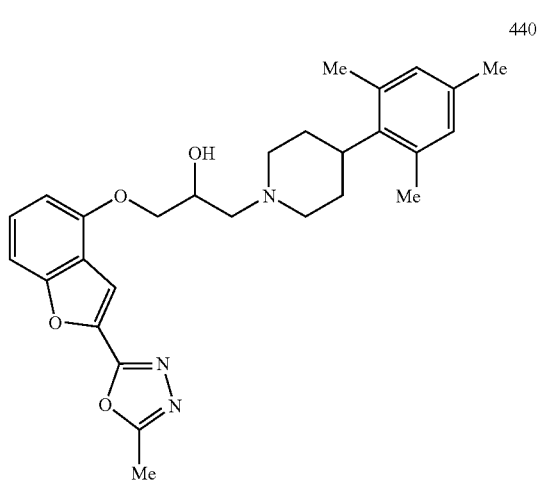

441
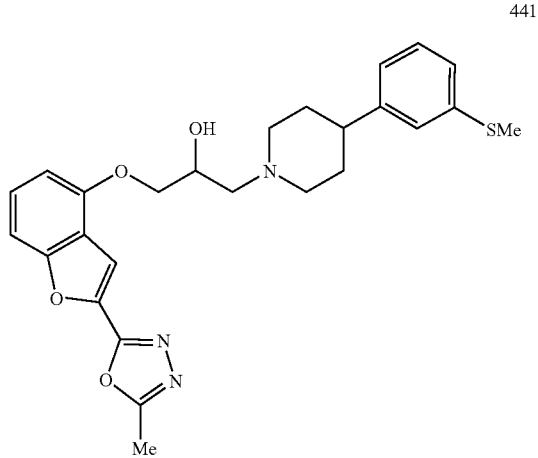
442
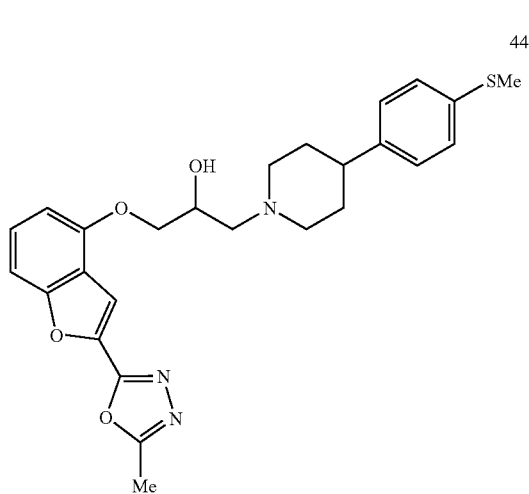
443
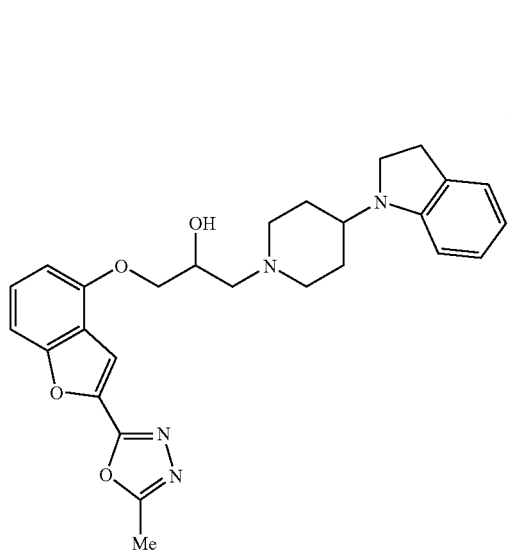
444
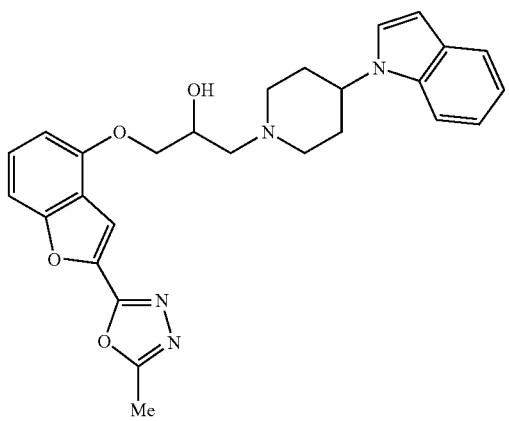
445
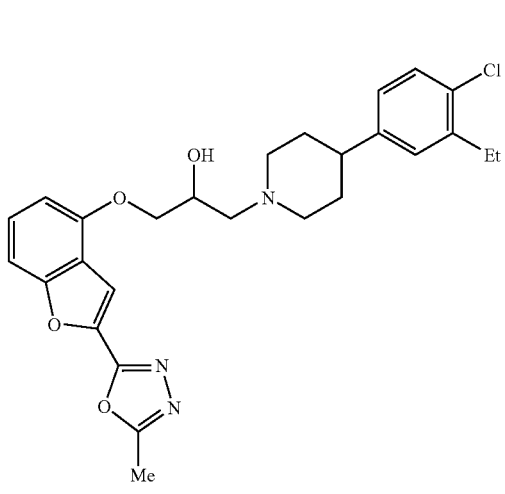
446
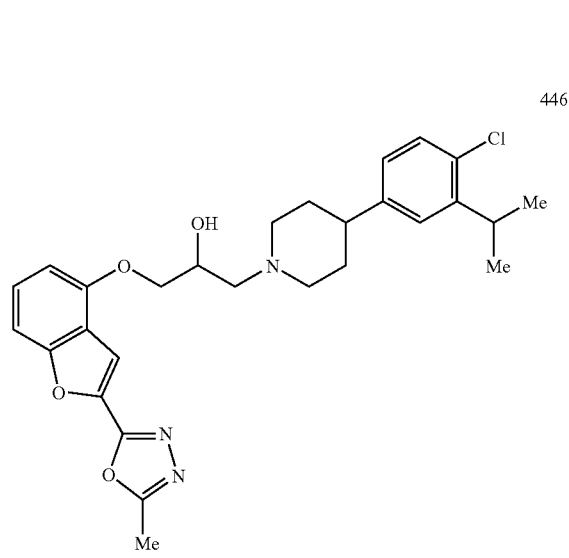

-continued

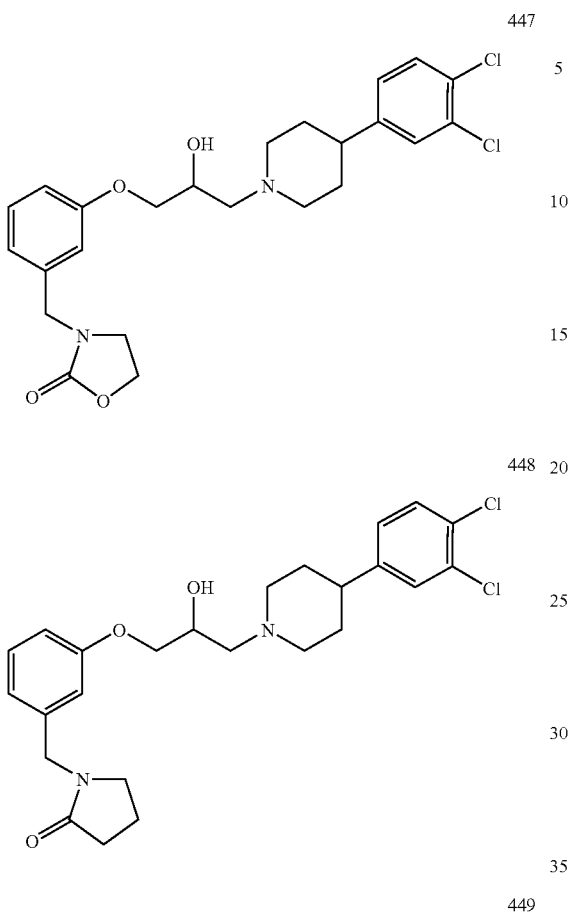

447

448

449

450

-continued

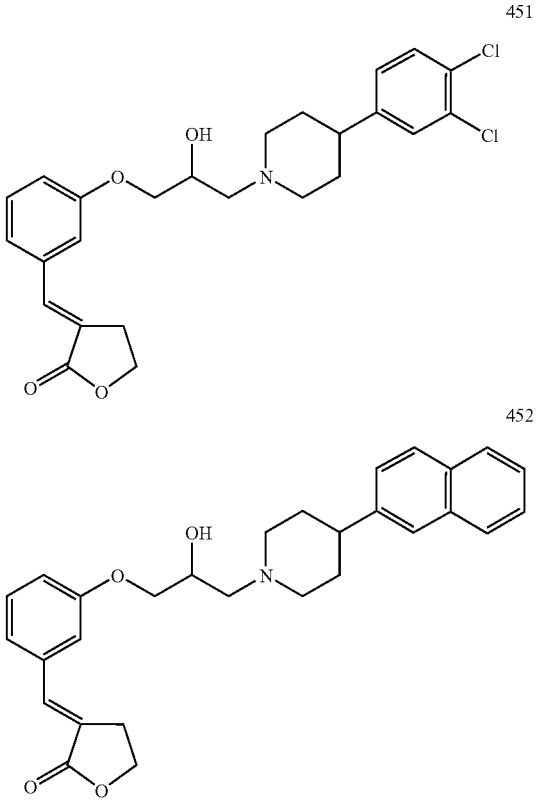

451

452

Formulation Example

Of the compounds of the present invention, a compound of the formula (I) (50 mg) is thoroughly kneaded with lactose (98 mg), cornstarch (45 mg) and hydroxypropylcellulose (3 mg) in a kneader. The kneaded product is passed through a 200 mesh sieve, dried at 50° C. and passed through a 24 mesh sieve. The resulting product is mixed with talc (3 mg) and magnesium stearate (1 mg) and compressed with a 9 mm diameter pounder to give a tablet weighing 200 mg. The tablets may be sugar coated or film coated as necessary.

Experimental Examples 1–5 are shown in the following. In Experimental Examples 1, 2 and 5, (S)-1-(4-indolyloxy)-3-[4-hydroxy-4-(2-naphthyl)piperidino]propan-2-ol described in WO97/48698 was used as a compound for comparison.

Experimental Example 1

5-HT$_{1A}$ Receptor Binding Test

The experiment was conducted according to the method of M. D. Hall et al (J. Neurochem. 44, 1685–1696 (1985)).

Cryopreserved rat hippocampus was homogenized in a 20-fold wet weight amount of 50 mM Tris-HCl buffer (pH 7.4), and the homogenate was centrifuged at 500×g for 10 min. The supernatant was centrifuged at 40000×g for 10 min and the sediment was incubated at 37° C. for 10 min, which was followed by centrifugation at 40000×g for 10 min. To the sediment was added a 20-fold amount of 50 mM Tris-HCl buffer (pH 7.4) and the mixture was homogenized, which was followed by centrifugation again at 40000×g for 10 min. 50 mM Tris-HCl buffer (pH 7.4, 100-fold volume) containing 1 mM $MnCl_2$ was added to the sediment and the mixture was homogenized, which was used as a membrane solution. To a 96 well plate were successively added a test solution (25 ml), ($^3$H)-8-OH-DPAT ((±)-8-hydroxy-2-(DL-N-propylamino)tetraline, Sigma, lot No. 57H4131) solution (final concentration 2 nM, 25 ml) and the membrane solution (0.45 ml) preincubated at 37° C., and incubated at 37° C. for 12 min. After completion, the reaction mixture was filtered through a GF/B glass filter and the filter was washed 5 times with 50 mM Tris-HCl buffer (pH 7.4). The radioactivity left on the filter was measured with a Top Count. For total binding measurement, 0.005N hydrochloric acid (25 ml) was used, and for the measurement of nonspecific binding, a test solution containing WAY-100635 (final concentration 1M, 25 ml) instead of the test substance was used. The total binding and nonspecific binding were measured in quadruplicate, and the test substance was measured in duplicate.

The $IC_{50}$ value was calculated by two-point interpolation and Ki value was calculated according to the following equation using Kd value obtained from each measurement.

$$Ki=IC_{50}/(1+C/Kd)$$

$IC_{50}$: concentration of 50% binding inhibition

C: concentration of ligand

The results are shown in Table 3 below.

Experimental Example 2

5-HT Transporter Binding Test

The experiment was conducted according to the method of Habert, E. et al (Eur. J. Pharmacol., 118; 107–114 (1985)).

Rat brain cortex was homogenized using Polytron in ice-cooled 50 mmol/L Tris-HCl buffer (pH 7.4). After centrifugation at 1000×g and 4° C. for 10 min, the supernatant was transferred to a different centrifugation tube. This was centrifuged at 40000×g and 4° C. for 20 min, and 50 mmol/L Tris-HCl buffer (pH 7.4) was added to the sediment to give a suspension. This was incubated at 37° C. for 10 min, centrifuged at 40000×g and 4° C. for 20 min, and suspended in 50 mmol/L Tris-HCl buffer (pH 7.4) (diluted 100-fold of brain wet weight) containing 120 mmol/L NaCl and 5 mmol/L KCl, which was used as a membrane solution. For binding inhibition test, it was reacted with ($^3$H) paroxetine prepared to the final concentration of 0.2 nmol/L in a plastic test tube at 25° C. for 90 min. For total binding, a solvent was used and for nonspecific binding, fluvoxamine having a final concentration of 10 μmol/L was used.

Using a cell harvester, the reaction mixture was filtered through a GF/B glass filter treated with 0.1% polyethyleneimine to stop the reaction and washed 3 times with 3 mL of ice-cooled 50 mmol/L Tris-HCl buffer (pH 7.4). The radioactivity was measured using a β plate.

The results are shown in Table 3.

TABLE 3

Test results of Experimental Examples 1 and 2

|  | 5-$HT_{1A}$ receptor binding Ki value (nM) | 5-HT transporter binding Ki value (nM) |
|---|---|---|
| compound for reference | 0.16 | 55 |
| compound of Example 6 | 2.3 | 1.10 |
| compound of Example 88 | 0.75 | 0.32 |
| compound of Example 136 | 0.37 | 0.18 |
| compound of Example 138 | 0.68 | 1.60 |

As is evident from Table 3, the compound of the present invention showed strong affinity for both 5-$HT_{1A}$ receptor and 5-HT transporter.

Experimental Example 3

Antagonistic Action Against Lowering of Body Temperature

From the antagonistic action of the test substance against decrease in the body temperature due to 8-OH-DPAT, transfer of the test substance into the brain was established. At the same time, it was clarified if the test substance acts as an agonist or as an antagonist on the 5-$HT_{1A}$ receptor.

The rectal temperature of male ddY mice was measured with a digital thermostat (KN-91, Natsume) (pre-value). Thereafter, the test substance was administered orally or parenterally, and after a certain time, 8-OH-DPAT (1 mg/kg) was subcutaneously administered. The rectal temperature was measured 30 min later (post-value).

The pre-value and post-value obtained by the measurement were compared, and the action of the test substance on the decrease of body temperature due to 8-OH-DPAT was observed.

The results of Experimental Example 3 establish that the compound of the present invention acts as an antagonist on 5-$HT_{1A}$ receptor, because the compound given orally in 0.1–100 mg/kg antagonizes the lowering of the body temperature due to 8-OH-DPAT. From the results, it is suggested that the compound of the present invention is superior in the bioavailability and transfer into the brain.

Experimental Example 4

Forced Swimming Test

The test substance was administered orally or parenterally to male ddY mice, and after a certain time, the mice were placed in a water tank (material: vinyl chloride, color: black, inner diameter: 10 cm, height: 25 cm, water depth: 15 cm, water temperature: 25° C.), and subjected to 6 min test trial. The movement of the animal was videotaped with a CCD camera set right above the water tank, and analyzed against immobility time during 4 minutes from 2 to 6 min after the start of swimming, using an image analysis system/forced swimming analysis program [Neuroscience Inc.: Videoimage motion analyzer (AXIS series)/(TARGET/7M)].

The results of Experimental Example 4 reveal that, while the conventional SSRI requires several days for expression of an action, the compound of the present invention significantly shortened the immobility time by the single oral administration of 0.1–100 mg/kg thereof. From this, it is suggested that the compound of the present invention can be a so-called rapid onset antidepressant that shows quick expression of the anti-depressive effect, as compared to conventional SSRI.

Experimental Example 5

Test for Electrophysical Evaluation of Agonist/Antagonist of 5-HT$_{1A}$ Receptor The experiment followed the method of Katayama et al (*Brain Res.*; 745, 283–292, 1997).

The brain of 2-week-old male Wistar rat was extracted, and a brain thin section (thickness 350 μm) containing dorsal raphe nuclei was prepared using a microslicer. The brain thin section was treated in Ringer's solution containing pronase (0.4 mg/mL) and protease type X (0.25 mg/mL) at 30° C. for 25 min and 15 min, respectively, and the dorsal raphe nuclei region was micropunched out. The brain thin section punched out was subjected to pipetting in a culture dish filled with the Ringer's solution to isolate the nerve cell. The isolated nerve cell (dorsal raphe nuclei cell) was subjected to nystatin perforated patch clamp method (Akaike & Harata, Jpn. J. Physiol.; 44, 433–437, 1994) and the inward K$^+$ current induced by the test substance and the like was measured under membrane voltage-clamp condition ($V_H$=−60 mV). For the measurement of the inward K$^+$ current via the 5-HT$_{1A}$ receptor, an extracellular solution and a patch pipette solution having the following compositions were used simultaneously.

extracellular solution (mmol/L): NaCl, 135; KCl, 20; MgCl$_2$, 1; CaCl$_2$, 2; D-glucose, 10; HEPES, 10; tetrodotoxin, 3×10$^{-4}$; LaCl$_3$, 10 patch pipette solution (mmol/L): KCl, 150; HEPES, 10

To the above-mentioned patch pipette solution was added nystatin. (Sigma, Lot No. 33H0762) to the final concentration of 75 μg/mL before the electric measurement.

The current response was measured with a voltage clamp amplifier (List Medical, L/M-EPC7), and the obtained results were recorded on a chart of a recticorder (Nihondenki Sanei, RECTIHORIZ-8K), digitized by a PCM recording device (NF electric Instruments, RP-882) and videotaped by a VCR (Panasonic, NV-G40).

The administration of the test substance and the like followed a Y-tube method (Murase et al., Brain Res.; 525, 84–91, 1990).

First, 8-OH-DPAT (10$^{-7}$ mol/L) was administered to the isolated nerve cell (dorsal raphe nuclei cell) obtained above, and the level of the inward K$^+$ current response was measured. The cells that showed an inward K$^+$ current response of not less than 15 pA were subjected to the following test.

8-OH-DPAT was washed out for 2 min from the above-mentioned cells and the test substance and pindolol (reference substance which is an antagonist) were administered for 1 min, and the level of the inward K$^+$ current response by each of them was measured. From immediately after administration of the test substance or the reference substance, a mixture of 8-OH-DPAT (10 mol/L) and the test substance or reference substance was administered, and the level of the induced inward K$^+$ current response was measured. The measurement results and the level of the current response in the same cell by 8-OH-DPAT alone were compared, based on which the antagonistic action on the 8-OH-DPAT induction current was considered. Every current response was expressed upon standardizing according to the following calculation equation based on the level of the 8-OH-DPAT (10$^{-7}$ mol/L) induction current in the same cell.

The inward K$^+$ current response inducing action (5-HT$_{1A}$ agonistic action) by the test substance alone was determined from the following equation.

inward K$^+$ current response inducing action (%) by test substance alone=(ITD÷IDPAT)×100

ITD: level of inward K$^+$ current response by test substance alone

IDPAT: level of 8-OH-DPAT (10$^{-7}$ mol/L) induced inward K$^+$ current in the same cell The suppressive effect (5-HT$_{1A}$ antagonistic action) on the 8-OH-DPAT induced inward K$^+$ current by the test substance was determined according to the following equation.

antagonistic action of test substance on 8-OH-DPAT induced inward K$^+$ current (% of control)= (IMIX÷IDPAT)×100

IMIX: level of 8-OH-DPAT (10$^{-7}$ mol/L) induced inward K$^+$ current in the presence of test substance IDPAT: as defined above According to the results of Experimental Example 5, the respective values of inward K$^+$ current inducing action (%) by the test substance alone at a concentration of 10$^{-7}$ mol/L and the antagonistic action (% of control) of the test substance on the 8-OH-DPAT induced inward K$^+$ current were almost nil, showing that the compounds of the present invention (compounds of Examples 6, 88, 136, 138 etc.) are silent antagonists of 5-HT$_{1A}$ receptor.

In contrast, the compound for reference showed an action of a partial agonist at a high dose (10$^{-7}$ mol/L).

EFFECT OF THE INVENTION

The compound of the present invention shows selective affinity for as well as simultaneous antagonistic activity against 5-HT$_{1A}$ receptor, and also shows a 5-HT reuptake inhibitory activity. Thus, the compound of the present invention is useful as a so-called rapid onset antidepressant that shows quick expression of an anti-depressive effect. It is also useful for the treatment of 5-HT mediated diseases of the central nervous system, such as schizophrenia, anxiety neurosis, obsessive-compulsive disorder (OCD), panic disorder, social anxiety disorder (social phobia), seasonal emotional disorder (seasonal affective disorder), Anorexia Nervosa, Bulimia Nervosa, nocturnal enuresis, children's hyperlocomotion, post-traumatic stress disorder (PTSD), senile dementia, hemicrania, stroke, Alzheimer's disease, recognition disorder, hypertension, gastrointestinal injury, feeding disorders, premenstrual syndrome (PMS), abnormal body temperature regulation and sexual disorder, pain, abnormality in the cardiovascular system, drug abuse and the like.

This application is based on patent application Nos. 142750/1999, 166160/1999, 277384/1999 and 018080/2000 filed in Japan, the contents of which are hereby incorporated by reference.

What is claimed is:

1. A compound selected from the group consisting of
2-(4-methoxybenzo(b)furan-2-yl)-5-methyl-1,3,4-oxadiazole,
2-(4-hydroxybenzo(b)furan-2-yl)-5-methyl-1,3,4-oxadiazole,
(S)-2-(4-glycidyloxybenzo(b)furan-2-yl)-5-methyl-1,3,4-oxadiazole, 2-(7-methoxybenzo(b)furan-2-yl)-5-methyl-1,3,4-oxadiazole,
2-(4-(methoxymethyloxy)benzo(b)thiophen-2-yl)-5-methyl-1,3,4-oxadiazole,
2-(4-hydroxybenzo(b)thiophen-2-yl)-5-methyl-1,3,4-oxadiazole,
4-benzyloxy-2-(5-methyl-1,3,4-oxadiazol-2-yl)-1H-indole,
2-(7-methoxybenzo(b)furan-2-yl)-5-phenyl-1,3,4-oxadiazole,
2-(4-methoxybenzo(b)furan-2-yl)-5-trifluoromethyl-1,3,4-oxadiazole,
2-(4-hydroxybenzo(b)furan-2-yl)-5-trifluoromethyl-1,3,4-oxadiazole,
(S)-2-(4-glycidyloxybenzo(b)furan-2-yl)-5-trifluoromethyl-1,3,4-oxadiazole,
2-(7-methoxybenzo(b)furan-2-yl)-5-trifluoromethyl-1,3,4-oxadiazole,
2-(7-hydroxybenzo(b)furan-2-yl)-5-trifluoromethyl-1,3,4-oxadiazole,
(S)-2-(7-glycidyloxybenzo(b)furan-2-yl)-5-trifluoromethyl-1,3,4-oxadiazole,
2-(4-methoxybenzo(b)furan-2-yl)-5-ethyl-1,3,4-oxadiazole,
2-(4-hydroxybenzo(b)furan-2-yl)-5-ethyl-1,3,4-oxadiazole,
(S)-2-(4-glycidyloxybenzo(b)furan-2-yl)-5-ethyl-1,3,4-oxadiazole,
5-ethoxycarbonyl-2-(4-methoxybenzo(b)furan-2-yl)-1,3,4-oxadiazole,
5-ethoxycarbonyl-2-(4-hydroxybenzo(b)furan-2-yl)-1,3,4-oxadiazole,
5-(4-(methoxymethyloxy)benzo(b)furan-2-yl)-2,3-dihydro-1,3,4-oxadiazole-2-thione,
5-(4-(methoxymethyloxy)benzo(b)furan-2-yl)-2-methylthio-1,3,4-oxadiazole,
5-(4-hydroxybenzo(b)furan-2-yl)-2-methylthio-1,3,4-oxadiazole,
5-(4-(methoxymethyloxy)benzo(b)furan-2-yl)-2,3-dihydro-1,3,4-oxadiazol-2-one,
5-(4-(methoxymethyloxy)benzo(b)furan-2-yl)-2-methoxy-1,3,4-oxadiazole,
(S)-5-(4-glycidyloxybenzo(b)furan-2-yl)-2-methoxy-1,3,4-oxadiazole,
2-ethoxy-5-(4-(methoxymethyloxy)benzo(b)furan-2-yl)-1,3,4-oxadiazole,
(S)-2-ethoxy-5-(4-glycidyloxybenzo(b)furan-2-yl)-1,3,4-oxadiazole,
2-(1-methylethyloxy)-5-(4-(methoxymethyloxy)benzo(b)furan-2-yl)-1,3,4-oxadiazole and
(S)-2-(1-methylethyloxy)-5-(4-glycidyloxybenzo(b)furan-2-yl)-1,3,4-oxadiazole.

2. 2-(4-hydroxybenzo(b)furan-2-yl)-5-methyl-1,3,4-oxadiazole.

3. (S)-2-(4-glycidyloxybenzo(b)furan-2-yl)-5-methyl-1,3,4-oxadiazole.

* * * * *